(12) United States Patent
Shum

(10) Patent No.: US 11,932,849 B2
(45) Date of Patent: Mar. 19, 2024

(54) WHOLE TRANSCRIPTOME ANALYSIS OF SINGLE CELLS USING RANDOM PRIMING

(71) Applicant: Cellular Research, Inc., San Jose, CA (US)

(72) Inventor: Eleen Shum, San Jose, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 367 days.

(21) Appl. No.: 16/677,012

(22) Filed: Nov. 7, 2019

(65) Prior Publication Data

US 2020/0149037 A1    May 14, 2020

Related U.S. Application Data

(60) Provisional application No. 62/757,757, filed on Nov. 8, 2018.

(51) Int. Cl.
*C12N 15/10* (2006.01)
*C40B 40/06* (2006.01)
*C40B 50/04* (2006.01)
*C40B 50/06* (2006.01)
*C40B 70/00* (2006.01)

(52) U.S. Cl.
CPC ..... *C12N 15/1096* (2013.01); *C12N 15/1006* (2013.01); *C40B 40/06* (2013.01); *C40B 50/04* (2013.01); *C40B 50/06* (2013.01); *C40B 70/00* (2013.01)

(58) Field of Classification Search
CPC ............ C12N 15/1096; C12N 15/1006; C40B 40/06; C40B 50/04; C40B 50/06; C40B 70/00; C12Q 2525/161; C12Q 2537/143; C12Q 2549/119; C12Q 2563/179
See application file for complete search history.

(56) References Cited

U.S. PATENT DOCUMENTS

| | | | |
|---|---|---|---|
| 4,510,244 A | 4/1985 | Parks et al. | |
| 4,725,536 A | 2/1988 | Fritsch et al. | |

(Continued)

FOREIGN PATENT DOCUMENTS

| | | |
|---|---|---|
| CA | 2474509 | 2/2003 |
| EP | 1473080 | 11/2004 |

(Continued)

OTHER PUBLICATIONS

"Reverse Transcriptases" information from New England Biolabs, Inc.; downloaded Sep. 22, 2021 from https://www.neb.com/products/rna-reagents/reverse-transcriptases-and-rt-pcr/reverse-transcriptases-and-rt-pcr/reverse-transcriptases (5 pages) (Year: 2021).*

(Continued)

*Primary Examiner* — Jeremy C Flinders
(74) *Attorney, Agent, or Firm* — Sheppard, Mullin, Richter & Hampton LLP

(57) ABSTRACT

Disclosed herein include systems, methods, compositions, and kits for whole transcriptome analysis (WTA) with random priming and extension (RPE). The RPE-based WTA method can comprise hybridizing random primers with a plurality of first strand barcoded polynucleotides associated with a solid support and extending the random primers to generate a plurality of extension products. The method can comprise amplifying the plurality of extension products to generate a sequencing library.

20 Claims, 47 Drawing Sheets

Specification includes a Sequence Listing.

(56) References Cited

U.S. PATENT DOCUMENTS

| | | |
|---|---|---|
| 5,124,246 A | 6/1992 | Urdea et al. |
| 5,149,625 A | 9/1992 | Church et al. |
| 5,200,314 A | 4/1993 | Urdea |
| 5,308,990 A | 5/1994 | Takahashi et al. |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchik et al. |
| 5,962,272 A | 10/1999 | Chenchik et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,214,558 B1 | 4/2001 | Shuber et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Willis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet et al. |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,181,582 B2 | 11/2015 | Kurn |
| 9,188,586 B2 | 11/2015 | Fan et al. |
| 9,228,229 B2 | 1/2016 | Olson et al. |
| 9,262,376 B2 | 2/2016 | Tsuto |
| 9,290,808 B2 | 3/2016 | Fodor et al. |
| 9,290,809 B2 | 3/2016 | Fodor et al. |
| 9,297,047 B2 | 3/2016 | Furchak et al. |
| 9,315,857 B2 | 4/2016 | Fu et al. |
| 9,371,598 B2 | 6/2016 | Chee |
| 9,567,645 B2 | 2/2017 | Fan et al. |
| 9,567,646 B2 | 2/2017 | Fan et al. |
| 9,582,877 B2 | 2/2017 | Fu et al. |
| 9,593,365 B2 | 3/2017 | Frisen et al. |
| 9,598,736 B2 | 3/2017 | Fan et al. |
| 9,637,799 B2 | 5/2017 | Fan et al. |

(56) References Cited

U.S. PATENT DOCUMENTS

| | | |
|---|---|---|
| 9,644,204 B2 | 5/2017 | Hindson et al. |
| 9,689,024 B2 | 6/2017 | Hindson et al. |
| 9,695,468 B2 | 7/2017 | Hindson et al. |
| 9,708,659 B2 | 7/2017 | Fodor et al. |
| 9,727,810 B2 | 8/2017 | Fodor et al. |
| 9,787,810 B1 | 10/2017 | Chiang |
| 9,816,137 B2 | 11/2017 | Fodor et al. |
| 9,845,502 B2 | 12/2017 | Fodor et al. |
| 9,850,515 B2 | 12/2017 | McCoy et al. |
| 9,856,530 B2 | 1/2018 | Hindson et al. |
| 9,868,979 B2 | 1/2018 | Chee et al. |
| 9,879,313 B2 | 1/2018 | Chee et al. |
| 9,905,005 B2 | 2/2018 | Fu et al. |
| 9,938,523 B2 | 4/2018 | LaBaer |
| 9,951,386 B2 | 4/2018 | Hindson et al. |
| 9,988,660 B2 | 6/2018 | Rashtchian et al. |
| 10,002,316 B2 | 6/2018 | Fodor et al. |
| 10,011,872 B1 | 7/2018 | Belgrader et al. |
| 10,017,761 B2 | 7/2018 | Weissman et al. |
| 10,023,910 B2 | 7/2018 | Drmanac et al. |
| 10,030,267 B2 | 7/2018 | Hindson et al. |
| 10,041,116 B2 | 8/2018 | Hindson et al. |
| 10,047,394 B2 | 8/2018 | Fodor et al. |
| 10,059,991 B2 | 8/2018 | Fodor et al. |
| 10,131,958 B1 | 11/2018 | Fan et al. |
| 10,138,518 B2 | 11/2018 | Chun |
| 10,151,003 B2 | 12/2018 | Fan et al. |
| 10,202,641 B2 | 2/2019 | Shum |
| 10,202,646 B2 | 2/2019 | Fodor et al. |
| 10,208,343 B2 | 2/2019 | Hindson et al. |
| 10,208,356 B1 | 2/2019 | Fan et al. |
| 10,227,648 B2 | 3/2019 | Hindson et al. |
| 10,246,703 B2 | 4/2019 | Church et al. |
| 10,253,364 B2 | 4/2019 | Hindson et al. |
| 10,253,375 B1 | 4/2019 | Fan et al. |
| 10,273,541 B2 | 4/2019 | Hindson et al. |
| 10,288,608 B2 | 5/2019 | Kozlov et al. |
| 10,294,511 B2 | 5/2019 | Sanches-Kuiper et al. |
| 10,301,677 B2 | 5/2019 | Shum et al. |
| 10,308,982 B2 | 6/2019 | Chee |
| 10,323,278 B2 | 6/2019 | Belgrader et al. |
| 10,337,061 B2 | 7/2019 | Hindson et al. |
| 10,338,066 B2 | 7/2019 | Fan et al. |
| 10,344,329 B2 | 7/2019 | Hindson et al. |
| 10,392,661 B2 | 8/2019 | Fodor et al. |
| 10,450,607 B2 | 10/2019 | Hindson et al. |
| 10,550,429 B2 | 2/2020 | Harada et al. |
| 10,619,186 B2 | 4/2020 | Betts et al. |
| 10,619,203 B2 | 4/2020 | Fodor et al. |
| 10,676,779 B2 | 6/2020 | Chang et al. |
| 11,092,607 B2 | 8/2021 | Gaublomme et al. |
| 2001/0024784 A1 | 9/2001 | Wagner |
| 2001/0036632 A1 | 11/2001 | Yu et al. |
| 2002/0019005 A1 | 2/2002 | Kamb |
| 2002/0051986 A1 | 5/2002 | Baez et al. |
| 2002/0065609 A1 | 5/2002 | Ashby |
| 2002/0072058 A1 | 6/2002 | Voelker et al. |
| 2002/0094116 A1 | 7/2002 | Forst et al. |
| 2002/0106666 A1 | 8/2002 | Hayashizaki |
| 2002/0132241 A1 | 9/2002 | Fan et al. |
| 2002/0168665 A1 | 11/2002 | Okawa |
| 2002/0172953 A1 | 11/2002 | Mirkin et al. |
| 2002/0187480 A1 | 12/2002 | Brandon |
| 2002/0192687 A1 | 12/2002 | Mirkin et al. |
| 2003/0003490 A1 | 1/2003 | Fan et al. |
| 2003/0013091 A1 | 1/2003 | Dimitrov |
| 2003/0032049 A1 | 2/2003 | Wagner |
| 2003/0049616 A1 | 3/2003 | Brenner et al. |
| 2003/0077611 A1 | 4/2003 | Slepnev |
| 2003/0082818 A1 | 5/2003 | Bahnson et al. |
| 2003/0087242 A1 | 5/2003 | Mirkin et al. |
| 2003/0104436 A1 | 6/2003 | Morris et al. |
| 2003/0165935 A1 | 9/2003 | Vann et al. |
| 2003/0175908 A1 | 9/2003 | Linnarsson |
| 2003/0186251 A1 | 10/2003 | Dunn et al. |
| 2003/0207296 A1 | 11/2003 | Park et al. |
| 2003/0207300 A1 | 11/2003 | Matray et al. |
| 2004/0047769 A1 | 3/2004 | Tanaami |
| 2004/0091864 A1 | 5/2004 | French et al. |
| 2004/0096368 A1 | 5/2004 | Davis et al. |
| 2004/0096892 A1 | 5/2004 | Wang et al. |
| 2004/0121342 A1 | 6/2004 | McKeown |
| 2004/0146901 A1 | 7/2004 | Morris et al. |
| 2004/0147435 A1 | 7/2004 | Hawiger et al. |
| 2004/0157243 A1 | 8/2004 | Huang et al. |
| 2004/0209298 A1 | 10/2004 | Kamberov et al. |
| 2004/0224325 A1 | 11/2004 | Knapp et al. |
| 2004/0259118 A1 | 12/2004 | Macevicz |
| 2005/0019776 A1 | 1/2005 | Callow et al. |
| 2005/0032110 A1 | 2/2005 | Shen et al. |
| 2005/0048500 A1 | 3/2005 | Lawton |
| 2005/0053952 A1 | 3/2005 | Hong et al. |
| 2005/0105077 A1 | 5/2005 | Padmanabhan et al. |
| 2005/0170373 A1 | 8/2005 | Monforte |
| 2005/0175993 A1 | 8/2005 | Wei |
| 2005/0196760 A1 | 9/2005 | Pemov et al. |
| 2005/0214825 A1 | 9/2005 | Stuelpnagel |
| 2005/0250146 A1 | 11/2005 | McMillan |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0057634 A1 | 3/2006 | Rye |
| 2006/0073506 A1 | 4/2006 | Christians et al. |
| 2006/0211030 A1 | 9/2006 | Brenner |
| 2006/0257902 A1 | 11/2006 | Mendoza et al. |
| 2006/0263709 A1 | 11/2006 | Matsumura et al. |
| 2006/0263789 A1 | 11/2006 | Kincaid |
| 2006/0280352 A1 | 12/2006 | Muschler et al. |
| 2006/0281092 A1 | 12/2006 | Wille et al. |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0065844 A1 | 3/2007 | Golub et al. |
| 2007/0105090 A1 | 5/2007 | Cassidy et al. |
| 2007/0117121 A1 | 5/2007 | Hutchison et al. |
| 2007/0117134 A1 | 5/2007 | Kou |
| 2007/0117177 A1 | 5/2007 | Luo et al. |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker et al. |
| 2007/0281317 A1 | 12/2007 | Becker et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0268508 A1 | 10/2008 | Sowlay |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053669 A1 | 2/2009 | Liu et al. |
| 2009/0061513 A1 | 3/2009 | Andersson Svahn et al. |
| 2009/0105959 A1 | 4/2009 | Braverman et al. |
| 2009/0131269 A1 | 5/2009 | Martin et al. |
| 2009/0137407 A1 | 5/2009 | Church et al. |
| 2009/0220385 A1 | 9/2009 | Brown et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal et al. |
| 2009/0298709 A1 | 12/2009 | Ma |
| 2009/0311694 A1 | 12/2009 | Gallagher et al. |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |

(56) References Cited

U.S. PATENT DOCUMENTS

| | | |
|---|---|---|
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |
| 2010/0255471 A1 | 10/2010 | Clarke |
| 2010/0267028 A1 | 10/2010 | Pasche |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2012/0004132 A1 | 1/2012 | Zhang et al. |
| 2012/0010091 A1 | 1/2012 | Linnarson |
| 2012/0014977 A1 | 1/2012 | Furihata et al. |
| 2012/0034607 A1 | 2/2012 | Rothberg et al. |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney et al. |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0004569 A1 | 1/2014 | Lambowitz et al. |
| 2014/0057799 A1 | 2/2014 | Johnson et al. |
| 2014/0066318 A1 | 3/2014 | Frisen et al. |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0322716 A1 | 10/2014 | Robins |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0011396 A1 | 1/2015 | Schroeder et al. |
| 2015/0017654 A1 | 1/2015 | Gorfinkel et al. |
| 2015/0066385 A1 | 3/2015 | Schnall-levin et al. |
| 2015/0072867 A1 | 3/2015 | Soldatov et al. |
| 2015/0072873 A1 | 3/2015 | Heinz et al. |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0152409 A1 | 6/2015 | Seitz et al. |
| 2015/0203897 A1 | 7/2015 | Robons et al. |
| 2015/0211050 A1 | 7/2015 | Iafrate et al. |
| 2015/0218620 A1 | 8/2015 | Behlke et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0253237 A1 | 9/2015 | Castellarnau et al. |
| 2015/0259734 A1 | 9/2015 | Asbury et al. |
| 2015/0275295 A1 | 10/2015 | Wang et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0010151 A1 | 1/2016 | Fan et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060621 A1 | 3/2016 | Agresti et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen et al. |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0153973 A1 | 6/2016 | Smith |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0253584 A1 | 9/2016 | Fodor et al. |
| 2016/0257993 A1 | 9/2016 | Fu et al. |

(56) References Cited

U.S. PATENT DOCUMENTS

| | | |
|---|---|---|
| 2016/0258012 A2 | 9/2016 | Fodor et al. |
| 2016/0265027 A1 | 9/2016 | Sanches-Kuiper et al. |
| 2016/0265069 A1 | 9/2016 | Fan et al. |
| 2016/0266094 A1 | 9/2016 | Ankrum et al. |
| 2016/0289669 A1 | 10/2016 | Fan et al. |
| 2016/0289670 A1 | 10/2016 | Samuels et al. |
| 2016/0289740 A1 | 10/2016 | Fu et al. |
| 2016/0298180 A1 | 10/2016 | Chee |
| 2016/0312276 A1 | 10/2016 | Fu et al. |
| 2016/0320720 A1 | 11/2016 | Murata et al. |
| 2016/0326584 A1 | 11/2016 | Fodor et al. |
| 2016/0355879 A1 | 12/2016 | Kamberov et al. |
| 2016/0376583 A1 | 12/2016 | Fodor et al. |
| 2016/0376648 A1 | 12/2016 | Fodor et al. |
| 2017/0044525 A1 | 2/2017 | Kaper et al. |
| 2017/0073730 A1 | 3/2017 | Betts et al. |
| 2017/0154421 A1 | 6/2017 | Fu et al. |
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0337459 A1 | 11/2017 | Fodor et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0002764 A1 | 1/2018 | Fan et al. |
| 2018/0016634 A1 | 1/2018 | Hindson et al. |
| 2018/0024139 A1 | 1/2018 | Peikon et al. |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0088112 A1 | 3/2018 | Fan et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Arson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0216174 A1 | 8/2018 | Shum et al. |
| 2018/0230527 A1 | 8/2018 | Fang et al. |
| 2018/0251825 A1 | 9/2018 | Stoeckius et al. |
| 2018/0258482 A1 | 9/2018 | Hindson et al. |
| 2018/0258500 A1 | 9/2018 | Fan et al. |
| 2018/0267036 A1 | 9/2018 | Fan et al. |
| 2018/0276332 A1 | 9/2018 | Fan et al. |
| 2018/0282803 A1 | 10/2018 | Belgrader et al. |
| 2018/0291470 A1 | 10/2018 | Fan et al. |
| 2018/0002738 A1 | 11/2018 | Wang et al. |
| 2018/0320241 A1 | 11/2018 | Nolan et al. |
| 2018/0327835 A1 | 11/2018 | Fodor et al. |
| 2018/0327836 A1 | 11/2018 | Fodor et al. |
| 2018/0327866 A1 | 11/2018 | Fan et al. |
| 2018/0327867 A1 | 11/2018 | Fan et al. |
| 2018/0340170 A1 | 11/2018 | Belhocine et al. |
| 2018/0346969 A1 | 12/2018 | Chang et al. |
| 2018/0346970 A1 | 12/2018 | Chang et al. |
| 2018/0371536 A1 | 12/2018 | Fu et al. |
| 2019/0010552 A1 | 1/2019 | Xu et al. |
| 2019/0025304 A1 | 1/2019 | Vigneault et al. |
| 2019/0032129 A1 | 1/2019 | Hindson et al. |
| 2019/0040474 A1 | 2/2019 | Fan et al. |
| 2019/0085412 A1 | 3/2019 | Fan et al. |
| 2019/0095578 A1 | 3/2019 | Shum et al. |
| 2019/0100798 A1 | 4/2019 | Fodor et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0161743 A1 | 5/2019 | Church et al. |
| 2019/0177788 A1 | 6/2019 | Hindson et al. |
| 2019/0177800 A1 | 6/2019 | Boutet et al. |
| 2019/0203270 A1 | 7/2019 | Amit et al. |
| 2019/0203291 A1 | 7/2019 | Hindson et al. |
| 2019/0211395 A1 | 7/2019 | Tsao et al. |
| 2019/0218276 A1 | 7/2019 | Regev et al. |
| 2019/0218607 A1 | 7/2019 | Love et al. |
| 2019/0221287 A1 | 7/2019 | Tsujimoto |
| 2019/0221292 A1 | 7/2019 | Tsujimoto |
| 2019/0256888 A1 | 8/2019 | Weissleder et al. |
| 2019/0256907 A1 | 8/2019 | Ryan et al. |
| 2019/0292592 A1 | 9/2019 | Shum et al. |
| 2019/0338278 A1 | 11/2019 | Shum et al. |
| 2019/0338353 A1 | 11/2019 | Belgrader et al. |
| 2019/0338357 A1 | 11/2019 | Fan et al. |
| 2019/0390253 A1 | 12/2019 | Kennedy et al. |
| 2020/0109437 A1 | 4/2020 | Chang et al. |
| 2020/0124601 A1 | 4/2020 | Fan et al. |
| 2020/0149037 A1 | 5/2020 | Shum |
| 2021/0198754 A1 | 7/2021 | Fan et al. |
| 2021/0214770 A1 | 7/2021 | Prosen et al. |
| 2021/0214784 A1 | 7/2021 | Prosen et al. |
| 2021/0222244 A1 | 7/2021 | Martin et al. |
| 2021/0230582 A1 | 7/2021 | Fu et al. |
| 2021/0230583 A1 | 7/2021 | Lam et al. |
| 2021/0230666 A1 | 7/2021 | Wu et al. |
| 2021/0246492 A1 | 8/2021 | Song et al. |
| 2021/0263019 A1 | 8/2021 | Martin et al. |
| 2021/0355484 A1 | 11/2021 | Jensen et al. |
| 2021/0371909 A1 | 12/2021 | Lazaruk |
| 2022/0010361 A1 | 1/2022 | Song et al. |
| 2022/0010362 A1 | 1/2022 | Campbell |
| 2022/0033810 A1 | 2/2022 | Song et al. |
| 2022/0154288 A1 | 5/2022 | Mortimer |
| 2022/0162695 A1 | 5/2022 | Sakofsky et al. |
| 2022/0162773 A1 | 5/2022 | Sakofsky et al. |
| 2022/0178909 A1 | 6/2022 | Huang et al. |
| 2022/0220549 A1 | 7/2022 | Shum et al. |

FOREIGN PATENT DOCUMENTS

| | | |
|---|---|---|
| EP | 1647600 | 4/2006 |
| EP | 1845160 | 10/2007 |
| EP | 2036989 | 3/2009 |
| EP | 1379693 | 5/2009 |
| EP | 2204456 | 7/2010 |
| EP | 2431465 | 3/2012 |
| EP | 2203749 | 8/2012 |
| EP | 2511708 | 10/2012 |
| EP | 2538220 | 12/2012 |
| EP | 2623613 | 8/2013 |
| EP | 2702146 | 3/2014 |
| EP | 1745155 | 10/2014 |
| EP | 2805769 | 11/2014 |
| EP | 2556171 | 9/2015 |
| EP | 2989215 | 3/2016 |
| EP | 2970958 | 12/2017 |
| EP | 3263715 | 1/2018 |
| EP | 3286326 | 2/2018 |
| EP | 3136103 | 8/2018 |
| EP | 2954102 | 12/2018 |
| EP | 3428290 | 1/2019 |
| EP | 2970957 | 4/2019 |
| EP | 3058092 | 5/2019 |
| EP | 3256606 | 5/2019 |
| EP | 3327123 | 8/2019 |
| GB | 2293238 A | 3/1996 |
| JP | H04108385 | 4/1992 |
| JP | 2001078768 | 3/2001 |
| JP | 2005233974 | 9/2005 |
| JP | 2007504831 | 3/2007 |
| JP | 2008256428 | 10/2008 |
| JP | 2013039275 | 2/2013 |
| WO | WO1989001050 | 2/1989 |
| WO | WO1996024061 | 8/1996 |
| WO | WO1997010365 | 3/1997 |
| WO | WO1999015702 | 4/1999 |

(56) References Cited

FOREIGN PATENT DOCUMENTS

| | | |
|---|---|---|
| WO | WO1999028505 | 6/1999 |
| WO | WO2000058516 | 10/2000 |
| WO | WO2001048242 | 7/2001 |
| WO | WO2001053539 | 7/2001 |
| WO | WO2002018643 | 3/2002 |
| WO | WO2002046472 | 6/2002 |
| WO | WO2002056014 | 7/2002 |
| WO | WO2002059355 | 8/2002 |
| WO | WO2002070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003035829 | 5/2003 |
| WO | WO2004017374 | 2/2004 |
| WO | WO2004021986 | 3/2004 |
| WO | WO2004033669 | 4/2004 |
| WO | WO2004066185 | 8/2004 |
| WO | WO2004081225 | 9/2004 |
| WO | WO2005017206 | 2/2005 |
| WO | WO2005021731 | 3/2005 |
| WO | WO2005042759 | 5/2005 |
| WO | WO2005071110 | 8/2005 |
| WO | WO2005080604 | 9/2005 |
| WO | WO2005111242 | 11/2005 |
| WO | WO2005111243 | 11/2005 |
| WO | WO2006026828 | 3/2006 |
| WO | WO2006071776 | 7/2006 |
| WO | WO2006102264 | 9/2006 |
| WO | WO2006137932 | 12/2006 |
| WO | WO2007087310 | 8/2007 |
| WO | WO2007087312 | 8/2007 |
| WO | WO2007147079 | 12/2007 |
| WO | WO2008047428 | 4/2008 |
| WO | WO2008051928 | 5/2008 |
| WO | WO2008057163 | 5/2008 |
| WO | WO2008096318 | 8/2008 |
| WO | WO2008104380 | 9/2008 |
| WO | WO2008147428 | 12/2008 |
| WO | WO2008150432 | 12/2008 |
| WO | WO2009048530 | 4/2009 |
| WO | WO2009148560 | 12/2009 |
| WO | WO2009152928 | 12/2009 |
| WO | WO2010059820 | 5/2010 |
| WO | WO2010117620 | 10/2010 |
| WO | WO2010131645 | 11/2010 |
| WO | WO2019076768 | 4/2011 |
| WO | WO2011091393 | 7/2011 |
| WO | WO2011106738 | 9/2011 |
| WO | WO2011123246 | 10/2011 |
| WO | WO2011127099 | 10/2011 |
| WO | WO2011143659 | 11/2011 |
| WO | WO2011155833 | 12/2011 |
| WO | WO2012038839 | 3/2012 |
| WO | WO2012041802 | 4/2012 |
| WO | WO2012042374 | 4/2012 |
| WO | WO2012047297 | 4/2012 |
| WO | WO2012048341 | 4/2012 |
| WO | WO2012083225 | 6/2012 |
| WO | WO2012099896 | 7/2012 |
| WO | WO2012103154 | 8/2012 |
| WO | WO2012108864 | 8/2012 |
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012149042 | 11/2012 |
| WO | WO2012156744 | 11/2012 |
| WO | WO2012162267 | 11/2012 |
| WO | WO2012177639 | 12/2012 |
| WO | WO2013019075 | 2/2013 |
| WO | WO2013070990 | 5/2013 |
| WO | WO 2013/096802 A1 * | 6/2013 |
| WO | WO2013117595 | 8/2013 |
| WO | WO2013130674 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |
| WO | WO2014071361 | 5/2015 |
| WO | WO2015061844 | 5/2015 |
| WO | WO2015103339 | 7/2015 |
| WO | WO2015117163 | 8/2015 |
| WO | WO2015134787 | 9/2015 |
| WO | WO2015160439 | 10/2015 |
| WO | WO2015168161 | 11/2015 |
| WO | WO2015179339 | 11/2015 |
| WO | WO2015200869 | 12/2015 |
| WO | WO2015200893 | 12/2015 |
| WO | WO2016044227 | 3/2016 |
| WO | WO2016049418 | 3/2016 |
| WO | WO2016061517 | 4/2016 |
| WO | WO2016100976 | 6/2016 |
| WO | WO2016118915 | 7/2016 |
| WO | WO2016130578 | 8/2016 |
| WO | WO2016160965 | 8/2016 |
| WO | WO2016138496 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018017949 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |

(56) References Cited

FOREIGN PATENT DOCUMENTS

| | | |
|---|---|---|
| WO | WO2018111872 | 6/2018 |
| WO | WO2018115852 | 6/2018 |
| WO | WO2018119447 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018174827 | 9/2018 |
| WO | WO2018217862 | 11/2018 |
| WO | WO2018218222 | 11/2018 |
| WO | WO2018222548 | 12/2018 |
| WO | WO2018226293 | 12/2018 |
| WO | WO2019055852 | 3/2019 |
| WO | WO2019084046 | 5/2019 |
| WO | WO2019099906 | 5/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |
| WO | WO2013137737 | 9/2019 |
| WO | WO2019178164 | 9/2019 |
| WO | WO2019213237 | 11/2019 |
| WO | WO2019213294 | 11/2019 |
| WO | WO2019218101 | 11/2019 |
| WO | WO2020028266 | 2/2020 |
| WO | WO2020033164 | 2/2020 |
| WO | WO2020037065 | 2/2020 |
| WO | WO2020046833 | 3/2020 |
| WO | WO2020072380 | 4/2020 |
| WO | WO2020097315 | 5/2020 |
| WO | WO2020123384 | 6/2020 |
| WO | WO2020131699 | 6/2020 |
| WO | WO2020154247 | 7/2020 |
| WO | WO2020167920 | 8/2020 |
| WO | WO2020214642 | 10/2020 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021247593 | 12/2021 |
| WO | WO2022015667 | 1/2022 |
| WO | WO2022026909 | 2/2022 |
| WO | WO2022040453 | 2/2022 |

OTHER PUBLICATIONS

10X Genomics, Inc., 2019, User Guide: Visium Spatial Gene Expression Reagent Kits, www.10xGenomics.com, 76 pp.
2018 Top 10 Innovations, The Scientist Magazine® (2018). Available at: https://www.thescientist.com/features/2018-top-10-innovations-65140, 16 pp.
Achim et al., "High-throughput spatial mapping of single-cell RNA-seq data to tissue of origin," Nature Biotechnology 2015, 33(5), 503-511.
Advisory Action dated Nov. 29, 2019 in U.S. Appl. No. 15/084,307.
Advisory Action dated Dec. 2, 2019 in U.S. Appl. No. 15/055,407.
Agasti et al., "Photocleavable DNA barcode-antibody conjugates allow sensitive and multiplexed protein analysis in single cell," J Am Chem Soc. 2012, 134(45), 18499-18502.
Alexandra M. Ewing of Richards, Layton and Finger, P.A., Entry of Appearance dated Jan. 18, 2019 in the USDC District of Delaware, C.A. No. 18-1800-RGA, 1 pp.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLID™ System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Atanur et al., "The genome sequence of the spontaneously hypertensive rat: Analysis and functional significance." Genome Res. 2010, 20(6), 791-803.
Audic et al., "The Significance of Digital Gene Expression Profiles," Genome Res. 1997, 7, 986-995.
Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Bendall et al., "Single-Cell Mass Cytometry of Differential Immune and Drug Responses Across a Human Hematopoietic Continuum," Science 2011, 332(6030), 687-696.
Bioscribe "Massively parallel sequencing technology for single-cell gene expression published" (press release), PhysOrg 2015, 1-2.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bonaldo et al., "Normalization and Subtraction: Two Approaches to facilitate Gene Discovery," Genome Res. 1996, 6, 791-806.
Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.
Brodin et al., "Challenges with Using Primer IDs to Improve Accuracy of Next Generation Sequencing," PLoS One 2015, 19(3), 1-12.
Buggenum et al., "A covalent and cleavable antibody DNA conjugation strategy for sensitive protein detection via immunoPCR," Scientific Reports 2016, 6(22675), 1-12.
Buschmann et al., Enhancing the detection of barcoded reads in high throughput DNA sequencing DNA by controlling the false discovery rate, BMC Bioinformatics, 15(1), 264, 1-16, (Year 2014).
Bustin, "Absolute quantification of mRNA using real-time reverse transcription polymerase chain reaction assays," Journal of Molecular Endocrinology 2000, 25, 169-193.

(56) References Cited

OTHER PUBLICATIONS

Butkus, "Cellular research set to launch first gene expression platform using 'molecular indexing' technology," GenomeWeb 2014, 1-5.
Cai, "Turning single cells in microarrays by super-resolution barcoding," Briefings in Functional Genomics 2012, 12(2), 75-80.
Cao et al., "Comprehensive single-cell transcriptional profiling of a multicellular organism," Science 2017, 357, 661-667.
Carr et al., "Inferring relative proportions of DNA variants from sequencing electropherograms," Bioinformatics 2009, 25(24), 3244-3250.
Caruccio et al., "Nextera (TM) Technology for NGS DNA Library Preparation: Simultaneous Fragmentation and Tagging by in Vitro Transposition." EpiBio 2009, 16(3), 4-6.
Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis," Small 2015, 11(4), 489-498.
Castle et al., "DNA copy number, including telomeres and mitochondria, assayed using next-generation sequencing," BMC Genomics 2010, 11(244), 1-11.
Chamberlain et al., "Deletion screening of the Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research, 8, 2580-2585.
Chapin et al., "Rapid microRNA Profiling on Encoded Gel Microparticles," Angew Chem Int Ed Engl. 2011, 50(10), 2289-2293.
Chee et al., "Accessing genetic information with high-density DNA arrays," Science 1996, 274, 610-614.
Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Church et al., "Multiplex DNA sequencing," Science 1988, 240(4849), 185-188.
Civil Cover Sheet filed Nov. 15, 2018 in the USDC for the District of Delaware, C.A. 18-1800-RGA, 1 pp.
Clontech Laboratories, Inc., "Smart™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Communication of a Notice of Opposition dated Jul. 21, 2016 in European Patent Application No. EP 10762102.1.
Complaint filed in *Becton, Dickinson and Company and Cellular Research Inc. v. 10X Genomics, Inc.* dated Nov. 15, 2018 in the USDC for the District of Delaware, C.A. 18-1800-RGA, 141 pp.
Costa et al., "Single-Tube Nested Real-Time PCR as a New Highly Sensitive Approach to Trace Hazelnut," Journal of Agricultural and Food Chemistry 2012, 60, 8103-8110.
Costello et al., "Discovery and characterization of artefactual mutations in deep coverage targeted capture sequencing data due to oxidative DNA damage during sample preparation," Nucleic Acids Res 2013, 41(6), e67, 1-12.
Cotten et al., "Selection of proteins with desired properties from natural proteome libraries using mRNA display," Nature Protocols 2011, 6, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.

Custom Antibody Services, Precision Antibody, accessed Apr. 16, 2014, 2 pp.
Daines et al., "High-throughput multiplex sequencing to discover copy number variants in *Drosophila*," Genetics 2009, 182(4), 182, 935-941.
Dalerba et al., "Single-cell dissection of transcriptional heterogeneity in human colon tumors," Nat Biotechnol. 2011, 29(12), 1120-1127.
D'Antoni et al., "Rapid quantitative analysis using a single molecule counting approach," Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
Decision of Refusal dated Aug. 21, 2017 in Japanese Patent Application No. 2014-558975.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomic's Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Defendant 10X Genomic's Notice of Service for Initial Disclosures served to Opposing Counsel, dated Jun. 7, 2019 in the USDC for the District of Delaware, C.A. 18-1800-RGA, 2 pp.
Defendant 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomics, Inc.'s Opening Brief in Support of its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomic's Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant 10X Genomic's Request for Oral Argument Under D. Del. LR 7.1.4, dated Apr. 18, 2019 in the USDC for the District of Delaware, C.A. 18-1800-RGA 2 pp.
Defendant 10X Genomic's Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.

(56) References Cited

OTHER PUBLICATIONS

Delley et al., "Combined aptamer and transcriptome sequencing of single cells," bioRxiv 2017, 1-10.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.
Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.
Examination Report dated Mar. 18, 2019 in Singapore Patent Application No. 11201405274W.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Fan et al., "Parallel Genotyping of Human SNPs Using Generic High-density Oligonucleotide Tag Arrays," Genome Research 2000, 10, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," Science 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.
Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.
Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.

(56) References Cited

OTHER PUBLICATIONS

Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
Gerry et al., "Universal DNA Microarray Method for Multiplex Detection of Low Abundance Point Mutations," Journal of Molecular Biology 1999, 292, 251-262.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Grant et al., "SNP genotyping on a genome-wide amplified DOP-PCR template," Nucleic Acids Res 2002, 30(22), e25, 1-6.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications." Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.

Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13, Molecules.
Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Preliminary Report on Patentability dated Mar. 26, 2019 in PCT Application No. PCT/US2017/053331.
International Preliminary Report on Patentability dated Aug. 15, 2019 in PCT Application No. PCT/US2018/014385.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.
International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.
International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.
International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.

(56) References Cited

OTHER PUBLICATIONS

International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
Invitation to Pay Fees dated Mar. 16, 2016 in PCT Application No. PCT/US2016/019971.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Fees dated May 7, 2020 in PCT Application No. PCT/US2020/017890.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from a retroviral population," Biology Lunch Bunch Series, Training Initiatives in Biomedical & Biological Sciences of the University of North Carolina at Chapel Hill 2010.
Jabara et al., "Accurate sampling and deep sequencing of the HIV-1 protease gene using a Primer ID," PNAS 2011, 108(50), 20166-20171.
Jason J. Rawnsley of Richards, Layton and Finger, P.A., Entry of Appearance dated Jan. 18, 2019 in the USDC District of Delaware, C.A. No. 18-1800-RGA, 1 pp.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to Submit Agreed Document Production Protocol, dated Jul. 11, 2019 in the USDC for the District of Delaware, C.A. 18-1800 (RGA), 1 pp.
Junker et al., "Single-Cell Transcriptomics Enters the Age of Mass Production," Molecular Cell 2015, 58, 563-564.
Kanagawa, "Bias and artifacts in multi-template polymerase chain reactions (PCR)," Journal of Bioscience and Bioengineering 2003, 96(4), 317-323.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells." Ann Biotechnol. 2018, 2(1007), 1-8.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336-343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting Drug Resistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.
Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kivioja et al., "Counting absolute Nos. of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an Escherichia coli cDNA library for small RNAs," Journal of Microbiological Methods 2006, 64, 297-304.
Koboldt et al., VarScan: variant detection in massively parallel sequencing of individual and pooled samples, Bioinformatics 2009, 25(17), 2283-2285.
Kolodziejczyk et al., 'The Technology and Biology of Single-Cell RNA Sequencing, Molecular Cell 2015, 58, 610-620.
Konig et al., iCLIP reveals the function of hnRNAP particles in splicing at individual nucleotide resolution, Nature Structural & Molecular Biology 2010, 17(7), 909-916.
Kotake et al., "A simple nested RT-PCR method for quantitation of the relative amounts of multiple cytokine mRNAs in small tissue samples," Journal of Immunological Methods 1996, 199, 193-203.
Kozlov et al., "A high-complexity, multiplexed solution-phase assay for profiling protease activity on microarrays," Comb Chem High Throughput Screen 2008, 11(1), 24-35.
Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.
Lamble et al., "Improved workflows for high throughput library preparation using the transposome-based nextera system," BMC Biotechnology 2013, 13, 104, 1-10.
Larson et al., "A single molecule view of gene expression," Trends Cell Biol. 2009, 19(11), 630-637.
Lass-Napiorkowska et al., "Detection methodology based on target molecule-induced sequence-specific binding to a single-stranded oligonucleotide." Anal Chem. 2012, 84(7), 3382-3389.
Leamon et al., A massively parallel Pico TiterPlate based platform for discrete picoliter-scale polymerase chain reactions, Electrophoresis 2003, 24, 3769-3777.
Lee et al., "Large-scale arrays of picolitre chambers for single-cell analysis of large cell populations," Lab Chip 2010, 10, 2952-2958.
Lee et al., "Highly Multiplexed Subcellular RNA Sequencing in Situ," Science 2014, 343, 1360-1363.
Lee et al., "Universal process-inert encoding architecture for polymer microparticles," Nature Materials 2014, 13(5), 524-529.
Letter regarding the opposition procedure dated Jul. 22, 2015 for European Patent Application No. 11810645.9.
Letter to Judge Richard G. Andrews Requesting a Rule 16 Conference, dated Apr. 15, 2019 in the USDC for the District of Delaware, C.A. 18-1800 (RGA), 1 pp.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.

(56) References Cited

OTHER PUBLICATIONS

Lin et al., "Self-Assembled Combinatorial Encoding Nanoarrays for Multiplexed Biosensin," Nano Lett. 2007, 7 (2), 507-512.

Liu et al., "Single-cell transcriptome sequencing: recent advances and remaining challenges," F1000Research 2016, 5(F1000 Faculty Rev)(182), 1-9.

Lizardi et al., "Mutation detection and single-molecule counting using isothermal rolling-circle amplification," Nat Genet. 1998, 19, 225-232.

Lockhart et al., "Expression monitoring by hybridization to high-density oligonucleotide arrays," Nature Biotechnology 1996, 14, 1675-1680.

Lovatt et al., "Transcriptome in vivo analysis (TIVA) of spatially defined single cells in live tissue," Nat Methods 2014, 11(2), 190-196.

Loy et al., "A rapid library preparation method with custom assay designs for detection of variants at 0.1% allelic frequency in liquid biopsy samples," Oct. 2, 2018, 1 p.

Lucito et al., "Representational Oligonucleotide Microarray Analysis: A High-Resolution Method to Detect Genome Copy Number Variation," Genome Research 2003, 13, 2291-2305.

Lundberg et al., "Practical innovations for high-throughput amplicon sequencing," Nature Methods 2013, 10(10), 999-1007.

Lundberg et al., "Supplementary Information for: Practical innovations for high-throughput amplicon sequencing," Nature Methods 2013, 1-24.

Maamar et al., "Noise in Gene Expression Determines Cell Fate in Bacillus subtilis," Science 2007, 317, 526-529.

Macaulay et al., "Single Cell Genomics: Advances and Future Perspectives," PLoS Genetics 2014, 10(1), 1-9.

Macaulay et al., "G&T-seq: parallel sequencing of single-cell genomes and transcriptomes," Nature Methods 2015, 1-7.

Macosko et al., "Highly parallel genome-wide expression profiling of individual cells using nanoliter droplets," Cell 2015, 161, 1202-1214.

Maeda et al., "Development of a DNA barcode tagging method for monitoring dynamic changes in gene expression by using an ultra high-throughput sequencer," BioTechniques 2008, 45(1), 95-97.

Makrigiorgos et al., "A PCR-Based amplification method retaining the quantitative difference between two complex genomes," Nature Biotech 2002, 20(9), 936-939.

Marcus et al., 2006, "Microfluidic single-cell mRNA isolation and analysis," Anal Chem. 2006, 78, 3084-3089.

Mardis, "Next-generation DNA sequencing methods", Annu. Rev. Genomics Hum. Genet. 2008, 9, 387-402.

Marguerat et al., "Next-generation sequencing: applications beyond genomes," Biochem. Soc. Trans. 2008, 36(5), 1091-1096.

Marguiles et al., Genome sequencing in microfabricated high-density picolitre reactors, Nature 2005, 437, 376-380.

Martinez et al., "A microfluidic approach to encapsulate living cells in uniform alginate hydrogel microparticles," Macromol. Biosci 2012, 12, 946-951.

Massachusetts General Hospital, Overview of Illumina Chemistry, http://nextgen.mgh.harvard.edu/IlluminaChemistry.html, downloaded Jan. 28, 2020, 2 pp.

McCloskey et al., "Encoding PCR products with batch-stamps and barcodes," Biochem Genet. 2007, 45(11-12), 761-767.

Medvedev et al., "Detecting copy number variation with mated short reads," Genome Res. 2010, 20, 1613-1622.

Mei et al., "Identification of recurrent regions of Copy-Number Variants across multiple individuals," BMC Bioinformatics 2010, 11, 147, 1-14.

Merriam-Webster, definition of associate: http://www.merriam-webster.com/dictionary/associate, accessed Apr. 5, 2016.

Meyer et al., "Parallel tagged sequencing on the 454 platform," Nature Protocols 2008, 3(2), 267-278.

Miller et al., Directed evolution by in vitro compartmentalization, Nature Methods 2006, 3(7), 561-570.

Miner et al., "Molecular barcodes detect redundancy and contamination in hairpin-bisulfite PCR," Nucleic Acids Research 2004, 32(17), e135, 1-4.

Mortazavi et al., "Mapping and quantifying mammalian transcriptomes by RNA-Seq," Nat. Methods 2008, 5(7), 621-628.

Motion and Order for Admission Pro Hac Vice Pursuant to Local Rule 83.5, dated Jan. 24, 2019 in the USDC District of Delaware, C.A. No. 18-1800-RGA, 7 pp.

Nadai et al., Protocol for nearly full-length sequencing of HIV-1 RNA from plasma, PLoS One 2008, 3(1), e1420, 1-6.

Nagai et al., "Development of a microchamber array for picoliter PCR," Anal. Chem. 2001, 73, 1043-1047.

Navin et al., "The first five years of single-cell cancer genomics and beyond," Genome Research 2015, 25, 1499-1507.

Newell et al., Cytometry by time-of-flight shows combinatorial cytokine expression and virus-specific cell niches within a continuum of CD8+ T cell phenotypes. Immunity 2012, 36(1), 142-152.

Non-Final Office Action dated Oct. 3, 2013 in U.S. Appl. No. 12/969,581.

Non-Final Office Action dated Feb. 18, 2015 for U.S. Appl. No. 14/540,007.

Non-Final Office Action dated Feb. 26, 2015 for U.S. Appl. No. 14/540,029.

Non-Final Office Action dated Mar. 19, 2015 in U.S. Appl. No. 14/540,018.

Non-Final Office Action dated May 7, 2015 for U.S. Appl. No. 13/327,526.

Non-Final Office Action dated Dec. 3, 2015 for U.S. Appl. No. 14/281,706.

Non-Final Office Action dated Dec. 31, 2015 for U.S. Appl. No. 14/800,526.

Non-Final Office Action dated Apr. 11, 2016 in U.S. Appl. No. 14/472,363.

Non-Final Office Action dated May 10, 2016 in U.S. Appl. No. 14/381,488.

Non-Final Office Action dated May 13, 2016 in U.S. Appl. No. 14/508,911.

Non-Final Office Action dated Aug. 17, 2016 for U.S. Appl. No. 14/800,526.

Non-Final Office Action dated Sep. 26, 2016 in U.S. Appl. No. 15/167,807.

Non-Final Office Action dated Oct. 11, 2016 in U.S. Appl. No. 15/224,460.

Non-Final Office Action dated Jan. 19, 2017 in U.S. Appl. No. 15/055,445.

Non-Final Office Action dated Mar. 24, 2017 in U.S. Appl. No. 15/409,355.

Non-Final Office Action dated Jun. 2, 2017 in U.S. Appl. No. 14/381,526.

Non-Final Office Action dated Jun. 7, 2017 in U.S. Appl. No. 14/381,488.

Non-Final Office Action dated Jul. 28, 2017 in U.S. Appl. No. 14/975,441.

Non-Final Office Action dated Sep. 8, 2017 in U.S. Appl. No. 15/046,225.

Non-Final Office Action dated Sep. 8, 2017 in U.S. Appl. No. 15/134,967.

Non-Final Office Action dated Nov. 1, 2017 in U.S. Appl. No. 15/667,125.

Non-Final Office Action dated Nov. 9, 2017 in U.S. Appl. No. 15/004,618.

Non-Final Office Action dated Jan. 9, 2018 in U.S. Appl. No. 15/217,896.

Non-Final Office Action dated Jan. 12, 2018 in U.S. Appl. No. 15/217,886.

Non-Final Office Action dated Mar. 8, 2018 in U.S. Appl. No. 15/608,780.

Non-Final Office Action dated Apr. 6, 2018 in U.S. Appl. No. 15/603,239.

Non-Final Office Action dated Jul. 25, 2018 in U.S. Appl. No. 15/108,268.

Non-Final Office Action dated Oct. 4, 2018 in U.S. Appl. No. 15/260,106.

(56) References Cited

OTHER PUBLICATIONS

Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.
Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.
Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Notice of Allowability dated Jun. 19, 2014 for U.S. Appl. No. 12/969,581.
Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Apr. 15, 2020 in U.S. Appl. No. 16/012,635.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 9, 2015 for European Patent Application No. 11810645.9.
Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.
Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.
Office Action dated Jun. 6, 2016 in Chinese Patent Application No. 201380022187.9.
Office Action dated Dec. 27, 2016 in Chinese Patent Application No. 201380022187.9.
Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.

(56) References Cited

OTHER PUBLICATIONS

Order Scheduling ADR Mediation Teleconference, filed May 13, 2019 in the USDC for the District of Delaware, C.A. 18-1800-RGA, 4pp.
Ozkumur et al., "Inertial Focusing for Tumor Antigen-Dependent and - Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) CNDA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Péres-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes and sample integrity: BestKeeper—Excel-based tool using pair-wise correlations," Biotechnology Letters, 26(6), 505-515, (Year: 2004).
Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.
Pinkel et al., "Comparative Genomic Hybridization," Annual Review of Genomics and Human Genetics 2005, 6, 331-354.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Pleasance et al., "A small-cell lung cancer genome with complex signatures of tobacco exposure," Nature 2010, 463(7278), 184-190.
Plessy et al., "Population transcriptomics with single-cell resolution: a new field made possible bymicrofluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) of the Federal Rules of Civil Procedure, filed Jun. 20, 2019 in the USDC for the District of Delaware, C.A. 18-1800 (RGA), 26 pp.
Qiu et al., "DNA Sequence-Based "Bar Codes" for Tracking the Origins of Expressed Sequence Tagsfrom a Maize cDNA Library Constructed Using Multiple mRNA Sources," Plant Physiol. 2003, 133, 475-481.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.

Report on the Filing or Determination of an Action Regarding a Patent or Trademark filed Nov. 15, 2018 in the USDC for the District of Delaware, C.A. 18-1800-RGA, 2 pp.
Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated Jun. 19, 2019 in U.S. Appl. No. 15/596,364.
Restriction Requirement dated Sep. 20, 2019 in U.S. Appl. No. 15/875,816.
Roche Diagnostics GmbH, "Genome Sequencer 20 System: First to the Finish," 2006, 1-40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-CooV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody-DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Scheduling Order pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Schmitt et al., "Detection of ultra-rare mutations by next-generation sequencing," Proc Natl Acad Sci 2012, 109(36), 1-6.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Sebat et al., "Large-Scale Copy Number Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4):1347-1352.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019, 1129, 63-79.
Simpson et al., "Copy number variant detection in inbred strains from short read sequence data," Bioinformatics 2010, 26(4), 565-567.
Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.

(56) References Cited

OTHER PUBLICATIONS

Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Soumillon et al., "Characterization of directed differentiation by high-throughput single-cell RNA-Seq," bioRxiv 2014, 1-13.
Speicher et al., "The new cytogenetics: blurring the boundaries with molecular biology," Nature Reviews Genetics 2005, 6(10), 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons in a Civil Action to Defendant 10X Genomics, Inc. filed Nov. 16, 2018 in the USDC for the District of Delaware, Civil Action No. 18-1800, 2 pp.
Sun et al., "Ultra-deep profiling of alternatively spliced *Drosophila* Dscam isoforms by circularization-assisted multi-segment sequencing," EMBO J. 2013, 32(14), 2029-2038.
Takahashi et al., "Novel technique of quantitative nested real-time PCR assay for mycobacterium tuberculosis DNA," Journal of Clinical Microbiology 2006, 44, 1029-1039.
Tan et al., "Genome-wide comparison of DNA hydroxymethylation in mouse embryonic stem cells and neural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy number estimation of the highly polymorphic human beta-defensin locus on 8p23 by 454 amplicon sequencing," BMC Genomics 2010, 11, 252, 1-14.
The Tibbs Times, UNC bioscience newsletter, Apr. 1-17, 2010.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
Treutlein et al., Reconstructing lineage hierarchies of the distal lung epithelium using single-cell RNA-seq, Nature 2014, 509, 371-375.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization of the Yeast Transcriptome," Cell 1997, 88, 243-251.
Vogelstein et al., "Digital PCR," Proc. Natl. Acad. Sci. 1999, 96, 9236-9241.
Vollbrecht et al., "Validation and comparison of two NGS assays for the detection of EGFR T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing." Proc Natl Acad Sci 2010, 107(28), 12629-12633.
Wang et al., "Combining Gold Nanoparticles with Real-Time Immuno-PCR for Analysis of HIV p24 Antigens," Proceedings of ICBBE 2007, 1198-1201.
Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91(5), 400-401.
Wodicka et al., "Genome-wide expression monitoring in *Saccharomyces cerevisiae*," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy numbervariation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Yandell et al., "A probabilistic disease-gene finder for personal genomes," Genome Res. 2011, 21(9), 1529-1542.
Ye et al., Fluorescent microsphere-based readout technology for multiplexed human single nucleotide polymorphism analysis and bacterial identification, Human Mutation 2001, 17(4), 305-316.
Yoon et al., Sensitive and accurate detection of copy number variants using read depth of coverage, Genome Res. 2009, 19, 1586-1592.
Zagordi et al., "Error correction of next-generation sequencing data and reliable estimation of HIV quasispecies," Nucleic Acids Research 2010, 38(21), 7400-7409.
Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung CarcinomasRevealed by Single Nucleotide Polymorphism Array Analysis," Cancer Research 2005, 65(13), 5561-5570.

(56) References Cited

OTHER PUBLICATIONS

Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by MALDI-TOF MS," Mol. BioSyst. 2012, 8, 2395-2404.
Zhu et al., "Reverse Transcriptase Template Switching: A Smart Approach for Full-Length cDNA Library Construction," BioTechniques 2001, 30(4), 892-897.
Advisory Action dated Aug. 25, 2020 in U.S. Appl. No. 15/084,307.
Biosciences Product Catalogue, Dynal® Catalog 1999, Oslo, Norway, 49-51.
Examination Report dated Jul. 6, 2020 in European Patent Application No. 17781265.8.
Examination Report dated Sep. 21, 2020 in European Patent Application No. 18703156.2.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
International Search Report and Written Opinion dated May 18, 2020 in PCT Application No. PCT/US2020/014339.
International Search Report and Written Opinion dated Jun. 30, 2020 in PCT Application No. PCT/US2020/017890.
Kooiker & Xue, "cDNA Library Preparation," Cereal Genomics 2013, 1099, 29-40.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Notice of Grant dated Sep. 23, 2020 in Korean Patent Application No. 10-2016-7008144.
Notice of Allowance dated Oct. 29, 2020 in U.S. Appl. No. 15/987,851.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Rhee et al., "Simultaneous detection of mRNA and protein stem cell markers in live cells," BMC Biotechnology 2009, 9(30), 1-10.
Search Report and Written Opinion dated Aug. 26, 2020 in Singapore Patent Application No. 10201806890V.
KO, "An 'equalized cDNA library' by the reassociation of short double-stranded cDNAs," Nucleic Acids Res. 1990, 18(19), 5705-5711.
Bionumbers, Aug. 21, 2010, "Useful fundamental numbers in molecular biology," http://bionumbers.hms.harvard.edu/KeyNumbers/aspx, 1-4.
Examination Report dated Nov. 12, 2020 in European Patent Application No. 18716877.8, 5 pgs.
Examination Report dated Dec. 3, 2020 in European Patent Application No. 16719706.0, 4 pgs.
Examination Report dated Mar. 25, 2021 in European Patent Application No. 17781265.8, 6 pgs.
Final Office Action dated Dec. 7, 2020 in U.S. Appl. No. 16/012,584, 36 pgs.
Final Office Action dated Feb. 11, 2021 in U.S. Appl. No. 15/134,967, 65 pgs.
Final Office Action dated Mar. 16, 2021 in U.S. Appl. No. 15/715,028, 12 pgs.
Final Office Action dated Mar. 25, 2021 in U.S. Appl. No. 16/374,626, 62 pgs.
International Preliminary Report on Patentability dated Nov. 3, 2020 in PCT Application No. PCT/US2019/030175, 7 pgs.
International Preliminary Report on Patentability dated Nov. 3, 2020 in PCT Application No. PCT/US2019/030245, 13 pgs.
International Preliminary Report on Patentability dated Feb. 9, 2021 in PCT Application No. PCT/US2019/043949, 8 pgs.
International Preliminary Report on Patentability dated Feb. 23, 2021 in PCT Application No. PCT/US2019/046549, 7 pgs.
International Preliminary Report on Patentability dated Mar. 2, 2021 in PCT Application No. PCT/US2019/048179, 14 pgs.
International Search Report and Written Opinion dated Nov. 12, 2020 in PCT Application No. PCT/US2020/042880, 16 pgs.
International Search Report and Written Opinion dated Jan. 19, 2021 in PCT Application No. PCT/US2020/059419, 13 pgs.
New COVID-19 Variants, Centers for Disease Control and Prevention 2021, accessed Jan. 21, 2021, 3 pp.
Non-Final Office Action dated Dec. 9, 2020 in U.S. Appl. No. 16/788,743, 96 pgs.
Non-Final Office Action dated Jan. 19, 2021 in U.S. Appl. No. 16/836,750, 12 pgs.
Non-Final Office Action dated Feb. 2, 2021 in U.S. Appl. No. 16/535,080, 67 pgs.
Non-Final Office Action dated Feb. 25, 2021 in U.S. Appl. No. 15/055,407, 44 pgs.
Non-Final Office Action dated Feb. 25, 2021 in U.S. Appl. No. 15/084,307, 15 pgs.
Non-Final Office Action dated Mar. 29, 2021 in U.S. Appl. No. 16/789,358, 14 pgs.
Notice of Allowance dated Jan. 13, 2021 in U.S. Appl. No. 14/381,488, 10 pgs.
Notice of Allowance dated Jan. 13, 2021 in U.S. Appl. No. 15/459,977, 14 pgs.
Office Action dated Oct. 29, 2020 in Chinese Patent Application No. 2018800377201, 10 pgs.
Office Action dated Jan. 4, 2021 in Japanese Patent Application No. 2017-549390, 5 pgs.
Office Action dated Jan. 6, 2021 in Chinese Patent Application No. 201680052330.2, 21 pgs.
Office Action dated Jan. 14, 2021 in Japanese Patent Application No. 2019-014564, 5 pgs.
Office Action dated Jan. 15, 2021 in Korean Patent Application No. 10-2020-7033213, 5 pgs.
Office Action dated Jan. 26, 2021 in Chinese Patent Application No. 201680007351.2, 9 pgs.
Office Action dated Feb. 4, 2021 in Canadian Patent Application No. 2,865,575, 4 pgs.
Office Action dated Feb. 20, 2021 in Chinese Patent Application No. 201680022865.5, 28 pgs.
Office Action dated Mar. 1, 2021 in Chinese Patent Application No. 201680007652.5, 9 pgs.
Office Action dated Mar. 2, 2021 in Chinese Patent Application No. 2016800157452, 34 pgs.
Office Action dated Mar. 8, 2021 in Japanese Patent Application No. 2018-512152, 5 pgs.
Office Action dated Mar. 16, 2021 in Chinese Patent Application No. 2018800377201, 7 pgs.
Stoeckius et al., "Cell Hashing with barcoded antibodies enables multiplexing and doublet detection for single cell genomics," Genome Biology 2018, 19(224), 1-12.
Summons to Attend Oral Proceedings dated Nov. 16, 2020 in European Patent Application No. 17202409.3, 11 pgs.
TotalSeq™-A0251 anti-human Hashtag 1 Antibody, BioLegend®, Jul. 1-10, 2018.
Zeberg et al., "The major genetic risk factor for severe COVID-19 is inherited from Neanderthals," Nature 2020, 587(7835), 1-13.

(56) References Cited

OTHER PUBLICATIONS

Adey et al., "Rapid, low-input, low-bias construction of shotgun fragment libraries by high-density in vitro transposition," Genome Biology 2010, 11(R19), in 17 pages.
Ahern, "Biochemical, Reagent Kits Offer Scientists Good Return on Investment," The Scientist 1995, 9(15), in 5 pages.
Brouilette et al., "A Simple and Novel Method for RNA-seq Library Preparation of Single Cell cDNA Analysis by Hyperactive Tn5 Transposase," Developmental Dynamics 2012, 241, 1584-1590.
Examination Report dated Oct. 8, 2021 in European Patent Application No. 18716877.8, 7 pgs.
Examination Report dated Nov. 18, 2021 in European Patent Application No. 19724003.9, 8 pgs.
Examination Report dated Nov. 24, 2021 in European Patent Application No. 19762517.1, 4 pgs.
Examination Report dated Dec. 6, 2021 in European Patent Application No. 18703156.2, 4 pgs.
Extended European Search Report dated May 6, 2021 in European Patent Application No. 20207621.2, 13 pgs.
Extended European Search Report dated May 28, 2021 in European Patent Application No. 20209777.0, 10 pgs.
Final Office Action dated Jun. 15, 2021 in U.S. Appl. No. 15/084,307.
Final Office Action dated Jul. 15, 2021 in U.S. Appl. No. 16/836,750.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
Fitzgerald and Grivel, "A Universal Nanoparticle Cell Secretion Capture Assay," Cytometry Part A 2012, 83A(2), 205-211.
GenBank Accession No. NM_000518.5 for *Homo sapiens* hemoglobin subunit beta (HBB), mRNA. Mar. 22, 2021 [online], [retrieved on Apr. 27, 2021], retrieved from the Internet: <URL: www.ncbi.nlm.nih.gov/nuccore/NM_000518.5?report=Genbank (Year: 2021).
Gertz et al., "Transposase mediated construction of RNA-seq libraries," Genome Research 2012, 22, 134-141.
Gratton et al., "Cell-permeable peptides improve cellular uptake and therapeutic gene delivery of replication-deficient viruses in cells and in vivo," Nature Medicine 2003, 9(3), 357-362.
International Search Report and Written Opinion dated Apr. 9, 2021 in PCT Application No. PCT/US2021/013137, 15 pgs.
International Search Report and Written Opinion dated Apr. 21, 2021 in PCT Application No. PCT/US2021/015571, 14 pgs.
International Search Report and Written Opinion dated May 4, 2021 in PCT Application No. PCT/US2021/013109, 16 pgs.
International Search Report and Written Opinion dated May 11, 2021 in PCT Application No. PCT/US2021/013748, 16 pgs.
International Search Report and Written Opinion dated Jul. 15, 2021 in PCT Application No. PCT/US2021/019475, 19 pgs.
International Search Report and Written Opinion dated Jul. 20, 2021 in PCT Application No. PCT/US2021/015898, 21 pgs.
International Search Report and Written Opinion dated Aug. 31, 2021 in PCT Application No. PCT/US2021/035270, 14 pgs.
International Search Report and Written Opinion dated Sep. 22, 2021, in PCT Application No. PCT/US2021/013747, 17 pgs.
International Search Report and Written Opinion dated Sep. 27, 2021, in PCT Application No. PCT/US2021/017719, 15 pgs.
International Search Report and Written Opinion dated Oct. 12, 2021, in PCT Application No. PCT/US2021/041327, 16 pgs.
International Search Report and Written Opinion dated Oct. 29, 2021, in PCT Application No. PCT/US2021/032319, 22 pgs.
International Search Report and Written Opinion dated Nov. 12, 2021, in PCT Application No. PCT/US2021/044036, 14 pgs.
Invitation to Pay Fees dated May 25, 2021 in PCT Application No. PCT/US2021/01598, 16 pgs.
Invitation to Pay Additional Search Fees dated Sep. 8, 2021 in PCT Application No. PCT/US2021/032319, 15 pgs.
Invitation to Provide Informal Clarification dated Jun. 9, 2021 in PCT Application No. PCT/US2021/019475, 5 pgs.

Janeway et al., "Structural variation in immunoglobulin constant regions," Immunology: The Immune System in Health and Disease 1999, 101-103.
Lan et al., "Droplet barcoding for massively parallel single-molecule deep sequencing," Nature Communications 2016, 7(11784), in 10 pages.
Livingstone, "rRNA depletion, poly(A) enrichment, or exonuclease treatment?" Tebu-Bio Blog 2015, 5 pgs.
Mair et al., "A Targeted Multi-omic Analysis Approach Measures Protein Expression and Low-Abundance Transcripts on the Single-Cell Level", Cell Reports 2020, 31(1), 107499, in 20 pages.
Non-Final Office Action dated Apr. 14, 2021 in U.S. Appl. No. 16/789,311.
Non-Final Office Action dated Apr. 20, 2021 in U.S. Appl. No. 15/875,816.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Non-Final Office Action dated Dec. 15, 2021 in U.S. Appl. No. 15/875,816.
Non-Final Office Action dated Dec. 21, 2021 in U.S. Appl. No. 15/055,407.
Notice of Allowance dated Apr. 26, 2021 in Japanese Patent Application No. 2019-014564, 4 pgs.
Notice of Allowance dated Jun. 10, 2021 in Chinese Patent Application No. 2018800377201, 3 pgs.
Notice of Allowance dated Aug. 16, 2021 in Japanese Patent Application No. 2018-512152, 4 pgs.
Notice of Allowance dated Sep. 10, 2021 in U.S. Appl. No. 16/535,080.
Notice of Allowance dated Nov. 17, 2021 in U.S. Appl. No. 16/836,750.
Novus Biologicals, "Fixation and Permeability in ICC IF," Novus Biologicals 2021, 1-3.
Office Action dated May 10, 2021 in Japanese Patent Application No. 2019-566787, 6 pgs.
Office Action dated May 21, 2021 in Chinese Patent Application No. 201680007351.2, 21 pgs.
Office Action dated Jul. 26, 2021 in Korean Patent Application No. 10-2019-7011635, 10 pgs.
Office Action dated Jul. 28, 2021 in Korean Patent Application No. 10-2020-7033213, 6 pgs.
Office Action dated Aug. 13, 2021 in Chinese Patent Application No. 2017800587991, 32 pgs.
Office Action dated Aug. 27, 2021 in Chinese Patent Application No. 2016800076525, 8 pgs.
Office Action dated Aug. 30, 2021 in Japanese Patent Application No. 2019-540515, 9 pgs.
Office Action dated Aug. 31, 2021, in Korean Patent Application No. 10-2019-7038794, 16 pgs.
Office Action dated Sep. 14, 2021, in Chinese Patent Application No. 2016800523302, 11 pgs.
Office Action dated Oct. 21, 2021, in Chinese Patent Application No. 2016800073512, 23 pgs.

(56) References Cited

OTHER PUBLICATIONS

O'Shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Quail et al., "SASI-Seq: sample assurance Spike-Ins, and highly differentiating 384 barcoding for Illumina sequencing," BMC Genomics 2014, 15(110), in 13 pages.
Restriction Requirement dated May 5, 2021 in U.S. Appl. No. 16/400,886.
Restriction Requirement dated May 28, 2021 in U.S. Appl. No. 16/781,814.
Restriction Requirement dated Jun. 4, 2021 in U.S. Appl. No. 16/551,620.
Restriction Requirement dated Sep. 20, 2021 in U.S. Appl. No. 16/525,054.
Restriction Requirement dated Oct. 1, 2021 in U.S. Appl. No. 16/232,287.
Restriction Requirement dated Dec. 27, 2021 in U.S. Appl. No. 16/747,737.
Schouten et al., "Relative quantification of 40 nucleic acid sequences by multiplex ligation-dependent probe amplification," Nucleic Acids Research 2002, 30(12), e57, 13 pgs.
Shapiro et al., "Single-cell sequencing-based technologies will revolutionize whole-organism science," Nature Reviews Genetics 2013, 14, 618-629.
Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Takara Bio, "SMARTer Human BCR IgG IgM H/K/L Profiling Kit User Manual," Takara Bio USA Inc. 2019, 1-22.
Trzupek et al., "Discovery of CD80 and CD86 as recent activation markers on regulatory T cells by protein-RNA single-cell analysis", Genome Medicine 2020, 12(1), in 22 pages.
Vestheim et al., "Application of Blocking Oligonucleotides to Improve Signal-to-Noise Ratio in a PCR," Methods in Molecular Biology 2011, 687, 265-274.
Wang et al., "Tagmentation-based whole-genome bisulfite sequencing," Nature Protocols 2013, 8(10), 2022-2032.
Zhao et al., "Methylated DNA Immunoprecipitation and High-Throughput Sequencing (MeDIP-seq) Using Low Amounts of Genomic DNA," Cellular Reprogramming 2014, 16(3), in 20 pages.
Bolivar et al., "Targeted next-generation sequencing of endometrial cancer and matched circulating tumor DNA: identification of plasma-based, tumor-associated mutations in early stage patients," Modern Pathology 2019, 32(3), 405-414.
Chang et al., "Single-cell protein and gene expression profiling of stem memory T cells by BD Ab-seq," Annual Joint Meeting of the American Society for Cell Biology and the European Molecular Biology Organization 2017, 28(26), P1896.
Chen et al., "High-throughput sequencing of the transcriptome and chromatin accessibility in the same cell," Nature Biotechnology 2019, 37, 1452-1457.
Dengl et al., "Engineered hapten-binding antibody derivatives for modulation of pharmacokinetic properties of small molecules and targeted payload delivery," Immunol Rev. 2016, 270, 165-177.
Examination Report dated Dec. 9, 2021 in European Patent Application No. 19723988.2.
Examination Report dated Apr. 7, 2022 in Singapore Patent Application No. 10201806890V.

Examination Report dated Apr. 8, 2022 in Australian Patent Application No. 2018281745.
Final Office Action dated Jan. 18, 2022 in U.S. Appl. No. 16/588,405.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Goodridge et al., "Synthesis of Albumin and Malic Enzyme in Wheat-Germ Lysates and *Xenopus laevis* Oocytes Programmed with Chicken-Liver Messenger RNA," Eur. J. Biochem. 1979, 96, 1-8.
International Search Report and Written Opinion dated Dec. 6, 2021, in PCT Application No. PCT/US2021/046750.
International Search Report and Written Opinion dated Mar. 10, 2022, in PCT Application No. PCT/US2021/060206.
International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
Jacobsen et al., "33rd Annual Meeting & Pre-Conference Programs of the Society for Immunotherapy of Cancer," Journal for Immunotherapy of Cancer 2018, 6(S1), 7-11.
Lake et al., "Integrative single-cell analysis of transcriptional and epigenetic states in the human adult brain," Nature Biotechnology 2018, 36(1), 70-80.
Lutz et al., "Isolation and analysis of high quality nuclear DNA with reduced organellar DNA for plant genome sequencing and resequencing," BMC Biotechnology 2011, 11(54), in 9 pages.
Monneron, "One-step Isolation and Characterization of Nuclear Membranes, 1974 Electron Microscopy and Composition of Biological Membranes and Envelops," The Royal Publishing Society 1974, 268, 101-108.
Non-Final Office Action dated Jan. 6, 2022 in U.S. Appl. No. 15/084,307.
Non-Final Office Action dated Feb. 2, 2022 in U.S. Appl. No. 16/747,737.
Non-Final Office Action dated Feb. 9, 2022 in U.S. Appl. No. 16/525,054.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Non-Final Office Action dated May 11, 2022 in U.S. Appl. No. 16/588,405.
Non-Final Office Action dated May 19, 2022 in U.S. Appl. No. 16/459,444.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Notice of Allowance dated Dec. 7, 2021 in Chinese Patent Application No. 201680007652.
Notice of Allowance dated Jan. 24, 2022 in Korean Patent Application No. 16/836,750.
Notice of Allowance dated Feb. 9, 2022 in U.S. Appl. No. 16/781,814.

(56) References Cited

OTHER PUBLICATIONS

Notice of Allowance dated Feb. 11, 2022 in Chinese Patent Application No. 201680007351.2.
Notice of Allowance dated Feb. 16, 2022 in U.S. Appl. No. 15/875,816.
Notice of Allowance dated Feb. 21, 2022 in Korean Patent Application No. 10-2020-7033213.
Notice of Allowance dated Apr. 11, 2022 in U.S. Appl. No. 15/134,967.
Notice of Allowance dated Apr. 25, 2022 in Korean Patent Application No. 10-2018-7008560.
Notice of Allowance dated Apr. 27, 2022 in U.S. Appl. No. 16/400,886.
Notice of Allowance dated May 9, 2022 in Australian Patent Application No. 2018281745.
Notice of Allowance dated May 15, 2022 in Japanese Patent Application No. 2019-540515.
Notice of Allowance dated May 23, 2022 in U.S. Appl. No. 15/715,028.
Notice of Allowance dated May 26, 2022 in Korean Patent Application No. 10-2019-7038794.
Notice of Allowance dated Jun. 6, 2022 in U.S. Appl. No. 16/789,358.
Notice of Allowance dated Jul. 20, 2022 in U.S. Appl. No. 16/707,780.
Notice of Allowance dated Aug. 9, 2022 in U.S. Appl. No. 16/232,287.
Notice of Allowance dated Sep. 26, 2022, 2022 in U.S. Appl. No. 16/232,287.
Nowak et al., "Does the KIR2DS5 gene protect from some human diseases?," PLoS One 2010, 5(8), in 6 pages.
Office Action dated Nov. 2, 2021, in Japanese Patent Application No. 2017-549390.
Office Action dated Dec. 23, 2021, in Japanese Patent Application No. 2019-566787.
Office Action dated Dec. 17, 2021 in Korean Patent Application No. 10-2018-7008560.
Office Action dated Jan. 13, 2022 in Chinese Patent Application No. 201780058799.1.
Office Action dated Feb. 9, 2022 in Japanese Patent Application No. 2019-540515.
Office Action dated Mar. 7, 2022 in Korean Patent Application No. 10-2022-7004715.
Office Action dated May 17, 2022 in Australian Patent Application No. 2019204928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
Restriction Requirement dated Aug. 8, 2022 in U.S. Appl. No. 17/163,177.
Restriction Requirement dated Aug. 11, 2022 in U.S. Appl. No. 17/091,639.
Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.
Yang & Zhao, "Quantitative Analysis of Nonoxynol-9 in Blood," Contraception 1991, 43(2), 161-166.
Zhang et al., "Immunoaffinity Purification of Plasma Membrane with Secondary Antibody Superparamagnetic Beads," Journal of Proteome 2006, 6, 34-43.

* cited by examiner

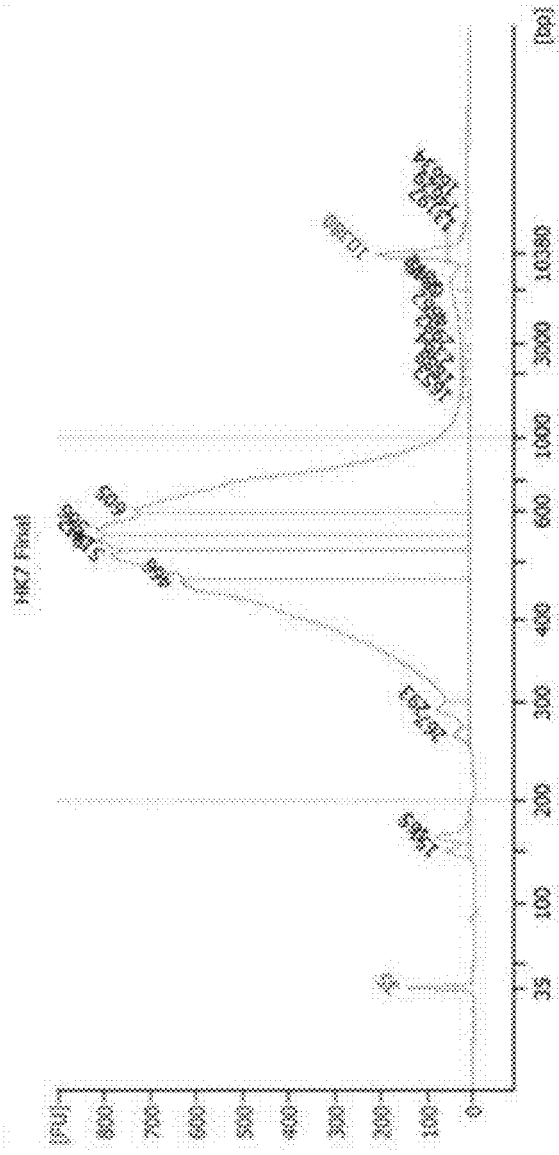
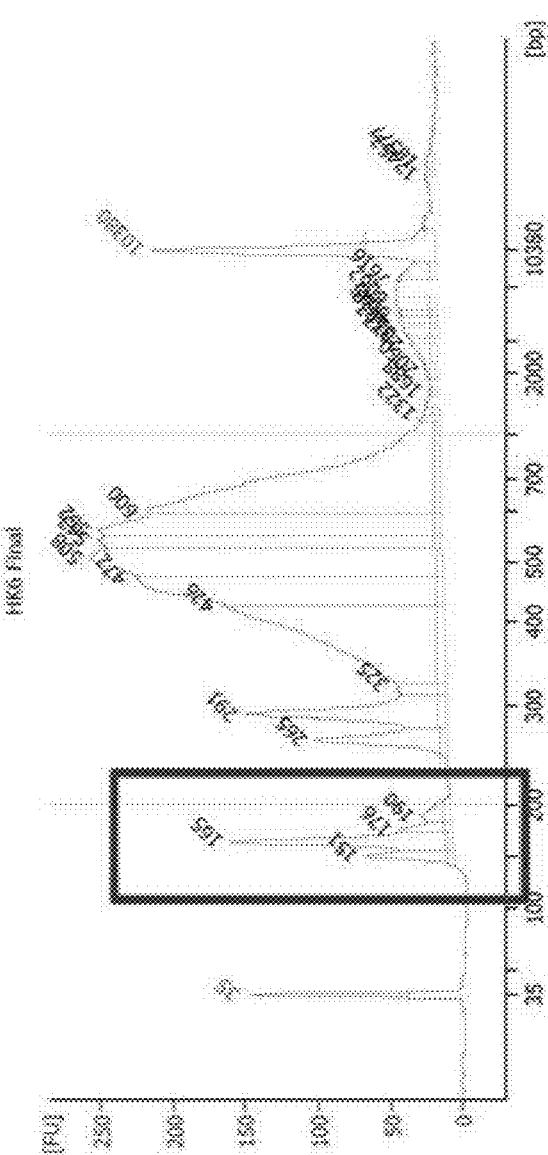
FIG. 16A
FIG. 16B

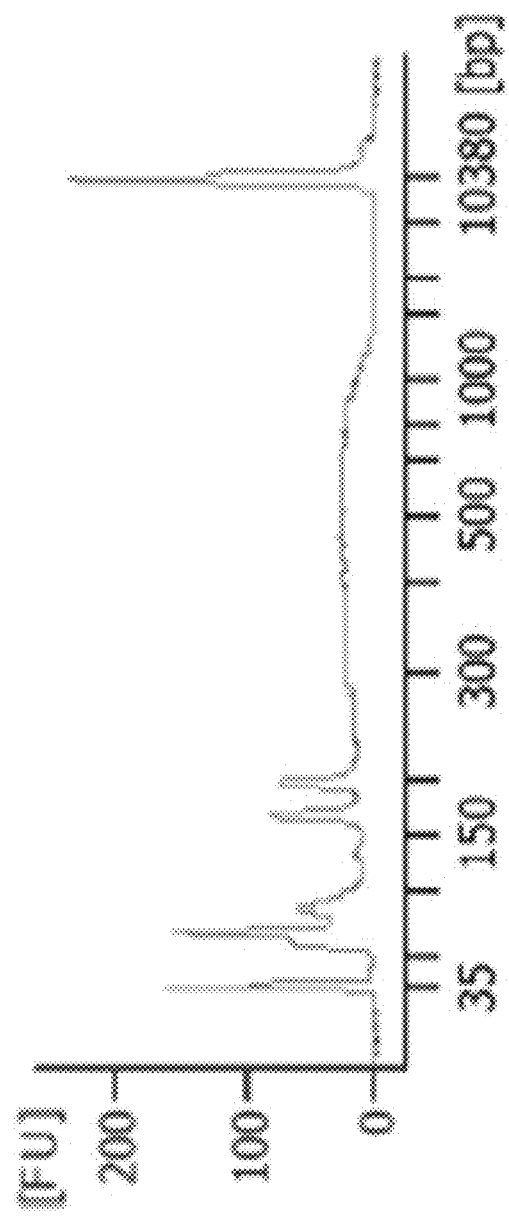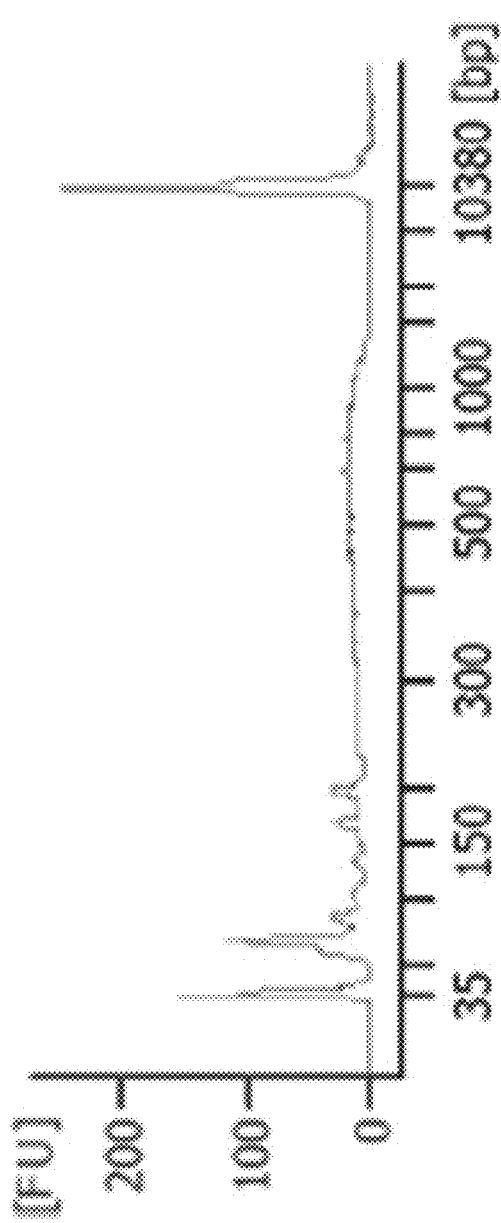
FIG. 21C
FIG. 21D

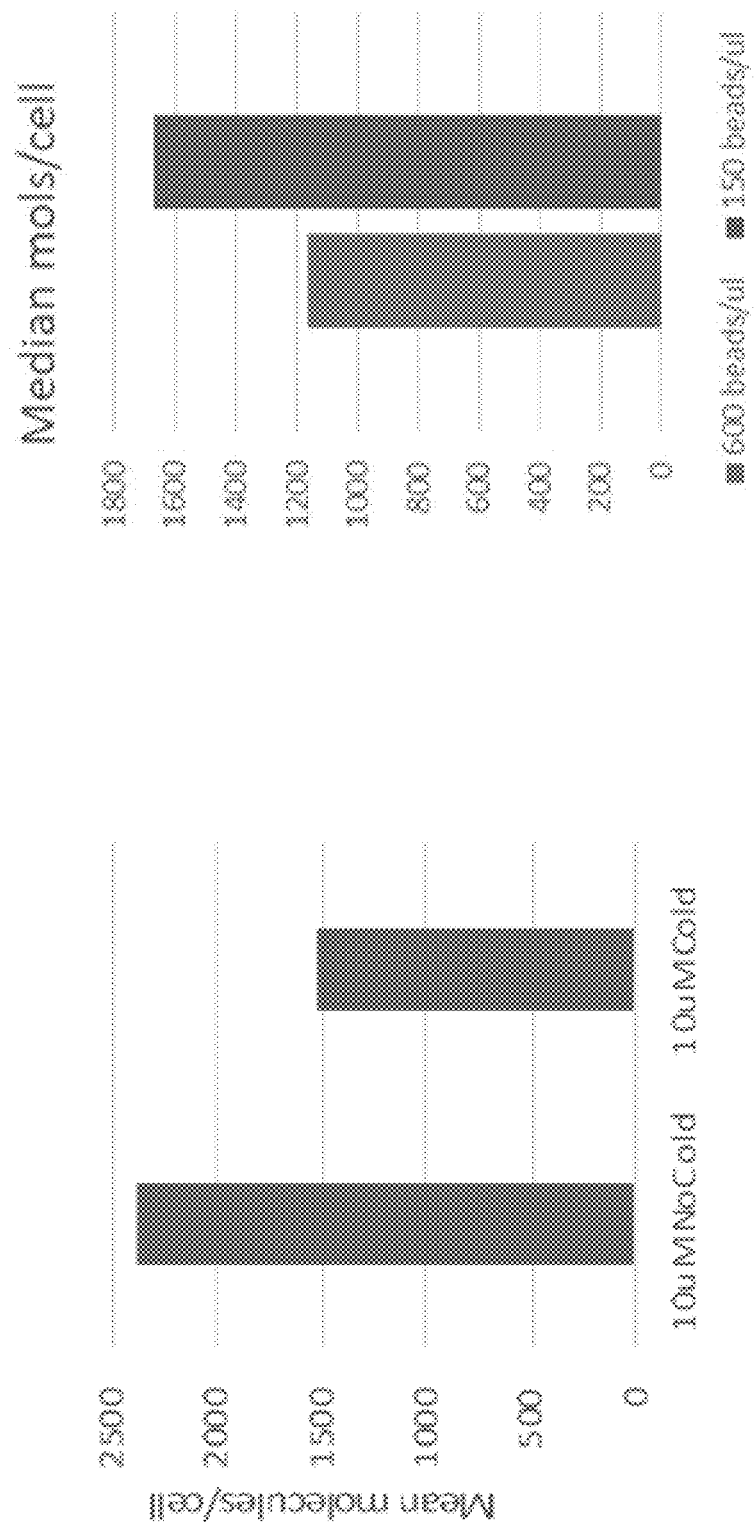

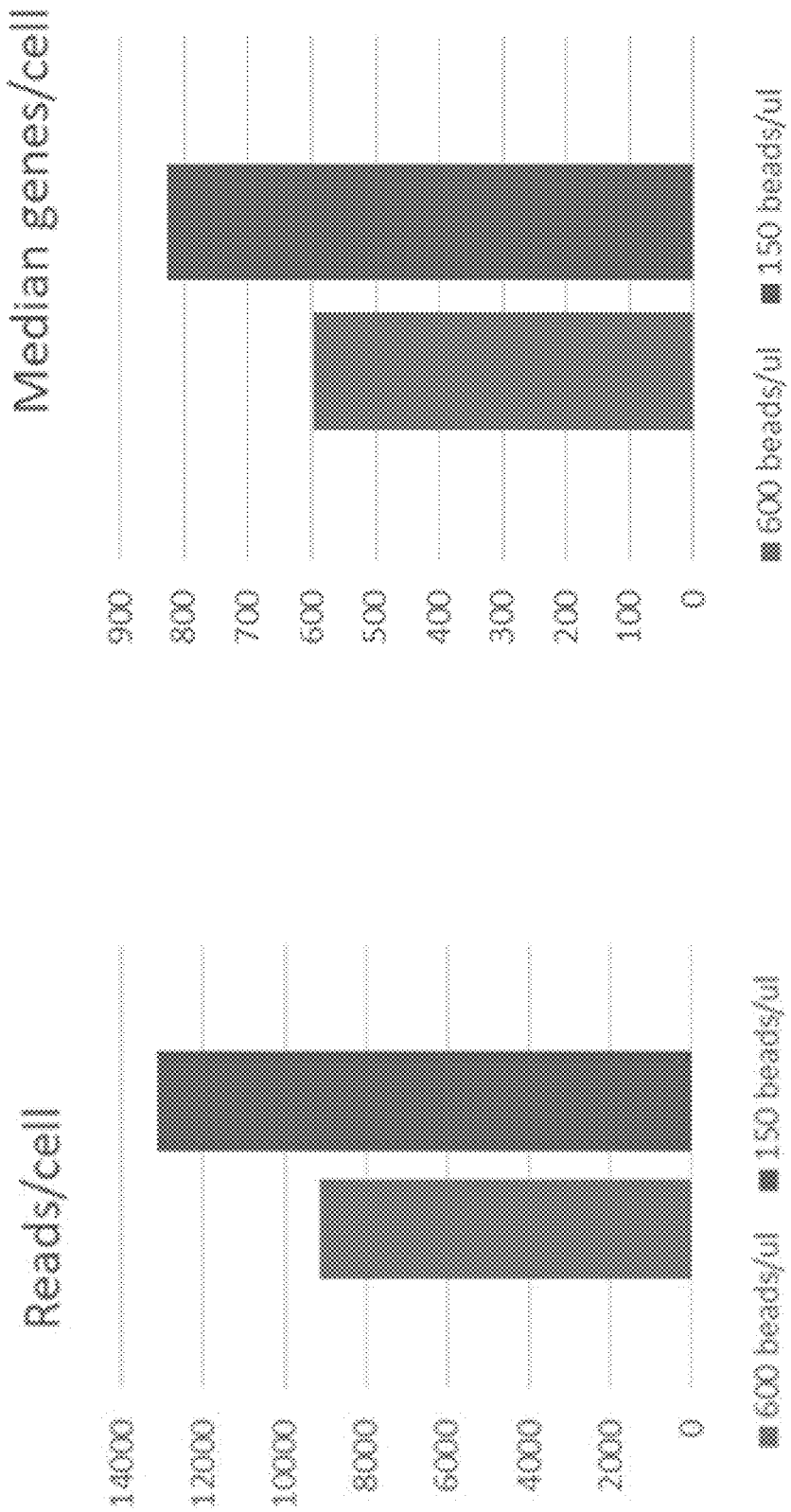

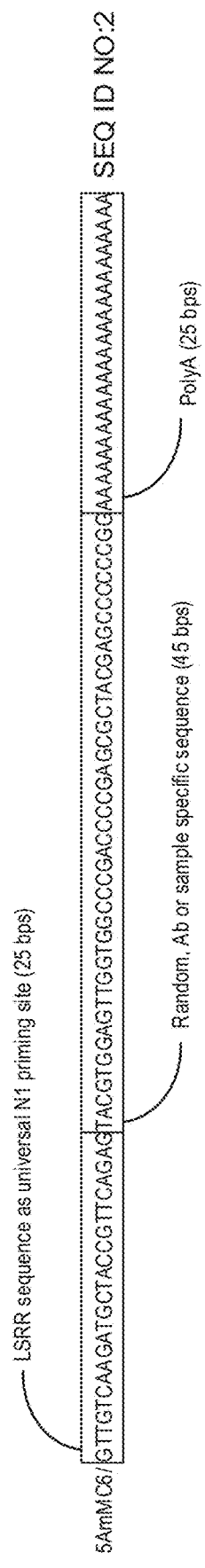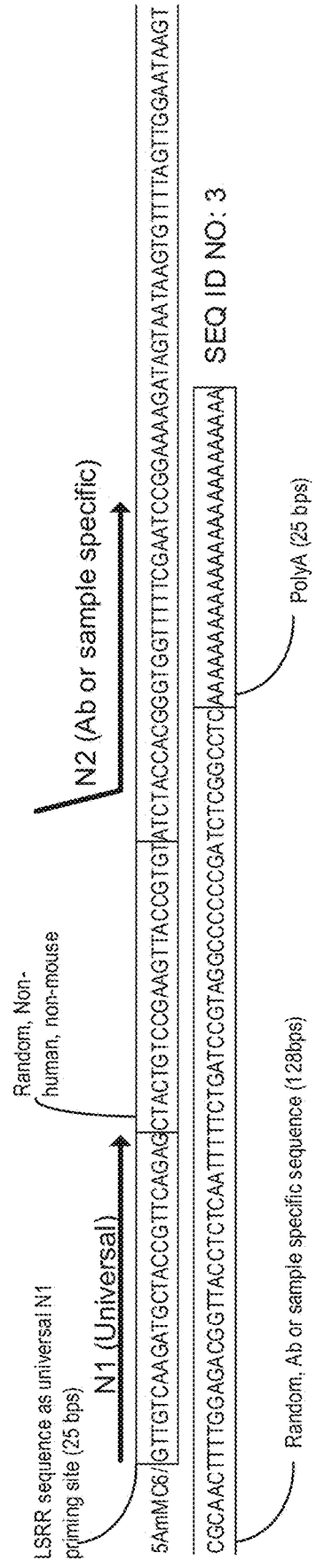

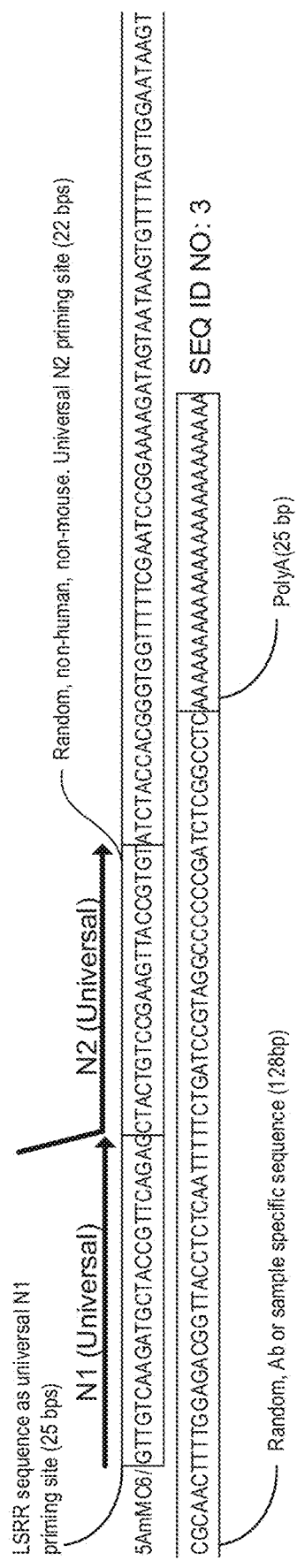
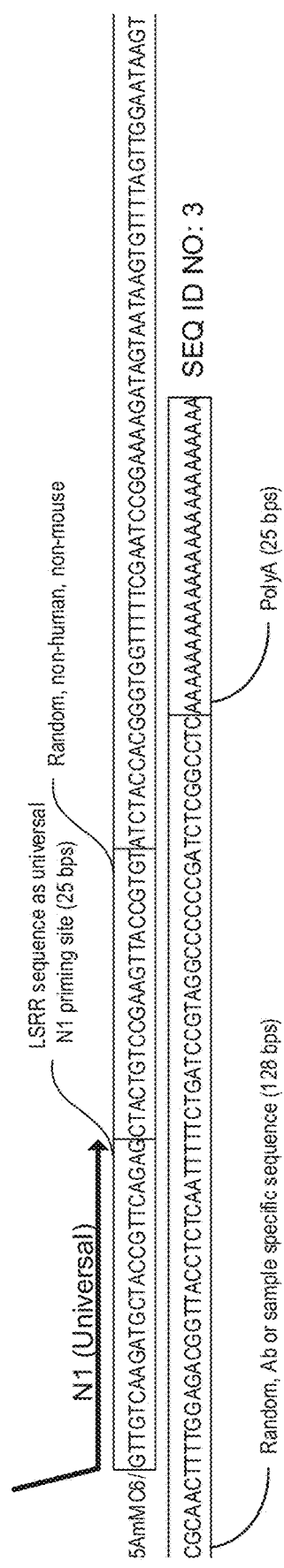
FIG. 29C
FIG. 29D

WHOLE TRANSCRIPTOME ANALYSIS OF SINGLE CELLS USING RANDOM PRIMING

RELATED APPLICATIONS

This application claims the benefit under 35 U.S.C. § 119(e) of U.S. Provisional Patent Application Ser. No. 62/757,757, filed Nov. 8, 2018, the content of this related application is incorporated herein by reference in its entirety for all purposes.

REFERENCE TO SEQUENCE LISTING

The present application is being filed along with a Sequence Listing in electronic format. The Sequence Listing is provided as a file entitled 68EB_298705_WO, created Nov. 7, 2019, which is 4 kilobytes in size. The information in the electronic format of the Sequence Listing is incorporated herein by reference in its entirety.

BACKGROUND

Field

The present disclosure relates generally to the field of molecular biology, for example determining gene expression profiles of cells using molecular barcoding.

Description of the Related Art

Current technology allows measurement of gene expression of single cells in a massively parallel manner (e.g., >10000 cells) by attaching cell specific oligonucleotide barcodes to poly(A) mRNA molecules from individual cells as each of the cells is co-localized with a barcoded reagent bead in a compartment. There is a need for systems and methods that can quantitatively analyze gene expression of cells efficiently.

SUMMARY

Disclosed herein include methods of labeling nucleic acid targets in a sample. In some embodiments, the method comprises: contacting copies of a nucleic acid target with a plurality of oligonucleotide barcodes, wherein each oligonucleotide barcode comprises a first universal sequence, a molecular label, and a target-binding region capable of hybridizing to the copies of the nucleic acid target; extending the plurality of oligonucleotide barcodes hybridized to the copies of the nucleic acid target to generate a plurality of first strand barcoded polynucleotides; contacting random primers with the plurality of first strand barcoded polynucleotides, wherein each of the random primers comprises a second universal sequence, or a complement thereof; and extending the random primers hybridized to the plurality of first strand barcoded polynucleotides to generate a plurality of extension products.

In some embodiments, the method comprises: amplifying the plurality of extension products using primers capable of hybridizing to the first universal sequence or complements thereof, and primers capable of hybridizing the second universal sequence or complements thereof, thereby generating a first plurality of barcoded amplicons. In some embodiments, amplifying the plurality of extension products comprises adding sequences of binding sites of sequencing primers and/or sequencing adaptors, complementary sequences thereof, and/or portions thereof, to the plurality of extension products. In some embodiments, the method comprises: determining the copy number of the nucleic acid target in the sample based on the number of molecular labels with distinct sequences associated with the first plurality of barcoded amplicons, or products thereof.

Disclosed herein include methods of determining the numbers of a nucleic acid target in a sample. In some embodiments, the method comprises: contacting copies of a nucleic acid target with a plurality of oligonucleotide barcodes, wherein each oligonucleotide barcode comprises a first universal sequence, a molecular label, and a target-binding region capable of hybridizing to the copies of the nucleic acid target; extending the plurality of oligonucleotide barcodes hybridized to the copies of the nucleic acid target to generate a plurality of first strand barcoded polynucleotides; contacting random primers with the plurality of first strand barcoded polynucleotides, wherein each of the random primers comprise a second universal sequence, or a complement thereof; extending the random primers hybridized to the plurality of first strand barcoded polynucleotides to generate a plurality of extension products; amplifying the plurality of extension products using primers capable of hybridizing to the first universal sequence or complements thereof, and primers capable of hybridizing the second universal sequence or complements thereof, thereby generating a first plurality of barcoded amplicons; and determining the copy number of the nucleic acid target in the sample based on the number of molecular labels with distinct sequences associated with the first plurality of barcoded amplicons, or products thereof.

In some embodiments, contacting copies of a nucleic acid target comprises contacting copies of a plurality of nucleic acid targets with a plurality of oligonucleotide barcodes, extending the plurality of oligonucleotide barcodes comprises extending the plurality of oligonucleotide barcodes hybridized to the copies of the plurality nucleic acid targets to generate a plurality of first strand barcoded polynucleotides, and determining the copy number of the nucleic acid target in the sample comprises determining the number of each of the plurality of nucleic acid targets in the sample based on the number of the molecular labels with distinct sequences associated with barcoded amplicons of the first plurality of barcoded amplicons comprising a sequence of the each of the plurality of nucleic acid targets. In some embodiments, the sequence of the each of the plurality of nucleic acid targets comprises a subsequence of the each of the plurality of nucleic acid targets. In some embodiments, the sequence of the nucleic acid target in the first plurality of barcoded amplicons comprises a subsequence of the nucleic acid target.

In some embodiments, the method comprises amplifying the first plurality of barcoded amplicons using primers capable of hybridizing to the first universal sequence or complements thereof, and primers capable of hybridizing the second universal sequence or complements thereof, thereby generating a second plurality of barcoded amplicons. In some embodiments, amplifying the first plurality of barcoded amplicons comprises adding sequences of binding sites of sequencing primers and/or sequencing adaptors, complementary sequences thereof, and/or portions thereof, to the first plurality of barcoded amplicons. In some embodiments, the method comprises determining the copy number of the nucleic acid target in the sample based on the number of molecular labels with distinct sequences associated with the second plurality of barcoded amplicons, or products thereof. In some embodiments, contacting copies of a nucleic acid target comprises contacting copies of a plurality of nucleic acid targets with a plurality of oligonucleotide barcodes, extending the plurality of oligonucleotide barcodes comprises extending the plurality of oligonucleotide barcodes hybridized to the copies of the plurality nucleic acid targets to generate a plurality of first strand barcoded polynucleotides, and/or wherein determining the copy number of the nucleic acid target in the sample comprises determining the number of each of the plurality of nucleic acid targets in the sample based on the number of the molecular labels with distinct sequences associated with barcoded amplicons of the second plurality of barcoded amplicons comprising a sequence of the each of the plurality of nucleic acid targets. In some embodiments, the sequence of the each of the plurality of nucleic acid targets comprises a subsequence of the each of the plurality of nucleic acid targets. In some embodiments, the sequence of the nucleic acid target in the second plurality of barcoded amplicons comprises a subsequence of the nucleic acid target.

In some embodiments, each one of the first plurality of barcoded amplicons and/or second plurality of barcoded amplicons comprises at least part of the first universal sequence, the second universal sequence, or both. In some embodiments, the first universal sequence and the second universal sequence are the same. In some embodiments, the first universal sequence and the second universal sequence are different. In some embodiments, the first universal sequence and/or the second universal sequence comprise the binding sites of sequencing primers and/or sequencing adaptors, complementary sequences thereof, and/or portions thereof. In some embodiments, the sequencing adaptors comprise a P5 sequence, a P7 sequence, complementary sequences thereof, and/or portions thereof. In some embodiments, the sequencing primers comprise a Read 1 sequencing primer, a Read 2 sequencing primer, complementary sequences thereof, and/or portions thereof.

In some embodiments, extending the plurality of oligonucleotide barcodes hybridized to the copies of the nucleic acid target comprises extending the plurality of oligonucleotide barcodes hybridized to the copies of the nucleic acid target using a reverse transcriptase. In some embodiments, the reverse transcriptase comprises a viral reverse transcriptase. In some embodiments, extending the plurality of oligonucleotide barcodes hybridized to the copies of the nucleic acid target comprises extending the plurality of oligonucleotide barcodes hybridized to the copies of the nucleic acid target using a DNA polymerase lacking at least one of 5' to 3' exonuclease activity and 3' to 5' exonuclease activity. In some embodiments, extending the random primers hybridized to the plurality of first strand barcoded polynucleotides comprises extending the random primers hybridized to the plurality of first strand barcoded polynucleotides using a DNA polymerase lacking at least one of 5' to 3' exonuclease activity and 3' to 5' exonuclease activity. In some embodiments, the DNA polymerase comprises a Klenow Fragment.

In some embodiments, the first plurality of barcoded amplicons and/or the second plurality of barcoded amplicons comprise whole transcriptome amplification (WTA) products. In some embodiments, the first plurality of barcoded amplicons and/or the second plurality of barcoded amplicons correspond to at least 10% of the mRNAs of a single cell. In some embodiments, the first plurality of barcoded amplicons and/or the second plurality of barcoded amplicons correspond to at least 50% or at least 90% of the mRNAs of a single cell. In some embodiments, one or more of the pluralities of nucleic acid targets comprises mRNAs of a low-expressing gene. In some embodiments, said random primers comprise a random sequence of nucleotides, optionally the random sequence of nucleotides is about 4 to about 30 nucleotides in length, and further optionally said random sequence of nucleotides is 6 or 9 nucleotides in length. In some embodiments, the target-binding region comprises an oligo dT sequence, a random sequence, a target-specific sequence, or a combination thereof. In some embodiments, the target-binding region comprises a poly (dT) region, and wherein the nucleic acid target comprises a poly(dA) region. In some embodiments, the method comprises: repeating the steps of contacting random primers with the plurality of first strand barcoded polynucleotides, extending the random primers hybridized to the plurality of first strand barcoded polynucleotides, and amplifying the plurality of extension products.

In some embodiments, the method comprises: synthesizing a third plurality of barcoded amplicons using the plurality of first strand barcoded polynucleotides as templates to generate a third plurality of barcoded amplicons. In some embodiments, synthesizing a third plurality of barcoded amplicons comprises performing polymerase chain reaction (PCR) amplification of the plurality of first stranded barcoded polynucleotides. In some embodiments, synthesizing a third plurality of barcoded amplicons comprises PCR amplification using primers capable of hybridizing to the first universal sequence, or a complement thereof, and a target-specific primer. In some embodiments, the method comprises: obtaining sequence information of the third plurality of barcoded amplicons, or products thereof, and optionally obtaining the sequence information comprises attaching sequencing adaptors to the third plurality of barcoded amplicons, or products thereof. In some embodiments, the target-specific primer specifically hybridizes to an immune receptor, optionally the immune receptor is a T cell receptor (TCR) and/or a B cell receptor (BCR) receptor.

In some embodiments, amplifying the plurality of extension products is not performed in the presence of a solid support. In some embodiments, the method does not comprise RNase H-induced priming, end repair, and/or adapter ligation. In some embodiments, the method does not comprise fragmentation, tagmentation, or both. In some embodiments, the first strand barcoded polynucleotides comprise barcoded deoxyribonucleic acid (DNA) molecules, barcoded ribonucleic acid (RNA) molecules, or both.

In some embodiments, the sample comprises a plurality of cells, a plurality of single cells, a tissue, a tumor sample, or any combination thereof. In some embodiments, the sample comprises peripheral blood mononuclear cells or immune cells, and optionally the immune cells comprise B cells, T cells or a combination thereof. In some embodiments, the nucleic acid target comprises a nucleic acid molecule, and optionally the nucleic acid molecule comprises ribonucleic acid (RNA), messenger RNA (mRNA), microRNA, small interfering RNA (siRNA), RNA degradation product, RNA comprising a poly(A) tail, or any combination thereof. In some embodiments, the mRNA encodes an immune receptor.

In some embodiments, the nucleic acid target comprises a cellular component binding reagent. In some embodiments, the nucleic acid molecule is associated with the cellular component binding reagent. In some embodiments, the method comprises: dissociating the nucleic acid molecule and the cellular component binding reagent. In some embodiments, at least 10 of the plurality of oligonucleotide barcodes comprise different molecular label sequences. In some embodiments, each molecular label of the plurality of oligonucleotide barcodes comprises at least 6 nucleotides.

In some embodiments, the plurality of oligonucleotide barcodes are associated with a solid support. In some embodiments, the plurality of oligonucleotide barcodes associated with the same solid support each comprise an identical sample label, and wherein each sample label of the plurality of oligonucleotide barcodes comprises at least 6 nucleotides. In some embodiments, the plurality of oligonucleotide barcodes each comprise a cell label, and optionally each cell label of the plurality of oligonucleotide barcodes comprises at least 6 nucleotides. In some embodiments, oligonucleotide barcodes associated with the same solid support comprise the same cell label. In some embodiments, oligonucleotide barcodes associated with different solid supports comprise different cell labels. In some embodiments, the solid support comprises a synthetic particle, a planar surface, or a combination thereof.

In some embodiments, the sample comprises a single cell, the method comprising associating a synthetic particle comprising the plurality of the oligonucleotide barcodes with the single cell in the sample. In some embodiments, the method comprises: lysing the single cell after associating the synthetic particle with the single cell, and optionally lysing the single cell comprises heating the sample, contacting the sample with a detergent, changing the pH of the sample, or any combination thereof. In some embodiments, the synthetic particle and the single cell are in the same partition, and optionally the partition is a well or a droplet. In some embodiments, at least one of the plurality of oligonucleotide barcodes is immobilized or partially immobilized on the synthetic particle. In some embodiments, at least one of the plurality of oligonucleotide barcodes is enclosed or partially enclosed in the synthetic particle. In some embodiments, the synthetic particle is disruptable, and optionally the synthetical particle is a disruptable hydrogel particle.

In some embodiments, the synthetic particle comprises a bead, and optionally the bead comprises a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a hydrogel bead, a gel bead, a silica-like bead, an anti-biotin microbead, an anti-fluorochrome microbead, or any combination thereof. In some embodiments, the synthetic particle comprises a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. In some embodiments, each of the plurality of oligonucleotide barcodes comprises a linker functional group, the synthetic particle comprises a solid support functional group, and/or the support functional group and the linker functional group are associated with each other. In some embodiments, the linker functional group and the support functional group are individually selected from the group consisting of C6, biotin, streptavidin, primary amine(s), aldehyde(s), ketone(s), and any combination thereof.

BRIEF DESCRIPTION OF THE DRAWINGS

FIGS. 16A-16D are non-limiting exemplary bioanalyzer plots depicting the performance of the RPE WTA method in Jurkat/Ramos cells and healthy donor peripheral blood mononuclear cells (PBMCs).

FIGS. 21A-21G are non-limiting exemplary bioanalyzer plots (RPE PCR, post-SPRI cleanup) showing the effects of varying random primer concentrations and RPE conditions on the performance of the RPE-based WTA method.

FIGS. 22A-22F are non-limiting exemplary sequencing data showing the effects of adding cold beads and varying bead density on the performance of the RPE WTA.

FIGS. 29A-29D show non-limiting exemplary designs of oligonucleotides for determining protein expression and gene expression simultaneously and for sample indexing.

DETAILED DESCRIPTION

Figure 1:
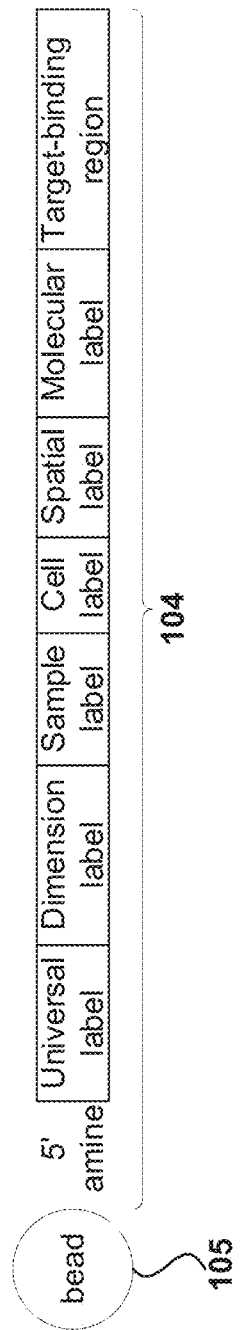
FIG. 1 illustrates a non-limiting exemplary stochastic barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids, for example messenger ribonucleic acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding such as the Precise™ assay (Cellular Research, Inc. (Palo Alto, CA)) can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular labels on poly(T) oligonucleotides to hybridize to all poly(A)-mRNAs in a sample during the RT step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular labels, and the numbers of mRNA molecules.

Methods for determining mRNA expression profiles of single cells can be performed in a massively parallel manner. For example, the Precise™ assay can be used to determine the mRNA expression profiles of more than 10000 cells simultaneously. The number of single cells (e.g., 100 s or 1000 s of singles) for analysis per sample can be lower than the capacity of the current single cell technology. Pooling of cells from different samples enables improved utilization of the capacity of the current single technology, thus lowering reagents wasted and the cost of single cell analysis. The disclosure provides methods of sample indexing for distinguishing cells of different samples for cDNA library preparation for cell analysis, such as single cell analysis. Pooling of cells from different samples can minimize the variations in cDNA library preparation of cells of different samples, thus enabling more accurate comparisons of different samples.

Disclosed herein include methods of labeling nucleic acid targets in a sample. In some embodiments, the method comprises: contacting copies of a nucleic acid target with a plurality of oligonucleotide barcodes, wherein each oligonucleotide barcode comprises a first universal sequence, a molecular label, and a target-binding region capable of hybridizing to the copies of the nucleic acid target; extending the plurality of oligonucleotide barcodes hybridized to the copies of the nucleic acid target to generate a plurality of first strand barcoded polynucleotides; contacting random primers with the plurality of first strand barcoded polynucleotides, wherein each of the random primers comprises a second universal sequence, or a complement thereof; and extending the random primers hybridized to the plurality of first strand barcoded polynucleotides to generate a plurality of extension products.

Disclosed herein include methods of determining the numbers of a nucleic acid target in a sample. In some embodiments, the method comprises: contacting copies of a nucleic acid target with a plurality of oligonucleotide barcodes, wherein each oligonucleotide barcode comprises a first universal sequence, a molecular label, and a target-binding region capable of hybridizing to the copies of the nucleic acid target; extending the plurality of oligonucleotide barcodes hybridized to the copies of the nucleic acid target to generate a plurality of first strand barcoded polynucleotides; contacting random primers with the plurality of first strand barcoded polynucleotides, wherein each of the random primers comprise a second universal sequence, or a complement thereof; extending the random primers hybridized to the plurality of first strand barcoded polynucleotides to generate a plurality of extension products; amplifying the plurality of extension products using primers capable of hybridizing to the first universal sequence or complements thereof, and primers capable of hybridizing the second universal sequence or complements thereof, thereby generating a first plurality of barcoded amplicons; and determining the copy number of the nucleic acid target in the sample based on the number of molecular labels with distinct sequences associated with the first plurality of barcoded amplicons, or products thereof.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, or barcode sequences (e.g., molecular labels). The adapters can be linear. The adapters can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein, an antibody can be a full-length (e.g., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

In some embodiments, an antibody is a functional antibody fragment. For example, an antibody fragment can be a portion of an antibody such as F(ab')2, Fab', Fab, Fv, sFv and the like. An antibody fragment can bind with the same antigen that is recognized by the full-length antibody. An antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (for example, CD8, CD34, and CD45), and therapeutic antibodies.

As used herein the term "associated" or "associated with" can mean that two or more species are identifiable as being co-located at a point in time. An association can mean that two or more species are or were within a similar container. An association can be an informatics association. For example, digital information regarding two or more species can be stored and can be used to determine that one or more of the species were co-located at a point in time. An association can also be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label. An association can comprise hybridization between two molecules (such as a target molecule and a label).

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This methodology, which can be stochastic in nature, transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different barcodes such that when the non-depleting reservoir is associated with a pool of targets each target is likely to be associated with a unique barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of barcodes detected then allows calculation of the number of target molecules present in the original collection or sample. When the ratio of the number of copies of a target molecule present to the number of unique barcodes is low, the labeled target molecules are highly unique (i.e., there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (e.g., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—CH$_2$), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g., adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2': 4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead."

As used herein, the term "stochastic barcode" can refer to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins, peptides, or polypeptides. In some embodiments, targets are lipids. As used herein, "target" can be used interchangeably with "species."

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the *Lactococcus lactis* LI.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

Barcodes

Barcoding, such as stochastic barcoding, has been described in, for example, US20150299784, WO2015031691, and Fu et al, Proc Natl Acad Sci U.S.A. 2011 May 31; 108(22):9026-31, the content of these publications is incorporated hereby in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5'amine that may link the barcode to a solid support 105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g., seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequences (e.g., molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20, or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or be at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were barcoded. For example, a population of cells can be barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a bead), but different for different solid supports (e.g., beads). In some embodiments, at least 60%, 70%, 80%, 85%, 90%, 95%, 97%, 99% or 100%, of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or be at most, 1, 2, 3, 4, 5, 10, 15, 20, 25, 30, 35, 40, 45, 50, 100, 200, or 300, nucleotides in length. A dimension label can comprise between about 5 to about 200 nucleotides, between about 10 to about 150 nucleotides, or between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example, a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g., a well, a container, or a droplet). In some embodiments, multiple spatial labels are used together to encode one or more positions in space.

The spatial label can be identical for all barcodes attached to a given solid support (e.g., a bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or be at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides, between about 10 to about 150 nucleotides, or about 20 to about 125 nucleotides in length.

Cell Labels

A barcode (e.g., a stochastic barcode) can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or be at most, 1, 2, 3, 4, 5, 10, 15, 20, 25, 30, 35, 40, 45, 50, 100, 200, or 300 nucleotides in length. For example, a cell label can comprise between about 5 to about 200 nucleotides, between about 10 to about 150 nucleotides, or between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or be at most, $10^2$, $10^3$, $10^4$, $10^5$, $10^6$, $10^7$, $10^8$, or $10^9$, unique barcode sequences. The unique molecular label sequences can be attached to a given solid support (e.g., a bead).

The length of a barcode can be different in different implementations. For example, a barcode can be, or be about, 1, 2, 3, 4, 5, 10, 15, 20, 25, 30, 35, 40, 45, 50, or a number or a range between any two of these values, nucleotides in length. As another example, a barcode can be at least, or be at most, 1, 2, 3, 4, 5, 10, 15, 20, 25, 30, 35, 40, 45, 50, 100, 200, or 300 nucleotides in length.

Molecular Labels

A barcode (e.g., a stochastic barcode) can comprise one or more molecular labels. Molecular labels can include barcode sequences. In some embodiments, a molecular label can comprise a nucleic acid sequence that provides identifying information for the specific type of target nucleic acid species hybridized to the barcode. A molecular label can comprise a nucleic acid sequence that provides a counter for the specific occurrence of the target nucleic acid species hybridized to the barcode (e.g., target-binding region).

In some embodiments, a diverse set of molecular labels are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, of unique molecular label sequences. For example, a plurality of barcodes can comprise about 6561 molecular labels with distinct sequences. As another example, a plurality of barcodes can comprise about 65536 molecular labels with distinct sequences. In some embodiments, there can be at least, or be at most, $10^2$, $10^3$, $10^4$, $10^5$, $10^6$, $10^7$, $10^8$, or $10^9$, unique molecular label sequences. Barcodes with unique molecular label sequences can be attached to a given solid support (e.g., a bead).

For stochastic barcoding using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or be at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g., target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g., an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A stochastic barcode (e.g., a stochastic barcode) can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode (e.g., a stochastic barcode) can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be labeled (e.g., stochastically labeled). The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length, for example 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequences, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, CA). In some implementation, a gel bead can comprise a polymer-based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be degradable. For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to, pH-mediated changes to the bead wall, disintegration of the bead wall via chemical cleavage of crosslink bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
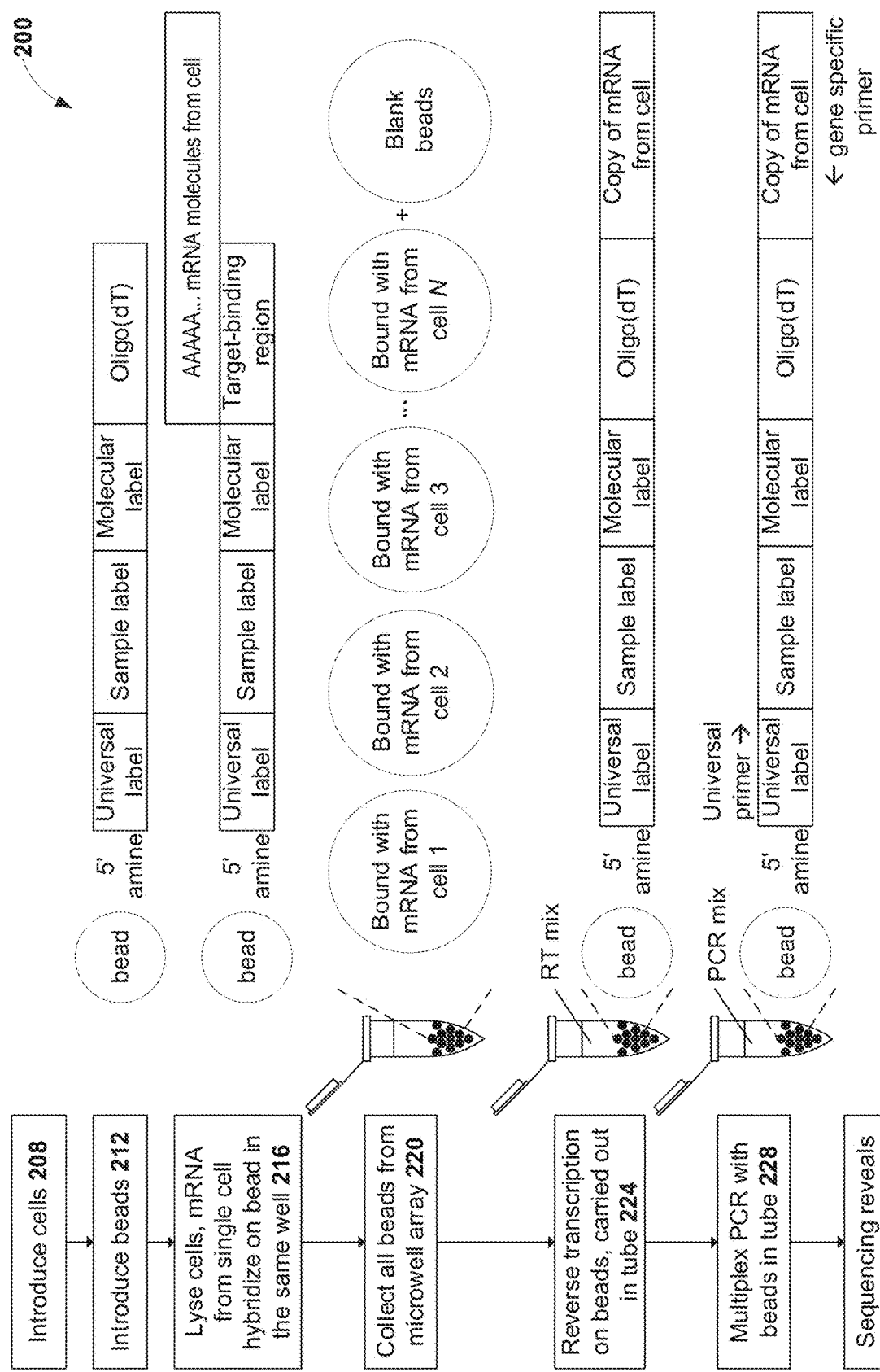
FIG. 2 shows a non-limiting exemplary workflow of stochastic barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode with different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or be at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized," are used interchangeably, and can refer to covalent or non-covalent means for attaching barcodes to a solid support. Any of a variety of different solid supports can be used as solid supports for attaching pre-synthesized barcodes or for in situ solid-phase synthesis of barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g., magnesium, molybdenum, lithium, and tantalum), superparamagnetic materials (e.g., ferrite ($Fe_3O_4$; magnetite) nanoparticles), ferromagnetic materials (e.g., iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example, beads). Each of the particles can comprise a plurality of oligonucleotides (e.g., barcodes). Each of the plurality of oligonucleotides can comprise a barcode sequence (e.g., a molecular label sequence), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometers. In some embodiments, the diameter of the bead can be, or be about, 0.1, 0.5, 1, 2, 3, 4, 5, 6, 7, 8, 9, 10, 20, 30, 40, 50 micrometers, or a number or a range between any two of these values.

The diameter of the bead can be related to the diameter of the wells of the substrate. In some embodiments, the diameter of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameter of the bead can be at least, or be at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameter of the bead, or the average diameter of the plurality of beads, can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g., impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example, due to swelling in an organic or inorganic solution. A bead can be hydrophobic. A bead can be hydrophilic. A bead can be biocompatible.

A solid support (e.g., a bead) can be visualized. The solid support can comprise a visualizing tag (e.g., fluorescent dye). A solid support (e.g., a bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lacks such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

Substrates and Microwell Array

As used herein, a substrate can refer to a type of solid support. A substrate can refer to a solid support that can comprise barcodes or stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a bead). A microwell can comprise barcode reagents of the disclosure.

Methods of Barcoding

The disclosure provides for methods for estimating the number of distinct targets at distinct locations in a physical sample (e.g., tissue, organ, tumor, cell). The methods can comprise placing barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two-dimensional map or a three-dimensional map of the sample. The two-dimensional map and the three-dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two-dimensional map or a three-dimensional map of the sample. The two-map and the three-dimensional map can be generated prior to or after barcoding the plurality of targets in the sample. in some embodiments, the two-dimensional map and the three-dimensional map can be generated before or after lysing the sample. Lysing the sample before or after generating the two-dimensional map or the three-dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., formsa planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be cross-linked to barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9, 10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7%, or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g., buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g., an EcoRI sticky-end overhang). The assay procedure can further comprise treating the target nucleic acids with a restriction enzyme (e.g., EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a target-barcode conjugate using reverse transcription (e.g., at block 224 of FIG. 2). The target-barcode conjugate can comprise the barcode and a complementary sequence of all or a portion of the target nucleic acid (i.e., a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular label and/or barcode sequence (e.g., a molecular label). The amplification reactions can comprise amplifying at least a portion of a sample tag, a cell label, a spatial label, a barcode sequence (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled amplicon (e.g., a stochastically labeled amplicon). The labeled amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholine and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photolabile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholine and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded targets (e.g., stochastically barcoded targets) or barcoded fragments of the targets. The barcode sequences of different barcodes (e.g., the molecular labels of different stochastic barcodes) can be different from one another. Generating an indexed library of the barcoded targets includes generating a plurality of indexed polynucleotides from the plurality of targets in the sample. For example, in an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Barcoding (e.g., stochastic barcoding) can include using nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 232 of FIG. 2.

Figure 3:
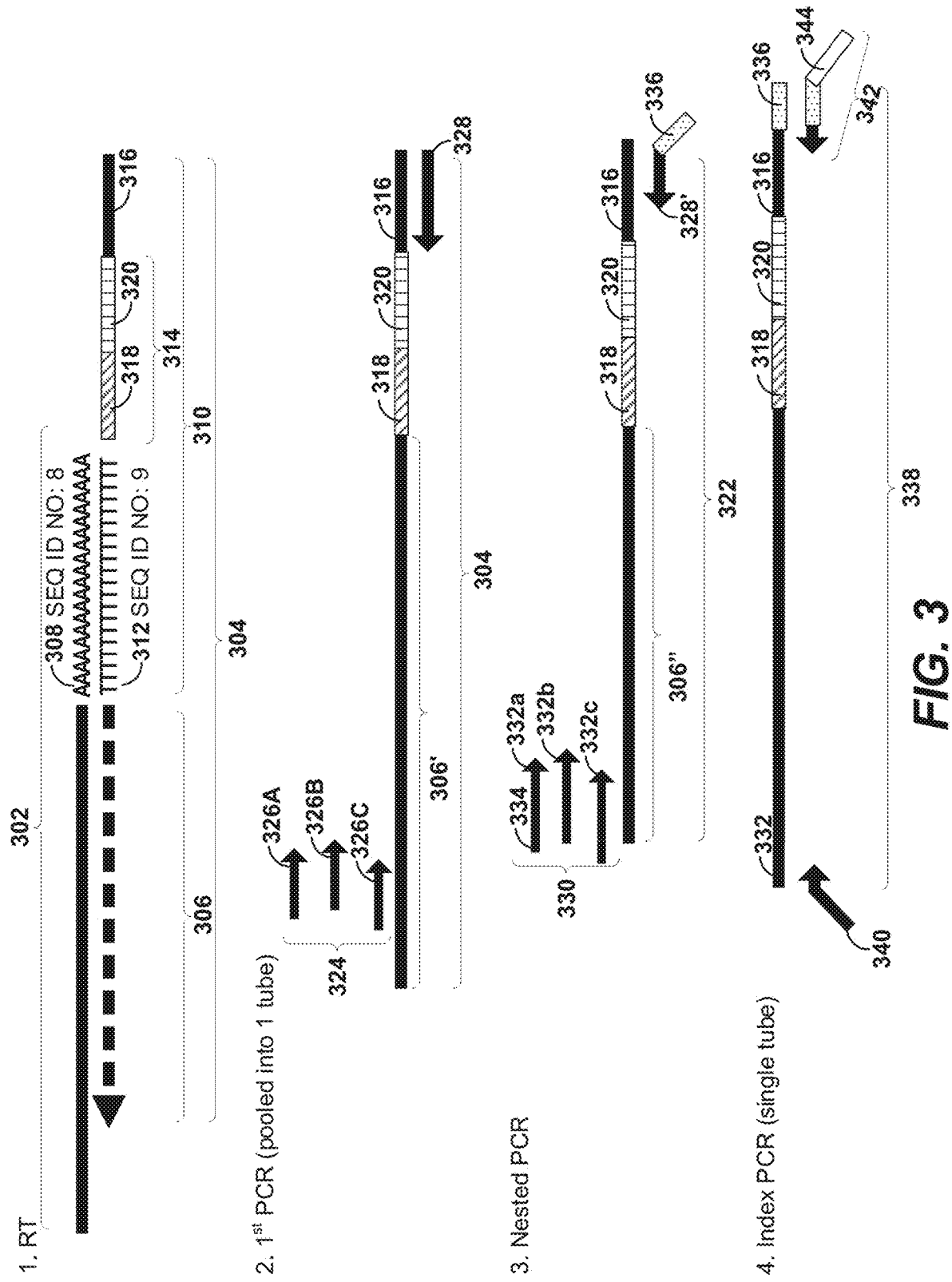
FIG. 3 is a schematic illustration showing a non-limiting exemplary process for generating an indexed library of the stochastically barcoded targets from a plurality of targets.

FIG. 3 is a schematic illustration showing a non-limiting exemplary process of generating an indexed library of the barcoded targets (e.g., stochastically barcoded targets), such as barcoded mRNAs or fragments thereof. As shown in step 1, the reverse transcription process can encode each mRNA molecule with a unique molecular label, a cell label, and a universal PCR site. In particular, RNA molecules 302 can be reverse transcribed to produce labeled cDNA molecules 304, including a cDNA region 306, by hybridization (e.g., stochastic hybridization) of a set of barcodes (e.g., stochastic barcodes) 310 to the poly(A) tail region 308 of the RNA molecules 302. Each of the barcodes 310 can comprise a target-binding region, for example a poly(dT) region 312, a label region 314 (e.g., a barcode sequence or a molecule), and a universal PCR region 316.

In some embodiments, the cell label can include 3 to 20 nucleotides. In some embodiments, the molecular label can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise using a $1^{st}$ PCR primer pool 324 comprising custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Compositions Comprising Cellular Component Binding Reagents Associated with Oligonucleotides Some embodiments disclosed herein provide a plurality of compositions each comprising a cellular component binding reagent (such as a protein binding reagent) that is conjugated with an oligonucleotide, wherein the oligonucleotide comprises a unique identifier for the cellular component binding reagent that it is conjugated with. Cellular component binding reagents (such as barcoded antibodies) and their uses (such as sample indexing of cells) have been described in U.S. Patent Application Publication No. 2018/0088112 and U.S. patent application Ser. No. 15/937,713; the content of each is incorporated by reference in its entirety.

In some embodiments, the cellular component binding reagent is capable of specifically binding to a cellular component target. For example, a binding target of the cellular component binding reagent can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component binding reagent (e.g., a protein binding reagent) is capable of specifically binding to an antigen target or a protein target. In some embodiments, each of the oligonucleotides can comprise a barcode, such as a stochastic barcode. A barcode can comprise a barcode sequence (e.g., a molecular label), a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., unanchored to a solid support or anchored to a solid support. The poly(A) tail can be from about 10 to 50 nucleotides in length, for example 18 nucleotides in length. The oligonucleotides can comprise deoxyribonucleotides, ribonucleotides, or both.

The unique identifiers can be, for example, a nucleotide sequence having any suitable length, for example, from about 4 nucleotides to about 200 nucleotides, or from 25 nucleotides to about 45 nucleotides, in length. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise, or comprise about, 20, 30, 40, 50, 60, 70, 80, 90, 100, 200, 300, 400, 500, 600, 700, 800, 900, 1000, 2000, 5000, or a number or a range between any two of these values, different unique identifiers. The diverse set of unique identifiers can comprise at least, or comprise at most, 20, 30, 40, 50, 60, 70, 80, 90, 100, 200, 300, 400, 500, 600, 700, 800, 900, 1000, 2000, or 5000, different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by, or by about, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a number or a range between any two of these values. In some embodiments, the sequences of the set of unique identifiers are different from each other, or the complement thereof, by at least, or by at most, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides. In some embodiments, the sequences of the set of unique identifiers are different from each other, or the complement thereof, by at least 3%, at least 5%, at least 8%, at least 10%, at least 15%, at least 20%, or more.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable cellular component binding reagents are contemplated in this disclosure, such as protein binding reagents, antibodies or fragments thereof, aptamers, small molecules, ligands, peptides, oligonucleotides, etc., or any combination thereof. In some embodiments, the cellular component binding reagents can be polyclonal antibodies, monoclonal antibodies, recombinant antibodies, single chain antibody (sc-Ab), or fragments thereof, such as Fab, Fv, etc. In some embodiments, the plurality of cellular component binding reagents can comprise, or comprise about, 20, 30, 40, 50, 60, 70, 80, 90, 100, 200, 300, 400, 500, 600, 700, 800, 900, 1000, 2000, 5000, or a number or a range between any two of these values, different cellular component reagents. In some embodiments, the plurality of cellular component binding reagents can comprise at least, or comprise at most, 20, 30, 40, 50, 60, 70, 80, 90, 100, 200, 300, 400, 500, 600, 700, 800, 900, 1000, 2000, or 5000, different cellular component reagents.

The oligonucleotide can be conjugated with the cellular component binding reagent through various mechanism. In some embodiments, the oligonucleotide can be conjugated with the cellular component binding reagent covalently. In some embodiment, the oligonucleotide can be conjugated with the cellular component binding reagent non-covalently. In some embodiments, the oligonucleotide is conjugated with the cellular component binding reagent through a linker. The linker can be, for example, cleavable or detachable from the cellular component binding reagent and/or the oligonucleotide. In some embodiments, the linker can comprise a chemical group that reversibly attaches the oligonucleotide to the cellular component binding reagents. The chemical group can be conjugated to the linker, for example, through an amine group. In some embodiments, the linker can comprise a chemical group that forms a stable bond with another chemical group conjugated to the cellular component binding reagent. For example, the chemical group can be a UV photocleavable group, a disulfide bond, a streptavidin, a biotin, an amine, etc. In some embodiments, the chemical group can be conjugated to the cellular component binding reagent through a primary amine on an amino acid, such as lysine, or the N-terminus. Commercially available conjugation kits, such as the Protein-Oligo Conjugation Kit (Solulink, Inc., San Diego, CA), the Thunder-Link® oligo conjugation system (Innova Biosciences, Cambridge, United Kingdom), etc., can be used to conjugate the oligonucleotide to the cellular component binding reagent.

The oligonucleotide can be conjugated to any suitable site of the cellular component binding reagent (e.g., a protein binding reagent), as long as it does not interfere with the specific binding between the cellular component binding reagent and its cellular component target. In some embodiments, the cellular component binding reagent is a protein, such as an antibody. In some embodiments, the cellular component binding reagent is not an antibody. In some embodiments, the oligonucleotide can be conjugated to the antibody anywhere other than the antigen-binding site, for example, the Fc region, the $C_H1$ domain, the $C_H2$ domain, the $C_H3$ domain, the $C_L$ domain, etc. Methods of conjugating oligonucleotides to cellular component binding reagents (e.g., antibodies) have been previously disclosed, for example, in U.S. Pat. No. 6,531,283, the content of which is hereby expressly incorporated by reference in its entirety. Stoichiometry of oligonucleotide to cellular component binding reagent can be varied. To increase the sensitivity of detecting the cellular component binding reagent specific oligonucleotide in sequencing, it may be advantageous to increase the ratio of oligonucleotide to cellular component binding reagent during conjugation. In some embodiments, each cellular component binding reagent can be conjugated with a single oligonucleotide molecule. In some embodiments, each cellular component binding reagent can be conjugated with more than one oligonucleotide molecule, for example, at least, or at most, 2, 3, 4, 5, 10, 20, 30, 40, 50, 100, 1000, or a number or a range between any two of these values, oligonucleotide molecules wherein each of the oligonucleotide molecule comprises the same, or different, unique identifiers. In some embodiments, each cellular component binding reagent can be conjugated with more than one oligonucleotide molecule, for example, at least, or at most, 2, 3, 4, 5, 10, 20, 30, 40, 50, 100, 1000, oligonucleotide molecules, wherein each of the oligonucleotide molecule comprises the same, or different, unique identifiers.

In some embodiments, the plurality of cellular component binding reagents are capable of specifically binding to a plurality of cellular component targets in a sample, such as a single cell, a plurality of cells, a tissue sample, a tumor sample, a blood sample, or the like. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components (e.g., proteins) in a cell or an organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components (e.g., proteins) in a cell or an organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, 10000, different cellular component targets.

Figure 4:
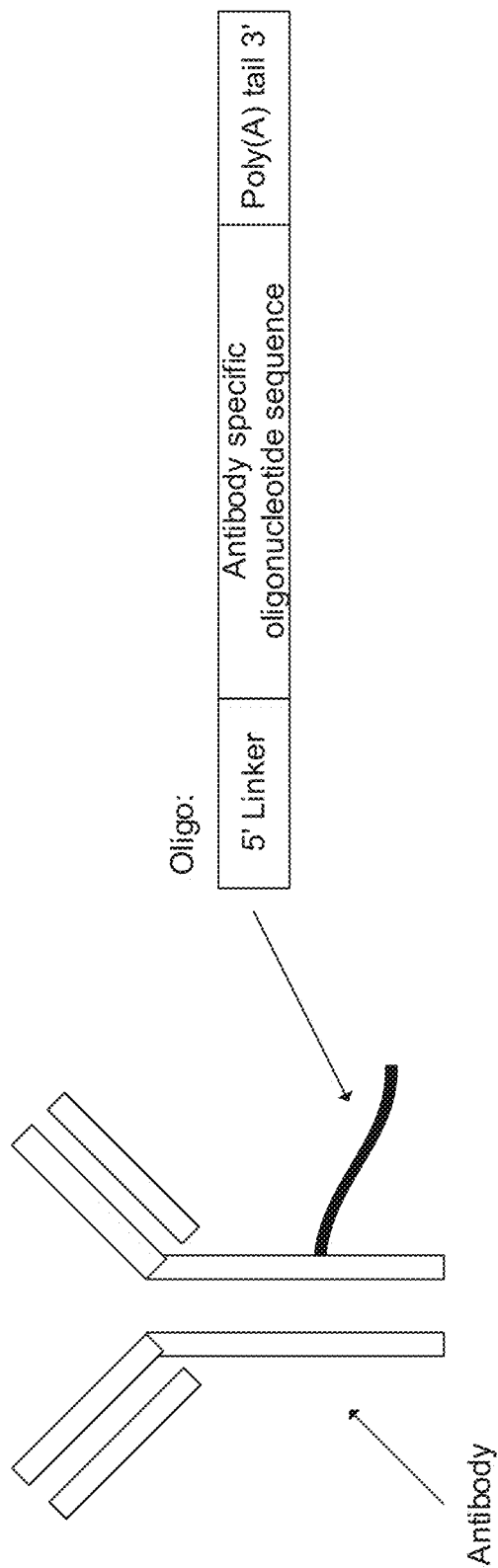
FIG. 4 shows a schematic illustration of an exemplary protein binding reagent (antibody illustrated here) conjugated with an oligonucleotide comprising a unique identifier for the protein binding reagent.

FIG. 4 shows a schematic illustration of an exemplary cellular component binding reagent, e.g., an antibody, that is conjugated with an oligonucleotide comprising a unique identifier sequence for the antibody. An oligonucleotide-conjugated with a cellular component binding reagent, an oligonucleotide for conjugation with a cellular component binding reagent, or an oligonucleotide previously conjugated with a cellular component binding reagent can be referred to herein as an antibody oligonucleotide (abbreviated as a binding reagent oligonucleotide). An oligonucleotide-conjugated with an antibody, an oligonucleotide for conjugation with an antibody, or an oligonucleotide previously conjugated with an antibody can be referred to herein as an antibody oligonucleotide (abbreviated as an "AbOligo" or "AbO"). The oligonucleotide can also comprise additional components, including but not limited to, one or more linker, one or more unique identifier for the antibody, optionally one or more barcode sequences (e.g., molecular labels), and a poly(A) tail. In some embodiments, the oligonucleotide can comprise, from 5' to 3', a linker, a unique identifier, a barcode sequence (e.g., a molecular label), and a poly(A) tail. An antibody oligonucleotide can be an mRNA mimic.

Figure 5:
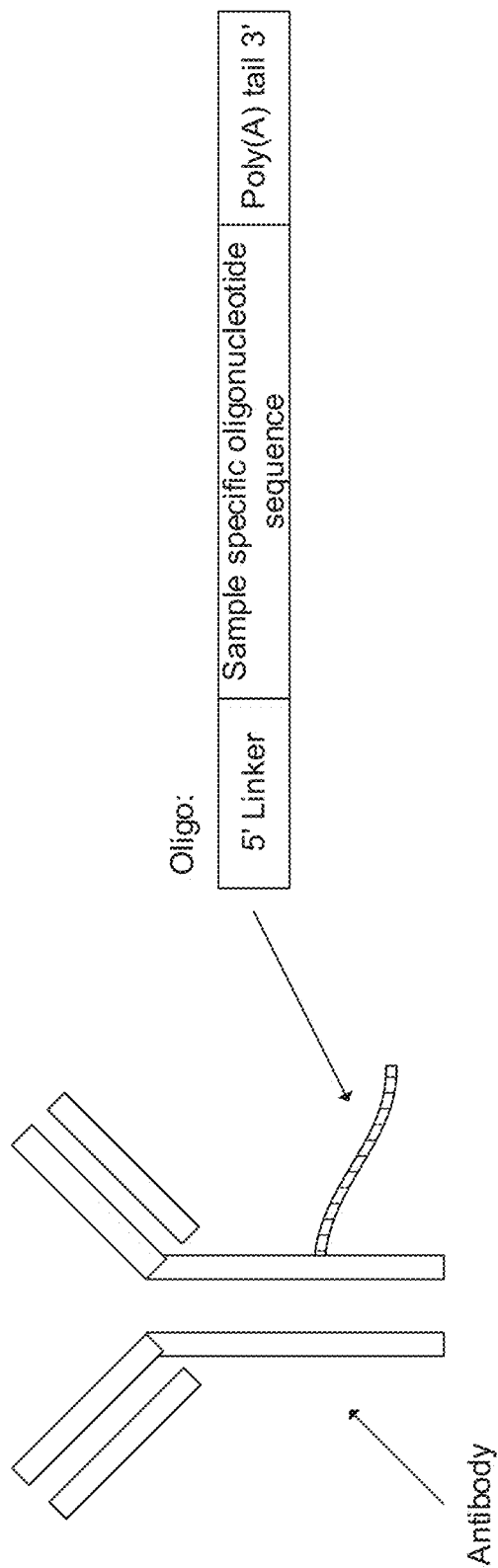
FIG. 5 shows a schematic illustration of an exemplary binding reagent (antibody illustrated here) conjugated with an oligonucleotide comprising a unique identifier for sample indexing to determine cells from the same or different samples.

FIG. 5 shows a schematic illustration of an exemplary cellular component binding reagent, e.g., an antibody, that is conjugated with an oligonucleotide comprising a unique identifier sequence for the antibody. The cellular component binding reagent can be capable of specifically binding to at least one cellular component target, such as an antigen target or a protein target. A binding reagent oligonucleotide (e.g., a sample indexing oligonucleotide, or an antibody oligonucleotide) can comprise a sequence (e.g., a sample indexing sequence) for performing the methods of the disclosure. For example, a sample indexing oligonucleotide can comprise a sample indexing sequence for identifying sample origin of one or more cells of a sample. Indexing sequences (e.g., sample indexing sequences) of at least two compositions comprising two cellular component binding reagents (e.g., sample indexing compositions) of the plurality of compositions comprising cellular component binding reagents can comprise different sequences. In some embodiments, the binding reagent oligonucleotide is not homologous to genomic sequences of a species. The binding reagent oligonucleotide can be configured to be detachable or non-detachable from the cellular component binding reagent.

The oligonucleotide conjugated to a cellular component binding reagent can, for example, comprise a barcode sequence (e.g., a molecular label sequence), a poly(A) tail, or a combination thereof. An oligonucleotide conjugated to a cellular component binding reagent can be an mRNA mimic. In some embodiments, the sample indexing oligonucleotide comprises a sequence complementary to a capture sequence of at least one barcode of the plurality of barcodes. A target binding region of the barcode can comprise the capture sequence. The target binding region can, for example, comprise a poly(dT) region. In some embodiments, the sequence of the sample indexing oligonucleotide complementary to the capture sequence of the barcode can comprise a poly(A) tail. The sample indexing oligonucleotide can comprise a molecular label.

In some embodiments, the binding reagent oligonucleotide (e.g., the sample oligonucleotide) comprises a nucleotide sequence of, or a nucleotide sequence of about, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, the binding reagent oligonucleotide comprises a nucleotide sequence of at least, or of at most, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

In some embodiments, the cellular component binding reagent comprises an antibody, a tetramer, an aptamer, a protein scaffold, or a combination thereof. The binding reagent oligonucleotide can be conjugated to the cellular component binding reagent, for example, through a linker. The binding reagent oligonucleotide can comprise the linker. The linker can comprise a chemical group. The chemical group can be reversibly, or irreversibly, attached to the molecule of the cellular component binding reagent. The chemical group can be selected from the group consisting of a UV photocleavable group, a disulfide bond, a streptavidin, a biotin, an amine, and any combination thereof.

In some embodiments, the cellular component binding reagent can bind to ADAM10, CD156c, ANO6, ATP1B2, ATP1B3, BSG, CD147, CD109, CD230, CD29, CD298, ATP1B3, CD44, CD45, CD47, CD51, CD59, CD63, CD97, CD98, SLC3A2, CLDND1, HLA-ABC, ICAM1, ITFG3, MPZL1, NA K ATPase alpha1, ATP1A1, NPTN, PMCA ATPase, ATP2B1, SLC1A5, SLC29A1, SLC2A1, SLC44A2, or any combination thereof.

In some embodiments, the protein target is, or comprises, an extracellular protein, an intracellular protein, or any combination thereof. In some embodiments, the antigen or protein target is, or comprises, a cell-surface protein, a cell marker, a B-cell receptor, a T-cell receptor, a major histocompatibility complex, a tumor antigen, a receptor, an integrin, or any combination thereof. The antigen or protein target can be, or comprise, a lipid, a carbohydrate, or any combination thereof. The protein target can be selected from a group comprising a number of protein targets. The number of antigen target or protein targets can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. The number of protein targets can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

The cellular component binding reagent (e.g., a protein binding reagent) can be associated with two or more binding reagent oligonucleotide (e.g., sample indexing oligonucleotides) with an identical sequence. The cellular component binding reagent can be associated with two or more binding reagent oligonucleotides with different sequences. The number of binding reagent oligonucleotides associated with the cellular component binding reagent can be different in different implementations. In some embodiments, the number of binding reagent oligonucleotides, whether having an identical sequence, or different sequences, can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of binding reagent oligonucleotides can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000.

The plurality of compositions comprising cellular component binding reagents (e.g., the plurality of sample indexing compositions) can comprise one or more additional cellular component binding reagents not conjugated with the binding reagent oligonucleotide (such as sample indexing oligonucleotide), which is also referred to herein as the binding reagent oligonucleotide-free cellular component binding reagent (such as sample indexing oligonucleotide-free cellular component binding reagent). The number of additional cellular component binding reagents in the plurality of compositions can be different in different implementations. In some embodiments, the number of additional cellular component binding reagents can be, or be about, 1, 2, 3, 4, 5, 6, 7, 8, 9, 10, 20, 30, 40, 50, 60, 70, 80, 90, 100, or a number or a range between any two of these values. In some embodiments, the number of additional cellular component binding reagents can be at least, or be at most, 1, 2, 3, 4, 5, 6, 7, 8, 9, 10, 20, 30, 40, 50, 60, 70, 80, 90, or 100. The cellular component binding reagent and any of the additional cellular component binding reagents can be identical, in some embodiments.

In some embodiments, a mixture comprising cellular component binding reagent(s) that is conjugated with one or more binding reagent oligonucleotides (e.g., sample indexing oligonucleotides) and cellular component binding reagent(s) that is not conjugated with binding reagent oligonucleotides is provided. The mixture can be used in some embodiments of the methods disclosed herein, for example, to contact the sample(s) and/or cell(s). The ratio of (1) the number of a cellular component binding reagent conjugated with a binding reagent oligonucleotide and (2) the number of another cellular component binding reagent (e.g., the same cellular component binding reagent) not conjugated with the binding reagent oligonucleotide (e.g., sample indexing oligonucleotide) or other binding reagent oligonucleotide(s) in the mixture can be different in different implementations. In some embodiments, the ratio can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the ratio can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

A cellular component binding reagent can be conjugated with a binding reagent oligonucleotide (e.g., a sample indexing oligonucleotide), or not. In some embodiments, the percentage of the cellular component binding reagent conjugated with a binding reagent oligonucleotide (e.g., a sample indexing oligonucleotide) in a mixture comprising the cellular component binding reagent that is conjugated with the binding reagent oligonucleotide and the cellular component binding reagent(s) that is not conjugated with the binding reagent oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the cellular component binding reagent conjugated with a sample indexing oligonucleotide in a mixture can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, the percentage of the cellular component binding reagent not conjugated with a binding reagent oligonucleotide (e.g., a sample indexing oligonucleotide) in a mixture comprising a cellular component binding reagent conjugated with a binding reagent oligonucleotide (e.g., a sample indexing oligonucleotide) and the cellular component binding reagent that is not conjugated with the sample indexing oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the cellular component binding reagent not conjugated with a binding reagent oligonucleotide in a mixture can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Cellular Component Cocktails

In some embodiments, a cocktail of cellular component binding reagents (e.g., an antibody cocktail) can be used to increase labeling sensitivity in the methods disclosed herein. Without being bound by any particular theory, it is believed that this may be because cellular component expression or protein expression can vary between cell types and cell states, making finding a universal cellular component binding reagent or antibody that labels all cell types challenging. For example, cocktail of cellular component binding reagents can be used to allow for more sensitive and efficient labeling of more sample types. The cocktail of cellular component binding reagents can include two or more different types of cellular component binding reagents, for example a wider range of cellular component binding reagents or antibodies. Cellular component binding reagents that label different cellular component targets can be pooled together to create a cocktail that sufficiently labels all cell types, or one or more cell types of interest.

In some embodiments, each of the plurality of compositions (e.g., sample indexing compositions) comprises a cellular component binding reagent. In some embodiments, a composition of the plurality of compositions comprises two or more cellular component binding reagents, wherein each of the two or more cellular component binding reagents is associated with a binding reagent oligonucleotide (e.g., a sample indexing oligonucleotide), wherein at least one of the two or more cellular component binding reagents is capable of specifically binding to at least one of the one or more cellular component targets. The sequences of the binding reagent oligonucleotides associated with the two or more cellular component binding reagents can be identical. The sequences of the binding reagent oligonucleotides associated with the two or more cellular component binding reagents can comprise different sequences. Each of the plurality of compositions can comprise the two or more cellular component binding reagents.

The number of different types of cellular component binding reagents (e.g., a CD147 antibody and a CD47 antibody) in a composition can be different in different implementations. A composition with two or more different types of cellular component binding reagents can be referred to herein as a cellular component binding reagent cocktail (e.g., a sample indexing composition cocktail). The number of different types of cellular component binding reagents in a cocktail can vary. In some embodiments, the number of different types of cellular component binding reagents in cocktail can be, or be about 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or a number or a range between any two of these values. In some embodiments, the number of different types of cellular component binding reagents in cocktail can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, or 100000. The different types of cellular component binding reagents can be conjugated to binding reagent oligonucleotides with the same or different sequences (e.g., sample indexing sequences).

Methods of Quantitative Analysis of Cellular Component Targets

In some embodiments, the methods disclosed herein can also be used for quantitative analysis of a plurality of cellular component targets (for example, protein targets) in a sample using the compositions disclosed herein and oligonucleotide probes that can associate a barcode sequence (e.g., a molecular label sequence) to the oligonucleotides of the cellular component binding reagents (e.g., protein binding reagents). The oligonucleotides of the cellular component binding reagents can be, or comprise, an antibody oligonucleotide, a sample indexing oligonucleotide, a cell identification oligonucleotide, a control particle oligonucleotide, a control oligonucleotide, an interaction determination oligonucleotide, etc. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, etc., or a mixture of cells from different subjects.

In some embodiments, the sample can comprise a plurality of single cells separated into individual compartments, such as microwells in a microwell array.

In some embodiments, the binding target of the plurality of cellular component target (i.e., the cellular component target) can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component target is a protein target. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular components can be at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90%, at least 95%, at least 98%, at least 99%, or more, of all the encoded cellular components in an organism. In some embodiments, the plurality of cellular component targets can comprise at least 2, at least 3, at least 4, at least 5, at least 10, at least 20, at least 30, at least 40, at least 50, at least 100, at least 1000, at least 10000, or more different cellular component targets.

In some embodiments, the plurality of cellular component binding reagents is contacted with the sample for specific binding with the plurality of cellular component targets. Unbound cellular component binding reagents can be removed, for example, by washing. In embodiments where the sample comprises cells, any cellular component binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1%, 5%, 10%, 15%, 20%, 25%, 30%, 35%, 40%, 45%, 50%, 55%, 60%, 65%, 70%, 75%, 80%, 85%, 90%, 95% or 100%, of wells of the substrate receive a single cell. The population of cells can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100%, of wells of the substrate receive a single cell. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. In some instances, the population of cells is diluted such that the number of cells is about 10% of the number of wells in the substrate.

Distribution of single cells into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one cell. There can be at least a 0.1%, 0.5%, 1%, 2%, 3%, 4%, 5%, 6%, 7%, 8%, 9%, or 10%, or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the cellular component binding reagents can be additionally conjugated with fluorescent molecules to enable flow sorting of cells into individual compartments.

In some embodiments, the methods disclosed herein provide contacting a plurality of compositions with the sample for specific binding with the plurality of cellular component targets. It would be appreciated that the conditions used may allow specific binding of the cellular component binding reagents, e.g., antibodies, to the cellular component targets. Following the contacting step, unbound compositions can be removed. For example, in embodiments where the sample comprises cells, and the compositions specifically bind to cellular component targets are cell-surface cellular components, such as cell-surface proteins, unbound compositions can be removed by washing the cells with buffer such that only compositions that specifically bind to the cellular component targets remain with the cells.

In some embodiments, the methods disclosed herein can comprise associating an oligonucleotide (e.g., a barcode, or a stochastic barcode), including a barcode sequence (such as a molecular label), a cell label, a sample label, etc., or any combination thereof, to the plurality of oligonucleotides associated with the cellular component binding reagents. For example, a plurality of oligonucleotide probes comprising a barcode can be used to hybridize to the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality associated with oligonucleotides of the cellular component binding reagents, the plurality of oligonucleotides of the cellular component binding reagents can hybridize to the oligonucleotide probes. The oligonucleotide probes can be contacted at a non-depletable ratio such that each distinct oligonucleotide of the cellular component binding reagents can associate with oligonucleotide probes having different barcode sequences (e.g., molecular labels) of the disclosure.

In some embodiments, the methods disclosed herein provide detaching the oligonucleotides from the cellular component binding reagents that are specifically bound to the cellular component targets. Detachment can be performed in a variety of ways to separate the chemical group from the cellular component binding reagent, such as UV photocleaving, chemical treatment (e.g., dithiothreitol treatment), heating, enzyme treatment, or any combination thereof. Detaching the oligonucleotide from the cellular component binding reagent can be performed either before, after, or during the step of hybridizing the plurality of oligonucleotide probes to the plurality of oligonucleotides of the compositions.

Methods of Simultaneous Quantitative Analysis of Cellular Component and Nucleic Acid Targets In some embodiments, the methods disclosed herein can also be used for simultaneous quantitative analysis of a plurality of cellular component targets (e.g., protein targets) and a plurality of nucleic acid target molecules in a sample using the compositions disclosed herein and oligonucleotide probes that can associate a barcode sequence (e.g., a molecular label sequence) to both the oligonucleotides of the cellular component binding reagents and nucleic acid target molecules. Other methods of simultaneous quantitative analysis of a plurality of cellular component targets and a plurality of nucleic acid target molecules are described in U.S. Patent Application Publication 20180088112A1; the content of which is incorporated herein by reference in its entirety. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, or a mixture of cells from the same subject or different subjects.

In some embodiments, the sample can comprise a plurality of single cells separated into individual compartments, such as microwells in a microwell array.

In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components, such as expressed proteins, in an organism, or one or more cell of the organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components, such as proteins could be expressed, in an organism, or one or more cells of the organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, or 10000, different cellular component targets.

In some embodiments, the plurality of cellular component binding reagents is contacted with the sample for specific binding with the plurality of cellular component targets. Unbound cellular component binding reagents can be removed, for example, by washing. In embodiments where the sample comprises cells, any cellular component binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. In some instances, the population of cells is diluted such that the number of cells is about 10% of the number of wells in the substrate.

Distribution of single cells into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one cell. There can be at least a 0.1%, 0.5%, 1%, 2%, 3%, 4%, 5%, 6%, 7%, 8%, 9%, or 10%, or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the cellular component binding reagents can be additionally conjugated with fluorescent molecules to enable flow sorting of cells into individual compartments.

In some embodiments, the methods disclosed herein provide contacting a plurality of compositions with the sample for specific binding with the plurality of cellular component targets. It would be appreciated that the conditions used may allow specific binding of the cellular component binding reagents, e.g., antibodies, to the cellular component targets. Following the contacting step, unbound compositions can be removed. For example, in embodiments where the sample comprises cells, and the compositions specifically bind to cellular component targets are on the cell surface, such as cell-surface proteins, unbound compositions can be removed by washing the cells with buffer such that only compositions that specifically bind to the cellular component targets remain with the cells.

In some embodiments, the methods disclosed herein can provide releasing the plurality of nucleic acid target molecules from the sample, e.g., cells. For example, the cells can be lysed to release the plurality of nucleic acid target molecules. Cell lysis may be accomplished by any of a variety of means, for example, by chemical treatment, osmotic shock, thermal treatment, mechanical treatment, optical treatment, or any combination thereof. Cells may be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof.

It would be appreciated by one of ordinary skill in the art that the plurality of nucleic acid molecules can comprise a variety of nucleic acid molecules. In some embodiments, the plurality of nucleic acid molecules can comprise, DNA molecules, RNA molecules, genomic DNA molecules, mRNA molecules, rRNA molecules, siRNA molecules, or a combination thereof, and can be double-stranded or single-stranded. In some embodiments, the plurality of nucleic acid molecules comprises, or comprise about, 100, 1000, 10000, 20000, 30000, 40000, 50000, 100000, 1000000, or a number or a range between any two of these values, species. In some embodiments, the plurality of nucleic acid molecules comprises at least, or comprise at most, 100, 1000, 10000, 20000, 30000, 40000, 50000, 100000, or 1000000, species. In some embodiments, the plurality of nucleic acid molecules can be from a sample, such as a single cell, or a plurality of cells. In some embodiments, the plurality of nucleic acid molecules can be pooled from a plurality of samples, such as a plurality of single cells.

In some embodiments, the methods disclosed herein can comprise associating a barcode (e.g., a stochastic barcode), which can include a barcode sequence (such as a molecular label), a cell label, a sample label, etc., or any combination thereof, to the plurality of nucleic acid target molecules and the plurality of oligonucleotides of the cellular component binding reagents. For example, a plurality of oligonucleotide probes comprising a stochastic barcode can be used to hybridize to the plurality of nucleic acid target molecules and the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes is in close proximity to the plurality of nucleic acid target molecules and the plurality of oligonucleotides of the cellular component binding reagents, the plurality of nucleic acid target molecules and the plurality of oligonucleotides of the cellular component binding reagents can hybridize to the oligonucleotide probes. The oligonucleotide probes can be contacted at a non-depletable ratio such that each distinct nucleic acid target molecules and oligonucleotides of the cellular component binding reagents can associate with oligonucleotide probes having different barcode sequences (e.g., molecular labels) of the disclosure.

In some embodiments, the methods disclosed herein provide detaching the oligonucleotides from the cellular component binding reagents that are specifically bound to the cellular component targets. Detachment can be performed in a variety of ways to separate the chemical group from the cellular component binding reagent, such as UV photocleaving, chemical treatment (e.g., dithiothreitol treatment), heating, enzyme treatment, or any combination thereof. Detaching the oligonucleotide from the cellular component binding reagent can be performed either before, after, or during the step of hybridizing the plurality of oligonucleotide probes to the plurality of nucleic acid target molecules and the plurality of oligonucleotides of the compositions.

Simultaneous Quantitative Analysis of Protein and Nucleic Acid Targets

Figure 6:
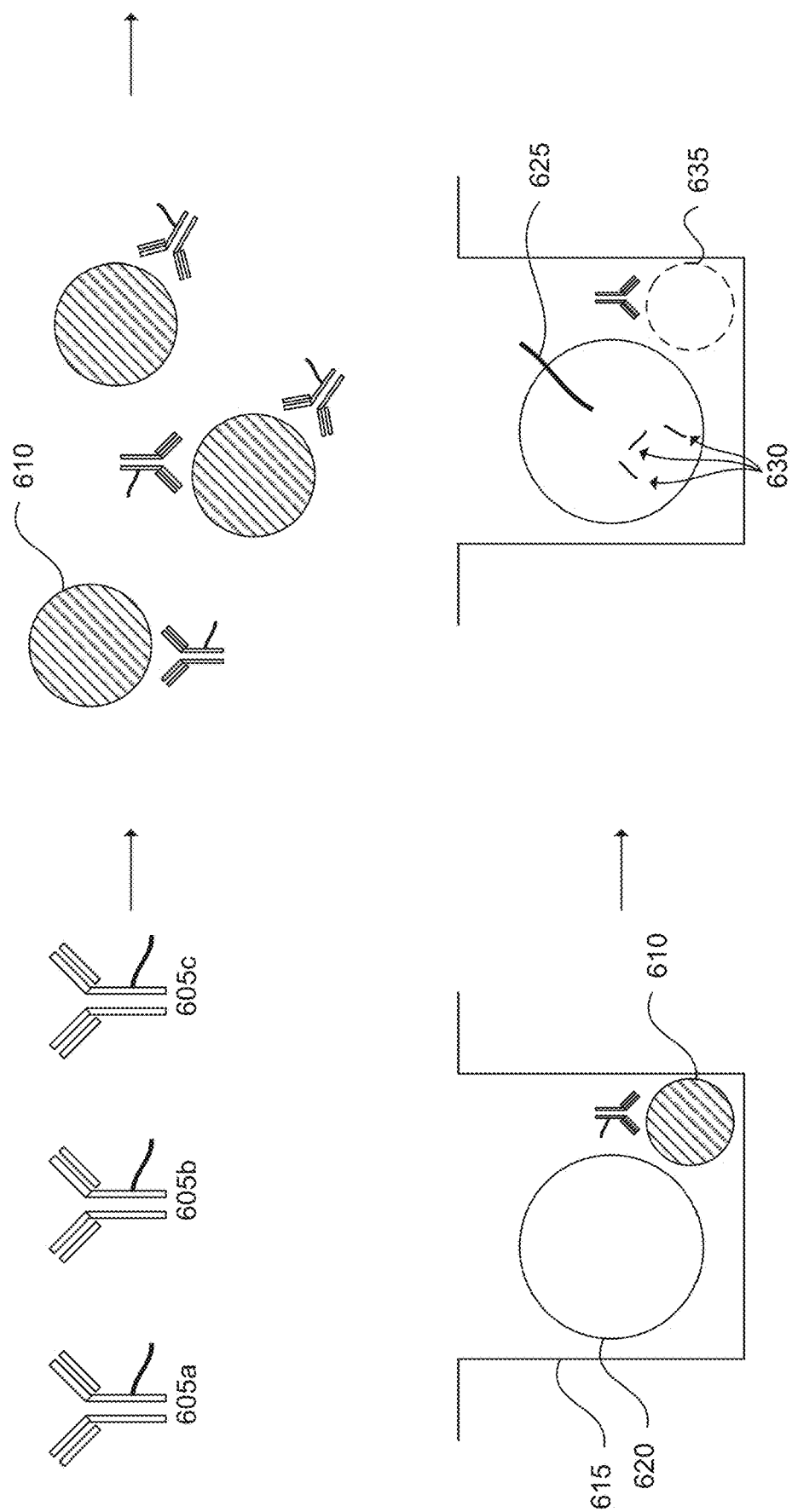
FIG. 6 shows a schematic illustration of an exemplary workflow using oligonucleotide-conjugated antibodies to determine protein expression and gene expression simultaneously in a high throughput manner.

In some embodiments, the methods disclosed herein also can be used for simultaneous quantitative analysis of multiple types of target molecules, for example protein and nucleic acid targets. For example, the target molecules can be, or comprise, cellular components. FIG. 6 shows a schematic illustration of an exemplary method of simultaneous quantitative analysis of both nucleic acid targets and other cellular component targets (e.g., proteins) in single cells. In some embodiments, a plurality of compositions 605, 605b, 605c, etc., each comprising a cellular component binding reagent, such as an antibody, is provided. Different cellular component binding reagents, such as antibodies, which bind to different cellular component targets are conjugated with different unique identifiers. Next, the cellular component binding reagents can be incubated with a sample containing a plurality of cells 610. The different cellular component binding reagents can specifically bind to cellular components on the cell surface, such as a cell marker, a B-cell receptor, a T-cell receptor, an antibody, a major histocompatibility complex, a tumor antigen, a receptor, or any combination thereof. Unbound cellular component binding reagents can be removed, e.g., by washing the cells with a buffer. The cells with the cellular component binding reagents can be then separated into a plurality of compartments, such as a microwell array, wherein a single compartment 615 is sized to fit a single cell and a single bead 620.

Each bead can comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The oligonucleotides 625 conjugated to the cellular component binding reagent can be detached from the cellular component binding reagent using chemical, optical or other means. The cell can be lysed 635 to release nucleic acids within the cell, such as genomic DNA or cellular mRNA 630. Cellular mRNA 630, oligonucleotides 625 or both can be captured by the oligonucleotide probes on bead 620, for example, by hybridizing to the poly(dT) sequence. A reverse transcriptase can be used to extend the oligonucleotide probes hybridized to the cellular mRNA 630 and the oligonucleotides 625 using the cellular mRNA 630 and the oligonucleotides 625 as templates. The extension products produced by the reverse transcriptase can be subject to amplification and sequencing. Sequencing reads can be subject to demultiplexing of sequences or identifies of cell labels, barcodes (e.g., molecular labels), genes, cellular component binding reagent specific oligonucleotides (e.g., antibody specific oligonucleotides), etc., which can give rise to a digital representation of cellular components and gene expression of each single cell in the sample.

Association of Barcodes

The oligonucleotides associated with the cellular component binding reagents (e.g., antigen binding reagents or protein binding reagents) and/or the nucleic acid molecules may randomly associate with the oligonucleotide probes. The oligonucleotides associated with the cellular component binding reagents, referred to herein as binding reagent oligonucleotides, can be, or comprise oligonucleotides of the disclosure, such as an antibody oligonucleotide, a sample indexing oligonucleotide, a cell identification oligonucleotide, a control particle oligonucleotide, a control oligonucleotide, an interaction determination oligonucleotide, etc. Association can, for example, comprise hybridization of an oligonucleotide probe's target binding region to a complementary portion of the target nucleic acid molecule and/or the oligonucleotides of the protein binding reagents. For example, an oligo(dT) region of a barcode (e.g., a stochastic barcode) can interact with a poly(A) tail of a target nucleic acid molecule and/or a poly(A) tail of an oligonucleotide of a protein binding reagent. The assay conditions used for hybridization (e.g., buffer pH, ionic strength, temperature, etc.) can be chosen to promote formation of specific, stable hybrids.

The disclosure provides for methods of associating a molecular label with a target nucleic acid and/or an oligonucleotide associated with a cellular component binding reagent using reverse transcription. As a reverse transcriptase can use both RNA and DNA as template. For example, the oligonucleotide originally conjugated on the cellular component binding reagent can be either RNA or DNA bases, or both. A binding reagent oligonucleotide can be copied and linked (e.g., covalently linked) to a cell label and a barcode sequence (e.g., a molecular label) in addition to the sequence, or a portion thereof, of the binding reagent sequence. As another example, an mRNA molecule can be copied and linked (e.g., covalently linked) to a cell label and a barcode sequence (e.g., a molecular label) in addition to the sequence of the mRNA molecule, or a portion thereof.

In some embodiments, molecular labels can be added by ligation of an oligonucleotide probe target binding region and a portion of the target nucleic acid molecule and/or the oligonucleotides associated with (e.g., currently, or previously, associated with) with cellular component binding reagents. For example, the target binding region may comprise a nucleic acid sequence that can be capable of specific hybridization to a restriction site overhang (e.g., an EcoRI sticky-end overhang). The methods can further comprise treating the target nucleic acids and/or the oligonucleotides associated with cellular component binding reagents with a restriction enzyme (e.g., EcoRI) to create a restriction site overhang. A ligase (e.g., T4 DNA ligase) may be used to join the two fragments.

Determining the Number or Presence of Unique Molecular Label Sequences

In some embodiments, the methods disclosed herein comprise determining the number or presence of unique molecular label sequences for each unique identifier, each nucleic acid target molecule, and/or each binding reagent oligonucleotides (e.g., antibody oligonucleotides). For example, the sequencing reads can be used to determine the number of unique molecular label sequences for each unique identifier, each nucleic acid target molecule, and/or each binding reagent oligonucleotide. As another example, the sequencing reads can be used to determine the presence or absence of a molecular label sequence (such as a molecular label sequence associated with a target, a binding reagent oligonucleotide, an antibody oligonucleotide, a sample indexing oligonucleotide, a cell identification oligonucleotide, a control particle oligonucleotide, a control oligonucleotide, an interaction determination oligonucleotide, etc. in the sequencing reads).

In some embodiments, the number of unique molecular label sequences for each unique identifier, each nucleic acid target molecule, and/or each binding reagent oligonucleotide indicates the quantity of each cellular component target (e.g., an antigen target or a protein target) and/or each nucleic acid target molecule in the sample. In some embodiments, the quantity of a cellular component target and the quantity of its corresponding nucleic acid target molecules, e.g., mRNA molecules, can be compared to each other. In some embodiments, the ratio of the quantity of a cellular component target and the quantity of its corresponding nucleic acid target molecules, e.g., mRNA molecules, can be calculated. The cellular component targets can be, for example, cell surface protein markers. In some embodiments, the ratio between the protein level of a cell surface protein marker and the level of the mRNA of the cell surface protein marker is low.

The methods disclosed herein can be used for a variety of applications. For example, the methods disclosed herein can be used for proteome and/or transcriptome analysis of a sample. In some embodiments, the methods disclosed herein can be used to identify a cellular component target and/or a nucleic acid target, i.e., a biomarker, in a sample. In some embodiments, the cellular component target and the nucleic acid target correspond to each other, i.e., the nucleic acid target encodes the cellular component target. In some embodiments, the methods disclosed herein can be used to identify cellular component targets that have a desired ratio between the quantity of the cellular component target and the quantity of its corresponding nucleic acid target molecule in a sample, e.g., mRNA molecule. In some embodiments, the ratio is, or is about, 0.001, 0.01, 0.1, 1, 10, 100, 1000, or a number or a range between any two of the above values. In some embodiments, the ratio is at least, or is at most, 0.001, 0.01, 0.1, 1, 10, 100, or 1000. In some embodiments, the methods disclosed herein can be used to identify cellular component targets in a sample that the quantity of its corresponding nucleic acid target molecule in the sample is, or is about, 1000, 100, 10, 5, 2 1, 0, or a number or a range between any two of these values. In some embodiments, the methods disclosed herein can be used to identify cellular component targets in a sample that the quantity of its corresponding nucleic acid target molecule in the sample is more than, or less than, 1000, 100, 10, 5, 2 1, or 0.

Compositions and Kits

Some embodiments disclosed herein provide kits and compositions for simultaneous quantitative analysis of a plurality of cellular components (e.g., proteins) and/or a plurality of nucleic acid target molecules in a sample. The kits and compositions can, in some embodiments, comprise a plurality of cellular component binding reagents (e.g., a plurality of protein binding reagents) each conjugated with an oligonucleotide, wherein the oligonucleotide comprises a unique identifier for the cellular component binding reagent, and a plurality of oligonucleotide probes, wherein each of the plurality of oligonucleotide probes comprises a target binding region, a barcode sequence (e.g., a molecular label sequence), wherein the barcode sequence is from a diverse set of unique barcode sequences. In some embodiments, each of the oligonucleotides can comprise a molecular label, a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., oligodA$_{18}$ (unanchored to a solid support) or oligoA$_{18}$V (anchored to a solid support). The oligonucleotides can comprise DNA residues, RNA residues, or both.

Disclosed herein includes a plurality of sample indexing compositions. Each of the plurality of sample indexing compositions can comprise two or more cellular component binding reagents. Each of the two or more cellular component binding reagents can be associated with a sample indexing oligonucleotide. At least one of the two or more cellular component binding reagents can be capable of specifically binding to at least one cellular component target. The sample indexing oligonucleotide can comprise a sample indexing sequence for identifying sample origin of one or more cells of a sample. Sample indexing sequences of at least two sample indexing compositions of the plurality of sample indexing compositions can comprise different sequences.

Disclosed herein include kits comprising sample indexing compositions for cell identification. In some embodiments. Each of two sample indexing compositions comprises a cellular component binding reagent (e.g., a protein binding reagent) associated with a sample indexing oligonucleotide, wherein the cellular component binding reagent is capable of specifically binding to at least one of one or more cellular component targets (e.g., one or more protein targets), wherein the sample indexing oligonucleotide comprises a sample indexing sequence, and wherein sample indexing sequences of the two sample indexing compositions comprise different sequences. In some embodiments, the sample indexing oligonucleotide comprises a molecular label sequence, a binding site for a universal primer, or a combination thereof.

Disclosed herein includes kits for cell identification. In some embodiments, the kit comprises: two or more sample indexing compositions. Each of the two or more sample indexing compositions can comprise a cellular component binding reagent (e.g., an antigen binding reagent) associated with a sample indexing oligonucleotide, wherein the cellular component binding reagent is capable of specifically binding to at least one of one or more cellular component targets, wherein the sample indexing oligonucleotide comprises a sample indexing sequence, and wherein sample indexing sequences of the two sample indexing compositions comprise different sequences. In some embodiments, the sample indexing oligonucleotide comprises a molecular label sequence, a binding site for a universal primer, or a combination thereof. Disclosed herein includes kits for multiplet identification. In some embodiments, the kit comprises two sample indexing compositions. Each of two sample indexing compositions can comprise a cellular component binding reagent (e.g., an antigen binding reagent) associated with a sample indexing oligonucleotide, wherein the antigen binding reagent is capable of specifically binding to at least one of one or more cellular component targets (e.g., antigen targets), wherein the sample indexing oligonucleotide comprises a sample indexing sequence, and wherein sample indexing sequences of the two sample indexing compositions comprise different sequences.

The unique identifiers (or oligonucleotides associated with cellular component binding reagents, such as binding reagent oligonucleotides, antibody oligonucleotides, sample indexing oligonucleotides, cell identification oligonucleotides, control particle oligonucleotides, control oligonucleotides, or interaction determination oligonucleotides) can have any suitable length, for example, from about 25 nucleotides to about 45 nucleotides long. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise, or comprise about, 20, 30, 40, 50, 60, 70, 80, 90, 100, 200, 300, 400, 500, 600, 700, 800, 900, 1000, 2000, 5000, or a number or a range between any two of these values, different unique identifiers. The diverse set of unique identifiers can comprise at least, or comprise at most, 20, 30, 40, 50, 60, 70, 80, 90, 100, 200, 300, 400, 500, 600, 700, 800, 900, 1000, 2000, or 5000, different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by, or by about, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a number or a range between any two of these values. In some embodiments, the sequences of the set of unique identifiers are different from each other, or the complement thereof, by at least, or by at most, 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable cellular component binding reagents are contemplated in this disclosure, such as any protein binding reagents (e.g., antibodies or fragments thereof, aptamers, small molecules, ligands, peptides, oligonucleotides, etc., or any combination thereof). In some embodiments, the cellular component binding reagents can be polyclonal antibodies, monoclonal antibodies, recombinant antibodies, single-chain antibody (scAb), or fragments thereof, such as Fab, Fv, etc. In some embodiments, the plurality of protein binding reagents can comprise, or comprise about, 20, 30, 40, 50, 60, 70, 80, 90, 100, 200, 300, 400, 500, 600, 700, 800, 900, 1000, 2000, 5000, or a number or a range between any two of these values, different protein binding reagents. In some embodiments, the plurality of protein binding reagents can comprise at least, or comprise at most, 20, 30, 40, 50, 60, 70, 80, 90, 100, 200, 300, 400, 500, 600, 700, 800, 900, 1000, 2000, or 5000, different protein binding reagents.

In some embodiments, the oligonucleotide is conjugated with the cellular component binding reagent through a linker. In some embodiments, the oligonucleotide can be conjugated with the protein binding reagent covalently. In some embodiment, the oligonucleotide can be conjugated with the protein binding reagent non-covalently. In some embodiments, the linker can comprise a chemical group that reversibly or irreversibly attached the oligonucleotide to the protein binding reagents. The chemical group can be conjugated to the linker, for example, through an amine group. In some embodiments, the linker can comprise a chemical group that forms a stable bond with another chemical group conjugated to the protein binding reagent. For example, the chemical group can be a UV photocleavable group, a disulfide bond, a streptavidin, a biotin, an amine, etc. In some embodiments, the chemical group can be conjugated to the protein binding reagent through a primary amine on an amino acid, such as lysine, or the N-terminus. The oligonucleotide can be conjugated to any suitable site of the protein binding reagent, as long as it does not interfere with the specific binding between the protein binding reagent and its protein target. In embodiments where the protein binding reagent is an antibody, the oligonucleotide can be conjugated to the antibody anywhere other than the antigen-binding site, for example, the Fc region, the $CH_1$ domain, the $C_H2$ domain, the $C_H3$ domain, the $C_L$ domain, etc. In some embodiments, each protein binding reagent can be conjugated with a single oligonucleotide molecule. In some embodiments, each protein binding reagent can be conjugated with, or with about, 2, 3, 4, 5, 10, 20, 30, 40, 50, 100, 1000, or a number or a range between any two of these values, oligonucleotide molecules, wherein each of the oligonucleotide molecule comprises the same unique identifier. In some embodiments, each protein binding reagent can be conjugated with more than one oligonucleotide molecule, for example, at least, or at most, 2, 3, 4, 5, 10, 20, 30, 40, 50, 100, or 1000, oligonucleotide molecules, wherein each of the oligonucleotide molecule comprises the same unique identifier.

In some embodiments, the plurality of cellular component binding reagents (e.g., protein binding reagents) are capable of specifically binding to a plurality of cellular component targets (e.g., protein targets) in a sample. The sample can be, or comprise, a single cell, a plurality of cells, a tissue sample, a tumor sample, a blood sample, or the like. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular proteins. In some embodiments, the plurality of cellular component targets can comprise intracellular proteins. In some embodiments, the plurality of cellular component targets can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values of all cellular component targets (e.g., proteins expressed or could be expressed) in an organism. In some embodiments, the plurality of cellular component targets can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all cellular component targets (e.g., proteins expressed or could be expressed) in an organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, or 10000, different cellular component targets.

Sample Indexing Using Oligonucleotide-Conjugated Cellular Component Binding Reagent Disclosed herein include methods for sample identification. In some embodiments, the method comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; barcoding (e.g., stochastically barcoding) the sample indexing oligonucleotides using a plurality of barcodes (e.g., stochastic barcodes) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

An oligonucleotide-conjugated with an antibody, an oligonucleotide for conjugation with an antibody, or an oligonucleotide previously conjugated with an antibody is referred to herein as an antibody oligonucleotide ("AbOligo"). Antibody oligonucleotides in the context of sample indexing are referred to herein as sample indexing oligonucleotides. An antibody conjugated with an antibody oligonucleotide is referred to herein as a hot antibody or an oligonucleotide antibody. An antibody not conjugated with an antibody oligonucleotide is referred to herein as a cold antibody or an oligonucleotide free antibody. An oligonucleotide-conjugated with a binding reagent (e.g., a protein binding reagent), an oligonucleotide for conjugation with a binding reagent, or an oligonucleotide previously conjugated with a binding reagent is referred to herein as a reagent oligonucleotide. Reagent oligonucleotides in the context of sample indexing are referred to herein as sample indexing oligonucleotides. A binding reagent conjugated with an antibody oligonucleotide is referred to herein as a hot binding reagent or an oligonucleotide binding reagent. A binding reagent not conjugated with an antibody oligonucleotide is referred to herein as a cold binding reagent or an oligonucleotide free binding reagent.

Figure 7:
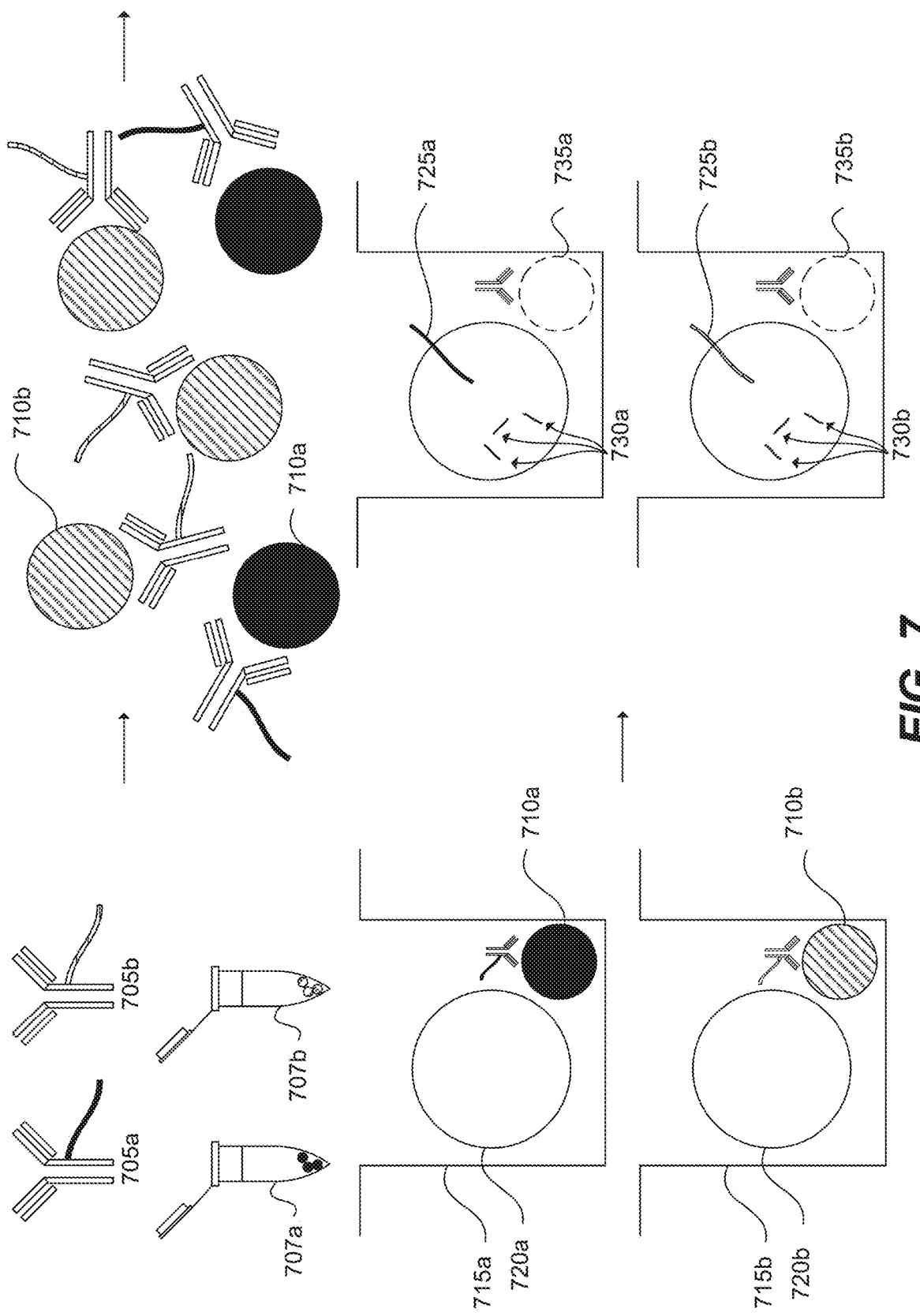
FIG. 7 shows a schematic illustration of an exemplary workflow of using oligonucleotide-conjugated antibodies for sample indexing.

FIG. 7 shows a schematic illustration of an exemplary workflow using oligonucleotide-conjugated cellular component binding reagents for sample indexing. In some embodiments, a plurality of compositions 705a, 705b, etc., each comprising a binding reagent is provided. The binding reagent can be a protein binding reagent, such as an antibody. The cellular component binding reagent can comprise an antibody, a tetramer, an aptamers, a protein scaffold, or a combination thereof. The binding reagents of the plurality of compositions 705a, 705b can bind to an identical cellular component target. For example, the binding reagents of the plurality of compositions 705, 705b can be identical (except for the sample indexing oligonucleotides associated with the binding reagents).

Different compositions can include binding reagents conjugated with sample indexing oligonucleotides with different sample indexing sequences. The number of different compositions can be different in different implementations. In some embodiments, the number of different compositions can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of different compositions can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

In some embodiments, the sample indexing oligonucleotides of binding reagents in one composition can include an identical sample indexing sequence. The sample indexing oligonucleotides of binding reagents in one composition may not be identical. In some embodiments, the percentage of sample indexing oligonucleotides of binding reagents in one composition with an identical sample indexing sequence can be, or be about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values. In some embodiments, the percentage of sample indexing oligonucleotides of binding reagents in one composition with an identical sample indexing sequence can be at least, or be at most, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9%.

The compositions 705a and 705b can be used to label samples of different samples. For example, the sample indexing oligonucleotides of the cellular component binding reagent in the composition 705a can have one sample indexing sequence and can be used to label cells 710a, shown as black circles, in a sample 707a, such as a sample of a patient. The sample indexing oligonucleotides of the cellular component binding reagents in the composition 705b can have another sample indexing sequence and can be used to label cells 710b, shown as hatched circles, in a sample 707b, such as a sample of another patient or another sample of the same patient. The cellular component binding reagents can specifically bind to cellular component targets or proteins on the cell surface, such as a cell marker, a B-cell receptor, a T-cell receptor, an antibody, a major histocompatibility complex, a tumor antigen, a receptor, or any combination thereof. Unbound cellular component binding reagents can be removed, e.g., by washing the cells with a buffer.

The cells with the cellular component binding reagents can be then separated into a plurality of compartments, such as a microwell array, wherein a single compartment 715a, 715b is sized to fit a single cell 710a and a single bead 720a or a single cell 710b and a single bead 720b. Each bead 720a, 720b can comprise a plurality of oligonucleotide probes, which can comprise a cell label that is common to all oligonucleotide probes on a bead, and molecular label sequences. In some embodiments, each oligonucleotide probe can comprise a target binding region, for example, a poly(dT) sequence. The sample indexing oligonucleotides 725a conjugated to the cellular component binding reagent of the composition 705a can be configured to be detachable or non-detachable from the cellular component binding reagent. The sample indexing oligonucleotides 725a conjugated to the cellular component binding reagent of the composition 705a can be detached from the cellular component binding reagent using chemical, optical or other means. The sample indexing oligonucleotides 725b conjugated to the cellular component binding reagent of the composition 705b can be configured to be detachable or non-detachable from the cellular component binding reagent. The sample indexing oligonucleotides 725b conjugated to the cellular component binding reagent of the composition 705b can be detached from the cellular component binding reagent using chemical, optical or other means.

The cell 710a can be lysed to release nucleic acids within the cell 710a, such as genomic DNA or cellular mRNA 730a. The lysed cell 735a is shown as a dotted circle. Cellular mRNA 730a, sample indexing oligonucleotides 725a, or both can be captured by the oligonucleotide probes on bead 720a, for example, by hybridizing to the poly(dT) sequence. A reverse transcriptase can be used to extend the oligonucleotide probes hybridized to the cellular mRNA 730a and the oligonucleotides 725a using the cellular mRNA 730a and the oligonucleotides 725a as templates. The extension products produced by the reverse transcriptase can be subject to amplification and sequencing.

Similarly, the cell 710b can be lysed to release nucleic acids within the cell 710b, such as genomic DNA or cellular mRNA 730b. The lysed cell 735b is shown as a dotted circle. Cellular mRNA 730b, sample indexing oligonucleotides 725b, or both can be captured by the oligonucleotide probes on bead 720b, for example, by hybridizing to the poly(dT) sequence. A reverse transcriptase can be used to extend the oligonucleotide probes hybridized to the cellular mRNA 730b and the oligonucleotides 725b using the cellular mRNA 730b and the oligonucleotides 725b as templates. The extension products produced by the reverse transcriptase can be subject to amplification and sequencing.

Sequencing reads can be subject to demultiplexing of cell labels, molecular labels, gene identities, and sample identities (e.g., in terms of sample indexing sequences of sample indexing oligonucleotides 725a and 725b). Demultiplexing of cell labels, molecular labels, and gene identities can give rise to a digital representation of gene expression of each single cell in the sample. Demultiplexing of cell labels, molecular labels, and sample identities, using sample indexing sequences of sample indexing oligonucleotides, can be used to determine a sample origin.

In some embodiments, cellular component binding reagents against cellular component binding reagents on the cell surface can be conjugated to a library of unique sample indexing oligonucleotides to allow cells to retain sample identity. For example, antibodies against cell surface markers can be conjugated to a library of unique sample indexing oligonucleotides to allow cells to retain sample identity. This will enable multiple samples to be loaded onto the same Rhapsody™ cartridge as information pertaining sample source is retained throughout library preparation and sequencing. Sample indexing can allow multiple samples to be run together in a single experiment, simplifying and shortening experiment time, and eliminating batch effect.

Disclosed herein include methods for sample identification. In some embodiments, the method comprise: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions. The method can include barcoding (e.g., stochastically barcoding) the sample indexing oligonucleotides using a plurality of barcodes (e.g., stochastic barcodes) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, the method for sample identification comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; and identifying sample origin of at least one cell of the one or more cells based on the sample indexing sequence of at least one sample indexing oligonucleotide of the plurality of sample indexing compositions.

In some embodiments, identifying the sample origin of the at least one cell comprises: barcoding (e.g., stochastically barcoding) sample indexing oligonucleotides of the plurality of sample indexing compositions using a plurality of barcodes (e.g., stochastic barcodes) to create a plurality of barcoded sample indexing oligonucleotides; obtaining sequencing data of the plurality of barcoded sample indexing oligonucleotides; and identifying the sample origin of the cell based on the sample indexing sequence of at least one barcoded sample indexing oligonucleotide of the plurality of barcoded sample indexing oligonucleotides. In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, identifying the sample origin of the at least one cell can comprise identifying the presence or absence of the sample indexing sequence of at least one sample indexing oligonucleotide of the plurality of sample indexing compositions. Identifying the presence or absence of the sample indexing sequence can comprise: replicating the at least one sample indexing oligonucleotide to generate a plurality of replicated sample indexing oligonucleotides; obtaining sequencing data of the plurality of replicated sample indexing oligonucleotides; and identifying the sample origin of the cell based on the sample indexing sequence of a replicated sample indexing oligonucleotide of the plurality of sample indexing oligonucleotides that correspond to the at least one barcoded sample indexing oligonucleotide in the sequencing data.

In some embodiments, replicating the at least one sample indexing oligonucleotide to generate the plurality of replicated sample indexing oligonucleotides comprises: prior to replicating the at least one barcoded sample indexing oligonucleotide, ligating a replicating adaptor to the at least one barcoded sample indexing oligonucleotide. Replicating the at least one barcoded sample indexing oligonucleotide can comprise replicating the at least one barcoded sample indexing oligonucleotide using the replicating adaptor ligated to the at least one barcoded sample indexing oligonucleotide to generate the plurality of replicated sample indexing oligonucleotides.

In some embodiments, replicating the at least one sample indexing oligonucleotide to generate the plurality of replicated sample indexing oligonucleotides comprises: prior to replicating the at least one barcoded sample indexing oligonucleotide, contacting a capture probe with the at least one sample indexing oligonucleotide to generate a capture probe hybridized to the sample indexing oligonucleotide; and extending the capture probe hybridized to the sample indexing oligonucleotide to generate a sample indexing oligonucleotide associated with the capture probe. Replicating the at least one sample indexing oligonucleotide can comprise replicating the sample indexing oligonucleotide associated with the capture probe to generate the plurality of replicated sample indexing oligonucleotides.

Cell Overloading and Multiplet Identification

Also disclosed herein include methods, kits and systems for identifying cell overloading and multiplet. Such methods, kits and systems can be used in, or in combination with, any suitable methods, kits and systems disclosed herein, for example the methods, kits and systems for measuring cellular component expression level (such as protein expression level) using cellular component binding reagents associated with oligonucleotides.

Using current cell-loading technology, when about 20000 cells are loaded into a microwell cartridge or array with ~60000 microwells, the number of microwells or droplets with two or more cells (referred to as doublets or multiplets) can be minimal. However, when the number of cells loaded increases, the number of microwells or droplets with multiple cells can increase significantly. For example, when about 50000 cells are loaded into about 60000 microwells of a microwell cartridge or array, the percentage of microwells with multiple cells can be quite high, such as 11-14%. Such loading of high number of cells into microwells can be referred to as cell overloading. However, if the cells are divided into a number of groups (e.g., 5), and cells in each group are labeled with sample indexing oligonucleotides with distinct sample indexing sequences, a cell label (e.g., a cell label of a barcode, such as a stochastic barcode) associated with two or more sample indexing sequences can be identified in sequencing data and removed from subsequent processing. In some embodiments, the cells are divided into a large number of groups (e.g., 10000), and cells in each group are labeled with sample indexing oligonucleotides with distinct sample indexing sequences, a sample label associated with two or more sample indexing sequences can be identified in sequencing data and removed from subsequent processing. In some embodiments, different cells are labeled with cell identification oligonucleotides with distinct cell identification sequences, a cell identification sequence associated with two or more cell identification oligonucleotides can be identified in sequencing data and removed from subsequent processing. Such higher number of cells can be loaded into microwells relative to the number of microwells in a microwell cartridge or array.

Disclosed herein includes methods for sample identification. In some embodiments, the method comprises: contacting a first plurality of cells and a second plurality of cells with two sample indexing compositions respectively, wherein each of the first plurality of cells and each of the second plurality of cells comprise one or more cellular components, wherein each of the two sample indexing compositions comprises a cellular component binding reagent associated with a sample indexing oligonucleotide, wherein the cellular component binding reagent is capable of specifically binding to at least one of the one or more cellular components, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying one or more cell label sequences that is each associated with two or more sample indexing sequences in the sequencing data obtained; and removing the sequencing data associated with the one or more cell label sequences that is each associated with two or more sample indexing sequences from the sequencing data obtained and/or excluding the sequencing data associated with the one or more cell label sequences that is each associated with two or more sample indexing sequences from subsequent analysis (e.g., single cell mRNA profiling, or whole transcriptome analysis). In some embodiments, the sample indexing oligonucleotide comprises a barcode sequence (e.g., a molecular label sequence), a binding site for a universal primer, or a combination thereof.

For example, the method can be used to load 50000 or more cells (compared to 10000-20000 cells) using sample indexing. Sample indexing can use oligonucleotide-conjugated cellular component binding reagents (e.g., antibodies) or cellular component binding reagents against a cellular component (e.g., a universal protein marker) to label cells from different samples with a unique sample index. When two or more cells from different samples, two or more cells from different populations of cells of a sample, or two or more cells of a sample, are captured in the same microwell or droplet, the combined "cell" (or contents of the two or more cells) can be associated with sample indexing oligonucleotides with different sample indexing sequences (or cell identification oligonucleotides with different cell identification sequences). The number of different populations of cells can be different in different implementations. In some embodiments, the number of different populations can be, or be about, 2, 3, 4, 5, 6, 7, 8, 9, 10, 20, 30, 40, 50, 60, 70, 80, 90, 100, or a number or a range between any two of these values. In some embodiments, the number of different populations can be at least, or be at most, 2, 3, 4, 5, 6, 7, 8, 9, 10, 20, 30, 40, 50, 60, 70, 80, 90, or 100. The number, or the average number, of cells in each population can be different in different implementations. In some embodiments, the number, or the average number, of cells in each population can be, or be about, 1, 2, 3, 4, 5, 6, 7, 8, 9, 10, 20, 30, 40, 50, 60, 70, 80, 90, 100, or a number or a range between any two of these values. In some embodiments, the number, or the average number, of cells in each population can be at least, or be at most, 1, 2, 3, 4, 5, 6, 7, 8, 9, 10, 20, 30, 40, 50, 60, 70, 80, 90, or 100. When the number, or the average number, of cells in each population is sufficiently small (e.g., equal to, or fewer than, 50, 25, 10, 5, 4, 3, 2, or 1 cell per population), the sample indexing composition for cell overloading and multiplet identification can be referred to as cell identification compositions.

Cells of a sample can be divided into multiple populations by aliquoting the cells of the sample into the multiple populations. A "cell" associated with more than one sample indexing sequence in the sequencing data can be identified as a "multiplet" based on two or more sample indexing sequences associated with one cell label sequence (e.g., a cell label sequence of a barcode, such as a stochastic barcode) in the sequencing data. The sequencing data of a combined "cell" is also referred to herein as a multiplet. A multiplet can be a doublet, a triplet, a quartet, a quintet, a sextet, a septet, an octet, a nonet, or any combination thereof. A multiplet can be any n-plet. In some embodiments, n is, or is about, 2, 3, 4, 5, 6, 7, 8, 9, 10, 11, 12, 13, 14, 15, 16, 17, 18, 19, 20, or a range between any two of these values. In some embodiments, n is at least, or is at most, 2, 3, 4, 5, 6, 7, 8, 9, 10, 11, 12, 13, 14, 15, 16, 17, 18, 19, or 20.

When determining expression profiles of single cells, two cells may be identified as one cell and the expression profiles of the two cells may be identified as the expression profile for one cell (referred to as a doublet expression profile). For example, when determining expression profiles of two cells using barcoding (e.g., stochastic barcoding), the mRNA molecules of the two cells may be associated with barcodes having the same cell label. As another example, two cells may be associated with one particle (e.g., a bead). The particle can include barcodes with the same cell label. After lysing the cells, the mRNA molecules in the two cells can be associated with the barcodes of the particle, thus the same cell label. Doublet expression profiles can skew the interpretation of the expression profiles.

A doublet can refer to a combined "cell" associated with two sample indexing oligonucleotides with different sample indexing sequences. A doublet can also refer to a combined "cell" associated with sample indexing oligonucleotides with two sample indexing sequences. A doublet can occur when two cells associated with two sample indexing oligonucleotides of different sequences (or two or more cells associated with sample indexing oligonucleotides with two different sample indexing sequences) are captured in the same microwell or droplet, the combined "cell" can be associated with two sample indexing oligonucleotides with different sample indexing sequences. A triplet can refer to a combined "cell" associated with three sample indexing oligonucleotides all with different sample indexing sequences, or a combined "cell" associated with sample indexing oligonucleotides with three different sample indexing sequences. A quartet can refer to a combined "cell" associated with four sample indexing oligonucleotides all with different sample indexing sequences, or a combined "cell" associated with sample indexing oligonucleotides with four different sample indexing sequences. A quintet can refer to a combined "cell" associated with five sample indexing oligonucleotides all with different sample indexing sequences, or a combined "cell" associated with sample indexing oligonucleotides with five different sample indexing sequences. A sextet can refer to a combined "cell" associated with six sample indexing oligonucleotides all with different sample indexing sequences, or a combined "cell" associated with sample indexing oligonucleotides with six different sample indexing sequences. A septet can refer to a combined "cell" associated with seven sample indexing oligonucleotides all with different sample indexing sequences, or a combined "cell" associated with sample indexing oligonucleotides with seven different sample indexing sequences. A octet can refer to a combined "cell" associated with eight sample indexing oligonucleotides all with different sample indexing sequences, or a combined "cell" associated with sample indexing oligonucleotides with eight different sample indexing sequences. A nonet can refer to a combined "cell" associated with nine sample indexing oligonucleotides all with different sample indexing sequences, or a combined "cell" associated with sample indexing oligonucleotides with nine different sample indexing sequences. A multiplet can occur when two or more cells associated with two or more sample indexing oligonucleotides of different sequences (or two or more cells associated with sample indexing oligonucleotides with two or more different sample indexing sequences) are captured in the same microwell or droplet, the combined "cell" can be associated with sample indexing oligonucleotides with two or more different sample indexing sequences.

As another example, the method can be used for multiplet identification, whether in the context of sample overloading or in the context of loading cells onto microwells of a microwell array or generating droplets containing cells. When two or more cells are loaded into one microwell, the resulting data from the combined "cell" (or contents of the two or more cells) is a multiplet with aberrant gene expression profile. By using sample indexing, one can recognize some of these multiplets by looking for cell labels that are each associated with or assigned to two or more sample indexing oligonucleotides with different sample indexing sequences (or sample indexing oligonucleotides with two or more sample indexing sequences). With sample indexing sequence, the methods disclosed herein can be used for multiplet identification (whether in the context of sample overloading or not, or in the context of loading cells onto microwells of a microwell array or generating droplets containing cells). In some embodiments, the method comprises: contacting a first plurality of cells and a second plurality of cells with two sample indexing compositions respectively, wherein each of the first plurality of cells and each of the second plurality of cells comprise one or more cellular components, wherein each of the two sample indexing compositions comprises a cellular component binding reagent associated with a sample indexing oligonucleotide, wherein the cellular component binding reagent is capable of specifically binding to at least one of the one or more cellular components, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a barcode sequence (e.g., a molecular label sequence), and a target-binding region, wherein barcode sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying one or more multiplet cell label sequences that is each associated with two or more sample indexing sequences in the sequencing data obtained.

The number of cells that can be loaded onto microwells of a microwell cartridge or into droplets generated using a microfluidics device can be limited by the multiplet rate. Loading more cells can result in more multiplets, which can be hard to identify and create noise in the single cell data. With sample indexing, the method can be used to more accurately label or identify multiplets and remove the multiplets from the sequencing data or subsequent analysis. Being able to identify multiplets with higher confidence can increase user tolerance for the multiplet rate and load more cells onto each microwell cartridge or generating droplets with at least one cell each.

In some embodiments, contacting the first plurality of cells and the second plurality of cells with the two sample indexing compositions respectively comprises: contacting the first plurality of cells with a first sample indexing compositions of the two sample indexing compositions; and contacting the first plurality of cells with a second sample indexing compositions of the two sample indexing compositions. The number of pluralities of cells and the number of pluralities of sample indexing compositions can be different in different implementations. In some embodiments, the number of pluralities of cells and/or sample indexing compositions can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of pluralities of cells and/or sample indexing compositions can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000. The number of cells can be different in different implementations. In some embodiments, the number, or the average number, of cells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number, or the average number, or cells can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the method comprises: removing unbound sample indexing compositions of the two sample indexing compositions. Removing the unbound sample indexing compositions can comprise washing cells of the first plurality of cells and the second plurality of cells with a washing buffer. Removing the unbound sample indexing compositions can comprise selecting cells bound to at least one cellular component binding reagent of the two sample indexing compositions using flow cytometry. In some embodiments, the method comprises: lysing the one or more cells from each of the plurality of samples.

In some embodiments, the sample indexing oligonucleotide is configured to be detachable or non-detachable from the cellular component binding reagent. The method can comprise detaching the sample indexing oligonucleotide from the cellular component binding reagent. Detaching the sample indexing oligonucleotide can comprise detaching the sample indexing oligonucleotide from the cellular component binding reagent by UV photocleaving, chemical treatment (e.g., using reducing reagent, such as dithiothreitol), heating, enzyme treatment, or any combination thereof.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises: amplifying the plurality of barcoded sample indexing oligonucleotides to produce a plurality of amplicons. Amplifying the plurality of barcoded sample indexing oligonucleotides can comprise amplifying, using polymerase chain reaction (PCR), at least a portion of barcode sequence (e.g., the molecular label sequence) and at least a portion of the sample indexing oligonucleotide. In some embodiments, obtaining the sequencing data of the plurality of barcoded sample indexing oligonucleotides can comprise obtaining sequencing data of the plurality of amplicons. Obtaining the sequencing data comprises sequencing at least a portion of the barcode sequence and at least a portion of the sample indexing oligonucleotide. In some embodiments, identifying the sample origin of the at least one cell comprises identifying sample origin of the plurality of barcoded targets based on the sample indexing sequence of the at least one barcoded sample indexing oligonucleotide.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, the method includes: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can include: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, the method for cell identification comprise: contacting a first plurality of one or more cells and a second plurality of one or more cells with two cell identification compositions respectively, wherein each of the first plurality of one or more cells and each of the second plurality of one or more cells comprise one or more cellular components, wherein each of the two cell identification compositions comprises a cellular component binding reagent associated with a cell identification oligonucleotide, wherein the cellular component binding reagent is capable of specifically binding to at least one of the one or more cellular components, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more cell label sequences that is each associated with two or more cell identification sequences in the sequencing data obtained; and removing the sequencing data associated with the one or more cell label sequences that is each associated with two or more cell identification sequences from the sequencing data obtained and/or excluding the sequencing data associated with the one or more cell label sequences that is each associated with two or more cell identification sequences from subsequent analysis (e.g., single cell mRNA profiling, or whole transcriptome analysis). In some embodiments, the cell identification oligonucleotide comprises a barcode sequence (e.g., a molecular label sequence), a binding site for a universal primer, or a combination thereof.

A multiplet (e.g., a doublet, triplet, etc.) can occur when two or more cells associated with two or more cell identification oligonucleotides of different sequences (or two or more cells associated with cell identification oligonucleotides with two or more different cell identification sequences) are captured in the same microwell or droplet, the combined "cell" can be associated with cell identification oligonucleotides with two or more different cell identification sequences.

Cell identification compositions can be used for multiplet identification, whether in the context of cell overloading or in the context of loading cells onto microwells of a microwell array or generating droplets containing cells. When two or more cells are loaded into one microwell, the resulting data from the combined "cell" (or contents of the two or more cells) is a multiplet with aberrant gene expression profile. By using cell identification, one can recognize some of these multiplets by looking for cell labels (e.g., cell labels of barcodes, such as stochastic barcodes) that are each associated with or assigned to two or more cell identification oligonucleotides with different cell identification sequences (or cell identification oligonucleotides with two or more cell identification sequences). With cell identification sequence, the methods disclosed herein can be used for multiplet identification (whether in the context of sample overloading or not, or in the context of loading cells onto microwells of a microwell array or generating droplets containing cells). In some embodiments, the method comprises: contacting a first plurality of one or more cells and a second plurality of one or more cells with two cell identification compositions respectively, wherein each of the first plurality of one or more cells and each of the second plurality of one or more cells comprise one or more cellular components, wherein each of the two cell identification compositions comprises a cellular component binding reagent associated with a cell identification oligonucleotide, wherein the cellular component binding reagent is capable of specifically binding to at least one of the one or more cellular components, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more multiplet cell label sequences that is each associated with two or more cell identification sequences in the sequencing data obtained.

The number of cells that can be loaded onto microwells of a microwell cartridge or into droplets generated using a microfluidics device can be limited by the multiplet rate. Loading more cells can result in more multiplets, which can be hard to identify and create noise in the single cell data. With cell identification, the method can be used to more accurately label or identify multiplets and remove the multiplets from the sequencing data or subsequent analysis. Being able to identify multiplets with higher confidence can increase user tolerance for the multiplet rate and load more cells onto each microwell cartridge or generating droplets with at least one cell each.

In some embodiments, contacting the first plurality of one or more cells and the second plurality of one or more cells with the two cell identification compositions respectively comprises: contacting the first plurality of one or more cells with a first cell identification compositions of the two cell identification compositions; and contacting the first plurality of one or more cells with a second cell identification compositions of the two cell identification compositions. The number of pluralities of cell identification compositions can be different in different implementations. In some embodiments, the number of cell identification compositions can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of cell identification compositions can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000. The number, or average number, of cells in each plurality of one or more cells can be different in different implementations. In some embodiments, the number, or average number, of cells in each plurality of one or more cells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number, or average number, of cells in each plurality of one or more cells can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the method comprises: removing unbound cell identification compositions of the two cell identification compositions. Removing the unbound cell identification compositions can comprise washing cells of the first plurality of one or more cells and the second plurality of one or more cells with a washing buffer. Removing the unbound cell identification compositions can comprise selecting cells bound to at least one cellular component binding reagent of the two cell identification compositions using flow cytometry. In some embodiments, the method comprises: lysing the one or more cells from each of the plurality of samples.

In some embodiments, the cell identification oligonucleotide is configured to be detachable or non-detachable from the cellular component binding reagent. The method can comprise detaching the cell identification oligonucleotide from the cellular component binding reagent. Detaching the cell identification oligonucleotide can comprise detaching the cell identification oligonucleotide from the cellular component binding reagent by UV photocleaving, chemical treatment (e.g., using reducing reagent, such as dithiothreitol), heating, enzyme treatment, or any combination thereof.

In some embodiments, barcoding the cell identification oligonucleotides using the plurality of barcodes comprises: contacting the plurality of barcodes with the cell identification oligonucleotides to generate barcodes hybridized to the cell identification oligonucleotides; and extending the barcodes hybridized to the cell identification oligonucleotides to generate the plurality of barcoded cell identification oligonucleotides. Extending the barcodes can comprise extending the barcodes using a DNA polymerase to generate the plurality of barcoded cell identification oligonucleotides. Extending the barcodes can comprise extending the barcodes using a reverse transcriptase to generate the plurality of barcoded cell identification oligonucleotides.

In some embodiments, the method comprises: amplifying the plurality of barcoded cell identification oligonucleotides to produce a plurality of amplicons. Amplifying the plurality of barcoded cell identification oligonucleotides can comprise amplifying, using polymerase chain reaction (PCR), at least a portion of barcode sequence (e.g., the molecular label sequence) and at least a portion of the cell identification oligonucleotide. In some embodiments, obtaining the sequencing data of the plurality of barcoded cell identification oligonucleotides can comprise obtaining sequencing data of the plurality of amplicons. Obtaining the sequencing data comprises sequencing at least a portion of the barcode sequence and at least a portion of the cell identification oligonucleotide. In some embodiments, identifying the sample origin of the at least one cell comprises identifying sample origin of the plurality of barcoded targets based on the cell identification sequence of the at least one barcoded cell identification oligonucleotide.

In some embodiments, barcoding the cell identification oligonucleotides using the plurality of barcodes to create the plurality of barcoded cell identification oligonucleotides comprises stochastically barcoding the cell identification oligonucleotides using a plurality of stochastic barcodes to create a plurality of stochastically barcoded cell identification oligonucleotides.

Whole Transcriptome Analysis (WTA) with Random Priming and Extension

Disclosed herein include methods for generating a whole transcriptome analysis (WTA) library from cDNA product (e.g., cDNA product of the BD Rhapsody Single Cell Analysis System) for sequencing on compatible sequencers (e.g., Illumina® sequencers). Currently, the standard BD Rhapsody RNA workflow first captures the RNA transcriptome via 3' capture and cDNA synthesis on the BD Rhapsody Cell Capture Beads (hereafter referred to as 'Beads'), followed by 2 multiplexed, nested PCR amplification to enrich for RNA targets of interest (targeted assay). In some embodiments of the method, targeted RNA analysis generally yields higher sensitivity for low expressing targets, while WTA RNA analysis provides a larger breadth of interrogated genes. Successful amplification of desired targets in some embodiments, may need a thorough understanding of each RNA's 3' end and its use of polyadenylation sites in model system of interest. The WTA method, for example using with BD Rhapsody, allows obtaining of several levels of information, including 1) identify interesting RNA targets in their model system to identify a panel of genes to design; 2) characterize the 3' ends of the transcriptome in their model system as an input to a new generation of PCR panel design for BD Rhapsody, and 3) allows users to do discovery biology by assaying a wider breath of genes compared to the standard BD Rhapsody targeted approach.

Figure 8:
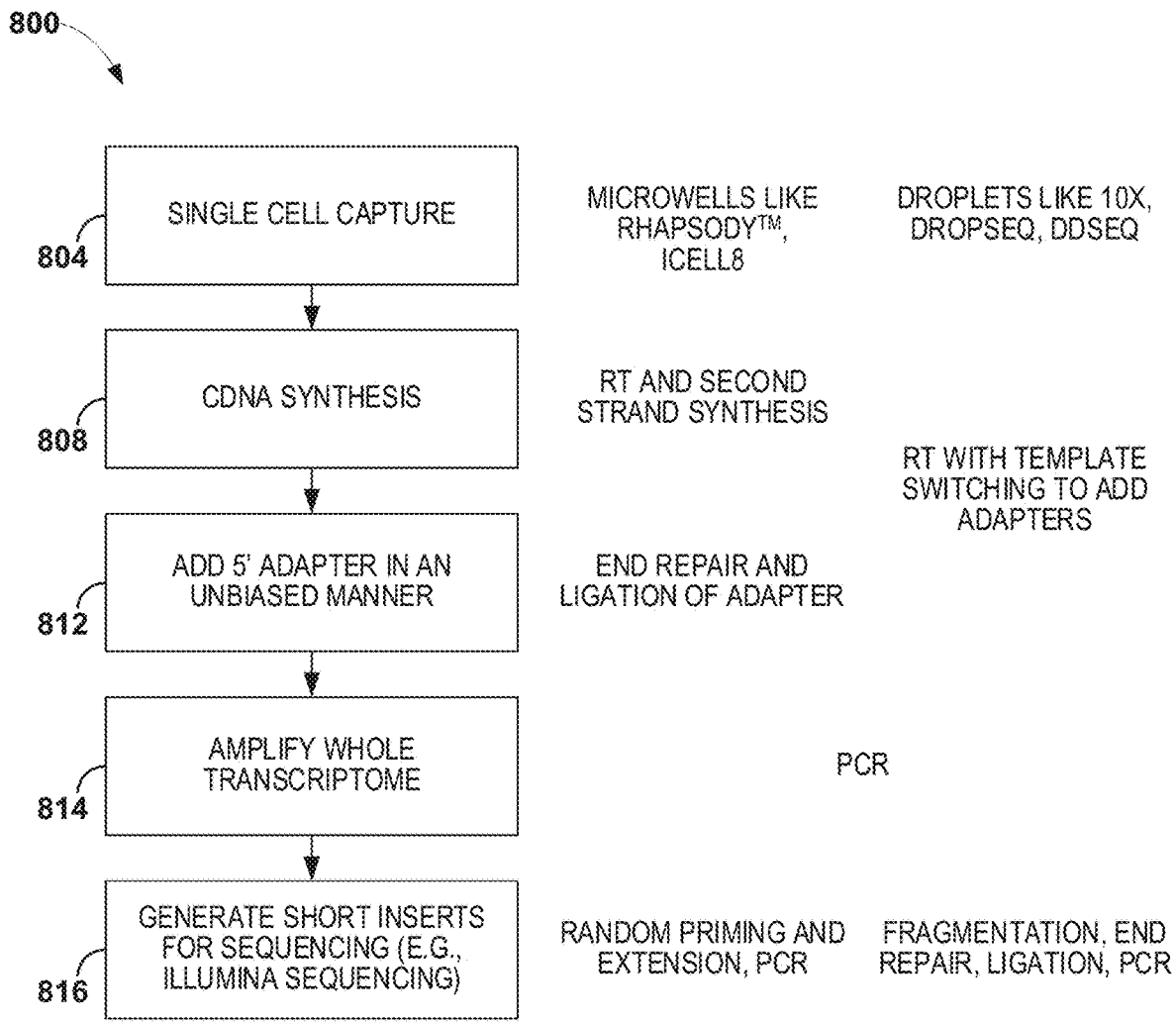
FIG. 8 is a schematic illustration of a non-limiting exemplary workflow of performing whole transcriptome analysis (WTA) of single cells.

FIG. 8 is a schematic illustration of a non-limiting exemplary workflow 800 of performing whole transcriptome analysis (WTA) of single cells. For single cell capture at block 804, microwells (such as Rhapsody or ICELL8) or droplets (such as dropseq, ddseq) can be employed. cDNA synthesis at block 808 can comprise reverse transcription and second strand synthesis followed by adding a 5' adapter in an unbiased manner at block 812 by end repair and ligation of the adapter. In some embodiments, block 808 and block 812 can comprise reverse transcription with the use of template switching to add adapters. Amplification of the whole transcriptome at block 814 can comprise polymerase chain reaction (PCR). The generation of short inserts for sequencing (e.g., Illumina sequencing) at block 816 can comprise random priming and extension followed by PCR. Block 816, in some embodiments, can comprise fragmentation, end repair, and ligation, followed by PCR.

Figure 9:
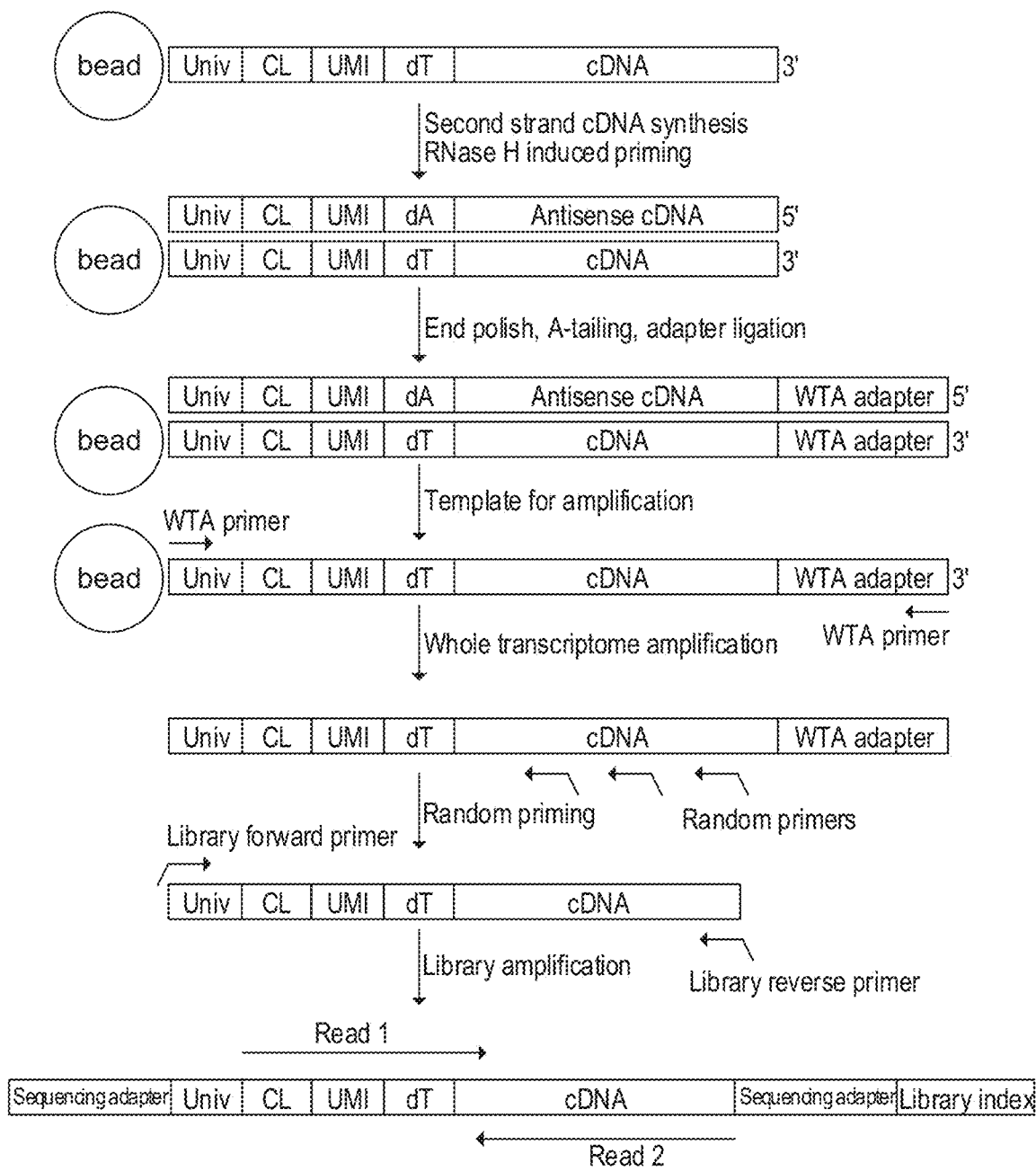
FIG. 9 is a schematic illustration of a non-limiting exemplary workflow of performing ligation-based whole transcriptome analysis of single cells.

FIG. 9 is a schematic illustration of a non-limiting exemplary workflow of performing ligation-based whole transcriptome analysis of single cells. The method can include performing reverse transcription using barcodes (e.g., barcodes each with a universal sequence (Univ), a unique molecular index (UMI), a cell label (CL), and an oligo(dT) sequence) second strand synthesis, end preparation, full-length cDNA amplification, random priming, and then sequencing library amplification.

As described herein, the main challenge for WTA methods disclosed in the past has been to effect WTA PCR amplification containing Beads, as the PCR yields have been low. The new RPE-based WTA approach disclosed herein can, for example in some embodiments, circumvent the need to do WTA PCR on Beads with a replacement random priming and DNA polymerase extension.

Figure 10:
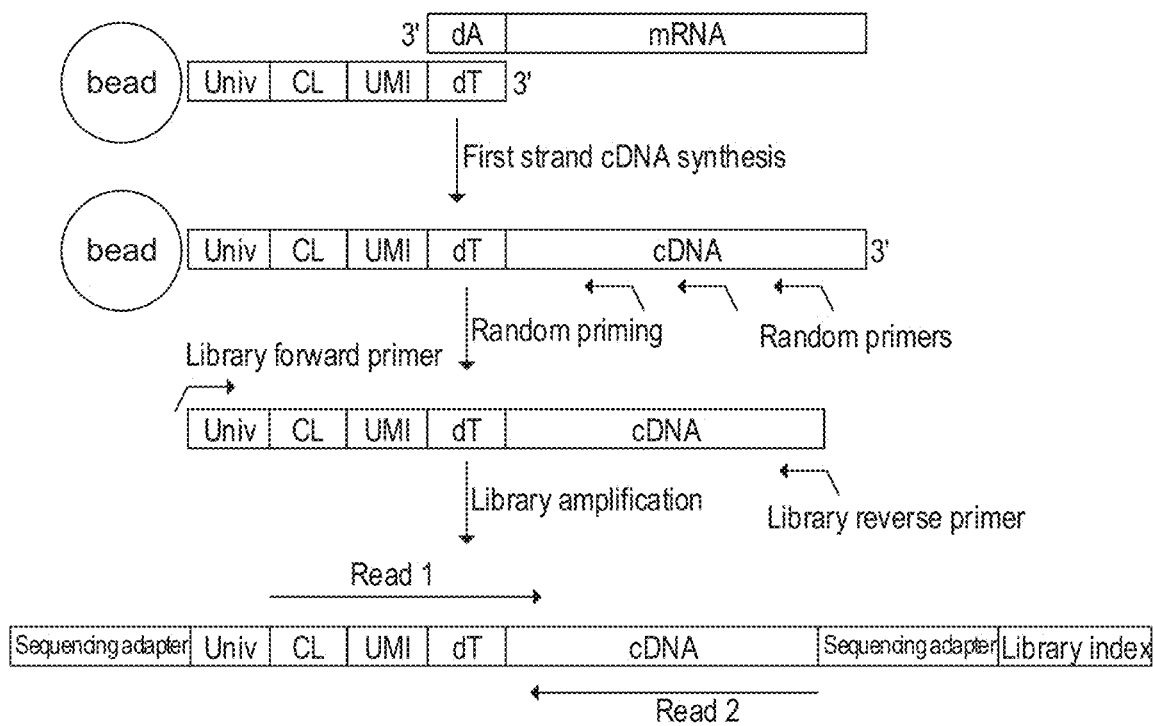
FIG. 10 is a schematic illustration of a non-limiting exemplary workflow of performing whole transcriptome analysis of single cells efficiently (e.g., in a shorter time compared to other whole transcriptome analysis methods) using random priming and primer extension.
Figure 11A:
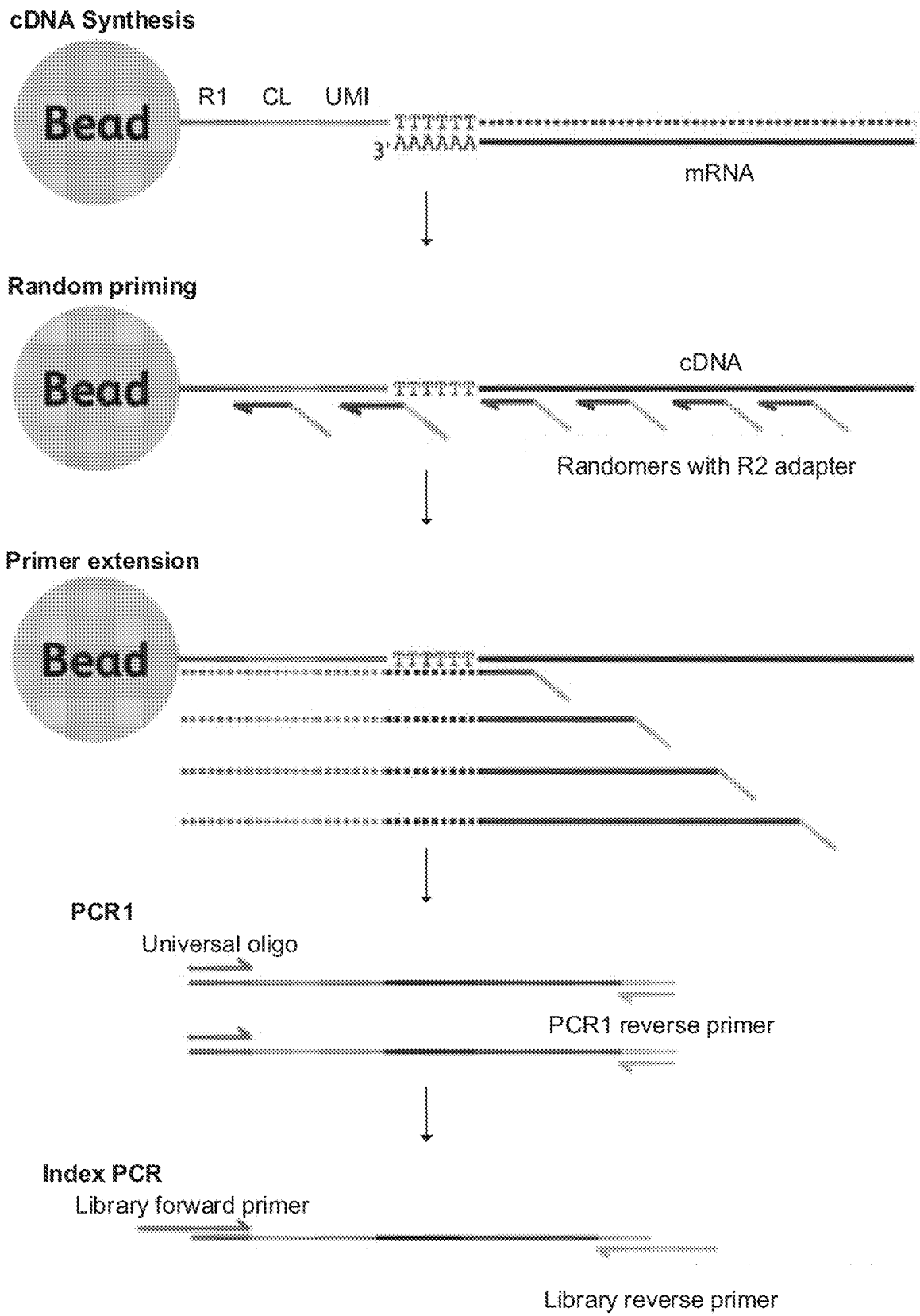
FIG. 11A is a schematic illustration of a non-limiting exemplary workflow of performing whole transcriptome analysis using random priming and primer extension.

FIG. 10 and FIG. 11A are schematic illustrations of non-limiting exemplary workflows of performing whole transcriptome analysis of single cells efficiently (e.g., in a shorter time compared to other whole transcriptome analysis methods) using random priming and primer extension (RPE). The method can include performing reverse transcription using barcodes (e.g., barcodes each with a universal sequence ("Univ", e.g., Read 1 (R1)), a unique molecular index (UMI), a cell label (CL), and an oligo(dT) sequence), first strand cDNA synthesis, random priming (e.g., using randomers comprising an Univ (e.g., an Read 2 (R2))), and random primer extension. The random primers can bind to different locations along the coding sequence of all transcripts and extend to generate an extension product (e.g., a linearly amplified product). The extension product can comprise cDNA which is of varying length depending on the binding site of random primer. The extension product can be amplified with sequencing library amplification primers. The workflow can comprise a single PCR amplification (as depicted in FIG. 10) or two or more rounds of PCR amplification (such as PCR1 followed by PCR2 ("index PCR") as shown in FIG. 11A). Sequencing library amplification can comprise using library forward and reverse primers adding sequencing adapters and/or library indices via overhangs. Library amplification can add sequencing adapters (e.g., P5 and P7 sequence) and sample index (e.g., i5, i7) via overhangs in a library forward primer and a library reverse primer. Library amplicons can be sequenced and subjected to downstream methods of the disclosure. Paired-end sequencing using to generate 150 bp×2 sequencing reads can reveal the cell label, unique molecular index, poly(A) tail, and/or gene (or a partial sequence of the gene) on read 1, the gene (or a partial sequence of the gene and/or poly(A) tail on read 2, and the sample index on index 1 read. Methods, compositions, systems, devices, and kits for whole transcriptome amplification using stochastic barcodes have been previously disclosed, for example, in U.S. Pat. Pub. No. 2016/0312276, the content of which is hereby expressly incorporated by reference in its entirety.

Figure 11B:
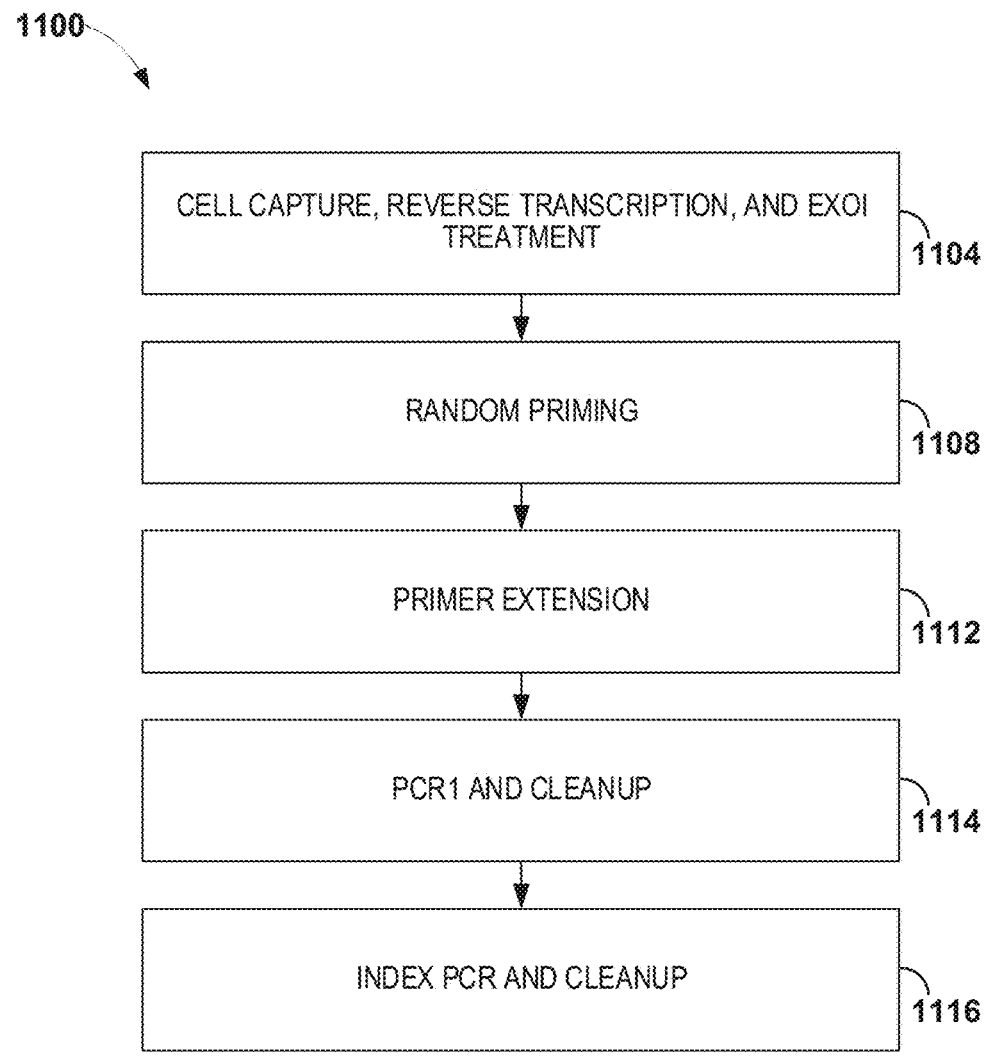
FIG. 11B is a non-limiting exemplary process of performing whole transcriptome analysis using random priming and primer extension.

FIG. 11B is a non-limiting exemplary process of performing whole transcriptome analysis using random priming and primer extension. For cell capture, reverse transcription, and ExoI treatment to remove unused primers at block 1104, parameters of the process include whether beads can be reused or whether beads are compatible with other analysis methods. Such analysis methods include sample indexing, tracking, or multiplexing with antibodies associated (e.g., conjugated with) with oligonucleotides ("AbOs"), single cell protein expression profiling with antibodies associated with oligonucleotides (also referred to herein as "AbSeq"), targeted single cell analysis methods (e.g., BD Rhapsody™ targeted assay), and methods for determining 5' transcript sequences (e.g., methods for determining the sequences of V(D)J regions of cells). Embodiments of using AbOs to determine protein expression profiles in single cells and sample tracking (e.g., tracking sample origins) have been described in U.S. patent application Ser. No. 15/715,028, published as U.S. Patent Application Publication No. 2018/0088112, and U.S. patent application Ser. No. 15/937,713; the content of each is incorporated herein by reference in its entirety. Embodiments of determining 5' transcript sequences have been described in U.S. Patent Application No. 62/739,795; the content of which is incorporated herein by reference in its entirety. For random priming extension at block 1108, parameters of the process include the number of beads per uL, polymerase used, length of reaction, concentration of Bovine serum albumin (BSA), and Ampure cleanup condition. For PCR1 and cleanup at block 1114, the parameters of the process include the polymerase used, cycle numbers for large or small cells, Ampure cleanup condition, and quality control (QC) method. For index PCR and cleanup at block 1116, the parameters of the process include the polymerase used, PCR input amount, Ampure cleanup condition, and quality control method.

Disclosed herein include methods of labeling nucleic acid targets in a sample. In some embodiments, the method comprises: contacting copies of a nucleic acid target with a plurality of oligonucleotide barcodes, wherein each oligonucleotide barcode comprises a first universal sequence, a molecular label, and a target-binding region capable of hybridizing to the copies of the nucleic acid target; extending the plurality of oligonucleotide barcodes hybridized to the copies of the nucleic acid target to generate a plurality of first strand barcoded polynucleotides; contacting random primers with the plurality of first strand barcoded polynucleotides, wherein each of the random primers comprises a second universal sequence, or a complement thereof; and extending the random primers hybridized to the plurality of first strand barcoded polynucleotides to generate a plurality of extension products. The first strand barcoded polynucleotides can comprise barcoded deoxyribonucleic acid (DNA) molecules, barcoded ribonucleic acid (RNA) molecules, or both. The number of cycles of random priming and extension can be different in different implementations. In some embodiments, the number of cycles of random priming and extension can comprise, or comprise about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or a number or a range between any two of these values, cycles of random priming and extension. In some embodiments, the number of cycles of random priming and extension can comprise at least, or at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100, cycles of random priming and extension.

The method can comprise amplifying the plurality of extension products using primers capable of hybridizing to the first universal sequence or complements thereof, and primers capable of hybridizing the second universal sequence or complements thereof, thereby generating a first plurality of barcoded amplicons. The number of cycles of amplification (e.g., linear amplification, PCR amplification) can be different in different implementations. In some embodiments, the amplification can comprise, or comprise about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or a number or a range between any two of these values, cycles of amplification. In some embodiments, the linear amplification can comprise at least, or at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100, cycles of amplification. The first plurality of barcoded amplicons can correspond to at least 10% of the mRNAs of a single cell. The first plurality of barcoded amplicons can correspond to at least 50% of the mRNAs of a single cell. The first plurality of barcoded amplicons can correspond to at least 90% of the mRNAs of a single cell. In some embodiments, the first plurality of barcoded amplicons can correspond to at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, of the mRNAs of a single cell. The first plurality of barcoded amplicons can comprise whole transcriptome amplification (WTA) products. Amplifying the plurality of extension products can comprise adding sequences of binding sites of sequencing primers and/or sequencing adaptors, complementary sequences thereof, and/or portions thereof, to the plurality of extension products. The method can comprise determining the copy number of the nucleic acid target in the sample based on the number of molecular labels with distinct sequences associated with the first plurality of barcoded amplicons, or products thereof. In some embodiments, amplifying the plurality of extension products is not performed in the presence of a solid support. In some embodiments, the method does not comprise RNase H-induced priming, end repair, and/or adapter ligation. In some embodiments, the method does not comprise fragmentation, tagmentation, or both.

Disclosed herein include methods of determining the numbers of a nucleic acid target in a sample. In some embodiments, the method comprises: contacting copies of a nucleic acid target with a plurality of oligonucleotide barcodes, wherein each oligonucleotide barcode comprises a first universal sequence, a molecular label, and a target-binding region capable of hybridizing to the copies of the nucleic acid target; extending the plurality of oligonucleotide barcodes hybridized to the copies of the nucleic acid target to generate a plurality of first strand barcoded polynucleotides; contacting random primers with the plurality of first strand barcoded polynucleotides, wherein each of the random primers comprise a second universal sequence, or a complement thereof; extending the random primers hybridized to the plurality of first strand barcoded polynucleotides to generate a plurality of extension products; amplifying the plurality of extension products using primers capable of hybridizing to the first universal sequence or complements thereof, and primers capable of hybridizing the second universal sequence or complements thereof, thereby generating a first plurality of barcoded amplicons; and determining the copy number of the nucleic acid target in the sample based on the number of molecular labels with distinct sequences associated with the first plurality of barcoded amplicons, or products thereof.

In some embodiments, contacting copies of a nucleic acid target comprises contacting copies of a plurality of nucleic acid targets with a plurality of oligonucleotide barcodes, extending the plurality of oligonucleotide barcodes comprises extending the plurality of oligonucleotide barcodes hybridized to the copies of the plurality nucleic acid targets to generate a plurality of first strand barcoded polynucleotides, and determining the copy number of the nucleic acid target in the sample comprises determining the number of each of the plurality of nucleic acid targets in the sample based on the number of the molecular labels with distinct sequences associated with barcoded amplicons of the first plurality of barcoded amplicons comprising a sequence of the each of the plurality of nucleic acid targets. The sequence of the each of the plurality of nucleic acid targets can comprise a subsequence of the each of the plurality of nucleic acid targets. The sequence of the nucleic acid target in the first plurality of barcoded amplicons can comprise a subsequence of the nucleic acid target.

The method can comprise amplifying the first plurality of barcoded amplicons using primers capable of hybridizing to the first universal sequence or complements thereof, and primers capable of hybridizing the second universal sequence or complements thereof, thereby generating a second plurality of barcoded amplicons. The method can comprise amplifying the plurality of extension products using primers capable of hybridizing to the first universal sequence or complements thereof, and primers capable of hybridizing the second universal sequence or complements thereof, thereby generating a first plurality of barcoded amplicons. The number of cycles of amplification (e.g., linear amplification, PCR amplification) can be different in different implementations. In some embodiments, the amplification can comprise, or comprise about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or a number or a range between any two of these values, cycles of amplification. In some embodiments, the linear amplification can comprise at least, or at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100, cycles of amplification. The second plurality of barcoded amplicons can correspond to at least 10% of the mRNAs of a single cell, at least 50% of the mRNAs of a single cell, or at least 90% of the mRNAs of a single cell. In some embodiments, the second plurality of barcoded amplicons can correspond to at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, of the mRNAs of a single cell. The second plurality of barcoded amplicons can comprise whole transcriptome amplification (WTA) products. Amplifying the first plurality of barcoded amplicons can comprise adding sequences of binding sites of sequencing primers and/or sequencing adaptors, complementary sequences thereof, and/or portions thereof, to the first plurality of barcoded amplicons.

The method can comprise determining the copy number of the nucleic acid target in the sample based on the number of molecular labels with distinct sequences associated with the second plurality of barcoded amplicons, or products thereof. In some embodiments, contacting copies of a nucleic acid target comprises contacting copies of a plurality of nucleic acid targets with a plurality of oligonucleotide barcodes, extending the plurality of oligonucleotide barcodes comprises extending the plurality of oligonucleotide barcodes hybridized to the copies of the plurality nucleic acid targets to generate a plurality of first strand barcoded polynucleotides, and/or wherein determining the copy number of the nucleic acid target in the sample comprises determining the number of each of the plurality of nucleic acid targets in the sample based on the number of the molecular labels with distinct sequences associated with barcoded amplicons of the second plurality of barcoded amplicons comprising a sequence of the each of the plurality of nucleic acid targets. The sequence of the each of the plurality of nucleic acid targets can comprise a subsequence of the each of the plurality of nucleic acid targets. The sequence of the nucleic acid target in the second plurality of barcoded amplicons can comprise a subsequence of the nucleic acid target.

Each one of the first plurality of barcoded amplicons and/or second plurality of barcoded amplicons can comprise at least part of the first universal sequence, the second universal sequence, or both. The first universal sequence and the second universal sequence can be the same or different. The first universal sequence and/or the second universal sequence can comprise the binding sites of sequencing primers and/or sequencing adaptors, complementary sequences thereof, and/or portions thereof. The sequencing adaptors can comprise a P5 sequence, a P7 sequence, complementary sequences thereof, and/or portions thereof. The sequencing primers can comprise a Read 1 sequencing primer, a Read 2 sequencing primer, complementary sequences thereof, and/or portions thereof.

The random primers can comprise a random sequence of nucleotides. The random sequence of nucleotides can be about 4 to about 30 nucleotides in length. In some embodiments, said random sequence of nucleotides is 6 or 9 nucleotides in length. The random sequence of nucleotides can have different lengths in different implementations. In some embodiments, the random sequence of nucleotides within the random primers is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or a number or a range between any two of these values, nucleotides in length. In some embodiments, the random sequence of nucleotides within the random primers is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, nucleotides in length. The random primers can have different concentrations during the random priming step in different implementations. In some embodiments, the random primer is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, or a number or a range between any two of these values, uM in concentration during the random priming.

Extending the plurality of oligonucleotide barcodes hybridized to the copies of the nucleic acid target can comprise extending the plurality of oligonucleotide barcodes hybridized to the copies of the nucleic acid target using a reverse transcriptase (e.g., a viral reverse transcriptase). Extending the plurality of oligonucleotide barcodes hybridized to the copies of the nucleic acid target can comprise extending the plurality of oligonucleotide barcodes hybridized to the copies of the nucleic acid target using a DNA polymerase lacking at least one of 5' to 3' exonuclease activity and 3' to 5' exonuclease activity. Extending the random primers hybridized to the plurality of first strand barcoded polynucleotides can comprise extending the random primers hybridized to the plurality of first strand barcoded polynucleotides using a DNA polymerase lacking at least one of 5' to 3' exonuclease activity and 3' to 5' exonuclease activity (e.g., a Klenow Fragment). In some embodiment, the extension enzyme is Klenow or Klenow exo-.

In some embodiments, the plurality of first strand barcoded polynucleotides can be reused as a template for additional extension and/or amplification reactions (following the random priming and extension). The method can comprise repeating the steps of contacting random primers with the plurality of first strand barcoded polynucleotides, extending the random primers hybridized to the plurality of first strand barcoded polynucleotides, and amplifying the plurality of extension products. The method can comprise synthesizing a third plurality of barcoded amplicons using the plurality of first strand barcoded polynucleotides as templates to generate a third plurality of barcoded amplicons. Synthesizing a third plurality of barcoded amplicons can comprise performing polymerase chain reaction (PCR) amplification of the plurality of first stranded barcoded polynucleotides. Synthesizing a third plurality of barcoded amplicons can comprise PCR amplification using primers capable of hybridizing to the first universal sequence, or a complement thereof, and a target-specific primer. The method can comprise obtaining sequence information of the third plurality of barcoded amplicons, or products thereof. Obtaining the sequence information can comprise attaching sequencing adaptors to the third plurality of barcoded amplicons, or products thereof. The target-specific primer can specifically hybridize to an immune receptor (e.g., a T cell receptor (TCR) and/or a B cell receptor (BCR) receptor).

Figure 12:
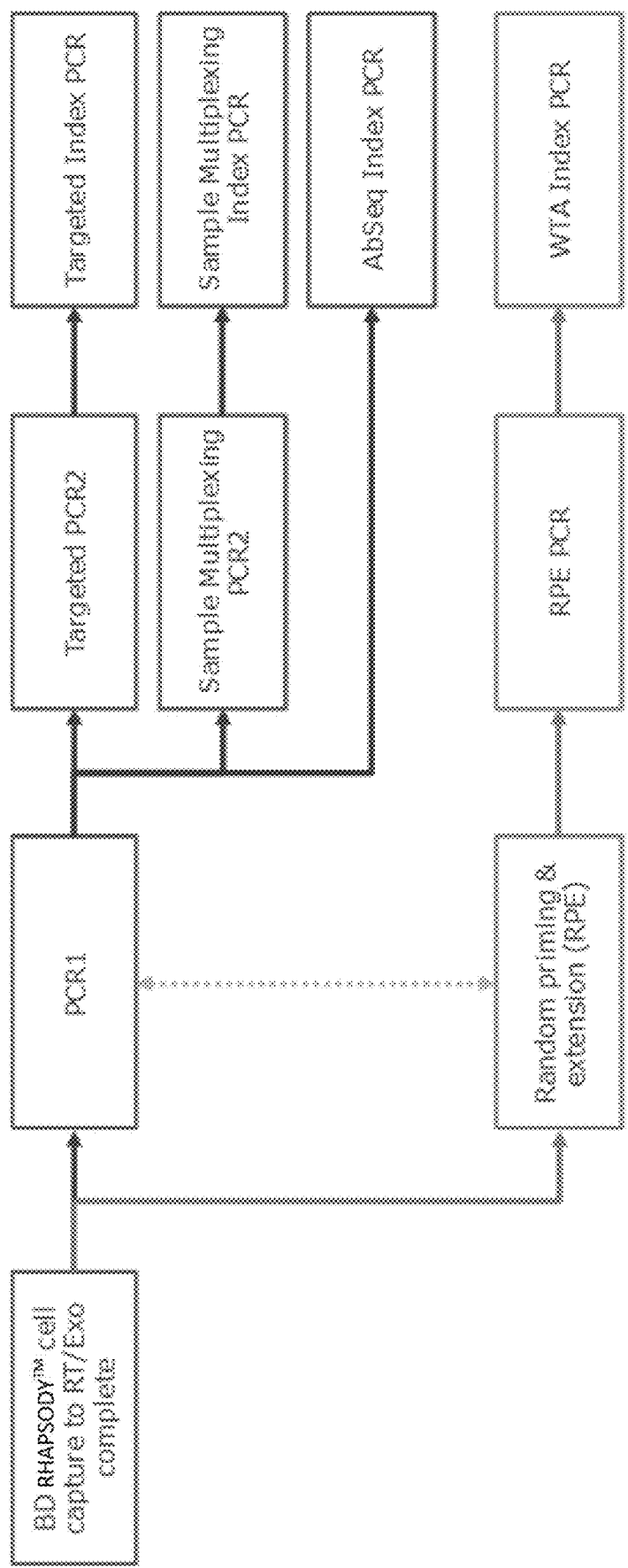
FIG. 12 is a schematic illustration of performing targeted gene expression profiling, sample multiplexing with AbOs, protein expression profiling with AbOs, and whole transcriptome analysis in one workflow.

FIG. 12 is a schematic illustration of performing targeted gene expression profiling, sample multiplexing with AbOs, protein expression profiling with AbOs, and whole transcriptome analysis in one workflow. In some embodiments, the whole transcriptome analysis can be compatible with one or more of targeted gene expression profiling, sample multiplexing with AbOs, and protein expression profiling with AbOs in one workflow and can be performed in one workflow. In some embodiments, a portion of the first strand barcoded polynucleotides (e.g., beads following cell capture and barcoding) are subsampled for RPE WTA and the remaining first strand barcoded polynucleotides are employed for targeted (e.g., gene-specific) amplification and analysis (e.g., targeted PCR2 and targeted index PCR). In some embodiments, following RPE WTA, the first strand barcoded polynucleotides can be reused for targeted (e.g., gene-specific) amplification and analysis using a multiplexed panel of primers as disclosed herein. In some embodiments, sequencing information derived from the RPE-based WTA methods provided herein are used to generate a panel of primers for targeted (e.g., gene-specific) amplification and analysis as disclosed herein.

The sample can comprise a plurality of cells, a plurality of single cells, a tissue, a tumor sample, or any combination thereof. The sample can comprise peripheral blood mononuclear cells or immune cells. The immune cells can comprise B cells, T cells or a combination thereof. The nucleic acid target can comprise a nucleic acid molecule. The nucleic acid molecule can comprise ribonucleic acid (RNA), messenger RNA (mRNA), microRNA, small interfering RNA (siRNA), RNA degradation product, RNA comprising a poly(A) tail, or any combination thereof. The mRNA encodes an immune receptor. One or more of the plurality of nucleic acid targets can comprise mRNAs of a low-expressing gene. The nucleic acid target can comprise a cellular component binding reagent. The nucleic acid molecule can be associated with the cellular component binding reagent. The method can comprise dissociating the nucleic acid molecule and the cellular component binding reagent. The target-binding region can comprise an oligo dT sequence, a random sequence, a target-specific sequence, or a combination thereof. The target-binding region can comprise a poly(dT) region and the nucleic acid target can comprise a poly(dA) region.

The method can comprise cleanup of the plurality of extension products, first plurality of barcoded amplicons, and/or second plurality of barcoded amplicons (e.g., ampure cleanup). The SPRI cleanup ratio can be different in different implementations. In some embodiments, the SPRI cleanup ratio is about 0.1× to about 3.0× (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.5, 2.7, 3.0, and ranges in between). The cleanup can be single-sided or double-sided.

At least 10 of the plurality of oligonucleotide barcodes can comprise different molecular label sequences. Each molecular label of the plurality of oligonucleotide barcodes can comprise at least 6 nucleotides. The plurality of oligonucleotide barcodes can be associated with a solid support. The plurality of oligonucleotide barcodes associated with the same solid support can each comprise an identical sample label. Each sample label of the plurality of oligonucleotide barcodes can comprise at least 6 nucleotides. The plurality of oligonucleotide barcodes can each comprise a cell label. Each cell label of the plurality of oligonucleotide barcodes can comprise at least 6 nucleotides. Oligonucleotide barcodes associated with the same solid support can comprise the same cell label. Oligonucleotide barcodes associated with different solid supports can comprise different cell labels. The solid support can comprise a synthetic particle, a planar surface, or a combination thereof. The solid support (e.g. bead) can have different densities in different implementations of the reactions provided herein. In some embodiments, the density of the solid support during the random priming and extension reaction is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, solid support/ul. In some embodiments, all of the solid supports are employed in the random priming and extension reaction. In some embodiments, only a portion of the solid supports are employed in the random priming and extension reaction (e.g., sub-sampling). In some such embodiments, sub-sampling comprises the addition of solid supports not comprising first strand barcoded polynucleotides (e.g., "cold" beads) to the sub-sampled solid supports.

The sample can comprise a single cell, the method comprising associating a synthetic particle comprising the plurality of the oligonucleotide barcodes with the single cell in the sample. The method can comprise lysing the single cell after associating the synthetic particle with the single cell. Lysing the single cell can comprise heating the sample, contacting the sample with a detergent, changing the pH of the sample, or any combination thereof. The synthetic particle and the single cell can be in the same partition (e.g., a well or a droplet). At least one of the plurality of oligonucleotide barcodes can be immobilized or partially immobilized on the synthetic particle. At least one of the plurality of oligonucleotide barcodes can be enclosed or partially enclosed in the synthetic particle. The synthetic particle can be disruptable (e.g., a disruptable hydrogel particle). The synthetic particle can comprise a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a hydrogel bead, a gel bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. Each of the plurality of oligonucleotide barcodes can comprise a linker functional group, the synthetic particle can comprise a solid support functional group, and/or the support functional group and the linker functional group are associated with each other. The linker functional group and the support functional group can be individually selected from the group consisting of C6, biotin, streptavidin, primary amine(s), aldehyde(s), ketone(s), and any combination thereof.

RPE-Based WTA Performance

The RPE-based WTA methods disclosed herein can yield increased sensitivity of low abundance transcripts, detection of new transcripts, detection of new cell types, and/or reduced sequencing costs. Some embodiments of the RPE-based WTA methods provided herein yield increased sensitivity of low abundance transcripts, detection of new transcripts, detection of new cell types, and/or reduced sequencing costs as compared to alternative non-RPE-based WTA methods (e.g., ligation-based or fragmentation-based WTA methods). As used herein, a "target" can be used interchangeably with a "species."

As used herein, a "species" refers to the polynucleotides (for example, single-stranded polynucleotides, such as cDNA molecules, sample indexing oligonucleotides for sample tracking, and protein-specific oligonucleotides for determining protein expression profiles) that are the same, the complement, or the reverse complement of one another, or are capable of hybridize to one another, or are transcripts from the same genetic locus, or encode the same protein or fragment thereof, etc. As used herein, "target" can be used interchangeably with "species." In some embodiments, members (e.g., copies or occurrences) of a species are at least 80%, at least 90%, at least 95%, at least 98%, at least 99%, or 100% homologous to one another, or complement thereof. In some embodiments, members of a species are transcripts from the same genetic locus and the transcripts can be of the same or different lengths. The species is, in some embodiments, cDNA or mRNA.

As used herein, a "high abundance species" refers to a species that is present in high amount, for example the species can be, be about, be at least, or be at least about 1%, 2%, 3%, 4%, 5%, 6%, 7%, 8%, 9%, 10%, 20%, 30%, 40%, 50%, or more. In some embodiments, a sample can comprise at least 1, at least 2, at least 3, at least 4, at least 5, at least 10, at least 20, at least 50, at least 100, at least 200, at least 500, at least 1,000, or more, high abundance species. In some embodiments, the total of all the high abundance species represents at least 10%, at least 20%, at least 30%, at least 40%, at least 50%, at least 60%, at least 70%, at least 80%, or more of the nucleic acid molecules or species in the sample. In some embodiments, high abundance species can comprise polynucleotides encoding one or more ribosomal proteins. In some embodiments, high abundance species can comprise polynucleotides encoding one or more mitochondrial proteins. In some embodiments, high abundance species can comprise polynucleotides encoding one or more housekeeping proteins. In some embodiments, the high abundance species can comprise the sequence of a sample indexing oligonucleotide (also referred to herein as sample tag sequences or sample indexing indices). In some embodiments, the high abundance species can comprise the sequence of an oligonucleotide used for sample tracking. In some embodiments, the high abundance species can comprise a sample indexing sequence for identifying sample origin of one or more cells of a sample. In some embodiments, the high abundance species can comprise a unique identifier sequence for a cellular component binding reagent (e.g., an antibody). In some embodiments, the high abundance species can comprise the sequence of an oligonucleotide conjugated (or previously conjugated) to a cellular component binding reagent. In some embodiments, the high abundance species can comprise the sequence of an oligonucleotide conjugated or previously conjugated with an antibody can be referred to herein as an antibody oligonucleotide (abbreviated as an "AbOligo" or "AbO").

As used herein, an "intermediate abundance species" refers to a species that is present in an amount that is lower than at least one species and is higher than at least one other species. In some embodiments, an intermediate abundance species can be, be at least, be about, or be at least about 10%, 5%, 4%, 3%, 2%, 1%, 0.1%, 0.01%, or a range between any two of the above values, of the nucleic acid molecules or species in the sample. In some embodiments, the sample can comprise at least 1, at least 2, at least 3, at least 4, at least 5, at least 10, at least 20, at least 50, at least 100, at least 200, at least 500, at least 1,000, or more, intermediate abundance species. In some embodiments, the total of all the intermediate abundance species represents about 1%, about 2%, about 3%, about 4%, about 5%, about 10%, about 20%, about 30%, or a range between any two of the above values, of the nucleic acid molecules in the sample. In some embodiments, intermediate abundance species can comprise polynucleotides encoding one or more housekeeping proteins. In some embodiments, the intermediate abundance species can comprise the sequence of an oligonucleotide used for sample tracking. In some embodiments, the intermediate abundance species can comprise a sample indexing sequence for identifying sample origin of one or more cells of a sample. In some embodiments, the intermediate abundance species can comprise a unique identifier sequence for a cellular component binding reagent (e.g., an antibody). In some embodiments, the intermediate abundance species can comprise the sequence of an oligonucleotide conjugated (or previously conjugated) to a cellular component binding reagent. In some embodiments, the intermediate abundance species can comprise the sequence of an oligonucleotide conjugated or previously conjugated with an antibody can be referred to herein as an antibody oligonucleotide (abbreviated as an "AbOligo" or "AbO").

As used herein, a "low abundance species" refers to a species that is present in low amount, for example the species can be, be about, be less than, or be less than about, 1%, 0.1%, 0.01%, 0.001%, 0.0001%, or less of the nucleic acid molecules or species in the sample. In some embodiments, the sample can comprise at least 1, at least 2, at least 3, at least 4, at least 5, at least 10, at least 20, at least 50, at least 100, at least 200, at least 500, at least 1,000, or more, low abundance species. In some embodiments, the total of all the low abundance species represents less than 20%, less than 10%, less than 5%, less than 4%, less than 3%, less than 2%, less than 1%, less than 0.1%, or less of the nucleic acid molecules in the sample. In some embodiments, low abundance species can comprise polynucleotides encoding one or more transcription factors. In some embodiments, low abundance species can comprise polynucleotides encoding one or more T cell receptors. In some embodiments, low abundance species can comprise polynucleotides encoding one or more antibodies.

In some embodiments, two or more of the plurality of nucleic acid targets comprises low abundance species. In some embodiments, two or more of the plurality of nucleic acid targets comprises low abundance and/or intermediate abundance species. In some embodiments, two or more of the plurality of nucleic acid targets comprises mRNAs of a low-expressing gene. In some embodiments, the percentage of nucleic acid targets that represent low abundance species can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of nucleic acid targets that represent low abundance species can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, a RPE WTA library comprises the products of RPE WTA library preparation as disclosed herein. In some embodiments, an RPE WTA library comprises the products of one or more downstream methods of the disclosure employing the products of RPE WTA library preparation as templates. In some embodiments, sequencing of an RPE WTA library generated by the RPE WTA methods of the disclosure yields an increase in the number of reads of one or more low abundance species (e.g., a nucleic acid target, a low-expressed mRNA) as compared to the sequencing of a library generated by alternative non-RPE-based WTA methods (e.g., ligation-based or fragmentation-based WTA methods). In some embodiments, the increase in the number of reads of one or more low abundance species in the RPE WTA library is at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to the non-RPE-based WTA library. In some embodiments, sequencing of a RPE WTA library generated by the methods of the disclosure yields an increase in the number of reads of one or more low abundance species (e.g., a nucleic acid target, a low-expressed mRNA) relative to the total number of reads as compared to the sequencing of an non-RPE WTA library. In some embodiments, the increase in the number of reads of one or more low abundance species relative to the total number of reads in the RPE WTA library is at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to the non-RPE WTA library. In some embodiments, sequencing of a RPE WTA library generated by the methods of the disclosure yields an increase in the number of molecular indexes (MIs) of one or more low abundance species (e.g., a nucleic acid target, a low-expressed mRNA) compared to the sequencing of an non-RPE WTA library. In some embodiments, the increase in the number of MIs of one or more low abundance species relative to the total number of reads in the RPE WTA library is at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to the non-RPE WTA library.

In some embodiments, the methods disclosed herein can increase the relative abundance of one or more low abundance species after RPE WTA library preparation (compared to non-RPE WTA library preparation, e.g., ligation-based or fragmentation-based WTA methods). For example, the methods disclosed herein can increase the relative abundance of at least 1, at least 2, at least 3, at least 4, at least 5, at least 10, at least 20, at least 50, at least 100, at least 200, at least 500, at least 1,000, or more, low abundance species after RPE WTA library preparation (compared to non-RPE WTA library preparation). In some embodiments, the methods disclosed herein can increase the relative abundance after RPE WTA library preparation (compared to non-RPE WTA library preparation) by at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 150%, 200%, 250%, 500%, 1000%, or higher and overlapping ranges therein) of each of the one or more low abundance species. In some embodiments, the methods disclosed herein can increase the relative abundance by at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 150%, 200%, 250%, 500%, 1000%, or higher and overlapping ranges therein) of at least one of the one or more low abundance species after RPE WTA library preparation (compared to non-RPE WTA library preparation). In some embodiments, the methods disclosed herein can increase the relative abundance of the total low abundance species after RPE WTA library preparation (compared to non-RPE WTA library preparation) by at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 150%, 200%, 250%, 500%, 1000%, or higher and overlapping ranges therein).

In some embodiments, the methods disclosed herein can selectively increase the relative abundance of one or more low abundance species after RPE WTA library (compared to non-RPE WTA library preparation) such that the abundance of the low abundance species relative to the one or more high abundance species increases after RPE WTA library preparation. In some embodiments, the methods and compositions disclosed herein can increase the relative abundance by, by about, by at least, or at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 150%, 200%, 250%, 500%, 1000%, or higher and overlapping ranges therein) of each of the one or more low abundance species after RPE WTA library preparation (compared to non-RPE WTA library) such that the abundance of the low abundance species relative to the one or more high abundance species increases after RPE WTA library preparation.

In some embodiments, sequencing of a RPE WTA library generated by the methods of the disclosure yields a similar gene expression profile and/or protein expression profile (e.g., gene expression panel results) of one or more targets as compared to the sequencing of a non-RPE WTA library. In some embodiments, the difference in the gene expression profile and/or protein expression profile of one or more targets between the RPE WTA and non-RPE WTA library can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, or a number or a range between any of these values. In some embodiments, the $R^2$ correlation between expression profile of the RPE WTA and non-RPE WTA libraries can be 0.6, 0.7, 0.8, 0.9, 0.990, 0.999, 1.0, and overlapping ranges therein. Methods of testing correlation between expression profiles of libraries results are well understood in the art (e.g., overlay of tSNE plots).

It would be appreciated the RPE WTA libraries can increase the efficiency of sequencing, by increasing the sequencing reads for intermediate or low abundance species in the RPE WTA library, and/or decreasing the sequencing reads for high abundance species in the non-RPE WTA library. In the RPE WTA library generated by methods of the disclosure, less abundant (e.g., rarer) nucleic acid targets can be identified more easily than in a non-RPE WTA library. Sequencing reads of less abundant targets in a RPE WTA library can comprise a larger portion of total reads of than in a non-RPE WTA library. Sequencing reads of one or more less abundant targets in a RPE WTA library can comprise at least 50, 100, 150, 200, 250, 300, 350, 400, 450 or 500% or more reads compared to reads of the same target in an non-RPE WTA library. Sequencing reads of one or more less abundant targets in a normalized library can be at least 1, 2, 3, 4, 5, or 6, or more fold than sequencing reads for the same target in a non-RPE WTA library.

The methods described herein for producing RPE WTA libraries can improve the sequencing reads for intermediate and/or low abundance nucleic acid targets in a plurality of nucleic acids (e.g., a nucleic acid library). For example, the sequencing reads for the plurality of intermediate abundance nucleic acid targets can be at least 30%, at least 20%, at least 10%, at least 5%, of the total sequencing reads of the RPE WTA library. In some embodiments, the sequencing reads for the plurality of low abundance nucleic acid targets can be at least 50%, at least 40%, at least 30%, at least 20%, at least 10%, at least 5%, at least 4%, at least 3%, at least 2%, at least 1%, of the total sequencing reads of the RPE WTA library. In some embodiments, the sequencing reads for the plurality of low abundance nucleic acid targets is at least 5% of the total sequencing reads of the RPE WTA library. In some embodiments, the sequencing reads for the plurality of low abundance nucleic acid targets is at least 10% of the total sequencing reads of the RPE WTA library. In some embodiments, the sequencing reads for the plurality of low abundance nucleic acid targets is at least 20% of the total sequencing reads of the RPE WTA library. In some embodiments, the sequencing reads for the plurality of low abundance nucleic acid targets is at least 30% of the total sequencing reads of the RPE WTA library. In some embodiments, the sequencing reads for the plurality of low abundance nucleic acid targets is at least 40% of the total sequencing reads of the RPE WTA library. In some embodiments, the sequencing reads for the plurality of low abundance nucleic acid targets is at least 50% of the total sequencing reads of the RPE WTA library.

Some embodiments of the RPE-based WTA methods disclosed herein advantageously have a shorter protocol time as compared to alternative non-RPE-based WTA methods (e.g., ligation-based or fragmentation-based WTA methods). In some embodiments, the time from single cell capture to cDNA synthesis and/or the time from library preparation to QC is reduced by at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to non-RPE-based WTA methods (e.g., ligation-based or fragmentation-based WTA methods).

EXAMPLES

Some aspects of the embodiments discussed above are disclosed in further detail in the following examples, which are not in any way intended to limit the scope of the present disclosure.

Random Priming and Extension (RPE) Protocol for Whole Transcriptome Analysis (WTA)

This protocol provided below outlines an illustrative embodiment for generating whole transcriptome libraries from Rhapsody beads using a random priming approach. Procedures similar to the protocol provided below were employed in Example 1.

Reagents

BD Rhapsody Targeted mRNA and AbSeq Amplification Kit (BD Biosciences, 633774); SPRIselect Reagent (Beckman Coulter Life Sciences, B23318); 100% Ethyl alcohol; Nuclease-Free Water; Klenow Fragment (3'→5' exo-) (New England Biolabs, M0212L); 10 mM dNTP (New England Biolabs); and Nonamer 2 (5' TCA GAC GTG TGC TCT TCC GAT CTNNNNNNNNN 3'; SEQ ID NO: 1) prediluted to 100 uM in concentration (mixed bases achieved by hand mixing of 25% per nucleotide content).

Consumables

Pipettes (P10, P20, P200, P1000); Low retention filtered pipette tips; 1.5 mL microcentrifuge tubes (Eppendorf, 022431021); DNA LoBind Tubes, 1.5 mL (Eppendorf, 0030108051); and 0.2 mL PCR strip tubes.

Equipment

Microcentrifuge for 1.5-2.0 mL tubes; Microcentrifuge for 0.2 mL tubes; Vortexer; Pipet-Aid; 6-tube magnetic separation rack for 1.5 mL tubes (New England Biolabs, S1506S); Low-profile magnetic separation stand for 0.2 mL, 8-strip tubes (V&P Scientific, Clontech; VP772F4-1, 635011); Digital timer; Multi-channel pipettes (P20, P200); Heat block; and Thermo mixer.

Procedure

Generating Beads without mRNA ("Cold" Beads)

1. One tube of Rhapsody beads (containing ~600,000 beads—enough cold beads to add to 3 sets of cartridge beads) was incubated with a magnet. All liquid was removed and the pellet was resuspended with 750 µl Sample Buffer.

2. The tube was incubated with a magnet and all liquid was discarded.

3. The beads were incubated with 42 µl 1× Lysis buffer (with 5 mM DTT) for 2 minutes. The lysis buffer with 5 mM DTT was made by combining 10 uL of 1M DTT and 2 mL Lysis Buffer.

4. Each were then diluted with 1 mL 1× lysis buffer (with 5 mM DTT), incubated with a magnet, and all liquid was removed.

5. 1.0 mL Bead Wash Buffer was added. After mixing and incubation with a magnet, all liquid was removed.

6. 1.0 mL Bead Wash Buffer was added.

7. RT buffer reaction mix was prepared as depicted in Table 1.

TABLE 1

RT BUFFER MIX

| Component | Final concentration | 1× | 1.05× | 2.1× |
|---|---|---|---|---|
| 5× RT Buffer (PN 650000067) | 1× | 120.0 | 126 | 252 |
| 100 mM DTT (PN 650000068) | 5 mM | 30.0 | 31.5 | 63 |
| 20 mg/mL BSA (NEB B9000S) | 1.2 mg/mL | 36.0 | 37.8 | 75.6 |
| Nuclease-free water | | 414.0 | 434.7 | 869.4 |
| Total | | 600.0 | 630 | 1260 |

8. The beads were incubated with a magnet and all liquid was removed.

9. 600 µL of RT Buffer Mix was added to the beads and mixed by pipetting.

10. The beads were incubated at 37° C. for 20 minutes with 1200 RPM shaking in ThermoMixer.

11. After placing the tubes on ice briefly, they were incubated with a magnet and all liquid was removed.

12. Exonuclease I mix was prepared as depicted in Table 2.

TABLE 2

EXONUCLEASE I REACTION MIX

| Component | Final concentration | 1× | 1.05× | 2.05× |
|---|---|---|---|---|
| 10× ExoI Buffer (NEB) | 1× | 60.0 | 63 | 123 |
| 20 U/uL Exonuclease I (NEB) | 1 U/µL | 30.0 | 31.5 | 61.5 |
| Nuclease-free Water | | 510.0 | 535.5 | 1045.5 |
| Total | | 600.0 | 630 | 1230 |

13. 600 µl Exo I Mix was added to the beads and mixed by pipetting.

14. The beads were incubated at 37° C. for 30 minutes with 1200 RPM shaking in ThermoMixer.

15. The beads were moved to 80° C. for 20 minutes without shaking and then placed on ice for 1 minute.

16. Beads were incubated with a magnet and all liquid was removed.

17. Each bead pellet was resuspended with 600 μL of Bead Resuspension Buffer. The resulting concentration was roughly 1000 beads/μL. In some instances, a Bead Count program on scanner was used to determine the final bead concentration.

Random Priming and Extension (RPE) on BD Rhapsody Beads with cDNA

1. In the pre-amplification workspace, in a new 1.5 mL LoBind tube, the components listed in Table 3 were pipetted in the order shown.

TABLE 3

RANDOM PRIMER MIX

| Component | Final concentration | 1× (200 uL) | 1.2× | 4.4× |
|---|---|---|---|---|
| Water | | 135 | 162 | 594 |
| 10× NEBuffer 2 | 1× | 20 | 24 | 88 |
| 100 μM Randomer 2 (Nonamer) | 10 μM | 20 | 24 | 88 |
| Total | | 175 | 211.2 | 774.4 |

2. The Random Primer Mix was mixed by gentle pipetting.

3. In some instances, random priming and extension was performed on the entire sample of Exonuclease I-treated BD Rhapsody Cell Capture beads and the procedure was skipped to step 7. In some instances, random priming and extension was performed on a subsample of Exonuclease I-treated BD Rhapsody Cell Capture beads and the user proceeded to step 4.

4. For sub-sampling the Exonuclease I-treated BD Rhapsody Cell Capture beads, based on the expected number of viable cells captured on beads in the final bead resuspension volume, the volume of beads to subsample for targeted sequencing was determined. In some instances, the remaining beads were stored at 4° C. for up to 3 months. The beads were completely resuspended by pipet mixing and then the calculated volume of bead suspension was pipetted into a new 1.5 mL LoBind tube. When using subsampled beads, the total volume was brought up to 100 μL with bead resuspension buffer.

5. The beads from cartridge experiment were combined with "cold" beads such that the final bead volume was 200 uL (total bead number was about 200,000). For example, in instances with 40 uL of beads with 2000 cells, 160 uL of cold beads was added. Alternatively, in some instances, the calculation was performed as follows: number of cold beads to add=200000*(1−(cells to subsample/total cells after bead wash)).

6. The tube with combined beads was placed in a 95° C. heat block for 2 minutes. Then the tube with BD Rhapsody Cell Capture beads was immediately placed on a 1.5 mL magnet and the supernatant was immediately removed and discarded. Drying out the BD Rhapsody Cell Capture beads was avoided.

7. The tube was removed from the magnet, and then a low retention tip was used to pipet 175 μL of Random Primer Mix into the tube. Pipette mixing was performed 10 times to resuspend beads.

8. The tube was placed in a 95° C. heat block for 2 minutes, 37° C. for 5 minutes at 1,200 rpm, 25° C. for 5 minutes at 1,200 rpm, and then the sample was spun down.

9. 25 μL of the Primer Extension Reaction Mix (shown in Table 4) was pipetted into the sample tube containing the beads (for a total volume of 200 μL). Pipette mixing was performed 10 times.

TABLE 4

PRIMER EXTENSION REACTION MIX

| Component | Final concentration | 1× (200 uL) | 1.2× | 4.4× |
|---|---|---|---|---|
| 10 mM dNTP | 0.45 mM | 9 | 10.8 | 39.6 |
| 20 mg/mL BSA (NEB B9000S) | 1.0 mg/mL | 10 | 12 | 44 |
| 5000 U/mL Klenow Exo- (NEB M0212S) | 150 U/mL | 6 | 7.2 | 26.4 |
| Total | | 25 | 30 | 110 |

10. The tube was placed in thermomixer at 1,200 rpm at 37° C. for 30 minutes.

11. The tube was placed in a 95° C. heat block for 2 minutes, was shaken for ~20 seconds on a Thermomixer, placed in a 1.5 mL magnet and the supernatant (Random Primer Extension Product, i.e. RPE Product) was immediately transferred to a new 1.5 mL LoBind tube and that tube was saved on ice.

12. In some instances, the beads were resuspended in 200 μL of Bead Resuspension Buffer (PN 650000066). The tube was placed in a 95° C. heat block for 2 minutes, placed in a 1.5 mL magnet and the supernatant was immediately transferred to a new tube.

13. In some instances, 200 μL of cold Bead Resuspension Buffer (PN 650000066) was pipetted into the tube with leftover beads. The beads were gently resuspended by pipette mixing only (and not vortexed). The beads were stored at 4° C. in the pre-amplification workspace. The leftover beads could be used for BD Rhapsody Targeted and BD AbSeq library generation.

Purifying RPE Product

1. In a new 5.0 mL LoBind tube, 5 mL of fresh 80% (v/v) ethyl alcohol was prepared by pipetting 4.0 mL of absolute ethyl alcohol to 1.0 mL of nuclease-free water. The tube was vortexed for 10 seconds. Fresh 80% ethyl alcohol was made and used in less than 24 hours.

2. The SPRI Select beads were vortexed at high speed for 1 minute before use. The beads appeared homogeneous and uniform in color.

3. 320 μL (1.6×) of SPRI Select beads were pipetted to the tube containing the 200 μL of RPE Product supernatant.

4. Pipet mixing was performed at least 10 times and then briefly centrifuged.

5. The suspension was incubated at room temperature for 10 minutes, and then it was placed on the 1.5 mL tube magnet for 5 minutes.

6. The supernatant was removed.

7. Keeping the original tube with the beads on the magnet, 600 μL of fresh 80% ethyl alcohol was gently pipetted to the tube.

8. The sample was incubated on the magnet for 30 seconds.

9. While on the magnet, the supernatant was carefully removed and appropriately discarded without disturbing the SPRI Select beads.

10. The ethanol wash steps were repeated for a total of two 80% ethanol washes.

11. While on the magnet, a small-volume pipette was used to remove any residual supernatant from the tube.

12. The tube was left open on the magnet to dry the SPRI Select beads at room temperature for 10-15 minutes or until beads no longer looked glossy.

13. The tube was removed from the magnet and 31 µL of Elution Buffer (PN 650000075) was pipetted into the tube. The suspension was pipette mixed at least 10 times until the solution appeared suspended and uniform in color.

14. The sample was incubated at room temperature for 2 minutes.

15. The tube was briefly centrifuged to collect the contents at the bottom.

16. The tube was placed on the magnet until the solution was clear (usually ≤30 seconds).

17. The entire eluate (~30 µL) was pipetted to a new PCR tube. This was the purified BD Rhapsody RPE Product. It was kept on ice or at 4° C. until PCR.

RPE PCR

1. In the pre-amplification workspace, in a new 1.5 mL LoBind tube, the components depicted in Table 5 were pipetted in the order shown.

TABLE 5

RPE PCR MIX

| Component | Final concentration | 1× | 1.2× | 4.4× |
|---|---|---|---|---|
| Random priming 1 product | | 30.0 | | |
| 2× PCR MasterMix | | 50.0 | 60 | 220 |
| Universal Oligo (10 µM) | 1 µM | 10.0 | 12 | 44 |
| AbSeq PCR1 Primer (10 µM) | 1 µM | 10.0 | 12 | 44 |
| Total | | 100.0 | 84 | 308 |

2. 70 µL of the RPE PCR Mix was combined with 30 µL of Purified RPE Product.

3. The RPE PCR Reaction was split into 2 PCR tubes with 50 µL of reaction mix per tube.

4. The PCR program depicted in Table 6 was run, wherein the number of PCR cycles was determined according to Table 7.

TABLE 6

PCR PROGRAM

| Step | Cycles | Temperature | Time |
|---|---|---|---|
| Hot start | 1 | 95° C. | 3 min |
| Denaturation | See Table 7 | 95° C. | 30 s |
| Annealing | | 60° C. | 1 min |
| Extension | | 72° C. | 1 min |
| Final extension | 1 | 72° C. | 2 min |
| Hold | 1 | 4° C. | ∞ |

TABLE 7

PCR CYCLE NUMBER

| Cell number in amplification | Recommended starting PCR cycles for resting PBMCs |
|---|---|
| 500 cells | 17 |
| 1,000 cells | 16 |
| 2,500 cells | 15 |

TABLE 7-continued

PCR CYCLE NUMBER

| Cell number in amplification | Recommended starting PCR cycles for resting PBMCs |
|---|---|
| 5,000-10,000 cells | 14 |
| 10,000 cells | 13 |

5. When the RPE PCR reaction was complete, the tubes were briefly centrifuged to collect contents at bottom of tubes.

6. The two reactions were combined into a new 0.2 mL PCR tube.

Purification of the RPE PCR Amplification Product (Single-Sided Cleanup)

1. In some instances, 2 µL of RPE PCR reaction product were taken for Bioanalyzer analysis (to compare with purified products later).

2. The SPRI Select beads were brought to room temperature, and the SPRI Select beads were vortexed at high speed for 1 minute. The beads appeared homogeneous and uniform in color.

3. The tubes with the final amplification product were briefly centrifuged.

4. 100.0 µL (1.0×) of SPRI Select beads were pipetted into the final amplification product.

5. Pipet mixing at least 10 times was performed and then the samples were briefly centrifuged.

6. The suspension was incubated at room temperature for 5 minutes, and then was placed on the strip tube magnet for 3-5 minutes.

7. While on the magnet, the user carefully removed and appropriately discarded only the supernatant without disturbing the SPRI Select beads.

8. Keeping the tubes on the magnet, 200 uL of fresh 80% ethyl alcohol was gently pipetted.

9. The samples were incubated for 30 seconds on the magnet.

10. While on the magnet, the user carefully removed and appropriately discarded only the supernatant without disturbing the SPRI Select beads.

11. The 80% ethanol wash was repeated for a total of two washes.

12. Keeping the tubes on the magnet, a small-volume pipette was used to remove any residual supernatant from the tube.

13. The tubes were left open on the magnet to dry the SPRI Select beads at room temperature for at least 5 minutes or until the beads no longer looked glossy.

14. 30 µL of Elution Buffer (PN 650000075) was pipetted into the tubes and pulse vortexed to completely resuspend the SPRI Select beads.

15. The samples were incubated at room temperature for 2 minutes.

16. The tubes were briefly centrifuged to collect the contents at the bottom.

17. The tubes were placed on the magnet until the solution was clear (usually ≤30 seconds).

18. The entire eluate (~30 µL) was pipetted into new 1.5 mL LoBind tubes. The RPE PCR eluate was now ready for Index PCR. In some instances, this step was a stopping point, and the RPE PCR libraries could be stored at −20° C. for ≤6 months.

19. The user quantified and performed quality control of the RPE PCR products with a Qubit™ Fluorometer using the Qubit dsDNA HS Assay and an Agilent 2100 Bioanalyzer using the Agilent High Sensitivity DNA Kit. The Bioanalyzer trace appropriately showed a broad peak from 200 to 1000 bp. The concentration from 200 to 1000 bp was used to calculate how much template to add in Index PCR. In some instances, a small peak around 70 bp may be observed. In some instances, if the 70 bp peak was significant, the yield after Index PCR was impacted.

WTA Index PCR

1. The RPE PCR eluate was diluted such that the concentration of the 200-1000 bp peak was ~1-2 nM. For example, if the Bioanalyzer measurement of the 200-1000 bp peak was ~6 nM, then the sample was diluted 1:3 to 2 nM.

2. The components depicted in Table 8 were pipetted in the order shown to a new 1.5 mL tube.

TABLE 8

WTA INDEX PCR MIX

| Component | Final concentration | 1× | 1.2× | 4.4× |
|---|---|---|---|---|
| RPE PCR eluate (template) | ~1-2 nM of 200-1000 bp peak (as measured by Bioanalyzer) | 3 | | |
| 2× PCR MasterMix | 1× | 25 | 30 | 110 |
| Library Forward Primer (10 µM) | 1 µM | 5 | 6 | 22 |
| Library Reverse Primer (10 µM) | 1 µM | 5 | 6 | 22 |
| Water | | 12 | 14.4 | 52.8 |
| Total | | 50 | 56.4 | 184.8 |

3. The WTA Index PCR Mix was combined with PCR1 template as follows: (a) for 1 sample, 47 µL WTA Index PCR Mix was combined with 3 µL of 1-2 nM of RPE PCR eluate (template); or (b) for multiple samples with different Reverse Library indices, WTA Index PCR Mixes were combined with 5 µL of Reverse Index and 3 µL of RPE PCR eluate (template).

4. The PCR program depicted in Table 9 was run.

TABLE 9

INDEX PCR PROGRAM

| Step | Cycles | Temperature | Time |
|---|---|---|---|
| Hot start | 1 | 95° C. | 5 min |
| Denaturation | 6-8 | 95° C. | 30 s |
| Annealing | | 60° C. | 30 s |
| Extension | | 72° C. | 30 s |
| Final extension | 1 | 72° C. | 1 min |
| Hold | 1 | 4° C. | ∞ |

5. When the WTA Index PCR was complete, the tubes were briefly centrifuged to collect contents at bottom of tubes.

Purification of the WTA Index PCR Product (Dual-Sided Cleanup)

1. In some instances, 2 µL of WTA Index PCR reaction product was taken for Bioanalyzer analysis (to compare with purified products later).

2. The SPRI Select beads were brought to room temperature, and the SPRI Select beads were vortexed at high speed for 1 minute. The beads appeared homogeneous and uniform in color.

3. The tubes with the WTA Index PCR product were briefly centrifuged.

4. 50 µL of water was added to the WTA Index PCR product for a final volume of 100 µL.

5. 55 µL (0.55×) of SPRI Select beads was pipetted into the WTA Index PCR product.

6. Pipet mixing was performed at least 10 times and then the samples were briefly centrifuged.

7. The suspensions were incubated at room temperature for 5 minutes, and then placed on the 0.2 mL strip tube magnet for 3 minutes.

8. While the strip tube in step 5 was still on the magnet, the user carefully, without disturbing the magneted beads, removed and transferred the 155 µL of supernatant into a new 0.2 mL strip tube and pipet mixed 10 times.

9. 15 µL (0.70×) of SPRI Select beads was pipetted into the new strip tube containing the supernatant.

10. The suspension was incubated at room temperature for 5 minutes, and the new tube was then placed on a 0.2 mL tube magnet for 5 minutes.

11. While on the magnet, the user carefully removed and appropriately discarded only the supernatant without disturbing the SPRI Select beads.

12. Keeping the tubes on the magnet, 200 uL of fresh 80% ethyl alcohol was gently pipetted.

13. The samples were incubated for 30 seconds on the magnet.

14. While on the magnet, the user carefully removed and appropriately discarded only the supernatant without disturbing the SPRI Select beads.

15. The 80% ethanol wash was repeated for a total of two washes.

16. Keeping the tubes on the magnet, a small-volume pipette was used to remove any residual supernatant from the tube.

17. The tubes were left open on the magnet to dry the SPRI Select beads at room temperature for 5 minutes.

18. 30 µL of Elution Buffer (PN 650000075) was pipetted into the tubes and pulse vortexed to completely resuspend the SPRI Select beads.

19. The samples were incubated at room temperature for 2 minutes.

20. The tubes were briefly centrifuged to collect the contents at the bottom.

21. The tubes were placed on the magnet until the solution was clear (usually ≤30 seconds).

22. The entire eluate (~30 µL) was pipetted into new 1.5 mL LoBind tubes. The WTA Index PCR eluate were the final sequencing libraries. In some instances, this step was a stopping point. The Index PCR libraries could be stored at −20° C. for ≤6 months until sequencing.

23. The user quantified and performed quality control of the Index PCR libraries with a Qubit™ Fluorometer using the Qubit dsDNA HS Assay and an Agilent 2100 Bioanalyzer using the Agilent High Sensitivity DNA Kit.

Sequencing

In some instances, sequencing was performed with 50,000 reads per cell and 20% PhiX load into sequencing run.

Example 1

Development and Refinement of a Random Priming and Extension (RPE)-Based Method for Performing Whole Transcriptome Analysis (WTA)

The random priming and extension (RPE)-based method for performing whole transcriptome analysis (WTA) provided herein was developed and optimized based, in part, on the non-limiting exemplary WTA performance metrics provided in Table 10 and comparisons to currently available WTA methods. For example, the RPE-based WTA method was developed taking into account: (1) common WTA metrics (e.g., genes/UMI per cell), though these may be biased since different WTA methods have inherent biases from different gene types; and (2) additional metrics, such as, for example, WTA dropout rates across different expression level genes and biases (ribosomal, mitochondrial, housekeeping genes, etc.). In some instances, identification of major immune cell types (B cells, NK, T cells, and myeloid cells) was done using tSNE and Feature Selection default settings on BD DataView.

TABLE 10

WTA PERFORMANCE METRICS

| Performance Metrics | Criteria |
|---|---|
| Bias | Ribosomal % reads per sample |
| | Mitochondrial % reads per sample |
| Sensitivity | Median genes per cell for at least 8000 reads per cell after pipeline is done |
| | Median genes per cell non-ribosomal, non-mitochondrial, non-pseudogene |
| WTA dropout rate | % total cells positive for housekeeping genes |
| | % T cells positive for CD4 |
| | % T cells positive for CD8A |
| | % T cells positive for TRBC2 |
| | % T cells positive for TRAC |
| | % T cells positive for CD3D |
| | % T cells positive for TBX21 |
| | % B cells positive for IGLC3 |
| Library yield and compatibility to Illumina sequencers | Final library nM |
| | Final library size (bp) |

Comparison of RPE-Based WTA Method Versus Ligation-Based WTA Method

Figures 13A, 13B:
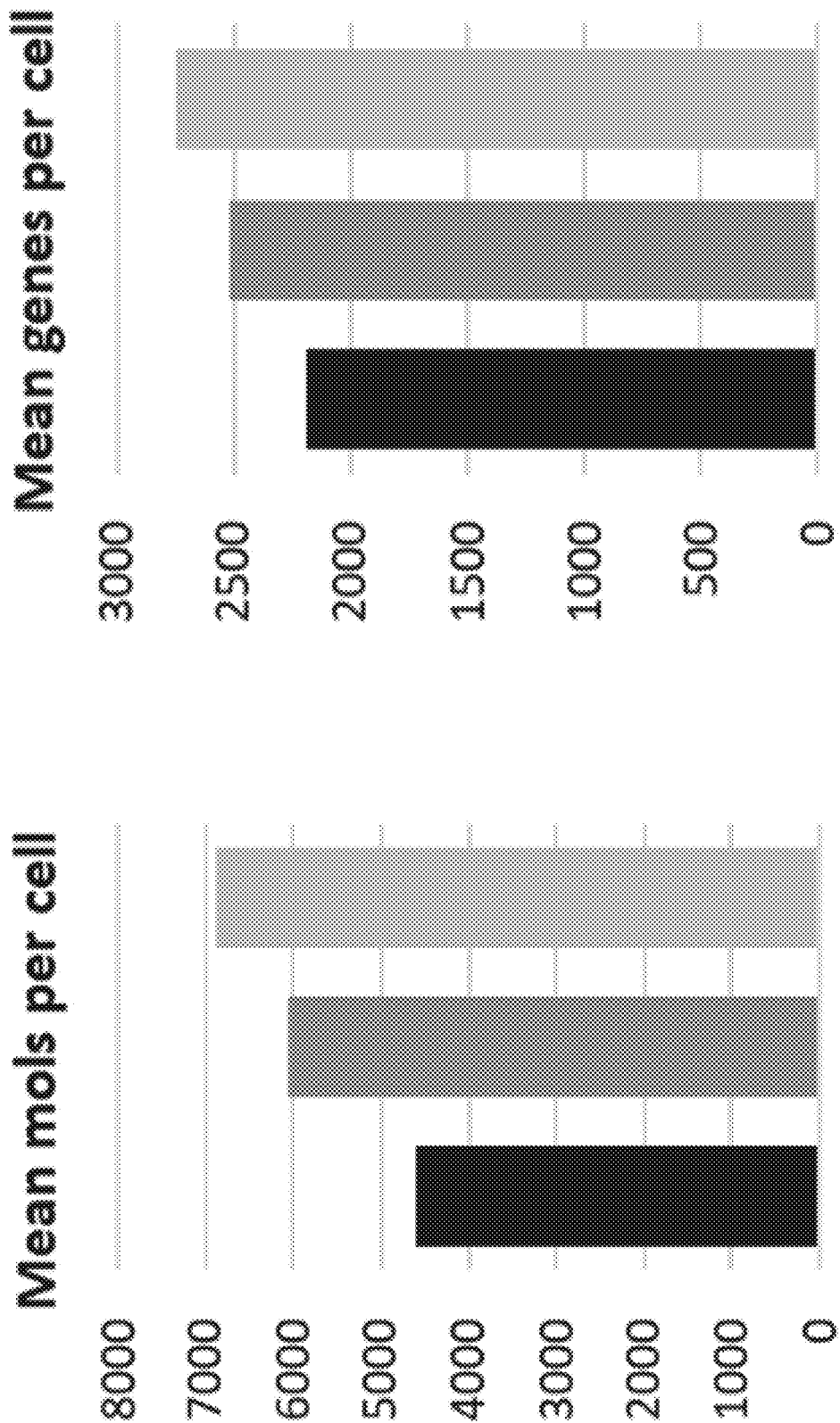
FIGS. 13A-B are plots showing non-exemplary sensitivity metrics of performing litigation-based whole transcriptome analysis, and whole transcriptome analysis with random priming and extension with 6mer randomers and 9mer randomers.

The RPE-based method for performing WTA provided herein, using either hexamers (ID010HK6) or nonamers (ID010NK6), was compared to a currently available ligation-based WTA method (ID010UG1) in Jurkat/Ramos cells (Table 11) and PMBCs (Table 12). FIGS. 13A-B are plots showing non-exemplary sensitivity metrics of performing litigation-based whole transcriptome analysis, and whole transcriptome analysis with random priming and extension with 6mer randomers and 9mer randomers. More genes and molecules were detected using the RPE-based WTA method in Jurkat/Ramos cells as compared to the ligation-based WTA method. Furthermore, more genes and molecules were detected using the nonamer-based RPE method as compared to the hexamer-based method. Some markers were not expressed in Jurkat cells. It was noted that the ligation-based method has better detection of IGLC3.

TABLE 11

COMPARING WTA PERFORMANCE IN JURKAT/RAMOS CELLS

| Criteria | RPE Hexamer | RPE Nonomer | Ligation-based WTA Protocol |
|---|---|---|---|
| Total genes detected | 21576 | 21986 | 21149 |
| Ribosomal % reads per sample | 11.02% | 11.13% | 13.09% |
| Mitochondrial % reads per sample | 15.14% | 15.61% | 11.60% |
| Median genes per cell for at least 8000 reads per cell after pipeline is done | 2495 | 2698 | 2154 |

TABLE 11-continued

COMPARING WTA PERFORMANCE IN JURKAT/RAMOS CELLS

| Criteria | RPE Hexamer | RPE Nonomer | Ligation-based WTA Protocol |
|---|---|---|---|
| Median genes per cell non-ribosomal, non-mitochondrial, non-pseudogene | 2362 | 2556 | 2003 |
| % total cells positive for housekeeping genes | — | — | — |
| % T cells positive for CD4 | 10.1% | 10.1% | 7.2% |
| % T cells positive for CD8A | — | — | — |
| % T cells positive for TRBC2 | 76.6% | 81.0% | 74.1% |
| % T cells positive for TRAC | 43.0% | 45.8% | 46.3% |
| % T cells positive for CD3D | 91.3% | 94.3% | 93.5% |
| % T cells positive for TBX21 | 0.5% | 0.3% | 0.1% |
| % B cells positive for IGLC3 | 22.1% | 65.8% | 72.4% |

TABLE 12

COMPARING WTA PERFORMANCE IN PBMCS

| Criteria | RPE Hexamer | RPE Nonomer | Ligation-based WTA Protocol |
|---|---|---|---|
| Total genes detected | 18419 | 18999 | 18958 |
| Ribosomal % reads per sample | 11.91% | 12.05% | 27.01% |
| Mitochondrial % reads per sample | 19.53% | 20.27% | 5.27% |
| Median genes per cell for at least 8000 reads per cell after pipeline is done | 569 | 651 | 391 |
| Median genes per cell non-ribosomal, non-mitochondrial, non-pseudogene | 564 | 489 | 276 |
| % total cells positive for housekeeping genes | — | — | — |
| % T cells positive for CD4 | 12.1% | 17.0% | 8.3% |
| % T cells positive for CD8A | 18.7% | 21.1% | 9.7% |
| % T cells positive for TRBC2 | 65.6% | 67.4% | 36.5% |
| % T cells positive for TRAC | 44.8% | 51.6% | 28.1% |
| % T cells positive for CD3D | 16.1% | 16.2% | 22.1% |
| % T cells positive for TBX21 | 7.0% | 11.2% | 5.9% |
| % B cells positive for IGLC3 | 0.0% | 0.7% | 8.5% |

Figure 14:
FIG. 14 is a t-Distributed Stochastic Neighbor Embedding (t-SNE) showing the exemplary performance of the random priming and extension-based WTA analysis of the disclosure compared to a ligation-based WTA method.

FIG. 14 is a t-Distributed Stochastic Neighbor Embedding (t-SNE) showing the exemplary performance of the random priming and extension-based WTA analysis of the disclosure compared to a ligation-based WTA method. The tSNE projection focused on 664 immune-related genes from predefined gene sets. The ID010HK6 (RPE hexamer) and ID010NK6 (RPE nonamer) samples had similar gene expression patterns, and appeared to have higher variability between cell clusters than ID010UG1 (ligation-based WTA method), although all appeared to be squished in a closer 2D space.

Figure 15A:
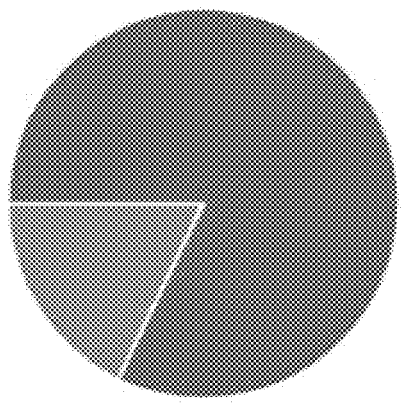
FIGS. 15A-15B are non-limiting exemplary pie charts showing that ID010NK6 (RPE WTA nonamer) appeared to capture more cell surface markers than ID010UG1 (a ligation-based WTA method).
Figure 15B:
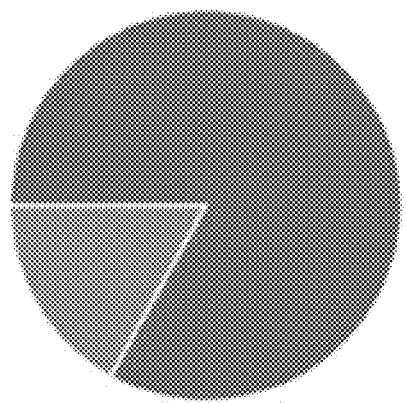

FIGS. 15A-15B are non-limiting exemplary pie charts showing that ID010NK6 (RPE WTA nonamer) appeared to capture more cell surface markers than ID010UG1 (a ligation-based WTA method). FIG. 15A is a pie chart showing that the number of cells expressing a particular gene that was higher in the RPE WTA nonamer method or ligation-based WTA method. FIG. 15B is a pie chart showing that UMI per cell expressing a particular gene that is higher in the RPE nonamer method or ligation-based WTA method. Further, as depicted in Tables 13 and 14, the nonamer RPE-based WTA method captured more cell surface markers than the ligation-based WTA method.

Accordingly, these data demonstrate the enhanced performance of the RPE-based method for performing WTA provided herein (using either hexamers or nonamers), as compared to a currently available ligation-based WTA method across multiple cell types and numerous performance metrics.

Additionally, the RPE-based WTA method disclosed herein can provide a shorter WTA protocol. From single cell capture to cDNA synthesis complete takes 85 minutes, 130 minutes, and 130 minutes, for an existing droplet-based WTA method, an existing ligation-based WTA method, and the RPE-based WTA method, respectively. From library preparation to QC takes 375 minutes, 520 minutes, and 330 minutes for an existing droplet-based WTA method, an existing ligation-based WTA method, and the RPE-based WTA method, respectively. Thus, the novel method of performing WTA provided herein advantageously shortens protocol time.

TABLE 13

GENE ONTOLOGY TERMS

| GO Term | Genes |
| --- | --- |
| GO:0009897-external side of plasma membrane | ENOX2, CD8A, ATP6AP2, CD88, CXCR3, TRDC1 IL7R. ADA, ALCAM. IFNG, CD4, IL2RG, CD24 . . . |
| GO:0098552-side of membrane | ENOX2, CD8A, ATP6AP2, CD88, CXCR3, TRDC, IL7R, ADA, BTK, ALCAM, IFNG, IL2RG, CD4 . . . |
| GO:0009986-cell surface | ENOX2, CD8A, ATP6AP2, CDBB, CXCR3, TRDC IL7R. TGFB1, ADA.,_ HMMR, ALCAM, CD44 . . . |
| GO:0043231-intracellular membrane-bounded organelle | HCCS, PNMA3, SLC9A7, SLC9A6, RP2, TRMT28, AURKA, HMGN5, USP51, SLC35A2, PRKX . . . |
| GO:0005622-intracellular | HCCS, PNMA3, SLC9A7, SLC9A6, RP2,. TRMT28, AURKA, HMGN5, SLC35A2, USP51. PRKX . . . |
| GO:0005768-endosome | PRF1, SLC9A7, SLC9A6, RAB9A, MMGT1, CD88, ATP6AP1, DIAPH2, TLR7, TLR8, RRAGB . . . |
| GO:0044459-plasma membrane part | PLXNA3, ENOX2, CD8A, CD88, ATP6AP2, RP2, TSPAN6, CASK, TSPAN7, CXCR3, TLR7, BTK . . . |
| GO:0044424- intracellular part | HCCS, PNMA3, SLC9A7, SLC9A6, RP2, TRMT28, AURKA, HMGN5, SLC35A2, USP51, PRKX . . . |
| GO:0005634-nucleus | PNMA3, AURKA, HMGN5, USP51, SLC35A2 PRKX, BTK, DNASE1L 1, PRIM1, MAGED1, ZFP9 . . . |
| GO:0043227-membrane-bounded organelle | HCCS, PNMA3, SLC9A7, SLC9A6, RP2, TRMT28, AURKA, HMGN5, SLC35A2, USP51, PRKX . . . |
| GO:0005773-vacuole | PRF1 SLC9A7, ARSD, SLC9A6, MMGT1, RAB9A, CD88 ATP6AP1 DIAPH2, UBQLN2, TLR7 . . . |
| GO:0044464-cell part | HCCS, SLC9A7, SLC9A6, RP2, USP51, BTK, MAGED1, SYP, CDCA7. CCR10, VMA21, PDHA1 . . . |

TABLE 14

GENE ONTOLOGY TERMS

| GO Term | Count | % | P value | Genes |
| --- | --- | --- | --- | --- |
| GO:0042571-immunoglobulin complex, circulating | 7 | 7.142857143 | 8.75644E-10 | IGHG1, IGHG3, IGHD, IGHA1, IGHA2, IGHM, IGLC3 |
| GO:0019814-immunoglobulin complex | 7 | 7.142857143 | 1.97463E-09 | IGHG1, IGHG3, IGHD, IGHA1, IGHA2, IGHM, IGLC3 |
| GO:0009897-external side of plasma membrane | 11 | 11.2244898 | 2.41164E-07 | IGHG1, SELP, IGHG3, IL2RA, IGHD, IGHA1, IGHA2, IGHM, ENG, LAG3, IGLC3 |
| GO:0098552-side of membrane | 12 | 12.24489796 | 7.5028E-06 | IGHG1, SELP, IGHG3, IL2RA, IGHD, IGHA1, IGHA2, CDH1, IGHM, ENG, LAG3, IGLC3 |
| GO:0072562-blood microparticle | 8 | 8.163265306 | 8.2479E-06 | IGHG1. IGHG3. IGHD, IGHA1. IGHA2, IGHM. ENG, IGLC3 |
| GO:0005615-extracellular space | 21 | 21.42857143 | 9.56996E-06 | MUC1, IGHG1, SELP, IGHG3. VPRE83, LGALS1, PRDX4, IGHM, RPL39, TIMP1, AZU1, CFP . . . |
| GO:0032991-macromolecular complex | 41 | 41.83673469 | 6.22817E-05 | IGHG1, IGHG3, RPS26P11, ERBB2, TIMM178, COX78, BEX1, CDH1, IGHM, RPL39, RPA4 . . . |
| GO:0043234-protein complex | 36 | 36.73469388 | 0.000127154 | IGHG1, IGHG3, ER882, TIMM17B, COX78, BEX1, CDH1, IGHM, RPA41 TIMP1, GATA1, NAA10 . . . |
| GO:0009986-cell surface | 12 | 12.24489796 | 0.000920806 | IGHG1, SELP, IGHG3, IL2RA, LGALS1, IGHD, IGHA1, IGHA2, IGHM, ENG, LAG3, IGLC3 |

TABLE 14-continued

GENE ONTOLOGY TERMS

| GO Term | Count | % | P value | Genes |
|---|---|---|---|---|
| GO:0044421-extracellular region part | 31 | 31.63265306 | 0.002477963 | IGHG1, IGHG3, VPRE83, PRDX4, CDH1, IGHM, OCRL, RPL39, TIMP1, AZU1, CFP, SERPINE1 . . . |
| GO:0005576-extracellular region | 34 | 34.69387755 | 0.005252573 | IGHG1, IGHG3, VPRE83, FAM3A, PRDX4, CDH1, IGHM, RPL39, OCRL1 TIMP1, AZU1, CFP . . . |

Model System

The RPE-based method for performing WTA provided herein, using either hexamers or nonamers, was tested in PBMCs and Jurkat/Ramos cells.

Figure 16C:
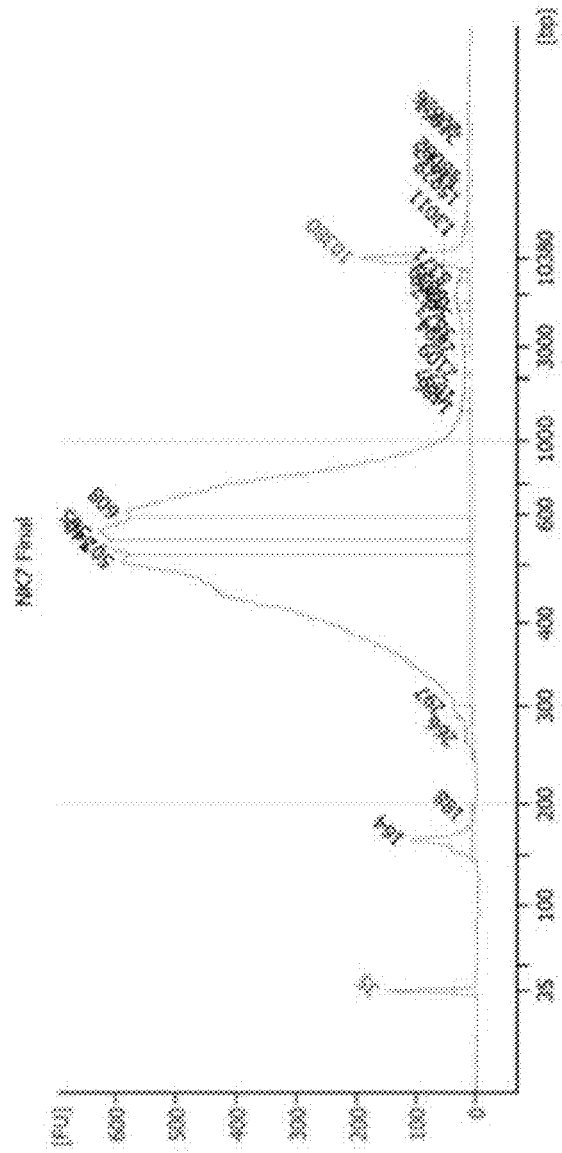
Figure 16D:
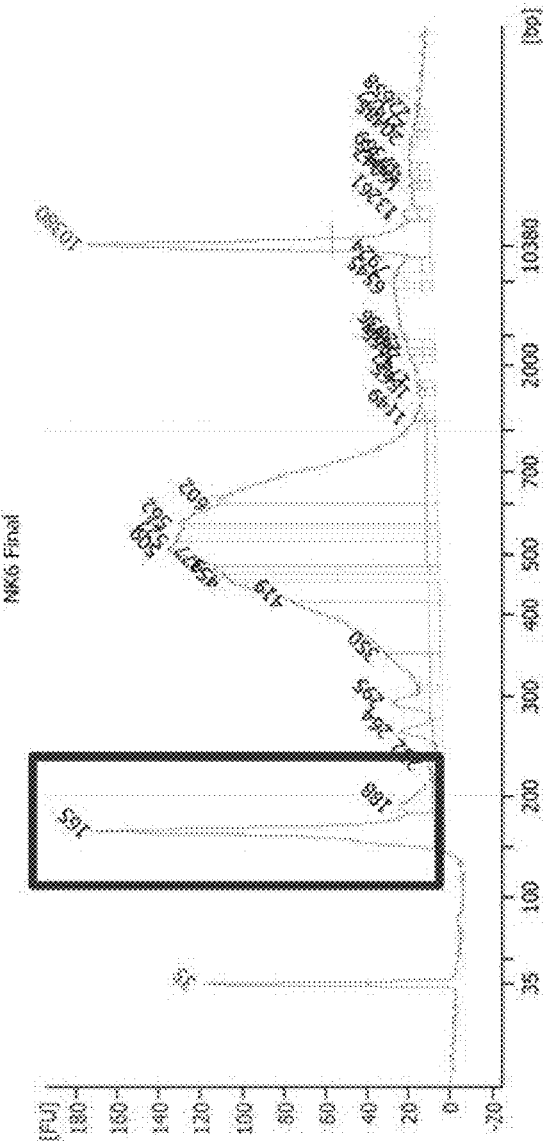

FIGS. 16A-16D are non-limiting exemplary bioanalyzer plots showing that when employing a RPE method comprising one random priming step and one PCR step, Jurkat/Ramos had higher RNA content than healthy donor peripheral blood mononuclear cells (PBMCs) (~5× when comparing UMI counts per cell) and PBMC libraries generated 165 bp contaminants, which were likely randomer dimers since it was possible to sequence these peaks. FIGS. 16A-16B depict hexamer RPE bioanalyzer plots in Jurkat/Ramos and PBMCs, respectively, while FIGS. 16C-16D depict nonamer RPE bioanalyzer plots in Jurkat/Ramos and PBMCs, respectively.

Table 15 depicts WTA performance of the hexamer-based and nonamer-based RPE WTA methods in Jurkat and PMBCs. Some markers were not expressed in Jurkat cells. PBMCs are a more challenging model system because RNA content is low. Developing the method in PBMCs hones on the sensitivity analysis more.

Extension Enzyme

The use of the extension enzyme for the RPE-based method for performing WTA provided herein, using either hexamers or nonamers, was investigated.

Figures 17A, 17B:
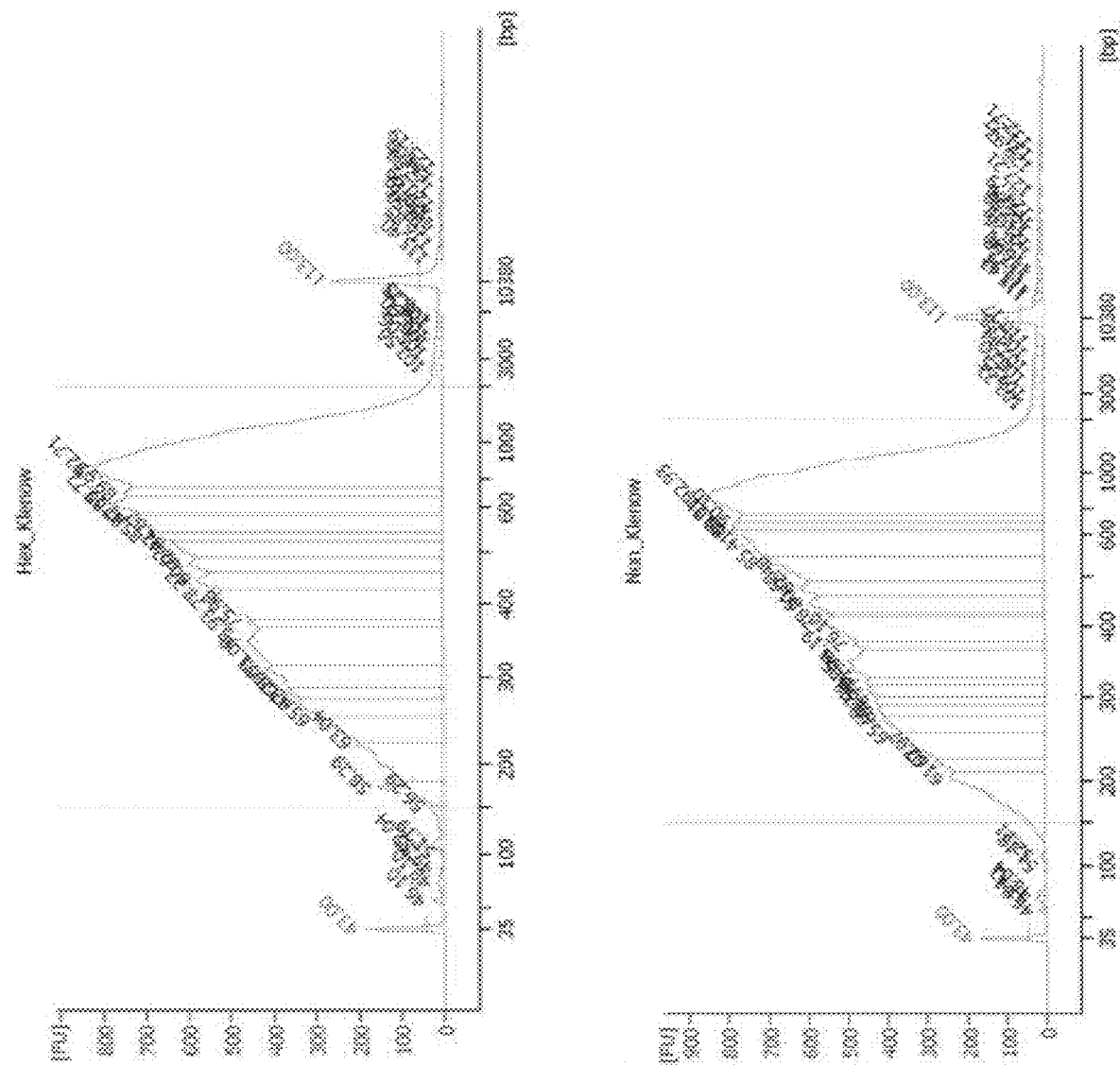
FIGS. 17A-17D are non-limiting exemplary bioanalyzer plots (RPE PCR) showing that Klenow Exo—with strand displacement activity is preferred over T4 DNA polymerase in some embodiments of performing WTA analysis with random priming and extension (employing a RPE method comprising one random priming step and one PCR step).
Figures 17C, 17D:
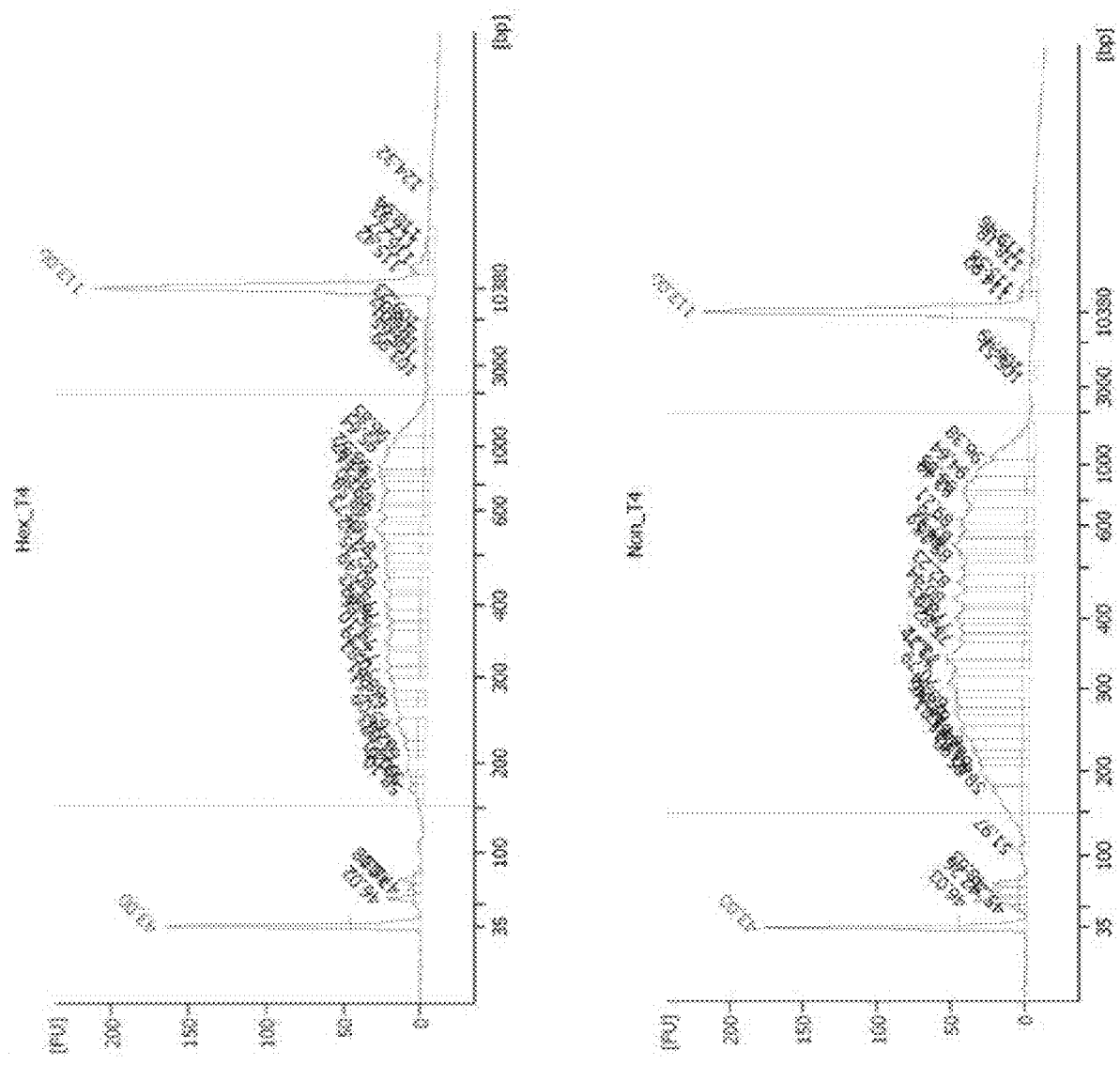

FIGS. 17A-17D are non-limiting exemplary bioanalyzer plots (RPE PCR) showing that Klenow Exo—with strand displacement activity is preferred over T4 DNA polymerase in some embodiments of performing WTA analysis with random priming and extension (employing a RPE method comprising one random priming step and one PCR step). Different polymerases were tested. The number of Jurkat/Ramos cells subsampled was 1000. FIGS. 17A-17B depict bioanalyzer plots for Klenow Exo—using hexamers and nonamers, respectively, while FIGS. 17C-17D depict bioanalyzer plots for T4 DNA polymerase using hexamers and nonamers, respectively. The plots show that Klenow Exo— had moderate strand displacement activity and T4 DNA polymerase had no strand displacement activity. There was also a difference in exonuclease activity between the two enzymes. Klenow Exo—generated higher yield for both hexamer and nonamer due to being able to generate multiple random priming extension products. In some embodiments,

TABLE 15

RPE-BASED WTA PERFORMANCE IN JURKAT CELLS AND PBMCS

| Criteria | RPE Hexamer, on Jurkat | RPE Nonamer on Jurkat | RPE Hexamer on PBMCs | RPE Nonamer on PBMCs |
|---|---|---|---|---|
| Total genes detected | 21576 | 21986 | 18419 | 18999 |
| Ribosomal % reads per sample | 11.02% | 11.13% | 11.91% | 12.05% |
| Mitochondrial % reads per sample | 15.14% | 15.61% | 19.53% | 20.27% |
| Median genes per cell for at least 8000 reads per cell after pipeline is done | 2495 | 2698 | 569 | 651 |
| Median genes per cell non-ribosomal, non-mitochondrial, non-pseudogene | 2362 | 2556 | 564 | 489 |
| % total cells positive for house-keeping genes | — | — | — | — |
| % T cells positive for CD4 | 10.1% | 10.1% | 12.1% | 17.0% |
| % T cells positive for CD8A | — | — | 18.7% | 21.1% |
| % T cells positive for TRBC2 | 76.6% | 81.0% | 65.6% | 67.4% |
| % T cells positive for TRAC | 43.0% | 45.8% | 44.8% | 51.6% |
| % T cells positive for CD3D | 91.3% | 94.3% | 16.1% | 16.2% |
| % T cells positive for TBX21 | 0.5% | 0.3% | 7.0% | 11.2% |
| % B cells positive for IGLC3 | 22.1% | 65.8% | 0.0% | 0.7% |

Klenow is used for extension. In some embodiments, Klenow exo— is employed for extension.

Figure 18B:
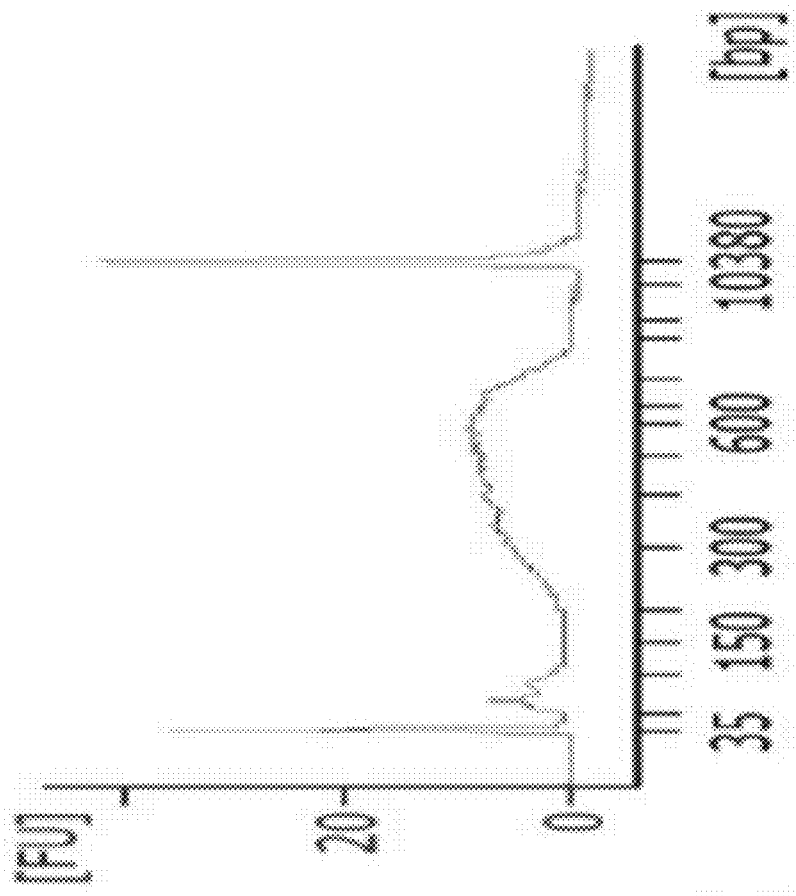
FIGS. 18A-18D are non-limiting exemplary bioanalyzer plots (RPE PCR) showing that Klenow exo—may not have as much strand displacement activity as previously thought.
Figure 18A:
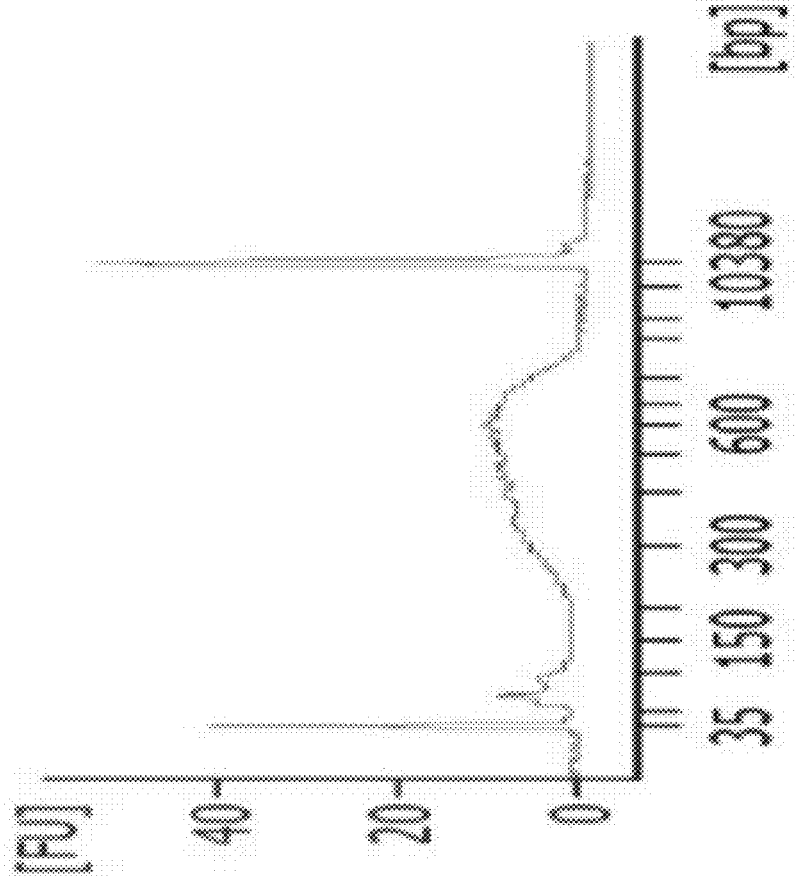
Figure 18D:
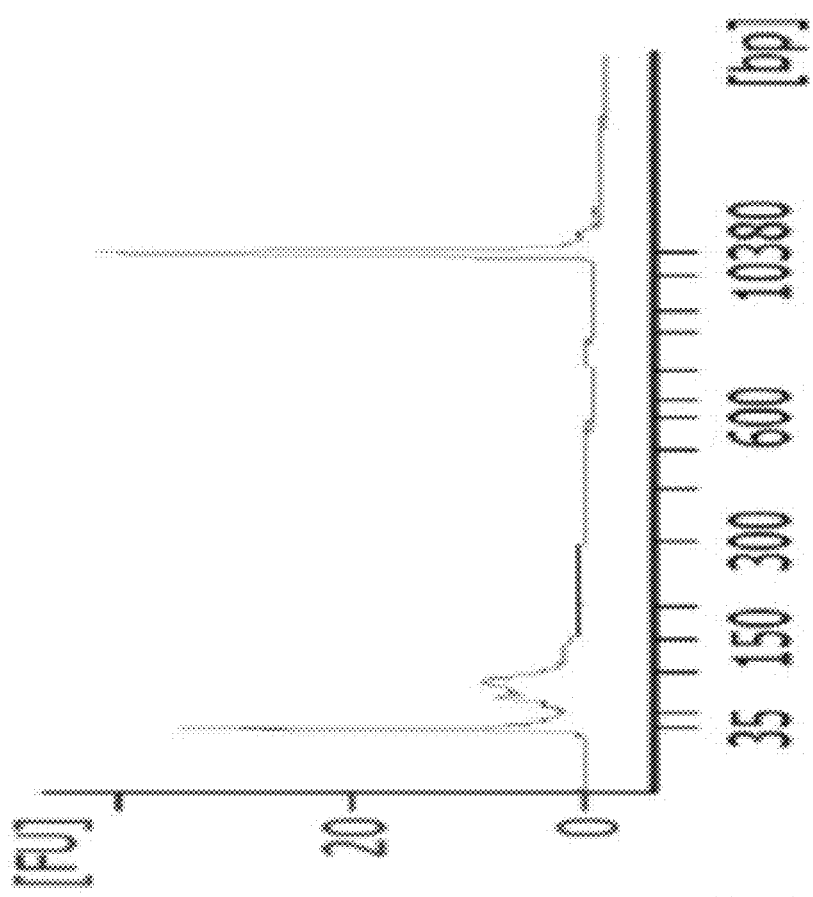
Figure 18C:
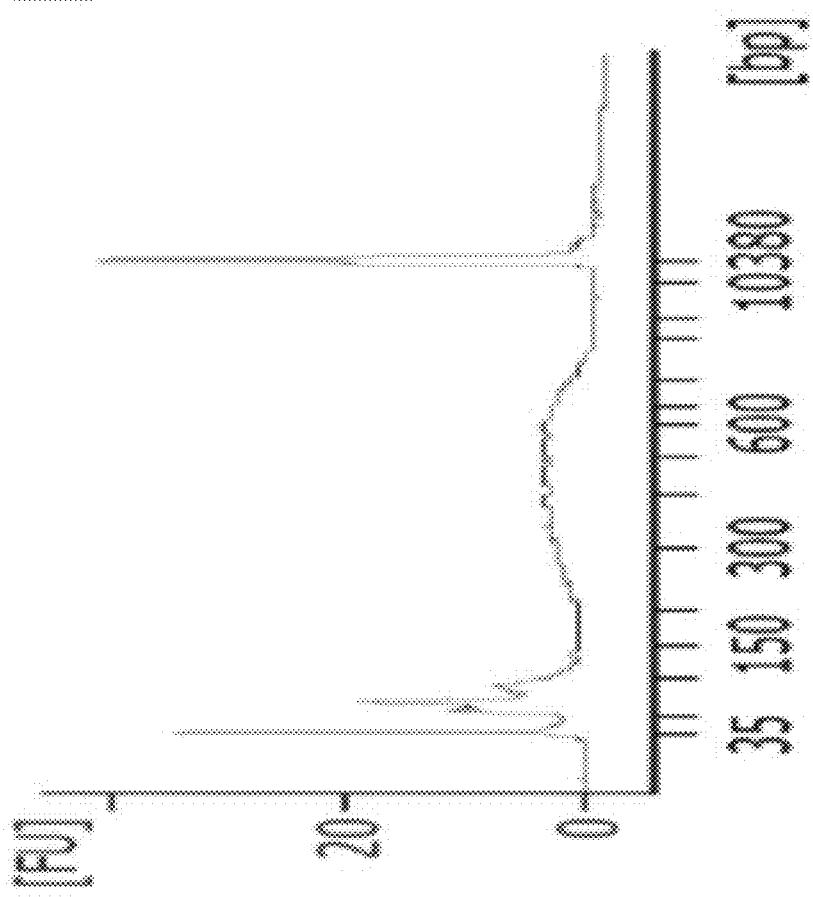

FIGS. 18A-18D are non-limiting exemplary bioanalyzer plots (RPE PCR) showing that Klenow exo—may not have as much strand displacement activity as previously thought. The number of PBMCs subsampled was 1000. Denaturation methods were tested for RPE before PCR1 showing that yields changed. The following were variables were tested: (i) denaturing at 95° C. for 2 min, then immediately take supernatant out (FIG. 18A); (ii) denaturing at 95° C. for 2 min, then wait 1 min to take supernatant out (FIG. 18B); (iii) treating with 0.1N NaOH 5 min, then neutralize with Tris Cl pH7 (FIG. 18C); and (iv) no denaturation (FIG. 18D). FIG. 18D shows that low RPE PCR yield suggests most of the product remains bound to cDNA beads, indicating that the enzyme may have little strand displacement activity. In some embodiments, other enzymes such as phi29 enzyme can be used.

RPE Primer Length and Random Priming Steps

The number of random priming steps and randomer length for the RPE-based method for performing WTA provided herein, using either hexamers or nonamers, was investigated.

Figure 19A:
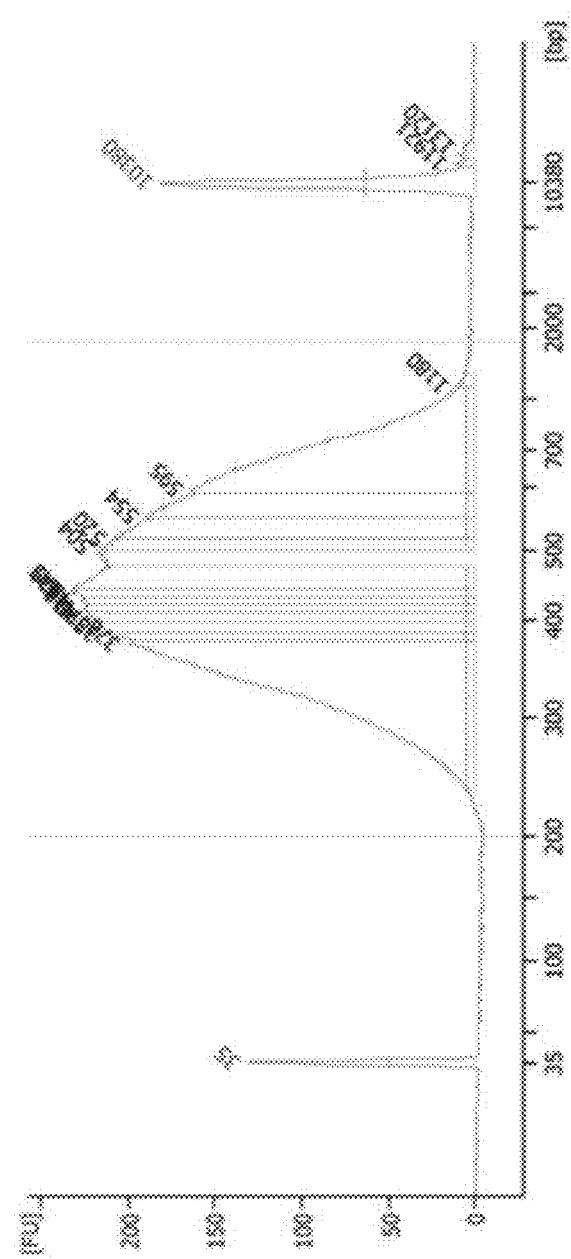
FIGS. 19A-19D are non-limiting exemplary bioanalyzer plots showing the effects of the number of random priming steps and randomer lengths on the performance of the RPE WTA method.
Figure 19B:
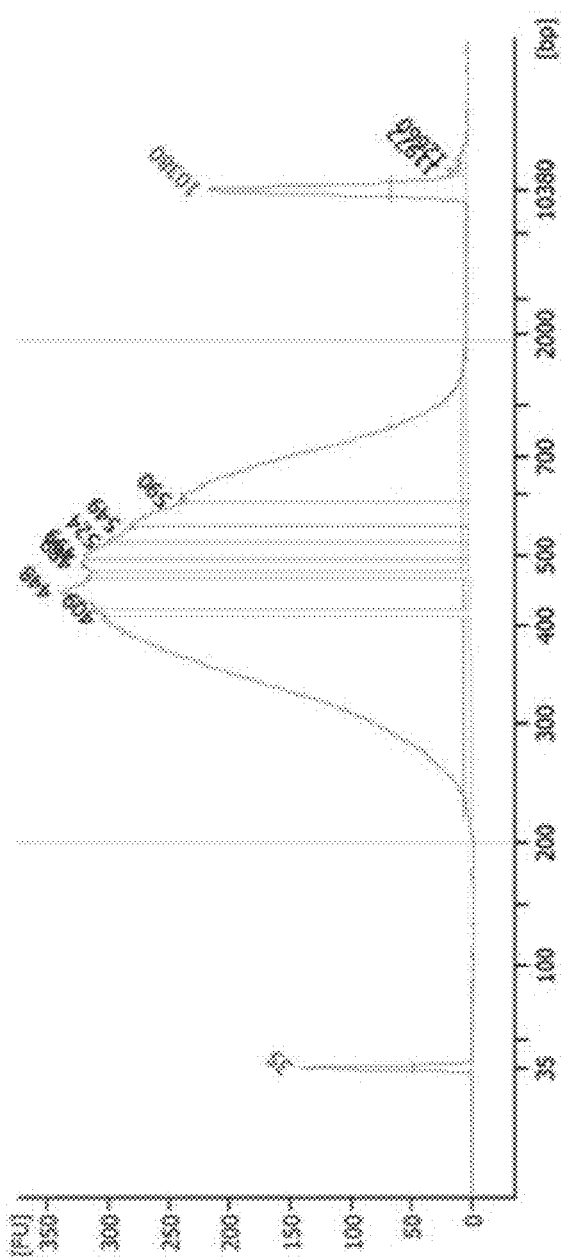
Figure 19C:
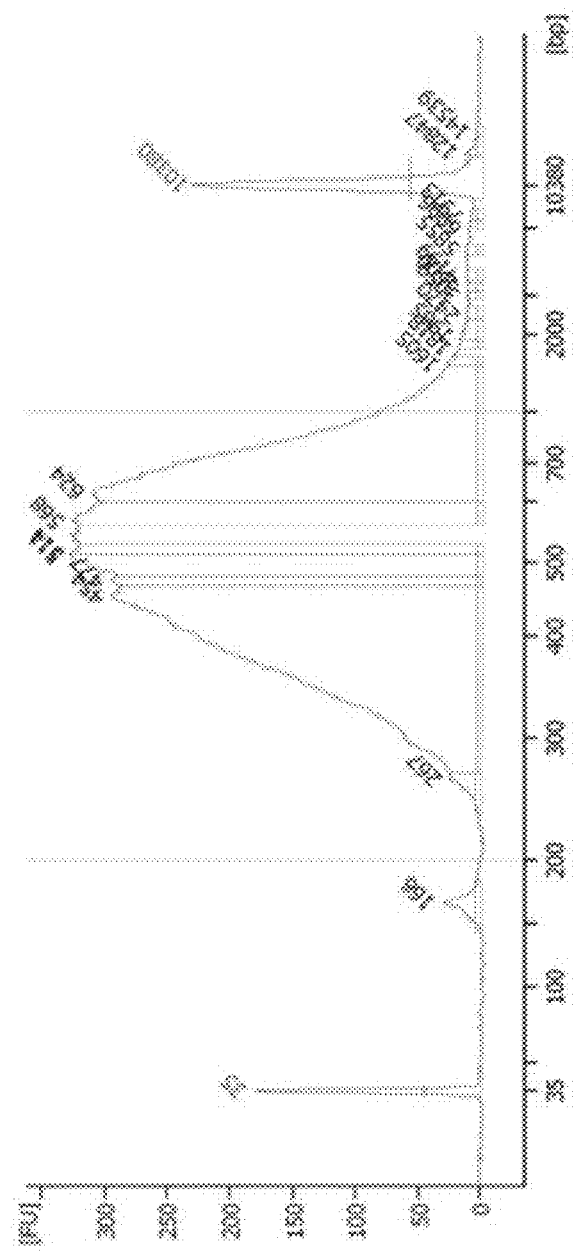
Figure 19D:
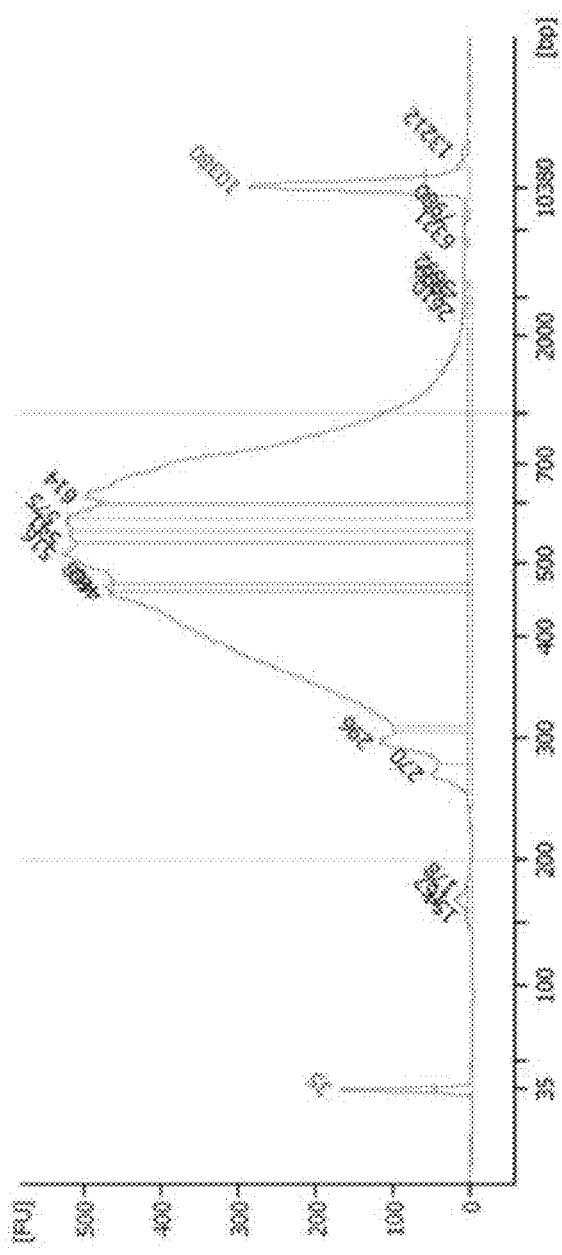

FIGS. 19A-19D are non-limiting exemplary bioanalyzer plots showing the effects of the number of random priming steps and randomer lengths on the RPE WTA method. The number of Jurkat/Ramos cells subsampled was 1000. An RPE-based WTA protocol comprising dual random priming (performing random priming and extension twice and two cycles of PCRs) was tested using hexamers and nonamers (FIGS. 19A and 19B, respectively). Additionally, an RPE-based WTA protocol comprising single random priming (performing random priming and extension one and one cycle of PCR) was tested using hexamers and nonamers (FIGS. 19C and 19D, respectively). With single random priming sequencible library can be generated as shown in the plots after index PCR. Contaminants of 165 bps were observed. Table 16 depicts WTA performance of the single random priming and dual random priming RPE variations above using hexamers and nonamers. While a single random priming step is much faster, 2 random priming steps appeared to have higher sensitivity. The nonamer appeared to have a better sensitivity for more genes. The remaining experiments provided herein employed 1 random priming step.

TABLE 16

RPE WTA PERFORMANCE USING 1 OR 2 RANDOM PRIMING STEPS AND HEXAMERS OR NONAMERS

| Criteria | Hexamer, 2 random priming steps | Hexamer, 1 random priming step | Nonomer, 2 random priming steps | Nonomer, 1 random priming step |
|---|---|---|---|---|
| Total genes detected | 17327 | 17380 | 17984 | 17474 |
| Ribosomal % reads per sample | 10.26% | 11.48% | 10.16% | 11.30% |
| Mitochondrial % reads per sample | 14.15% | 15.12 | 14.45% | 16.53% |
| Median genes per cell for at least 8000 reads per cell after pipeline is done | 2579 | 2069 | 2637 | 1897 |
| Median genes per cell non-ribosomal, non-mitochondrial, non-pseudogene | 2458 | 1951 | 2503 | 1779 |
| % total cells positive for house-keeping genes | — | — | — | — |
| % T cells positive for CD4 | 5.4% | 6.3% | 3.0% | 3.9% |
| % T cells positive for CD8A | — | — | — | — |
| % T cells positive for TRBC2 | 81.3% | 75.3% | 86.7% | 78.3% |
| % T cells positive for TRAC | 40.1% | 28.9% | 42.1% | 28.1% |
| % T cells positive for CD3D | 97.6% | 83.7% | 97.5% | 78.3% |
| % T cells positive for TBX21 | 0.6% | 0.0% | 0.6% | 0.0% |
| % B cells positive for IGLC3 | 18.6% | 16.3% | 55.9% | 41.9% |

RPE Cleanup

The optimal SPRI cleanup ratio for the RPE-based method for performing WTA provided herein was investigated.

Figure 20A:
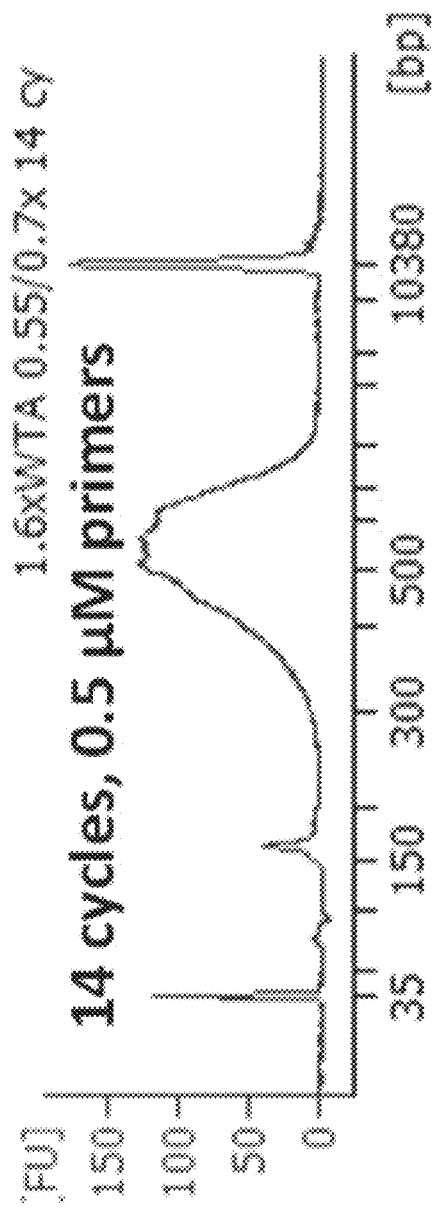
FIGS. 20A-20F are non-limiting exemplary data showing the effects of SPRI cleanup ratio on the performance of the RPE-based WTA method.
Figure 20B:
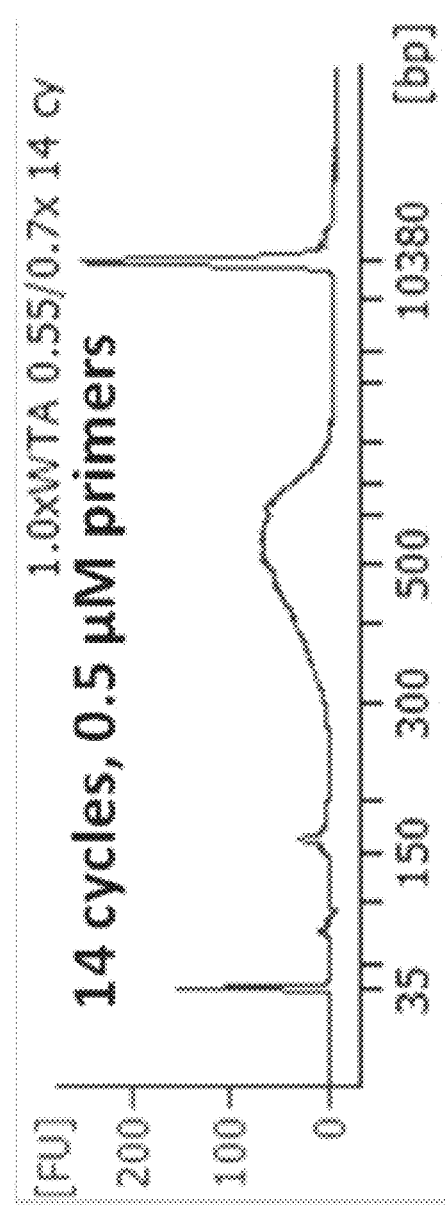
Figure 20E:
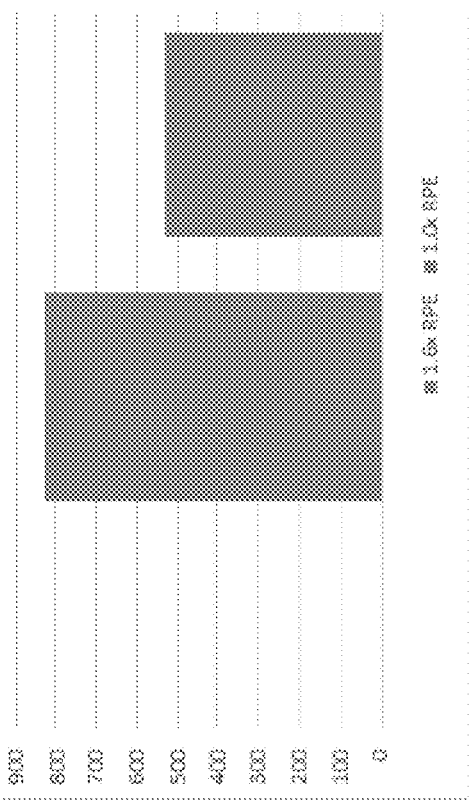
Figure 20F:
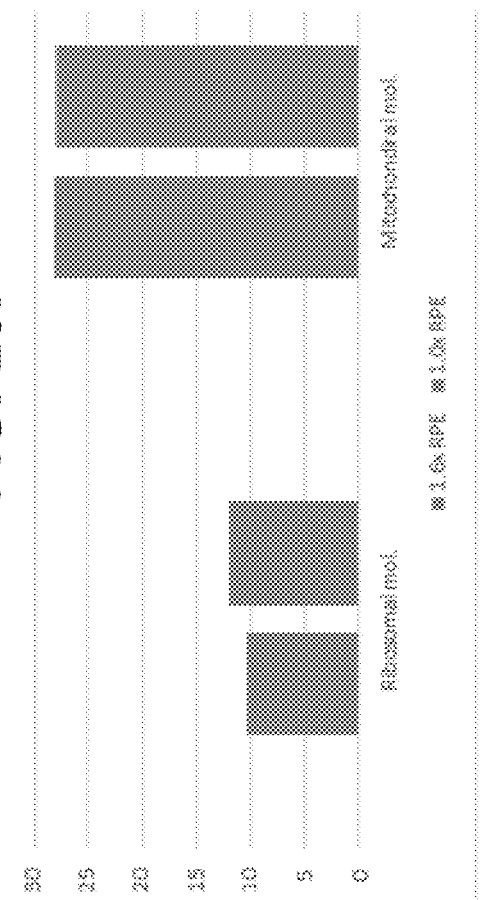
Figure 20C:
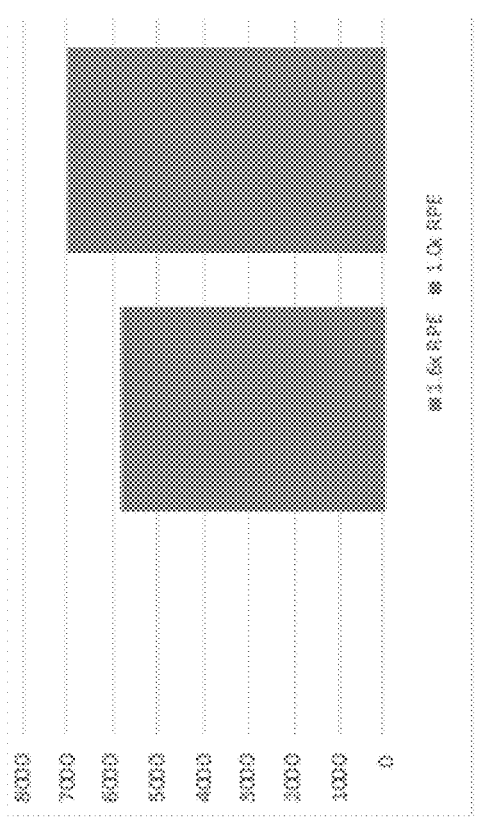
Figure 20D:
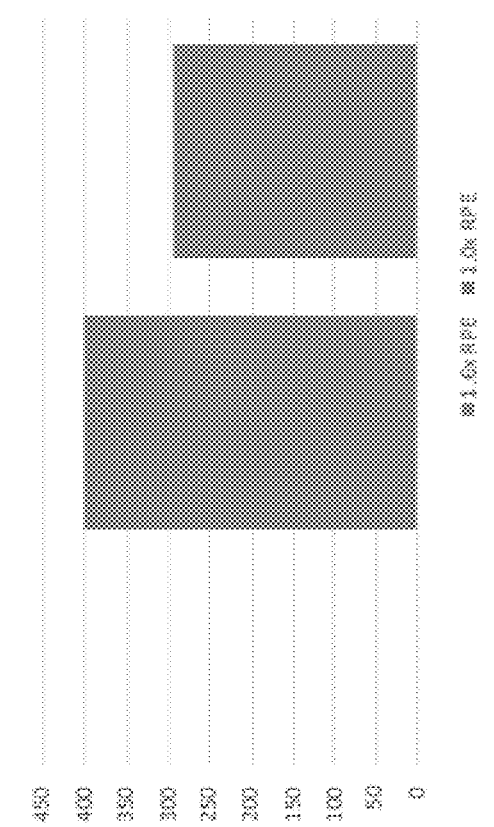
Figure 21A:
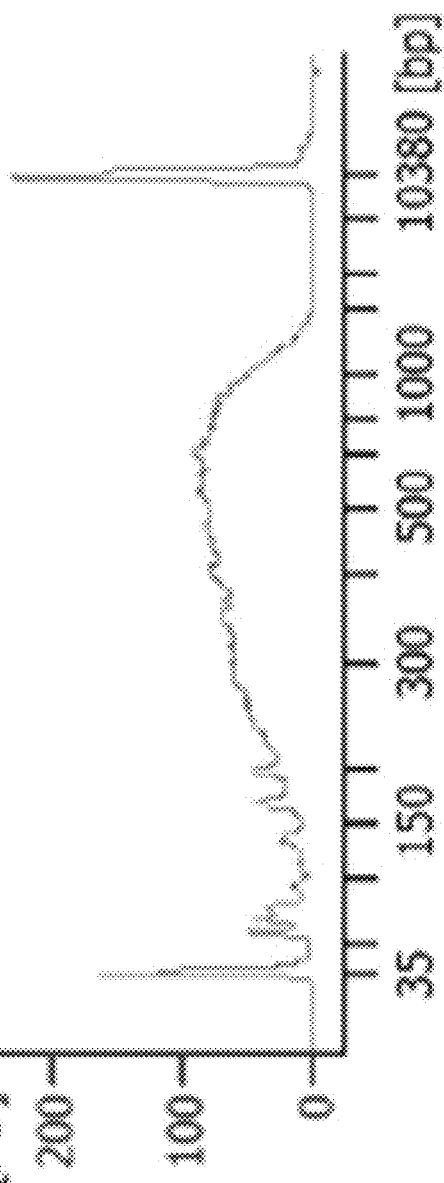
Figure 21B:
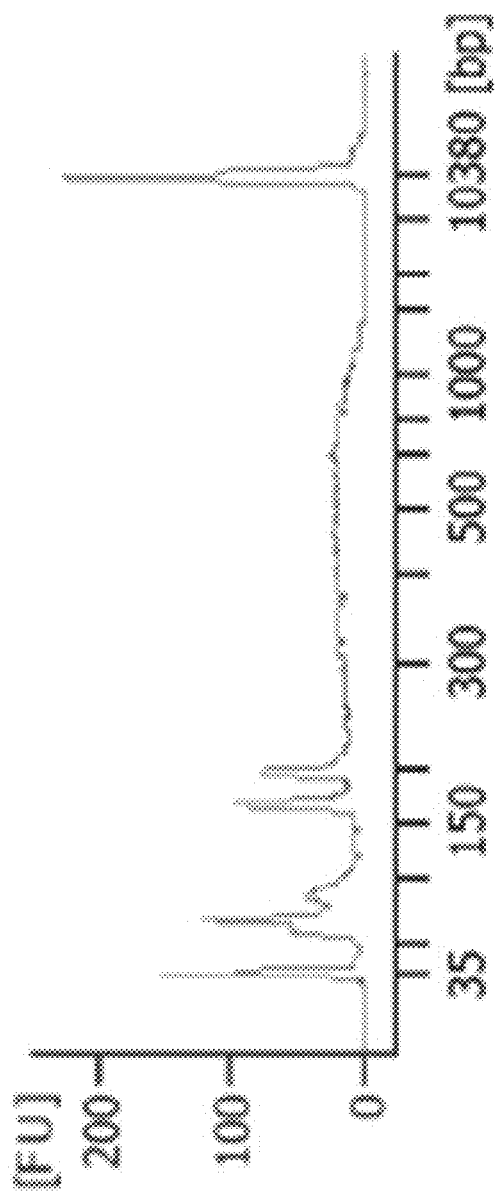
Figure 21E:
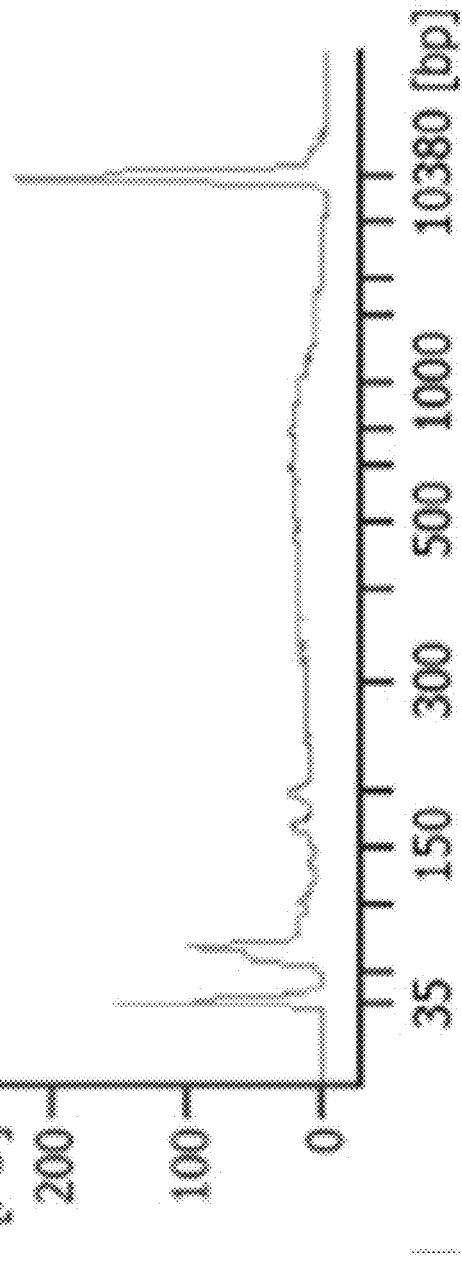
Figure 21F:
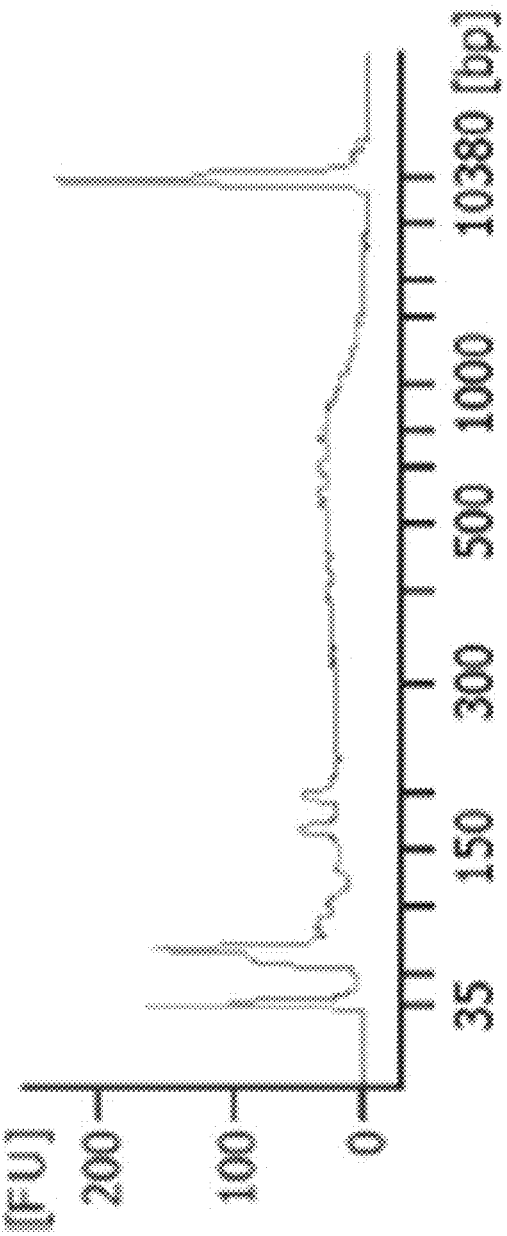
Figure 21G:
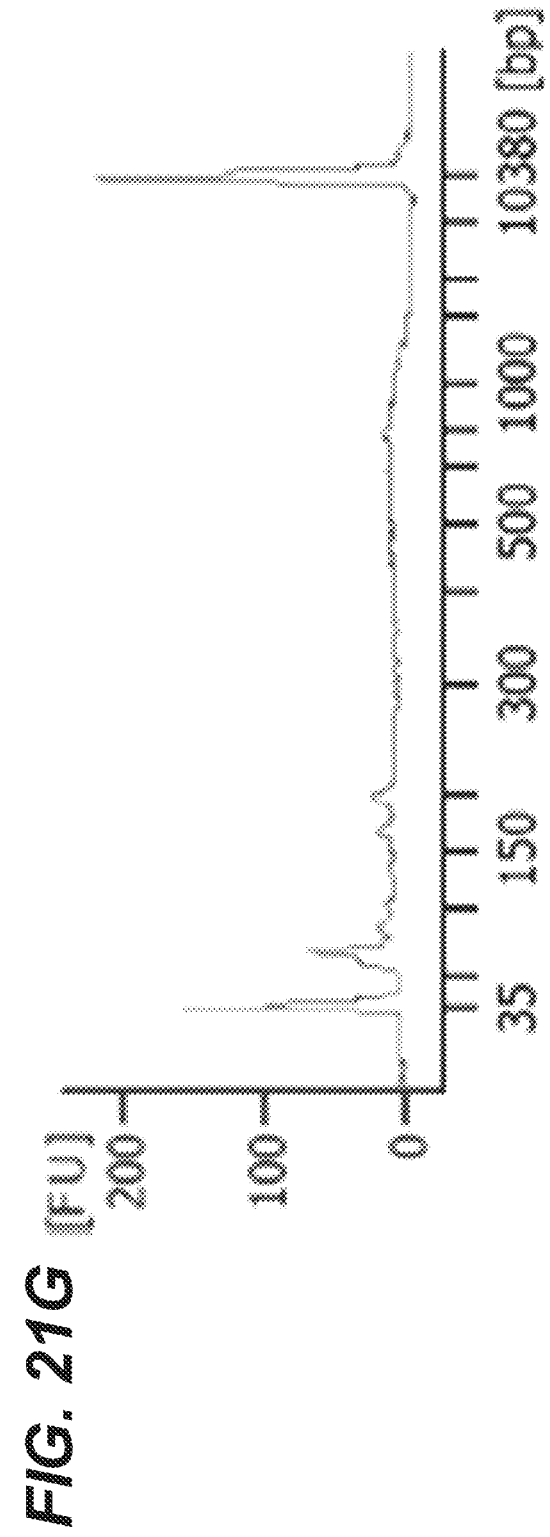
Figure 22B:
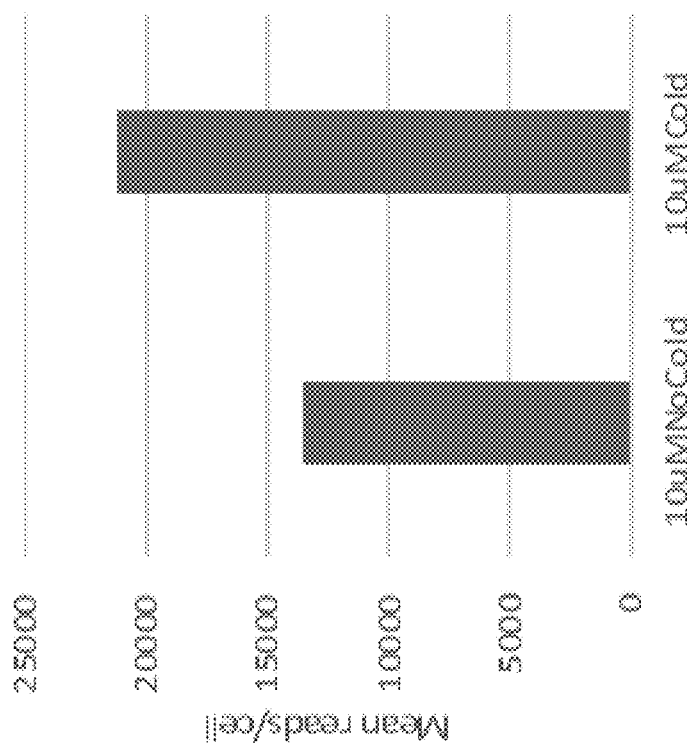
Figure 22A:
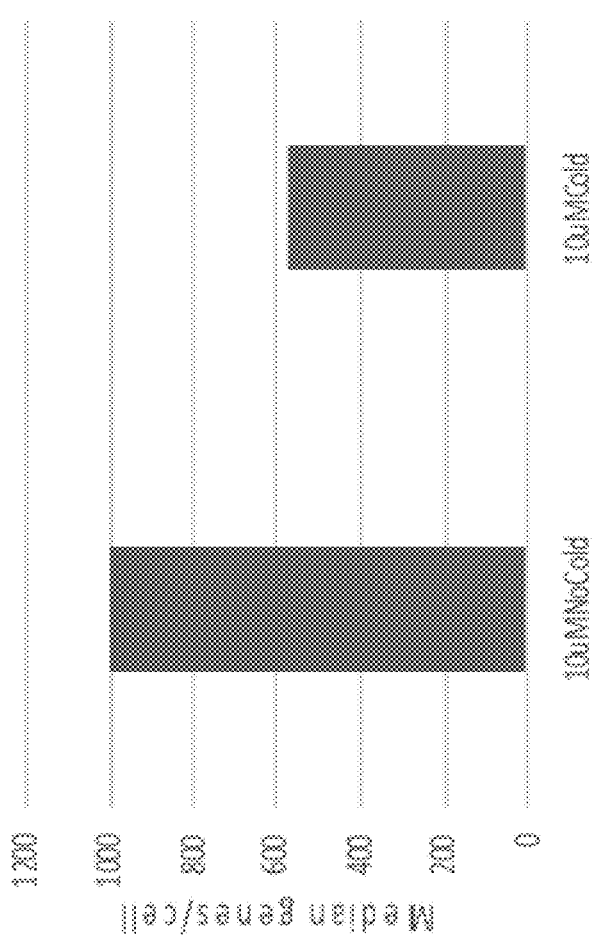

FIGS. 20A-20F are non-limiting exemplary data showing the effects of SPRI cleanup ratio on the performance of the RPE-based WTA method. FIGS. 20A-20B are non-limiting exemplary bioanalyzer plots comparing 1.6× (FIG. 20A) and 1.0× (FIG. 20B) SPRI cleanup ratios. Additionally, the reads/cell (FIG. 20C), median genes/cell (FIG. 20D), median molecules/cell (FIG. 20E), and % ribosomal and mitochondrial molecules (FIG. 20F) were compared for SPRI cleanup ratios of 1.6× and 1.0×. These data demonstrate that the 1.6×RPE cleanup ratio generates a higher yield than the 1.0× cleanup ratio, and that the 1.6× cleanup ratio also yields more molecules and genes/cell detected than the 1.0× cleanup ratio, despite having fewer reads/cell.

Random Primer Concentrations and RPE Conditions

Different random primer concentrations and RPE conditions for the RPE-based method for performing WTA provided herein were investigated.

FIGS. 21A-21G are non-limiting exemplary bioanalyzer plots (RPE PCR, post-SPRI cleanup) showing the effects of varying random primer concentrations and RPE conditions on the RPE-based WTA method. Specifically, the experiment compared the following conditions: ID019-1 (FIG. 21A, 10 uM random primer; no cold beads added, 6.186 nM), ID019-2 (FIG. 21B, 10 uM random primer, cold beads added, 2.138 nM), ID019-3 (FIG. 21C, 5 uM random primer, cold beads added, 0.538 nM), ID019-4 (FIG. 21D, 1 uM random primer, cold beads added, 0.314 nM), ID019-5 (FIG. 21E, 0.5 uM random primer, cold beads added, 0.438 nM), ID019-6 (FIG. 21F, 1 uM random primer, cold beads added, 0.652 nM), and ID019-7 (FIG. 21G, 0.5 uM random primer, cold beads added, 0.242 nM). Comparing FIGS. 21A and 21B, it is observed that adding cold bead decreases the yield of RPE PCR desired product. While ID017 (described below) had opposing PCR yield results, this could be due to PCR conditions being different, and RPE cleanup conditions were modified in ID019 to a 1-sided cleanup.

FIGS. 22A-22F are non-limiting exemplary sequencing data showing the effects of adding cold beads and varying bead density on RPE WTA. As shown FIGS. 22A-22C (ID019), adding cold beads decreased the sensitivity of the RPE WTA assay. The median number of genes per cell (FIG. 22A, non-ribosomal, non-mitochondrial, non-pseudogene), the mean reads/cell (FIG. 22B), and the mean molecules/cell (FIG. 22C) were assayed. Further, as shown FIGS. 22D-22F (ID017), higher bead density in RPE decreases the sensitivity of the RPE WTA assay. The median molecules/cell (FIG. 22D), the reads/cell (FIG. 22E) and the median genes/cell (FIG. 22F) were assayed.

Figure 23A:
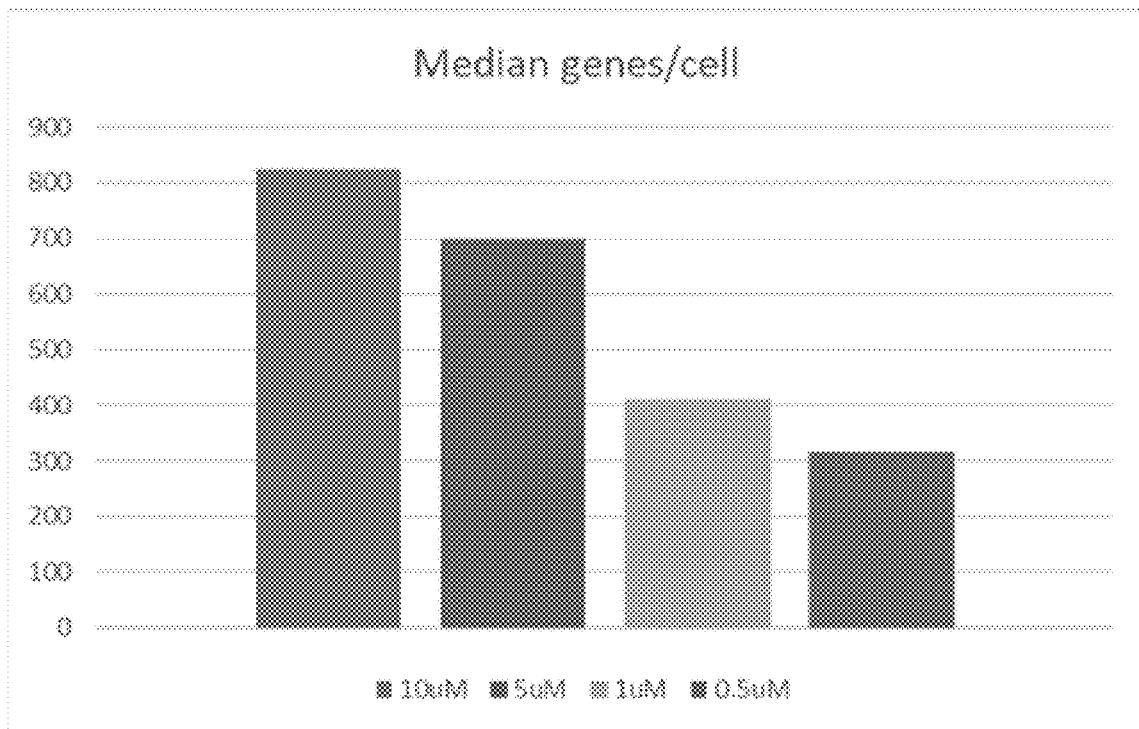
FIGS. 23A-23B are non-limiting exemplary sequencing data showing the effects of random primer concentration and cold beads on the performance of the RPE WTA.
Figure 23B:
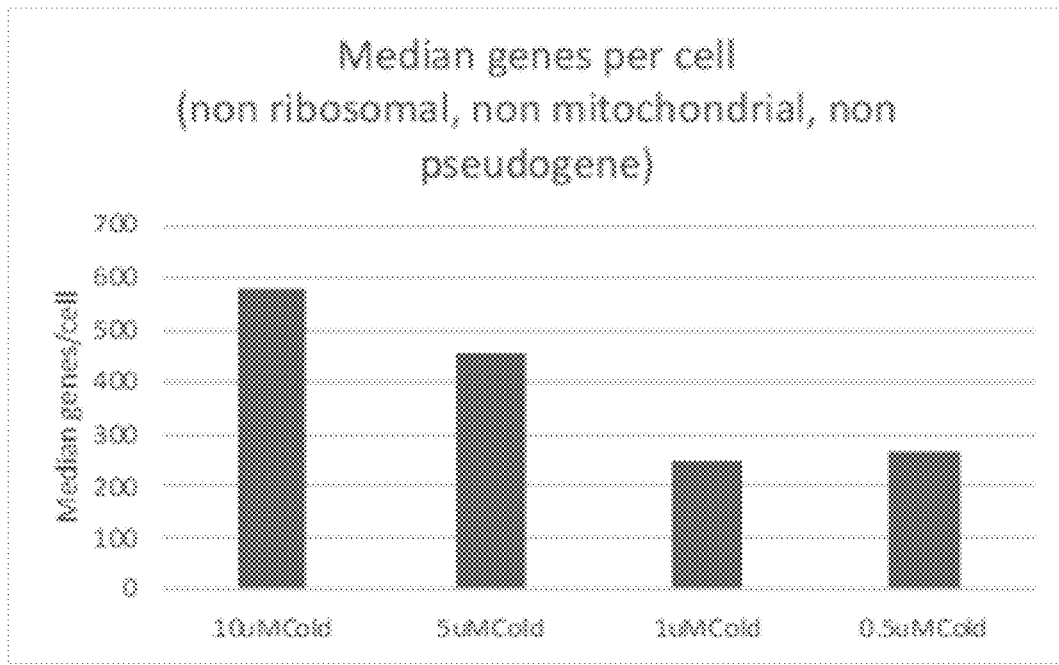
Figure 24A:
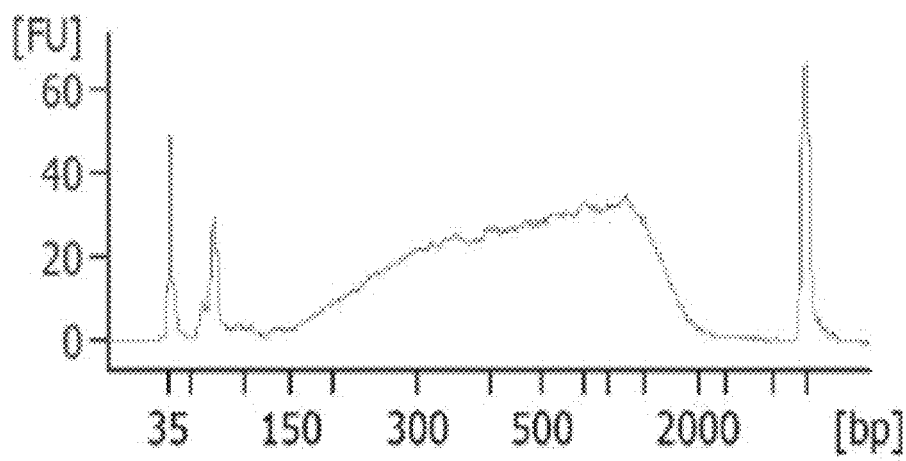
FIGS. 24A-24E are non-limiting exemplary bioanalyzer plots (RPE PCR) showing the effects of varying cell number on the RPE WTA method.
Figure 24B:
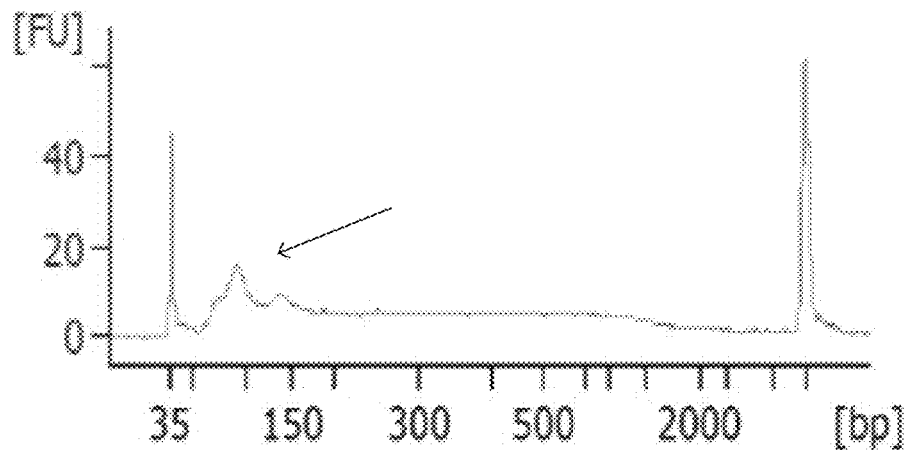
Figure 24C:
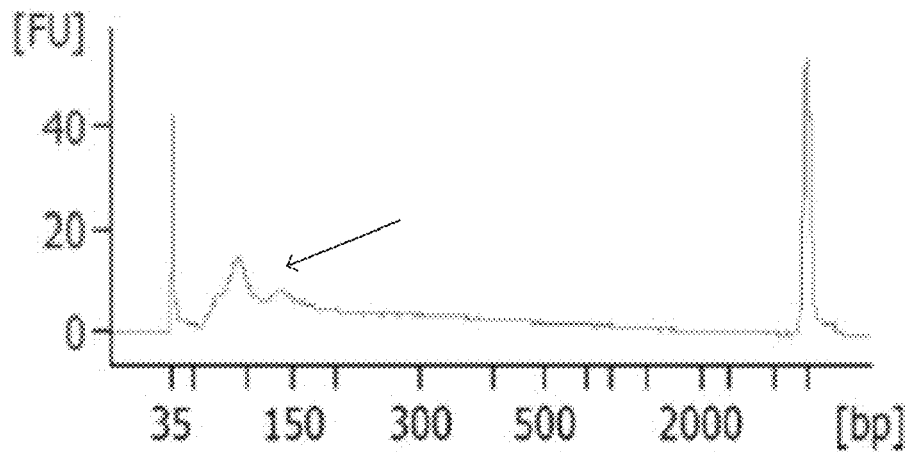
Figure 24D:
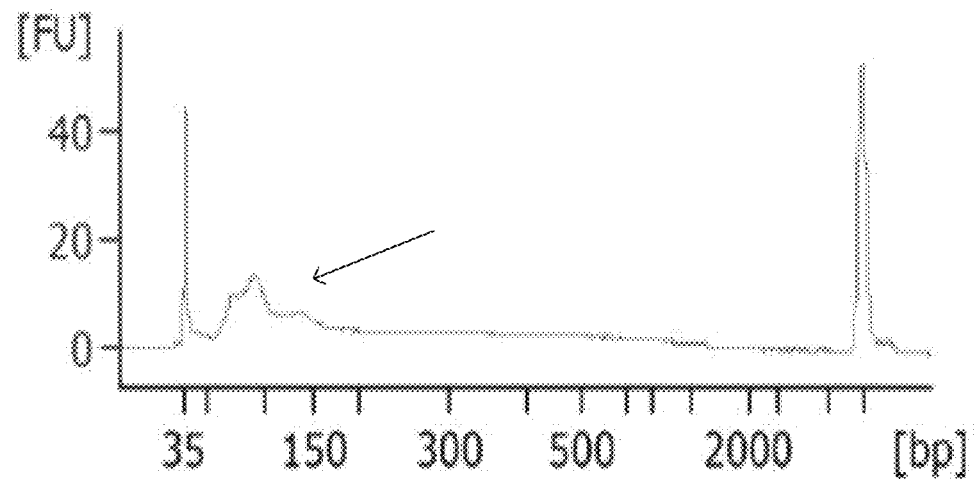
Figure 24E:
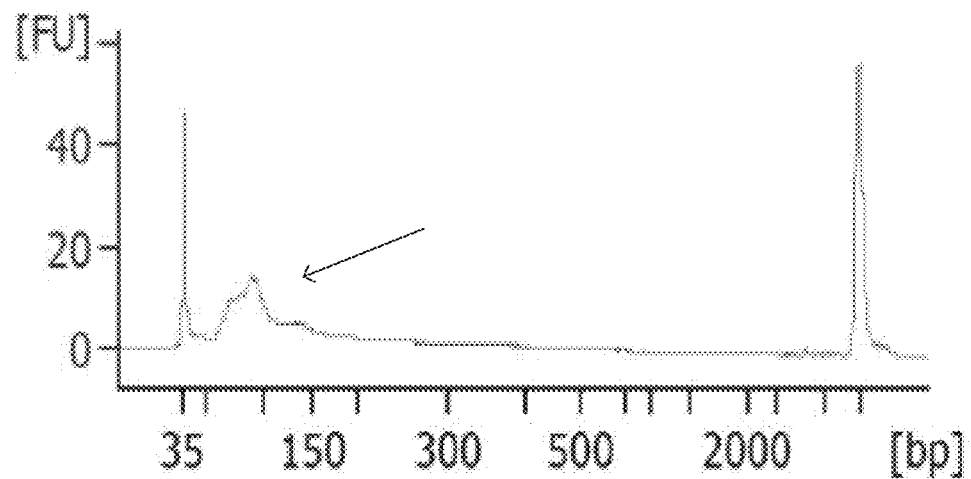
Figure 25A:
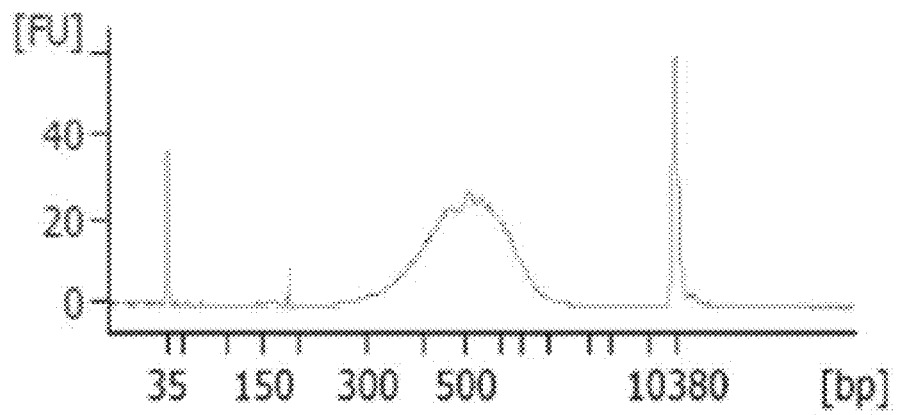
FIGS. 25A-25E are non-limiting exemplary bioanalyzer plots (Index PCR) showing the effects of varying cell number on the performance of the RPE WTA method.
Figure 25B:
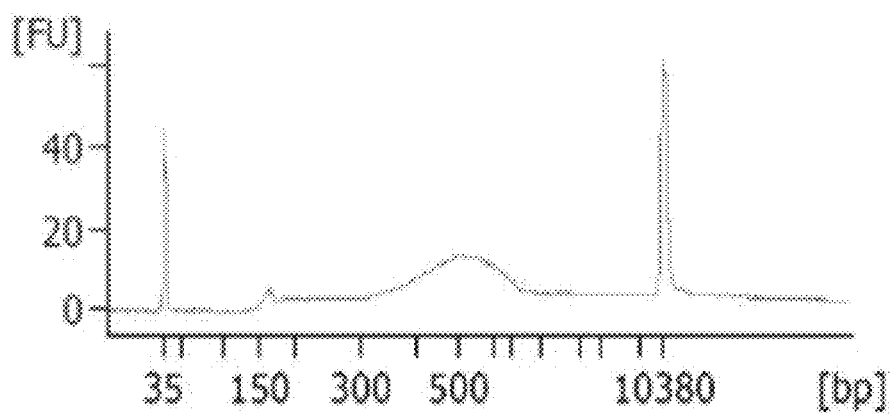
Figure 25C:
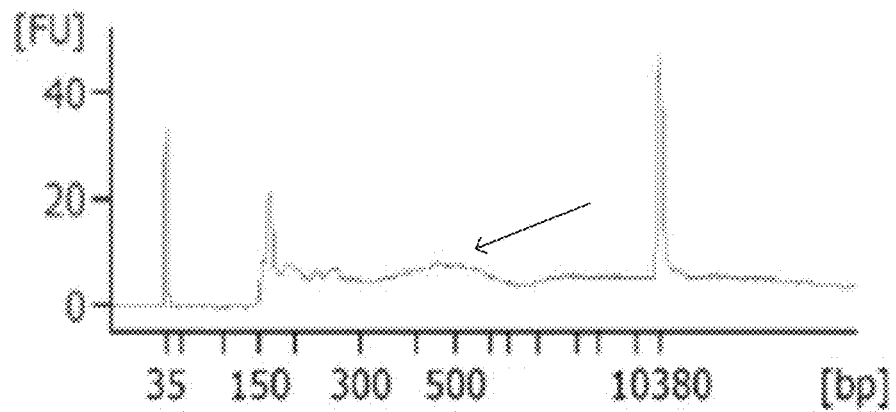
Figure 25D:
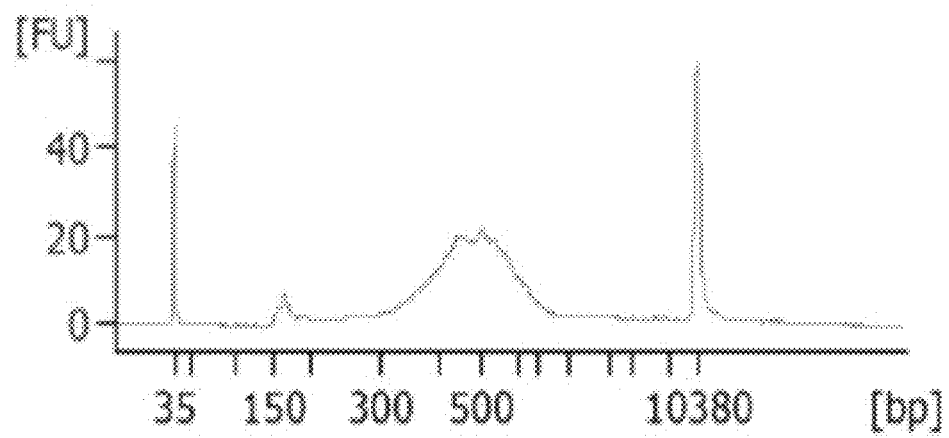
Figure 25E:
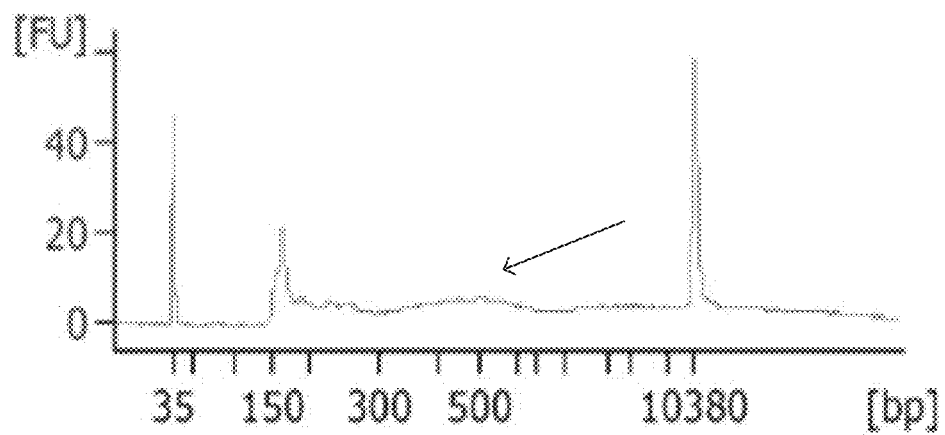

FIGS. 23A-23B are non-limiting exemplary sequencing data showing the effects of random primer concentration and cold beads on RPE WTA. FIG. 23A shows the median genes per cell (ID017, without cold beads) and FIG. 23B shows the median number of genes per cell (non-ribosomal, non-mitochondrial, non-pseudogene) with cold beads (ID019). In both the ID017 and ID019 single cell experiments, a 10 uM random primer concentration yielded consistently highest sensitivity. Table 17 provides a comparison of the WTA performance metrics of an existing WTA method to the RPE WTA methods employing varying random primer concentrations and bead densities.

TABLE 17

RPE WTA PERFORMANCE USING VARYING RANDOM PRIMER CONCENTRATIONS AND BEAD DENSITIES

| Criteria | Existing WTA Protocol Average Metric | WTA RPE Metric (random primer and bead concentrations) | | | | |
|---|---|---|---|---|---|---|
| | | 10 uM Primer (600 beads/ul) | 10 uM Primer (150 beads/ul) | 5 uM Primer (150 beads/ul) | 1 uM Primer (150 beads/ul) | 0.5 uM Primer (150 beads/ul) |
| Total genes detected | 14,757-19,919 (AVG. 16,485) | 16,766 | 19,109 | 18,584 | 16,521 | 15,454 |
| Ribosomal % reads per sample | 27.38-44.79% (AVG. 37%) | 17.95 | 18.76 | 17.89 | 15.3 | 13.71 |
| Mitochondria l% reads per sample | 2.24-4.15% (AVG. 3%) | 22.26 | 19.62 | 20.93 | 23.49 | 24.76 |
| % total cells positive for house-keeping genes | 65.06-81.76% (AVG. 75%) | 57.84 | 66.88 | 59.76 | 36.83 | 30.61 |
| % T cells positive for CD4 | 1.9-10% (AVG. 6%) | 23.1 | 27 | 20.5 | 12.6 | 7.7 |
| % T cells positive for CD8A | 7.5-19.7% (AVG. 14%) | 15.1 | 18.5 | 14.6 | 8.7 | 4.4 |
| % T cells positive for TRBC2 | 44.5-75.4% (AVG. 59%) | 67.6 | 72.8 | 67.7 | 46.8 | 43.4 |
| % T cells positive for TRAC | 51.1-85.9% (AVG. 71%) | 63.5 | 67.9 | 65.9 | 51.9 | 36 |
| % T cells positive for CD3D | 65.7-84.5% (AVG. 75%) | 27.8 | 38.7 | 31.1 | 15.8 | 8.2 |
| % T cells positive for TBX21 | 1.5-5.9% (AVG. 4%) | 3.8 | 5.8 | 3 | 2.9 | 2.5 |
| % B cells positive for IGLC3 | 26.1-43.9% (AVG. 35%) | 5.5 | 11.9 | 8.8 | 3.9 | 5.3 |

FIGS. 24A-24E are non-limiting exemplary bioanalyzer plots (RPE PCR) showing the effects of varying cell number on the RPE WTA method. Specifically, the experiment compared the following conditions: ID018-1 (FIG. 24A, 7970 cells, 14 cycles, 2.62 ng/uL), ID018-2 (FIG. 24B, 872 cells, 18 cycles, 1.14 ng/uL), ID018-3 (FIG. 24C, 75 cells, 18 cycles, 0.774 ng/uL), ID018-4 (FIG. 24D, 872 cells subsampled and cold beads added, 18 cycles, 0.892 ng/uL) and ID018-5 (FIG. 24E, 75 cells subsampled and cold beads added, 18 cycles, 0.572 ng/uL). Arrows indicate broad beads, possibly overamplification. FIGS. 25A-25E are non-limiting exemplary bioanalyzer plots (Index PCR) showing the effects of varying cell number on the RPE WTA method. Specifically, the experiment compared the following conditions: ID018-1 (FIG. 25A, 7970 cells, 6.36 ng/uL), ID018-2 (FIG. 25B, 872 cells, 1.14 ng/uL) ID018-3 (FIG. 25C, 75 cells, 0.774 ng/uL), ID018-4 (FIG. 25D, 872 cells subsampled and cold beads added, 0.892 ng/uL) and ID018-5 (FIG. 25E, 75 cells subsampled and cold beads added, 0.572 ng/uL). Cell libraries of approximately 100 cells were found not to have good quality in some instances. Table 18 shows the WTA performance metrics of the above-mentioned conditions. Library quality was found to have a tendency to diminish when the cell to bead ratio is low. Higher bead concentration may reduce sensitivity of assay, and the user may want to increase RPE volume. Library quality tends to be worse when cell:bead ratio is low. A random primer concentration of 10 uM was found to have highest sensitivity, and in some instances an even higher concentration may be desirable.

TABLE 18

RPE WTA PERFORMANCE USING VARYING CELL NUMBERS

| | # cell captured in cartridge | Putative # cell | # Reads/cell | % cellular reads assigned to cell label | % cellular reads uniquely aligned to transcriptome | Median mole/cell | Median gene/cell |
|---|---|---|---|---|---|---|---|
| ID018-1 | 7,970 | 6597 | 10657 | 74.22 | 39.74 | 965 | 531 |
| ID018-2 | 872 | 789 | 5917 | 28.2 | 9.26 | 1114 | 572 |
| ID018-3 | 75 | 72 | 2947.71 | 16.75 | 2 | 896 | 441.5 |
| ID018-4 | 872 | 640 | 11820 | 42.55 | 18.74 | 819.5 | 450.5 |
| ID018-5 | 75 | 57 | 4622.32 | 18.14 | 2.5 | 487 | 297 |

Figure 26A:
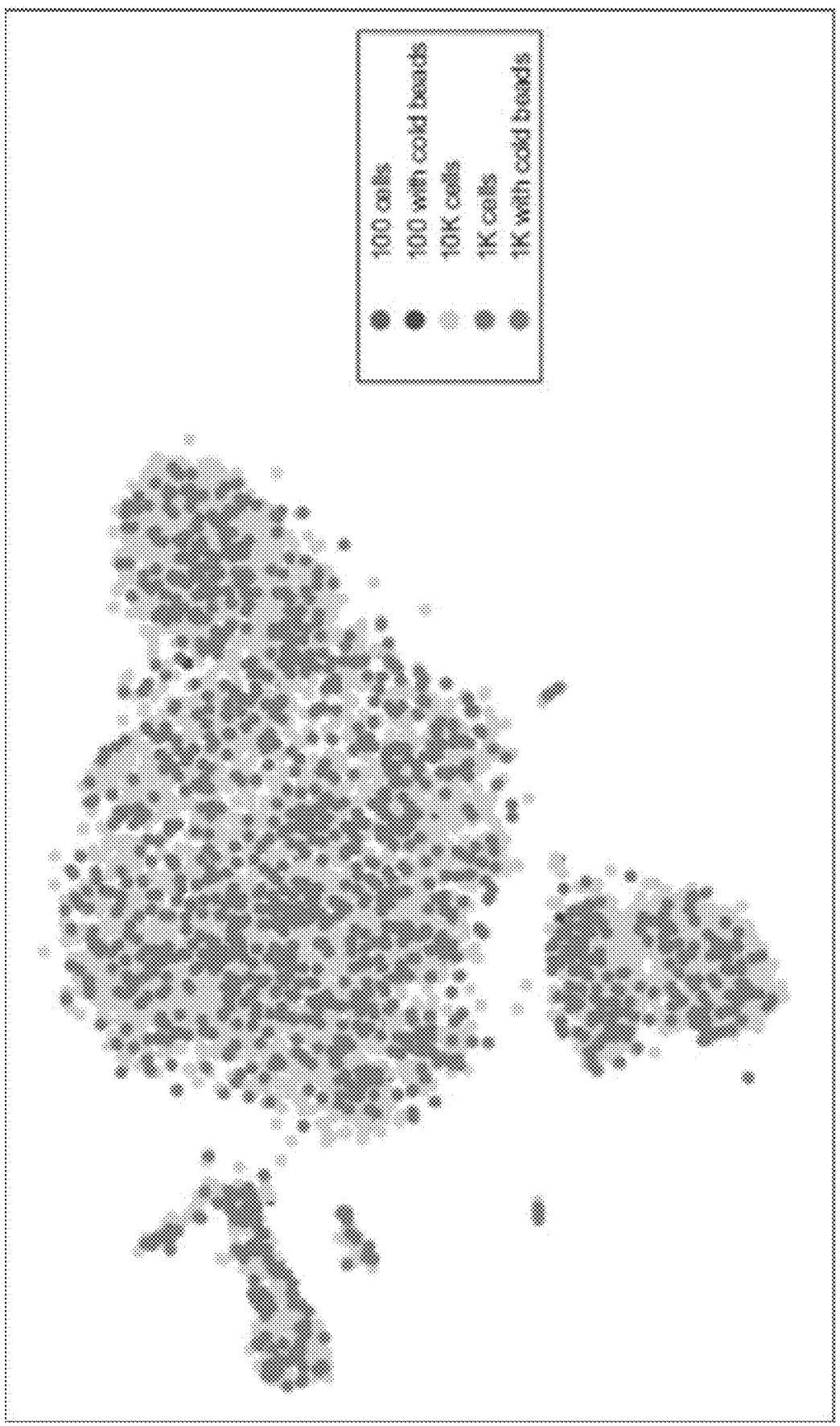
FIGS. 26A-26F depict t-Distributed Stochastic Neighbor Embedding (t-SNE) projections showing the exemplary performance of the random priming and extension-based WTA analysis of the disclosure with varying cell numbers.
Figure 26D:
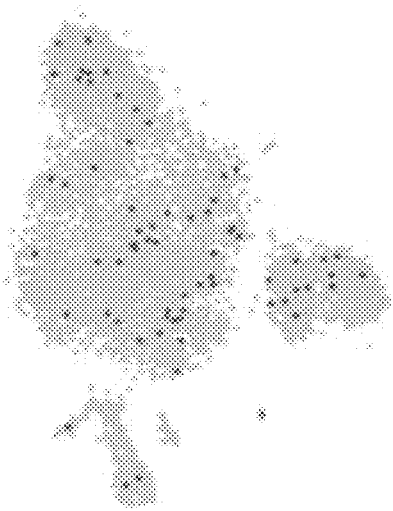
Figure 26C:
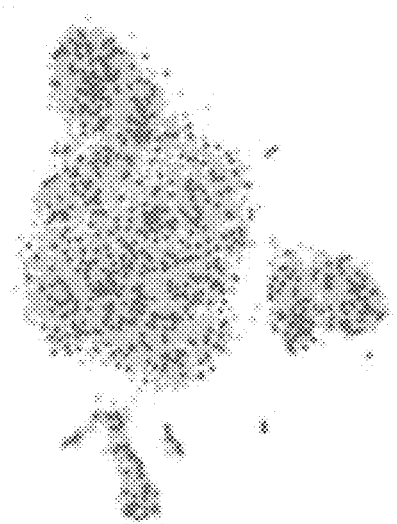
Figure 26B:
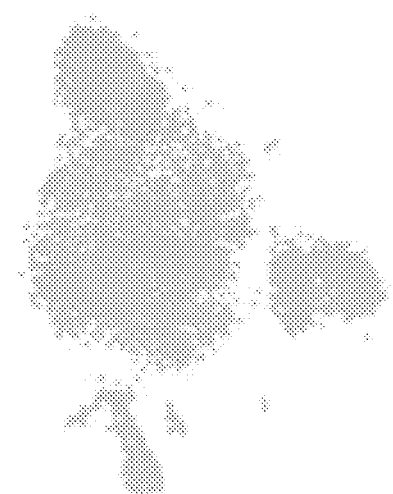
Figure 26F:
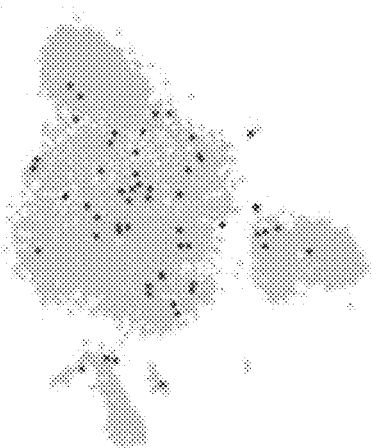
Figure 26E:
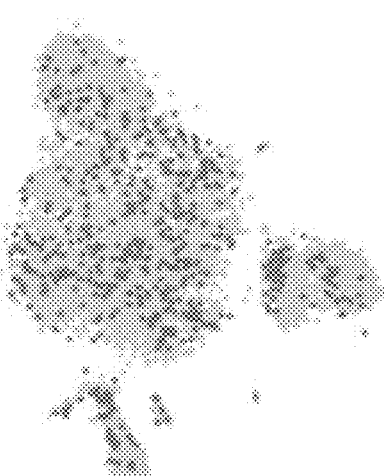

FIGS. 26A-26F depict t-Distributed Stochastic Neighbor Embedding (t-SNE) projections showing the exemplary performance of the random priming and extension-based WTA analysis of the disclosure with varying cell numbers. FIG. 26B depicts ID018-1 (10,000 cells), FIG. 26C depicts ID018-2 (1,000 cells), FIG. 26D depicts ID018-3 (100 cells), FIG. 26E depicts ID018-4 (1,000 cells with subsampling and cold beads added), FIG. 26F depicts ID018-5 (100 cells with subsampling and cold beads added), and FIG. 26A depicts an overlay of all the aforementioned conditions. Little batch effects were observed.

Figure 27A:
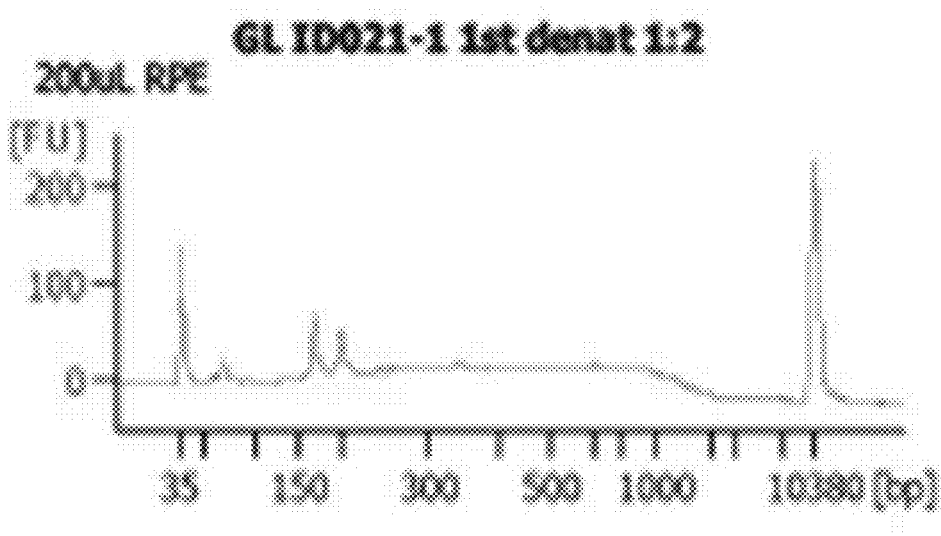
FIGS. 27A-27D are non-limiting exemplary bioanalyzer plots showing the effects of sequential RPE denaturation and RPE reaction volumes on the performance of the RPE WTA method.
Figure 27B:
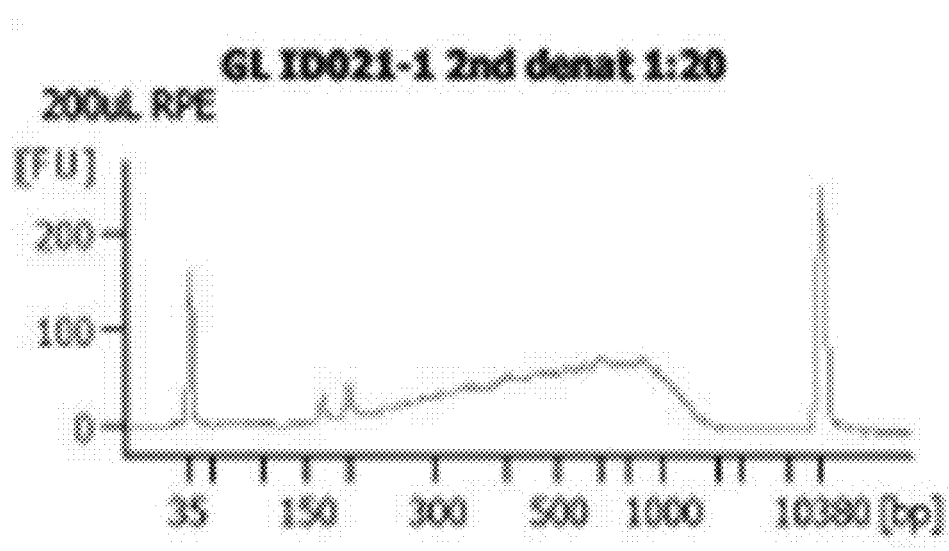
Figure 27C:
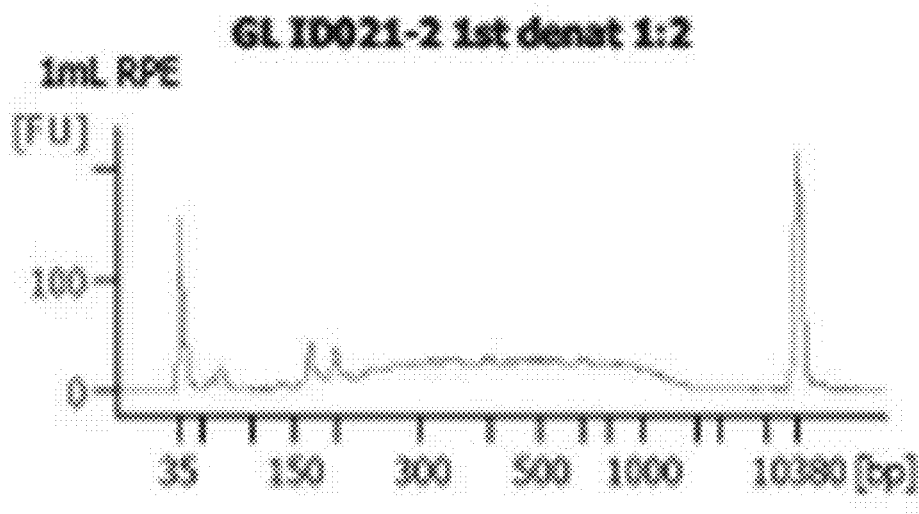
Figure 27D:
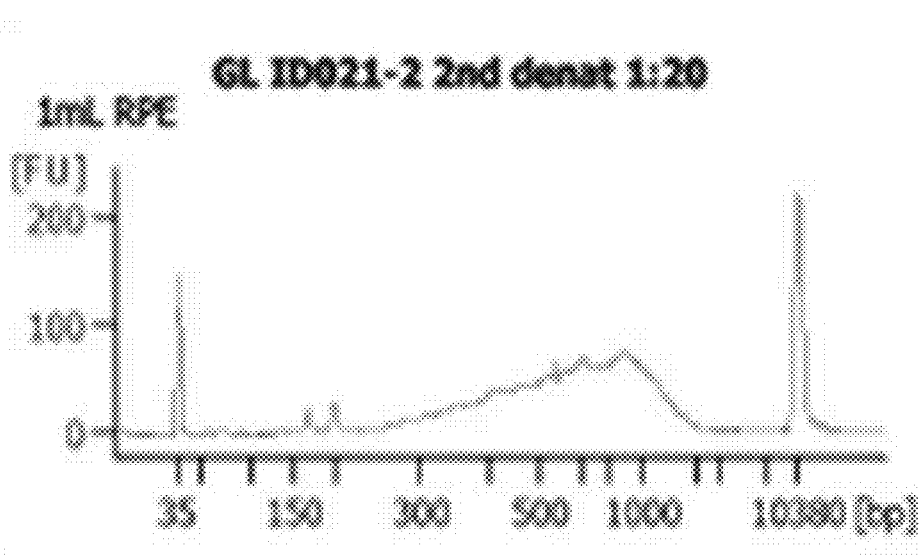

FIGS. 27A-27D are non-limiting exemplary bioanalyzer plots showing the effects of sequential RPE denaturation and RPE reaction volumes on the RPE WTA method. A single denaturation protocol (comprising denaturing with 95° C. in RPE reaction mix), shown in FIGS. 27A and 27C, was compared with a sequential denaturation protocol (further comprising denaturing a second time with 95 C in bead resuspension buffer), shown in FIGS. 27B and 27D. Further, the use of a 200 uL RPE volume (FIGS. 27A-27B) versus the use of a 1 mL RPE volume (FIGS. 27C-27D) were compared. The experiments were performed under the following conditions: FIG. 27A (12971 cells; 13 cycles; 4.64 ng/uL); FIG. 27B (12971 cells; 17 cycles; 68.07 ng/uL); FIG. 27C (12522 cells; 13 cycles; 5.44 ng/uL); and FIG. 27D (12522 cells; 17 cycles; 49.30 ng/uL). The second denaturation was found to yield roughly the same amount of PCR materials with both the 1 mL and 200 uL RPE volumes.

Number of PCR Amplifications

Figure 28A:
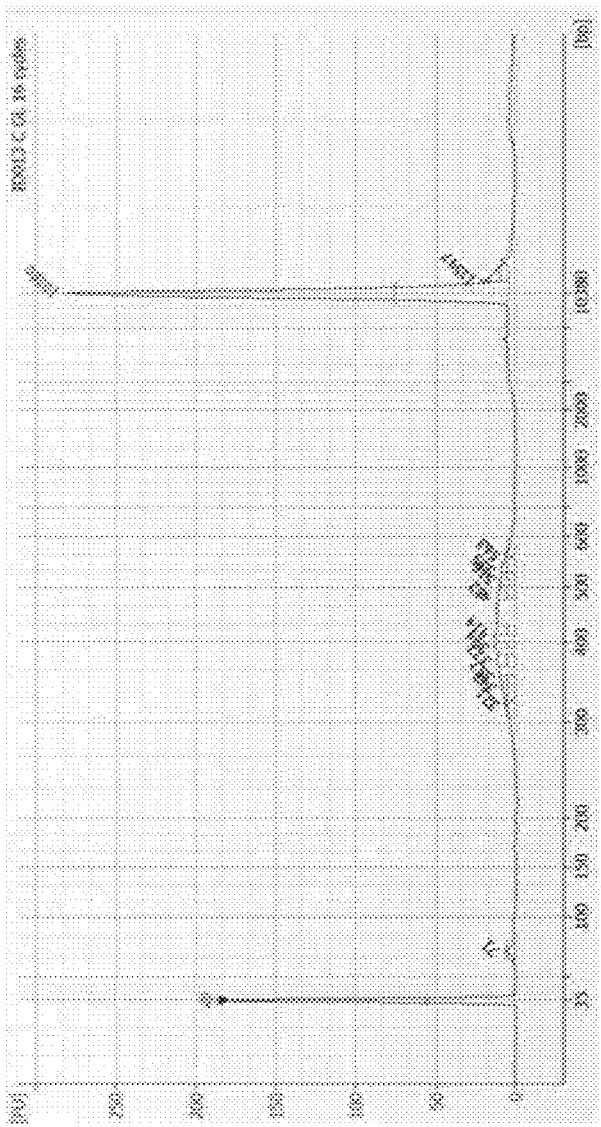
FIGS. 28A-28C are exemplary bioanalyzer plots showing the exemplary performance of the random priming and extension-based WTA analysis of the disclosure with a 2 PCR library generation protocol (FIGS. 28A-28B) and 1 PCR library generation protocol (FIG. 28C).
Figure 28B:
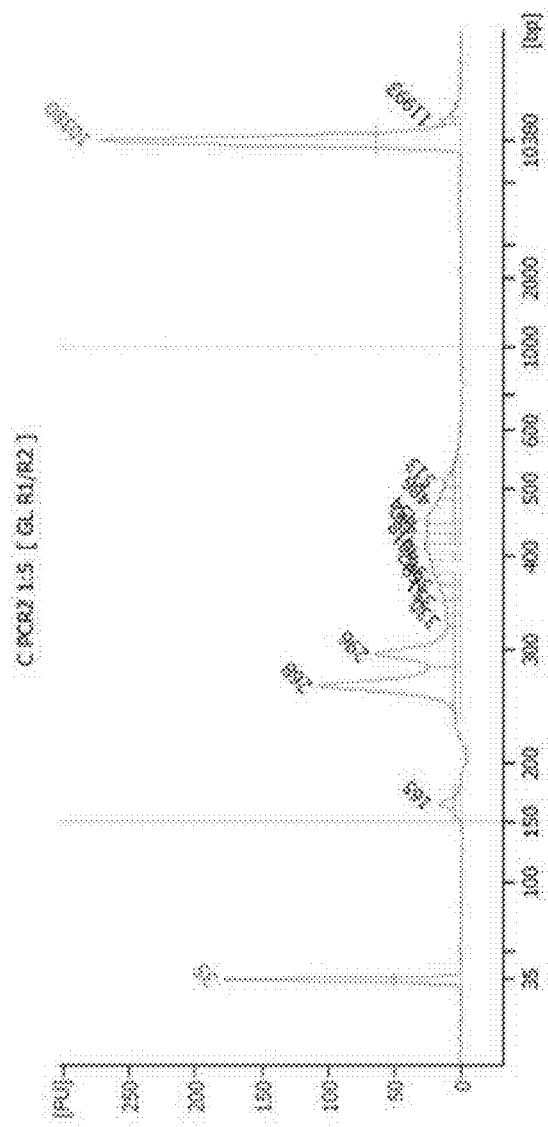
Figure 28C:
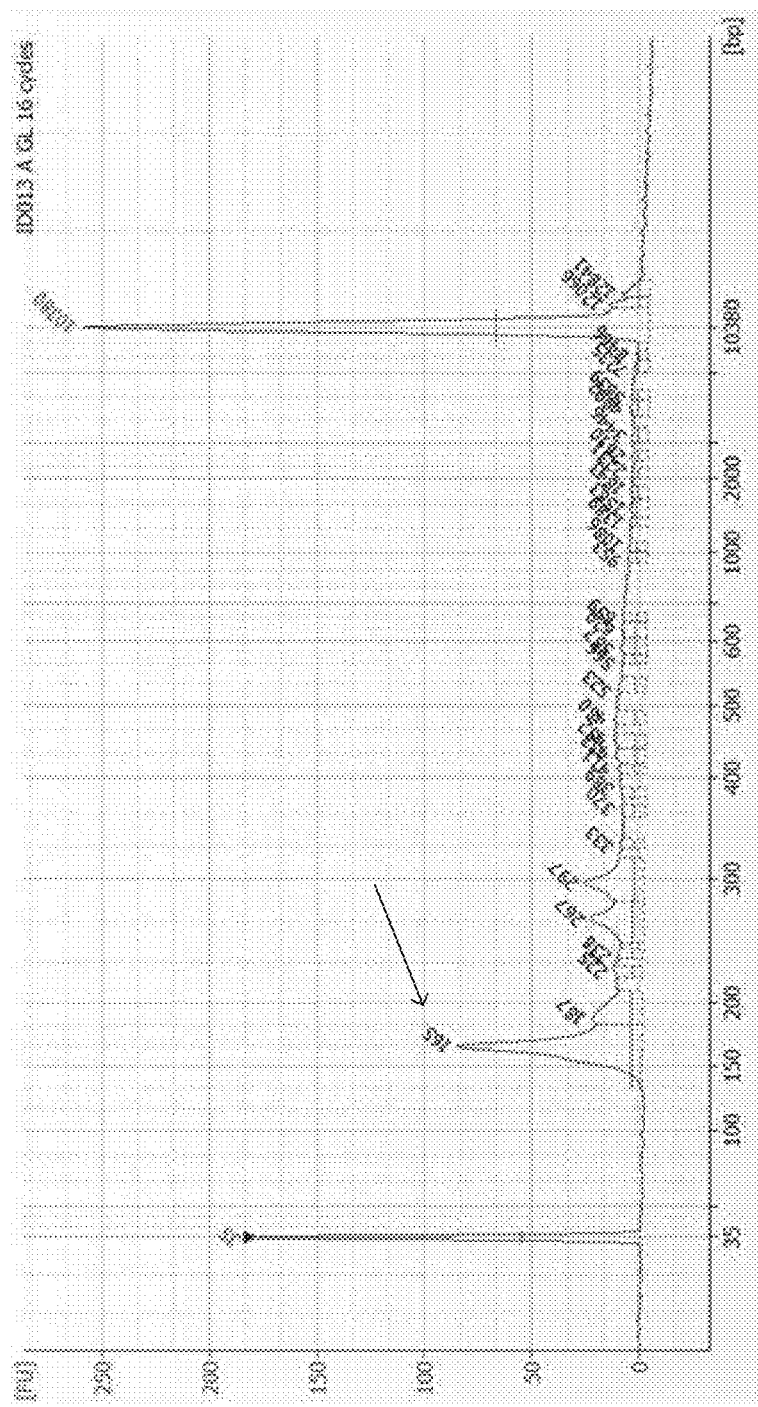

FIGS. 28A-28C are exemplary bioanalyzer plots showing the exemplary performance of the random priming and extension-based WTA analysis of the disclosure with a 2 PCR library generation protocol (FIGS. 28A-28B) and 1 PCR library generation protocol (FIG. 28C). FIG. 28A depicts PCR1 (e.g., RPE PCR) and FIG. 28B depicts PCR2 (e.g., index PCR) of the 2 PCR library generation protocol, while FIG. 28C depicts the results of the single PCR step. In first PCR of the 2 PCR library generation protocol (RPE PCR), Read 1&2 primers were used. In the first PCR of the 1 PCR library generation protocol, index P5/P7 primers were used. The use of index primers generated high 165 bp peak, <1 ng/uL after 16 cycles (elution in 30 uL). Using index primers in PCR1 (the 1 PCR library generation protocol) led to high amount of 165 bp peak (indicated by arrow in FIG. 28C). This peak was less prominent in the Read 1/Read 2 sample (FIG. 28A) (showed up as 71 bp). Thus, the use of R1/R2 primers in PCR1 generates less 165 bp peak and slightly less product in PCR1, but the user can generate more yield in the second PCR. Thus, the 2 PCR library generation protocol had less 165 bp contaminant peak and more total library yields. Therefore, 2 PCR-based RPE WTA method can allow cleaner library generation.

Example 2

Oligonucleotides for Associating with Protein Binding Reagents

This example demonstrates designing of oligonucleotides that can be conjugated with protein binding reagents. The oligonucleotides can be used to determine protein expression and gene expression simultaneously. The oligonucleotides can also be used for sample indexing to determine cells of the same or different samples.

95mer Oligonucleotide Design

The following method was used to generate candidate oligonucleotide sequences and corresponding primer sequences for simultaneous determination of protein expression and gene expression or sample indexing.

1. Sequence Generation and Elimination

The following process was used to generate candidate oligonucleotide sequences for simultaneous determination of protein expression and gene expression or sample indexing.

Step 1a. Randomly generate a number of candidate sequences (50000 sequences) with the desired length (45 bps).

Step 1b. Append the transcriptional regulator LSRR sequence to the 5' end of the sequences generated and a poly(A) sequence (25 bps) to the 3' end of the sequences generated.

Step 1c. Remove sequences generated and appended that do not have GC contents in the range of 40% to 50%.

Step 1d. Remove remaining sequences with one or more hairpin structures each.

The number of remaining candidate oligonucleotide sequences was 423.

2. Primer Design

The following method was used to design primers for the remaining 423 candidate oligonucleotide sequences.

2.1 N1 Primer: Use the universal N1 sequence: 5'-GTTGTCAAGATGCTACCGTTCAGAG-3' (LSRR sequence; SEQ ID NO. 4) as the N1 primer.

2.2 N2 Primer (for amplifying specific sample index oligonucleotides; e.g., N2 primer in FIGS. 29B-29D):

2.2a. Remove candidate N2 primers that do not start downstream of the N1 sequence.

2.2b. Remove candidate N2 primers that overlap in the last 35 bps of the candidate oligonucleotide sequence.

2.2c. Remove the primer candidates that are aligned to the transcriptome of the species of cells being studied using the oligonucleotides (e.g., the human transcriptome or the mouse transcriptome).

2.2d. Use the ILR2 sequence as the default control (ACACGACGCTCTTCCGATCT; SEQ ID NO. 5) to minimize or avoid primer-primer interactions.

Of the 423 candidate oligonucleotide sequences, N2 primers for 390 candidates were designed.

3. Filtering

The following process was used to filter the remaining 390 candidate primer sequences.

3a. Eliminate any candidate oligonucleotide sequence with a random sequence ending in As (i.e., the effective length of the poly(A) sequence is greater than 25 bps) to keep poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 29A shows a non-limiting exemplary candidate oligonucleotide sequence generated using the method above.

200mer Oligonucleotide Design

The following method was used to generate candidate oligonucleotide sequences and corresponding primer sequences for simultaneous determination of protein expression and gene expression and sample indexing.

1. Sequence Generation and Elimination

The following was used to generate candidate oligonucleotide sequences for simultaneous determination of protein expression and gene expression and sample indexing.

1a. Randomly generate a number of candidate sequences (100000 sequences) with the desired length (128 bps).

1b. Append the transcriptional regulator LSRR sequence and an additional anchor sequence that is non-human, non-mouse to the 5' end of the sequences generated and a poly(A) sequence (25 bps) to the 3' end of the sequences generated.

1c. Remove sequences generated and appended that do not have GC contents in the range of 40% to 50%.

1d. Sort remaining candidate oligonucleotide sequences based on hairpin structure scores.

1e. Select 1000 remaining candidate oligonucleotide sequences with the lowest hairpin scores.

2. Primer Design

The following method was used to design primers for 400 candidate oligonucleotide sequences with the lowest hairpin scores.

2.1 N1 Primer:

Use the universal N1 sequence: 5'-GTTGTCAAGATGC-TACCGTTCAGAG-3' (LSRR sequence; SEQ ID NO. 4) as the N1 primer.

2.2 N2 Primer (for amplifying specific sample index oligonucleotides; e.g., N2 primer in FIGS. 29B and 29C):

2.2a. Remove candidate N2 primers that do not start 23 nts downstream of the N1 sequence (The anchor sequence was universal across all candidate oligonucleotide sequences).

2.2b. Remove candidate N2 primers that overlap in the last 100 bps of the target sequence. The resulting primer candidates can be between the 48th nucleotide and 100th nucleotide of the target sequence.

2.2c. Remove the primer candidates that are aligned to the transcriptome of the species of cells being studied using the oligonucleotides (e.g., the human transcriptome or the mouse transcriptome).

2.2d. Use the ILR2 sequence, 5'-ACACGACGCTCTTCCGATCT-3' (SEQ ID NO. 5) as the default control to minimize or avoid primer-primer interactions.

2.2e. Remove N2 primer candidates that overlap in the last 100 bps of the target sequence.

Of the 400 candidate oligonucleotide sequences, N2 primers for 392 candidates were designed.

3. Filtering

The following was used to filter the remaining 392 candidate primer sequences.

3a. Eliminate any candidate oligonucleotide sequence with a random sequence ending in As (i.e., the effective length of the poly(A) sequence is greater than 25 bps) to keep poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 29B shows a non-limiting exemplary candidate oligonucleotide sequence generated using the method above. The nested N2 primer shown in FIG. 29B can bind to the antibody or sample specific sequence for targeted amplification. FIG. 29C shows the same non-limiting exemplary candidate oligonucleotide sequence with a nested universal N2 primer that corresponds to the anchor sequence for targeted amplification. FIG. 29D shows the same non-limiting exemplary candidate oligonucleotide sequence with a N2 primer for one step targeted amplification.

Altogether, these data indicate that oligonucleotide sequences of different lengths can be designed for simultaneous determination of protein expression and gene expression or sample indexing. The oligonucleotide sequences can include a universal primer sequence, an antibody specific oligonucleotide sequence or a sample indexing sequence, and a poly(A) sequence.

Example 3

Oligonucleotide-Associated Antibody Workflow

This example demonstrates a workflow of using an oligonucleotide-conjugated antibody for determining the expression profile of a protein target.

Figure 30:
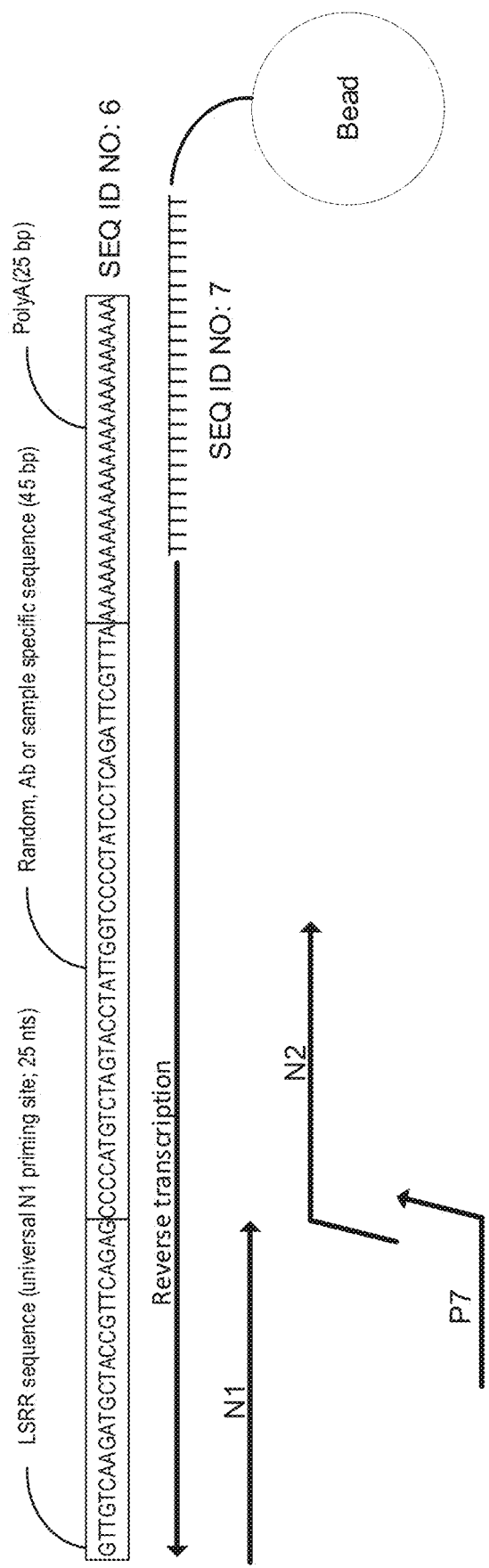
FIG. 30 shows a schematic illustration of a non-limiting exemplary oligonucleotide sequence for determining protein expression and gene expression simultaneously and for sample indexing.

Frozen cells (e.g., frozen peripheral blood mononuclear cells (PBMCs)) of a subject are thawed. The thawed cells are stained with an oligonucleotide-conjugated antibody (e.g., an anti-CD4 antibody at 0.06 µg/100 µl (1:333 dilution of an oligonucleotide-conjugated antibody stock)) at a temperature for a duration (e.g., room temperature for 20 minutes). The oligonucleotide-conjugated antibody is conjugated with 1, 2, or 3 oligonucleotides ("antibody oligonucleotides"). The sequence of the antibody oligonucleotide is shown in FIG. 30. The cells are washed to remove unbound oligonucleotide-conjugated antibody. The cells are optionally stained with Calcein AM (BD (Franklin Lake, New Jersey)) and Drag7™ (Abcam (Cambridge, United Kingdom)) for sorting with flow cytometry to obtain cells of interest (e.g., live cells). The cells are optionally washed to remove excess Calcein AM and Drag7™. Single cells stained with Calcein AM (live cells) and not Drag7™ (cells that are not dead or permeabilized) are sorted, using flow cytometry, into a BD Rhapsody™ cartridge.

Of the wells containing a single cell and a bead, the single cells in the wells (e.g., 3500 live cells) are lysed in a lysis buffer (e.g., a lysis buffer with 5 mM DTT). The mRNA expression profile of a target (e.g., CD4) is determined using BD Rhapsody™ beads. The protein expression profile of a target (e.g., CD4) is determined using BD Rhapsody™ beads and the antibody oligonucleotides. Briefly, the mRNA molecules are released after cell lysis. The Rhapsody™ beads are associated with barcodes (e.g., stochastic barcodes) each containing a molecular label, a cell label, and an oligo(dT) region. The poly(A) regions of the mRNA molecules released from the lysed cells hybridize to the poly(T) regions of the stochastic barcodes. The poly(dA) regions of the antibody oligonucleotides hybridize to the oligo(dT) regions of the barcodes. The mRNA molecules were reverse transcribed using the barcodes. The antibody oligonucleotides are replicated using the barcodes. The reverse transcription and replication optionally occur in one sample aliquot at the same time.

The reverse transcribed products and replicated products are PCR amplified using primers for determining mRNA expression profiles of genes of interest, using N1 primers, and the protein expression profile of a target, using the antibody oligonucleotide N1 primer. For example, the reverse transcribed products and replicated products can be PCR amplified for 15 cycles at 60 degrees annealing temperature using primers for determining the mRNA expression profiles of 488 blood panel genes, using blood panel N1 primers, and the expression profile of CD4 protein, using the antibody oligonucleotide N1 primer ("PCR 1"). Excess barcodes are optionally removed with Ampure cleanup. The products from PCR 1 are optionally divided into two aliquots, one aliquot for determining the mRNA expression profiles of the genes of interest, using the N2 primers for the genes of interest, and one aliquot for determining the protein expression profile of the target of interest, using the antibody oligonucleotide N2 primer ("PCR 2"). Both aliquots are PCR amplified (e.g., for 15 cycles at 60 degrees annealing temperature). The protein expression of the target in the cells are determined based on the antibody oligonucleotides as illustrated in FIG. 30 ("PCR 2"). Sequencing data is obtained and analyzed after sequencing adaptor addition ("PCR 3"), such as sequencing adaptor ligation. Cell types are determined based on the mRNA expression profiles of the genes of interest.

Altogether, this example describes using an oligonucleotide-Conjugated antibody for determining the protein expression profile of a target of interest. This example further describes that the protein expression profile of the target of interest and the mRNA expression profiles of genes of interest can be determine simultaneously.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof.

Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of labeling nucleic acid targets in a sample, the method comprising:
   contacting copies of a nucleic acid target with a plurality of oligonucleotide barcodes, wherein each oligonucleotide barcode comprises a first universal sequence, a molecular label, and a target-binding region capable of hybridizing to the copies of the nucleic acid target, wherein the nucleic acid target is an mRNA of a gene;
   extending the plurality of oligonucleotide barcodes hybridized to the copies of the nucleic acid target to generate a plurality of first strand barcoded polynucleotides;
   contacting random primers with the plurality of first strand barcoded polynucleotides, wherein each of the random primers comprises a second universal sequence, or a complement thereof,
   extending the random primers hybridized to the plurality of first strand barcoded polynucleotides to generate a plurality of extension products;
   amplifying the plurality of extension products using primers capable of hybridizing to the first universal sequence or complements thereof, and primers capable of hybridizing to the second universal sequence or complements thereof, thereby generating a first plurality of barcoded amplicons; and
   synthesizing a plurality of gene-specific barcoded amplicons using the plurality of first strand barcoded polynucleotides as templates, wherein synthesizing a plurality of gene-specific barcoded amplicons comprises PCR amplification using primers capable of hybridizing to the first universal sequence, or a complement thereof, and a gene-specific primer.

2. The method of claim 1, wherein amplifying the plurality of extension products comprises adding sequences of binding sites of sequencing primers and/or sequencing adaptors, complementary sequences thereof, and/or portions thereof, to the plurality of extension products.

3. The method of claim 1, comprising obtaining sequence information of the plurality of first plurality of barcoded amplicons, or products thereof, and wherein the number of distinct sequences associated with the first plurality of barcoded amplicons, or products thereof, indicates the copy number of the nucleic acid target in the sample.

4. The method of claim 3,
   wherein contacting copies of a nucleic acid target comprises contacting copies of a plurality of nucleic acid targets with a plurality of oligonucleotide barcodes,
   wherein extending the plurality of oligonucleotide barcodes comprises extending the plurality of oligonucleotide barcodes hybridized to the copies of the plurality nucleic acid targets to generate a plurality of first strand barcoded polynucleotides, and
   wherein the number of the molecular labels with distinct sequences associated with barcoded amplicons of the first plurality of barcoded amplicons comprising a sequence of the each of the plurality of nucleic acid targets indicates the number of each of the plurality of nucleic acid targets in the sample.

5. The method of claim 1, comprising amplifying the first plurality of barcoded amplicons using primers capable of hybridizing to the first universal sequence or complements thereof, and primers capable of hybridizing to the second universal sequence or complements thereof, thereby generating a second plurality of barcoded amplicons, wherein amplifying the first plurality of barcoded amplicons comprises adding sequences of binding sites of sequencing primers and/or sequencing adaptors, complementary sequences thereof, and/or portions thereof, to the first plurality of barcoded amplicons.

6. The method of claim 5, comprising obtaining sequence information of the plurality of second plurality of barcoded amplicons, or products thereof, and wherein the number of distinct sequences associated with the second plurality of barcoded amplicons, or products thereof, indicates the copy number of the nucleic acid target in the sample.

7. The method of claim 5,
   wherein contacting copies of a nucleic acid target comprises contacting copies of a plurality of nucleic acid targets with a plurality of oligonucleotide barcodes,
   wherein extending the plurality of oligonucleotide barcodes comprises extending the plurality of oligonucleotide barcodes hybridized to the copies of the plurality nucleic acid targets to generate a plurality of first strand barcoded polynucleotides, and
   wherein the number of the molecular labels with distinct sequences associated with barcoded amplicons of the second plurality of barcoded amplicons comprising a sequence of the each of the plurality of nucleic acid targets indicates the number of each of the plurality of nucleic acid targets in the sample.

8. The method of claim 1, wherein the first universal sequence and the second universal sequence are different.

9. The method of claim 1, wherein extending the plurality of oligonucleotide barcodes hybridized to the copies of the nucleic acid target comprises extending the plurality of oligonucleotide barcodes hybridized to the copies of the nucleic acid target using a reverse transcriptase.

10. The method of claim 1, wherein extending the plurality of oligonucleotide barcodes hybridized to the copies of the nucleic acid target comprises extending the plurality of oligonucleotide barcodes hybridized to the copies of the nucleic acid target using a DNA polymerase lacking at least one of 5' to 3' exonuclease activity and 3' to 5' exonuclease activity.

11. The method of claim 1, wherein extending the random primers hybridized to the plurality of first strand barcoded polynucleotides comprises extending the random primers hybridized to the plurality of first strand barcoded polynucleotides using a DNA polymerase lacking at least one of 5' to 3' exonuclease activity and 3' to 5' exonuclease activity.

12. The method of claim 1, wherein said random primers comprise a random sequence of nucleotides, and wherein the random sequence of nucleotides is 4 to 30 nucleotides in length.

13. The method of claim 1, comprising:
   providing additional random primers;
   contacting the additional random primers with the plurality of first strand barcoded polynucleotides, wherein each of the additional random primers comprises a second universal sequence, or a complement thereof,
   extending the additional random primers hybridized to the plurality of first strand barcoded polynucleotides to generate an additional plurality of extension products; and
   amplifying the additional plurality of extension products using primers capable of hybridizing to the first universal sequence or complements thereof, and primers capable of hybridizing to the second universal sequence or complements thereof.

14. The method of claim 1, wherein the sample comprises peripheral blood mononuclear cells or immune cells, and optionally the immune cells comprise B cells, T cells or a combination thereof.

15. The method of claim 1, wherein the nucleic acid target encodes an immune receptor.

16. The method of claim 15, wherein the immune receptor is a T cell receptor (TCR) or a B cell receptor (BCR).

17. The method of claim 1, wherein the sample comprises a single cell, the method comprising physically associating a synthetic particle comprising the plurality of the oligonucleotide barcodes with the single cell in the sample.

18. The method of claim 17, comprising lysing the single cell after physically associating the synthetic particle with the single cell.

19. The method of claim 17, wherein the synthetic particle and the single cell are in the same partition.

20. The method of claim 1, comprising obtaining sequence information of the plurality of gene-specific barcoded amplicons, or products thereof, wherein obtaining the sequence information comprises attaching sequencing adaptors to the plurality of gene-specific barcoded amplicons, or products thereof.

* * * * *

SEQUENCE LISTING

```
<160> NUMBER OF SEQ ID NOS: 9

<210> SEQ ID NO 1
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (24)..(32)
<223> OTHER INFORMATION: n is a, c, g, or t

<400> SEQUENCE: 1
tcagacgtgt gctcttccga tctnnnnnnn nn                              32

<210> SEQ ID NO 2
<211> LENGTH: 95
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: 5'AmMC6
<222> LOCATION: (1)..(1)
<223> OTHER INFORMATION: 5' Amino Modifier C6

<400> SEQUENCE: 2
gttgtcaaga tgctaccgtt cagagtacgt ggagttggtg gcccgacccc gagcgctacg     60 agcccccgg aaaaaaaaaa aaaaaaaaaa aaaaa                                 95

<210> SEQ ID NO 3
<211> LENGTH: 200
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: 5AmMC6
<222> LOCATION: (1)..(1)
<223> OTHER INFORMATION: 5' Amino Modifier C6

<400> SEQUENCE: 3
gttgtcaaga tgctaccgtt cagagctact gtccgaagtt accgtgtatc taccacgggt     60
ggtttttcga atccggaaaa gatagtaata agtgttttag ttggaataag tcgcaacttt    120
tggagacggt tacctctcaa tttttctgat ccgtaggccc cccgatctcg gcctcaaaaa    180
aaaaaaaaaa aaaaaaaaa                                                 200

<210> SEQ ID NO 4
<211> LENGTH: 25
<212> TYPE: DNA
<213> ORGANISM: Artificial Sequence
<220> FEATURE:
<223> OTHER INFORMATION: Synthetic Oligonucleotide
```

<400> SEQUENCE: 4
gttgtcaaga tgctaccgtt cagag                                                  25

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
acacgacgct cttccgatct                                                        20

<210> SEQ ID NO 6
<211> LENGTH: 95
<212> TYPE: DNA
<213> ORGANISM: Artificial Sequence
<220> FEATURE:
<223> OTHER INFORMATION: Synthetic Oligonucleotide

<400> SEQUENCE: 6
gttgtcaaga tgctaccgtt cagagccccca tgtctagtac ctattggtcc cctatcctca          60
gattcgttta aaaaaaaaaa aaaaaaaaaa aaaaa                                       95

<210> SEQ ID NO 7
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 7
tttttttttt tttttttttt tttttt                                                 26

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
aaaaaaaaaa aaaaaaaaaa                                                        20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tttttttttt tttttttttt                                                        20